US009029359B2

(12) United States Patent
Bui et al.

(10) Patent No.: US 9,029,359 B2
(45) Date of Patent: May 12, 2015

(54) HETEROARYL BTK INHIBITORS

(75) Inventors: Minna Bui, Oakland, CA (US); Patrick Conlon, Wakefield, MA (US); Daniel A. Erlanson, San Francisco, CA (US); Junfa Fan, Foster City, CA (US); Bing Guan, Needham, MA (US); Brian T. Hopkins, Newton, MA (US); Alexey Ishchenko, Somerville, MA (US); Tracy J. Jenkins, Belmont, MA (US); Gnanasambandam Kumaravel, Westford, MA (US); Doug Marcotte, Worcester, MA (US); Noel Powell, Westford, MA (US); Daniel Scott, Weston, MA (US); Art Taveras, Southborough, MA (US); Deping Wang, Sharon, MA (US); Min Zhong, Palo Alto, CA (US)

(73) Assignees: Biogen Idec MA, Inc., Cambridge, MA (US); Sunesis Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 13/393,191

(22) PCT Filed: Sep. 3, 2010

(86) PCT No.: PCT/US2010/047879
§ 371 (c)(1),
(2), (4) Date: Mar. 1, 2012

(87) PCT Pub. No.: WO2011/029043
PCT Pub. Date: Mar. 10, 2011

(65) Prior Publication Data
US 2012/0157442 A1    Jun. 21, 2012

Related U.S. Application Data

(60) Provisional application No. 61/240,003, filed on Sep. 4, 2009.

(51) Int. Cl.
C07D 473/34    (2006.01)
C07D 471/04    (2006.01)
C07D 239/70    (2006.01)
C07D 401/04    (2006.01)
C07D 487/04    (2006.01)

(52) U.S. Cl.
CPC .......... *C07D 473/34* (2013.01); *C07D 471/04* (2013.01); *C07D 239/70* (2013.01); *C07D 401/04* (2013.01); *C07D 487/04* (2013.01)

(58) Field of Classification Search
None
See application file for complete search history.

(56) References Cited

U.S. PATENT DOCUMENTS

| 4,861,760 | A | 8/1989 | Mazuel et al. |
| 4,911,920 | A | 3/1990 | Jani et al. |
| 5,212,162 | A | 5/1993 | Missel et al. |
| 5,403,841 | A | 4/1995 | Lang et al. |
| 6,696,567 | B2 * | 2/2004 | Blumenkopf et al. ........ 544/280 |
| 8,178,131 | B2 * | 5/2012 | Le Huerou et al. .......... 424/649 |
| 2007/0135461 | A1 | 6/2007 | Rodgers et al. |
| 2009/0099165 | A1 | 4/2009 | Hurley et al. |
| 2012/0157443 | A1 | 6/2012 | Bui et al. |
| 2013/0345192 | A1 | 12/2013 | Hopkins et al. |

FOREIGN PATENT DOCUMENTS

| WO | WO-96/05309 A2 | 2/1996 |
| WO | WO-02/00661 A1 | 1/2002 |
| WO | WO-03000695 A1 | 1/2003 |
| WO | WO-2005/068468 A2 | 7/2005 |
| WO | WO-2006044504 A1 | 4/2006 |
| WO | WO-2006/135383 A2 | 12/2006 |
| WO | WO 2006135383 A2 * | 12/2006 |
| WO | WO-2008/116064 A2 | 9/2008 |
| WO | WO-2009/108670 A1 | 9/2009 |
| WO | WO-2009/140320 A1 | 11/2009 |
| WO | WO-2010/068806 A1 | 6/2010 |
| WO | WO-2010/075273 A1 | 7/2010 |
| WO | WO-2011/003418 A1 | 1/2011 |
| WO | WO-2011/013785 A1 | 2/2011 |
| WO | WO-2011/029046 A1 | 3/2011 |
| WO | WO-2011/050202 A1 | 4/2011 |
| WO | WO-2011/082268 A2 | 7/2011 |
| WO | WO-2012/022045 A1 | 2/2012 |
| WO | WO-2012/022265 A1 | 2/2012 |
| WO | WO-2012/058645 A1 | 5/2012 |

OTHER PUBLICATIONS

Neidle, ed. Cancer Drug Design and Discovery, Elsevier/Academic Press, 2008, pp. 427-431.*
Advani et al., "Bruton Tyrosine Kinase Inhibitor Ibrutinib (PCI-32765) Has Significant Activity in Patients With Relapsed/Refractory B-Cell Malignancies", J.Clin.Oncol., 2013, vol. 31, No. 1, pp. 88-94.*
International Search Report for PCT/US2010/047879 mailed Nov. 23, 2010.
Vassilev et al. Therapeutic Potential of Inhibiting Bruton's Tyrosine Kinase, (BTK), in Current Pharmamaceutical Design, 2004, vol. 10, pp. 1757-1766.
U.S. Appl. No. 14/316,710, Bui et al.
Berge S.M. et al., Pharmaceutical salts, Journal of Pharmaceutical Sciences, 66(1):1-19 (1977).
Carpino, L.A. and El-Faham, A., Tetramethylfluoroformamidinium Hexafluorophosphate: A rapid-acting peptide coupling reagent for solution and solid phase peptide synthesis, Journal of the American Chemical Society, 117:5401 (1995).

(Continued)

*Primary Examiner* — Jeffrey S Lundgren
*Assistant Examiner* — Stephanie Springer
(74) *Attorney, Agent, or Firm* — Choate, Hall & Stewart, LLP; Andrea L. C. Reid; John P. Rearick

(57) ABSTRACT

The present invention provides compounds useful as inhibitors of Btk, compositions thereof, and methods of using the same.

18 Claims, No Drawings

(56) References Cited

OTHER PUBLICATIONS

Carpino, L.A., 1-Hydroxy-7-azabenzotriazole, An efficient peptide coupling additive, Journal of the American Chemical Society, 115:4397 (1993).

Extended European Search Report for EP 10814583.0 dated Jan. 8, 2013 (11 pages).

Hu, X et al., Synthesis of trans-(3S)-amino-(4R)-alkyl- and -(4S)-aryl-piperidines via ring-closing metathesis reaction, Organic Letters, 4(25):4499-502 (2002).

Huang, P. et al., First Asymmetric Synthesis of (2R, 3R)-3-Amino-1-benzyl-2-methyl-pyrrolidine via a highly diastereoselective reductive alkylation, Tetrahedron Letters, 38:271 (1997).

Kitas, E.A. et al., Substituted 2-oxo-azepane derivatives are potent, orally active gamma-secretase inhibitors, Bioorganic and Medicinal Chemistry Letters, 18(1):304-8 (2008).

Li, P. and Xu, JC. The development of highly efficient onium-type peptide coupling reagents based upon rational molecular design, Journal of Peptide Research, 58(2):129-39 (2001).

Mehrotra, M.M. et al., Spirocyclic nonpeptide glycoprotein IIb-IIIa antagonists. Part 3: synthesis and SAR of potent and specific 2,8-diazaspiro[4.5]decanes, Bioorganic and Medicinal Chemistry Letters, 12(7):1103-1107 (2002).

Shafir, A. and Buchwald, S.L., Highly selective room-temperature copper-catalyzed C-N coupling reactions, Journal of the American Chemical Society, 128(27):8742-3 (2006).

Wang, X. et al., Synthesis and biological activity of 5-fluorotubercidin, Nucleosides, Nucleotides, and Nucleic Acids, 23(1-2):161-70 (2004).

* cited by examiner

HETEROARYL BTK INHIBITORS

The present application is a U.S. national phase application under 35 U.S.C. 371 of international patent application no. PCT/US2010/047879, filed Sep. 3, 2010, which claims priority to U.S. provisional application Ser. No. 61/240,003, filed Sep. 4, 2009, the entirety of each of which is hereby incorporated by reference.

BACKGROUND OF THE INVENTION

Protein kinases are a large multigene family consisting of more than 500 proteins which play a critical role in the development and treatment of a number of human diseases in oncology, neurology and immunology. The Tec kinases are non-receptor tyrosine kinases which consists of five members (Tec (tyrosine kinase expressed in hepatocellular carcinoma), Btk (Bruton's tyrosine kinase), Itk (interleukin-2 (IL-2)-inducible T-cell kinase; also known as Emt or Tsk), $R^{1k}$ (resting lymphocyte kinase; also known as Txk) and Bmx (bone-marrow tyrosine kinase gene on chromosome X; also known as Etk)) and are primarily expressed in haematopoietic cells, although expression of Bmx and Tec has been detected in endothelial and liver cells. Tec kinases (Itk, Rlk and Tec) are expressed in T cell and are all activated downstream of the T-cell receptor (TCR). Btk is a downstream mediator of B cell receptor (BCR) signaling which is involved in regulating B cell activation, proliferation, and differentiation. More specifically, Btk contains a PH domain that binds phosphatidylinositol (3,4,5)-trisphosphate (PIP3). PIP3 binding induces Btk to phosphorylate phospholipase C (PLCγ), which in turn hydrolyzes PIP2 to produce two secondary messengers, inositol triphosphate (IP3) and diacylglycerol (DAG), which activate protein kinase PKC, which then induces additional B-cell signaling. Mutations that disable Btk enzymatic activity result in XLA syndrome (X-linked agammaglobulinemia), a primary immunodeficiency. Given the critical roles which Tec kinases play in both B-cell and T-cell signaling, Tec kinases are targets of interest for autoimmune disorders.

Consequently, there is a great need in the art for effective inhibitors of Btk. The present invention fulfills these and other needs.

SUMMARY OF THE INVENTION

In certain embodiments, the present invention provides a compound of formula I:

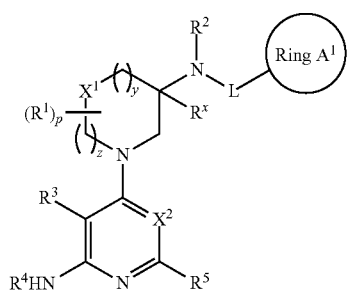

wherein each of $R^1$, $R^2$, $R^3$, $R^4$, $R^5$, $R^x$, $X^1$, $X^2$, L, Ring $A^1$, y, z, and p are as defined and described herein. These compounds are inhibitors of a number of protein kinases, in particular family members such as Itk, Txk, Tec, Bmx, and Btk (Bruton's tyrosine kinase). Accordingly, provided compounds can be used in a variety of methods including in vitro screening and activity assays as well as in vivo pre-clinical, clinical, and therapeutic settings, as described in detail herein.

In certain embodiments, the present invention provides pharmaceutical compositions comprising provided compounds.

In certain embodiments, the present invention provides methods of decreasing Btk enzymatic activity. Such methods include contacting a Btk with an effective amount of a Btk inhibitor.

In certain embodiments, the present invention provides methods of treating a disorder responsive to Btk inhibition in a subject in need thereof. Such disorders and methods are described in detail herein.

DETAILED DESCRIPTION OF CERTAIN EMBODIMENTS

In certain embodiments, the present invention provides a compound of formula I:

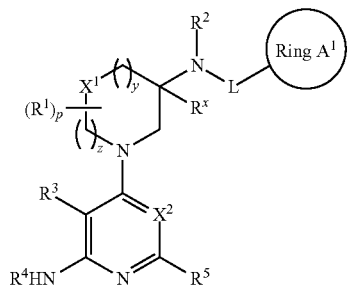

wherein:
  $X^1$ is —O—, —$CR^6R^7$— or —$NR^8$—;
  $X^2$ is =$CR^9$— or =N—;
  p is 0-5;
  y is 0, 1, or 2;
  z is 0, 1, or 2, wherein z is 0 or 1 when y is 2, and z is 1 or 2 when y is 0;
  each $R^1$ is independently halogen, —$NO_2$, —CN, —OR, —SR, —N(R)$_2$, —C(O)R, —$CO_2$R, —C(O)C(O)R, —C(O)CH$_2$C(O)R, —S(O)R, —S(O)$_2$R, —C(O)N(R)$_2$, —SO$_2$N(R)$_2$, —OC(O)R, —N(R)C(O)R, —N(R)N(R)$_2$, —N(R)C(=NR)N(R)$_2$, —C(=NR)N(R)$_2$, —C=NOR, —N(R)C(O)N(R)$_2$, —N(R)SO$_2$N(R)$_2$, —N(R)SO$_2$R, —OC(O)N(R)$_2$, or an optionally substituted group selected from $C_{1-12}$ aliphatic, phenyl, a 3-7 membered saturated or partially unsaturated monocyclic carbocyclic ring, a 7-10 membered saturated or partially unsaturated bicyclic carbocyclic ring, a 3-7 membered saturated or partially unsaturated monocyclic heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, an 8-10 membered bicyclic aryl ring, a 5-6 membered heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur; or:
  two $R^1$ groups on adjacent carbon atoms are taken together with their intervening atoms to form an optionally substituted ring selected from phenyl, a 3-7 membered saturated or partially unsaturated monocyclic carbocyclic ring, a 7-10 membered saturated or partially unsaturated bicyclic carbocyclic ring, a 3-7 membered saturated or partially unsaturated monocyclic heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, an 8-10 membered bicyclic aryl ring, a 5-6 membered heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur, or:

two $R^1$ groups on non-adjacent carbon atoms are taken together with their intervening atoms to form an optionally substituted bridge of a bridged bicyclic group, wherein the bridge is a $C_{1-3}$ hydrocarbon chain wherein one methylene unit is optionally replaced by —NR—, —O—, —C(O)—, —OC(O)—, —C(O)O—, —S—S—, or —S—, or:

two $R^1$ groups on the same carbon atom are taken together with their intervening atoms to form an optionally substituted spiro fused ring selected from a 3-7 membered saturated or partially unsaturated carbocyclic ring, or a 3-7 membered saturated or partially unsaturated monocyclic heterocyclic ring having 1-2 heteroatoms independently selected from nitrogen, oxygen, or sulfur;

each R is independently hydrogen or an optionally substituted group selected from $C_{1-6}$ aliphatic, phenyl, a 3-7 membered saturated or partially unsaturated carbocyclic ring, a 3-7 membered saturated or partially unsaturated monocyclic heterocyclic ring having 1-2 heteroatoms independently selected from nitrogen, oxygen, or sulfur, or a 5-6 membered heteroaryl ring having 1-3 heteroatoms independently selected from nitrogen, oxygen, or sulfur, or:

two R groups on the same nitrogen are taken together with their intervening atoms to form an optionally substituted 3-7 membered saturated, partially unsaturated, or heteroaryl ring having 1-4 heteroatoms independently selected from nitrogen, oxygen, or sulfur;

each of $R^2$, $R^4$, and $R^8$ is independently R, —CN, —C(O)R, —CO$_2$R, —C(O)C(O)R, —C(O)CH$_2$C(O)R, —C(O)N(R)$_2$, —S(O)R, —S(O)$_2$R, or —S(O)$_2$N(R)$_2$, or:

$R^2$ and $R^1$ are optionally taken together with their intervening atoms to form an optionally substituted ring selected from a 4-8 membered saturated or partially unsaturated monocyclic heterocyclic ring having 1-2 heteroatoms independently selected from nitrogen, oxygen, or sulfur, or a 7-10 membered saturated or partially unsaturated bicyclic heterocyclic ring having 1-3 heteroatoms independently selected from nitrogen, oxygen, or sulfur, or:

$R^2$ and $R^7$ are optionally taken together with their intervening atoms to form an optionally substituted ring selected from a 4-8 membered saturated or partially unsaturated monocyclic heterocyclic ring having 1-2 heteroatoms independently selected from nitrogen, oxygen, or sulfur, or a 7-10 membered saturated or partially unsaturated bicyclic heterocyclic ring having 1-3 heteroatoms independently selected from nitrogen, oxygen, or sulfur, or:

$R^2$ and $R^8$ are optionally taken together with their intervening atoms to form an optionally substituted ring selected from a 4-8 membered saturated or partially unsaturated monocyclic heterocyclic ring having 1-3 heteroatoms independently selected from nitrogen, oxygen, or sulfur, or a 7-10 membered saturated or partially unsaturated bicyclic heterocyclic ring having 1-3 heteroatoms independently selected from nitrogen, oxygen, or sulfur;

each of $R^3$, $R^5$, $R^6$, $R^7$, and $R^9$ is independently R, halogen, —NO$_2$, —CN, —OR, —SR, —N(R)$_2$, —C(O)R, —CO$_2$R, —C(O)C(O)R, —C(O)CH$_2$C(O)R, —S(O)R, —S(O)$_2$R, —C(O)N(R)$_2$, —SO$_2$N(R)$_2$, —OC(O)R, —N(R)C(O)R, —N(R)N(R)$_2$, —N(R)C(=NR)N(R)$_2$, —C(=NR)N(R)$_2$, —C=NOR, —N(R)C(O)N(R)$_2$, —N(R)SO$_2$N(R)$_2$, —N(R)SO$_2$R, or —OC(O)N(R)$_2$, or:

$R^3$ and $R^4$ are optionally taken together with their intervening atoms to form an optionally substituted ring selected from a 3-7 membered saturated or partially unsaturated monocyclic heterocyclic ring having 1-2 heteroatoms independently selected from nitrogen, oxygen, or sulfur, or a 7-10 membered saturated or partially unsaturated bicyclic heterocyclic ring having 1-3 heteroatoms independently selected from nitrogen, oxygen, or sulfur;

$R^x$ is hydrogen or optionally substituted $C_{1-6}$ aliphatic, or:

$R^x$ and $R^2$ are taken together to form an optionally substituted spirocyclic heterocyclic ring selected from a 4-8 membered saturated or partially unsaturated monocyclic heterocyclic ring having 1-2 heteroatoms independently selected from nitrogen, oxygen, or sulfur, or a 7-10 membered saturated or partially unsaturated bicyclic heterocyclic ring having 1-3 heteroatoms independently selected from nitrogen, oxygen, or sulfur;

Ring $A^1$ is an optionally substituted ring selected from phenyl, a 3-7 membered saturated or partially unsaturated monocyclic carbocyclic ring, a 7-10 membered saturated or partially unsaturated bicyclic carbocyclic ring, a 3-7 membered saturated or partially unsaturated monocyclic heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, an 8-10 membered bicyclic aryl ring, a 5-6 membered heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur;

L is a covalent bond or an optionally substituted, bivalent $C_{1-8}$ saturated or unsaturated, straight or branched, hydrocarbon chain, wherein one, two, or three methylene units of L are optionally and independently replaced by -Cy-, —C(R)$_2$—, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, —C(=NR)—, —N=N—, or —C(=N$_2$)—; and each Cy is independently an optionally substituted bivalent ring selected from phenylene, a 3-7 membered saturated or partially unsaturated carbocyclylene, a 3-7 membered saturated or partially unsaturated monocyclic heterocyclylene having 1-2 heteroatoms independently selected from nitrogen, oxygen, or sulfur, or a 5-6 membered heteroarylene having 1-3 heteroatoms independently selected from nitrogen, oxygen, or sulfur.

DEFINITIONS

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The abbreviations used herein have their conventional meaning within the chemical and biological arts. The chemical structures and formulae set forth herein are constructed according to the standard rules of chemical valency known in the chemical arts.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen).

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

As used herein, the term "bivalent $C_{x-y}$ (e.g., $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—. In some embodiments, n is from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cycloalkylenyl" refers to a bivalent cycloalkyl group of the following structure:

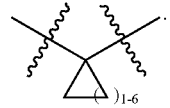

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring."

The term "aryl" used alone or as part of a larger moiety as in "aralkyl," "aralkoxy," or "aryloxyalkyl," refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As used herein and unless otherwise specified, the suffix "-ene" is used to describe a bivalent group. Thus, any of the terms above can be modified with the suffix "-ene" to describe a bivalent version of that moiety. For example, a bivalent carbocycle is "carbocycylene", a bivalent aryl ring is "arylene", a bivalent benzene ring is "phenylene", a bivalent heterocycle is "heterocyclylene", a bivalent heteroaryl ring is "heteroarylene", a bivalent alkyl chain is "alkylene", a bivalent alkenyl chain is "alkenylene", a bivalent alkynyl chain is "alkynylene", and so forth.

As described herein, compounds of the invention may, when specified, contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R$^\circ$; —(CH$_2$)$_{0-4}$OR$^\circ$; —O(CH$_2$)$_{0-4}$R$^\circ$, —O—(CH$_2$)$_{0-4}$C(O)OR$^\circ$; —(CH$_2$)$_{0-4}$CH(OR$^\circ$)$_2$; —(CH$_2$)$_{0-4}$SR$^\circ$; —(CH$_2$)$_{0-4}$Ph, which may be substituted with R$^\circ$; —(CH$_2$)$_{0-4}$O(CH$_2$)$_{0-1}$Ph which may be substituted with R$^\circ$; —CH═CHPh, which may be substituted with R$^\circ$; —(CH$_2$)$_{0-4}$O(CH$_2$)$_{0-1}$-pyridyl which may be substituted with R$^\circ$; —NO$_2$; —CN; —N$_3$; —(CH$_2$)$_{0-4}$N(R$^\circ$)$_2$; —(CH$_2$)$_{0-4}$N(R$^\circ$C(O)R$^\circ$; —N(R$^\circ$C(S)R$^\circ$; —(CH$_2$)$_{0-4}$N(R$^\circ$C(O) NR$^\circ_2$; —N(R$^\circ$C(S)NRO$_2$; —(CH$_2$)$_{0-4}$N(R$^\circ$C(O)OR$^\circ$; —N(R$^\circ$N(R$^\circ$C(O)R$^\circ$; —N(R$^\circ$N(R$^\circ$C(O)NRO$_2$; —N(R$^\circ$N(R$^\circ$C(O)OR$^\circ$; —(CH$_2$)$_{0-4}$C(O)R$^\circ$; —C(S)R$^\circ$; —(CH$_2$)$_{0-4}$C(O)OR$^\circ$; —(CH$_2$)$_{0-4}$C(O)SR$^\circ$; —(CH$_2$)$_{0-4}$C(O)OSiR$^\circ_3$; —(CH$_2$)$_{0-4}$OC(O)R$^\circ$; —OC(O)(CH$_2$)$_{0-4}$SR—, SC(S)SR$^\circ$; —(CH$_2$)$_{0-4}$SC(O)R$^\circ$; —(CH$_2$)$_{0-4}$C(O)NRO$_2$; —C(S)NRO$_2$; —C(S)SR$^\circ$; —SC(S)SR$^\circ$, —(CH$_2$)$_{0-4}$OC(O)NR$^\circ_2$; —C(O)N(OR$^\circ$)R$^\circ$; —C(O)C(O)R$^\circ$; —C(O)CH$_2$C(O)R$^\circ$; —C(NOR$^\circ$)R$^\circ$; —(CH$_2$)$_{0-4}$SSR$^\circ$; —(CH$_2$)$_{0-4}$S(O)$_2$R$^\circ$; —(CH$_2$)$_{0-4}$S(O)$_2$OR$^\circ$; —(CH$_2$)$_{0-4}$OS(O)$_2$R$^\circ$; —S(O)$_2$NRO$_2$; —(CH$_2$)$_{0-4}$S(O)R$^\circ$; —N(R$^\circ$S(O)$_2$NRO$_2$; —N(R$^\circ$S(O)$_2$R$^\circ$; —N(OR$^\circ$)R$^\circ$; —C(NH)NRO$_2$; —P(O)$_2$R$^\circ$; —P(O)R$^\circ_2$; —OP(O)R$^\circ_2$; —OP(O)(OR$^\circ$)$_2$; SiR$^\circ_3$; —(C$_{1-4}$ straight or branched)alkylene)O—N(R$^\circ$)$_2$; or —(C$_{1-4}$ straight or branched)alkylene)C(O)O—N(R$^\circ$)$_2$, wherein each R$^\circ$ may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R$^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R$^\circ$ (or the ring formed by taking two independent occurrences of R$^\circ$ together with their intervening atoms), are independently halogen, —(CH$_2$)$_{0-2}$R$^\circ$, -(haloR$^\circ$), —(CH$_2$)$_{0-2}$OH, —(CH$_2$)$_{0-2}$OR$^\circ$, —(CH$_2$)$_{0-2}$CH(OR$^\circ$)$_2$; —O(haloR$^\circ$), —CN, —N$_3$, —(CH$_2$)$_{0-2}$C(O)R$^\circ$, —(CH$_2$)$_{0-2}$C(O)OH, —(CH$_2$)$_{0-2}$C(O)OR$^\circ$, —(CH$_2$)$_{0-2}$SR$^\circ$, —(CH$_2$)$_{0-2}$SH, —(CH$_2$)$_{0-2}$NH$_2$, —(CH$_2$)$_{0-2}$NHR$^\circ$, —(CH$_2$)$_{0-2}$NR$^\circ_2$, —NO$_2$, —SiR$^\circ_3$, —OSiR$^\circ_3$, —C(O)SR$^\circ$, —(C$_{1-4}$ straight or branched alkylene)C(O)OR$^\circ$, or —SSR$^\circ$ wherein each R$^\circ$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\circ$ include =O and =S.

Suitable divalent substituents on a saturated carbon atom of an "optionally substituted" group include the following: =O, =S, =NNR$^\circ$$_2$, =NNHC(O)R$^\circ$, =NNHC(O)OR$^\circ$, =NNHS(O)$_2$R$^\circ$, =NR$^\circ$, =NOR$^\circ$, —O(C(R$^\circ$$_2$))$_{2-3}$O—, or —S(C(R$^\circ$$_2$))$_{2-3}$S—, wherein each independent occurrence of R$^\circ$ is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR$^\circ$$_2$)$_{2-3}$O—, wherein each independent occurrence of R$^\circ$ is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R$^\circ$ include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O) R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference.

In certain embodiments, the neutral forms of the compounds are regenerated by contacting the salt with a base or acid and isolating the parent compound in the conventional manner. In some embodiments, the parent form of the compound differs from the various salt forms in certain physical properties, such as solubility in polar solvents.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

The term "oxo," as used herein, means an oxygen that is double bonded to a carbon atom, thereby forming a carbonyl.

One of ordinary skill in the art will appreciate that the synthetic methods, as described herein, utilize a variety of protecting groups. By the term "protecting group," as used herein, it is meant that a particular functional moiety, e.g., O, S, or N, is masked or blocked, permitting, if desired, a reaction to be carried out selectively at another reactive site in a multifunctional compound. Suitable protecting groups are well known in the art and include those described in detail in *Protecting Groups in Organic Synthesis, T. W. Greene and P. G. M. Wuts*, 3$^{rd}$ edition, John Wiley & Sons, 1999, the entirety of which is incorporated herein by reference. In certain embodiments, a protecting group reacts selectively in good yield to give a protected substrate that is stable to the projected reactions; the protecting group is preferably selectively removable by readily available, preferably non-toxic reagents that do not attack the other functional groups; the protecting group forms a separable derivative (more preferably without the generation of new stereogenic centers); and the protecting group will preferably have a minimum of additional functionality to avoid further sites of reaction. As detailed herein, oxygen, sulfur, nitrogen, and carbon protecting groups may be utilized. By way of non-limiting example, hydroxyl protecting groups include methyl, methoxylmethyl (MOM), methylthiomethyl (MTM), benzyloxymethyl (BOM), p-methoxybenzyloxymethyl (PMBM), t-butoxymethyl, siloxymethyl, 2-methoxyethoxymethyl (MEM), 2,2,2-trichloroethoxymethyl, tetrahydropyranyl (THP), 4-methoxytetrahydropyranyl (MTHP), 1-methyl-1-methoxyethyl, 1-methyl-1-benzyloxyethyl, 2-trimethylsilylethyl, allyl, p-chlorophenyl, p-methoxyphenyl, 2,4-dinitrophenyl, benzyl, p-methoxybenzyl, 3,4-dimethoxybenzyl, p-nitrobenzyl, 2,6-dichlorobenzyl, p-phenylbenzyl, 4-picolyl, diphenylmethyl, p,p'-dinitrobenzhydryl, triphenylmethyl, p-methoxyphenyldiphenylmethyl, 1,1-bis(4-methoxyphenyl)-1'-pyrenylmethyl, trimethylsilyl (TMS), triethylsilyl (TES), triisopropylsilyl (TIPS), dimethylisopropylsilyl (IPDMS), dimethylthexylsilyl, t-butyldimethylsilyl (TBDMS), t-butyldiphenylsilyl (TBDPS), triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, pivaloate, adamantoate, crotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, o-(dibromomethyl)benzoate, 2-(methylthiomethoxy)ethyl, 2-(methylthiomethoxymethyl)benzoate, 2,6-dichloro-4-methylphenoxyacetate, 2,6-dichloro-4-(1,1,3,3-tetramethylbutyl)phenoxyacetate, chlorodiphenylacetate, isobutyrate, monosuccinoate, o-(methoxycarbonyl)benzoate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 3,4-dimethoxybenzylidene acetal, 2-nitrobenzylidene acetal, methoxymethylene acetal, ethoxymethylene acetal, α-methoxybenzylidene ortho ester, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), cyclic carbonates, cyclic boronates, ethyl boronate, and phenyl boronate. Amino-protecting groups include methyl carbamate, 9-fluorenylmethyl carbamate (Fmoc), 9-(2,7-dibromo)fluoroenylmethyl carbamate, 4-methoxyphenacyl carbamate (Phenoc), 2,2,2-trichloroethyl carbamate (Troc), 2-trimethylsilylethyl carbamate (Teoc), 1-methyl-1-(4-biphenyl)ethyl carbamate (Bpoc), 2-(2'- and 4'-pyridyl)ethyl carbamate (Pyoc), 2-(N,N-dicyclohexylcarboxamido)ethyl carbamate, t-butyl carbamate (BOC), allyl carbamate (Alloc), 4-nitrocinnamyl carbamate (Noc), N-hydroxypiperidinyl carbamate, alkyldithio carbamate, benzyl carbamate (Cbz), p-nitrobenzyl carbamate, p-chlorobenzyl carbamate, diphenylmethyl carbamate, 2-methylsulfonylethyl carbamate, 2-(p-toluenesulfonyl)ethyl carbamate, 2,4-dimethylthiophenyl carbamate (Bmpc), 2-triphenylphosphonioisopropyl carbamate (Ppoc), m-chloro-p-acyloxybenzyl carbamate, p-(dihydroxyboryl)benzyl carbamate, m-nitrophenyl carbamate, 3,5-dimethoxybenzyl carbamate, o-nitrobenzyl carbamate, phenyl(o-nitrophenyl)methyl carbamate, N'-p-toluenesulfonylaminocarbonyl derivative, N'-phenylaminothiocarbonyl derivative, t-amyl carbamate, p-cyanobenzyl carbamate, cyclohexyl carbamate, cyclopentyl carbamate, p-decyloxybenzyl carbamate, 2,2-dimethoxycarbonylvinyl carbamate, 2-furanylmethyl carbamate, isobornyl carbamate, isobutyl carbamate, 1-methyl-1-phenylethyl carbamate, 1-methyl-1-(4-pyridyl)ethyl carbamate, phenyl carbamate, formamide, acetamide, chloroacetamide, trichloroacetamide, trifluoroacetamide, phenylacetamide, 3-phenylpropanamide, picolinamide, N-benzoylphenylalanyl derivative, benzamide, p-phenylbenzamide, o-nitrophenoxyacetamide, acetoacetamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-2,5-dimethylpyrrole, N-methylamine, N-allylamine, N-[2-(trimethylsilyl)ethoxy]methylamine (SEM), N-3-acetoxypropylamine, N-benzylamine, N-triphenylmethylamine (Tr), N-2-picolylamino N'-oxide, N-1,1-dimethylthiomethyleneamine, N-benzylideneamine, N-p-methoxybenzylideneamine, N—(N',N'-dimethylaminomethylene)amine, N,N'-isopropylidenediamine, N-p-nitrobenzylideneamine, N-(5-chloro-2-hydroxyphenyl)phenylmethylene amine, N-cyclohexylidene amine, N-(5,5-dimethyl-3-oxo-1-cyclohexenyl)amine, N-borane derivative, N-diphenylborinic acid derivative, N-nitroamine, N-nitrosoamine, amine N-oxide, diphenylphosphinamide (Dpp), dimethylthiophosphinamide (Mpt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), methanesulfonamide (Ms), β-trimethylsilylethanesulfonamide (SES), benzylsulfonamide, trifluoromethylsulfonamide, and phenacylsulfonamide Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described by Greene and Wuts (supra).

The symbol "⌇" denotes the point of attachment of a chemical moiety to the remainder of a molecule or chemical formula.

In some embodiments, a provided compound is of formula I:

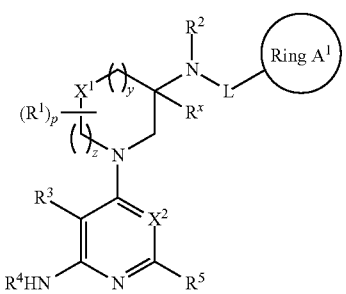

wherein each of $R^1$, $R^2$, $R^3$, $R^4$, $R^5$, $R^x$, $X^1$, $X^2$, L, Ring $A^1$, y, z, and p are as defined above and described in classes and subclasses herein.

In some embodiments, p is 0. In some embodiments, p is 1. In some embodiments, p is 2. In some embodiments, p is 3. In some embodiments, p is 4. In some embodiments, p is 5.

In some embodiments, y is 0. In some embodiments, y is 1. In some embodiments, y is 2.

In some embodiments, z is 0. In some embodiments, z is 1. In some embodiments, z is 2.

In certain embodiments, each $R^1$ is independently halogen, —NO₂, —CN, —OR, —SR, —N(R)₂, —C(O)R, —CO₂R, —C(O)C(O)R, —C(O)CH₂C(O)R, —S(O)R, —S(O)₂R, —C(O)N(R)₂, —SO₂N(R)₂, —OC(O)R, —N(R)C(O)R, —N(R)N(R)₂, —N(R)C(=NR)N(R)₂, —C(=NR)N(R)₂, —C=NOR, —N(R)C(O)N(R)₂, —N(R)SO₂N(R)₂, —N(R)SO₂R, —OC(O)N(R)₂, or optionally substituted $C_{1-12}$ aliphatic. In some embodiments, each $R^1$ is independently halogen, —NO₂, —CN, —OR, —SR, —N(R)₂, —C(O)R, —CO₂R, —C(O)C(O)R, —S(O)R, —S(O)₂R, —C(O)N(R)₂, —SO₂N(R)₂, —OC(O)R, —N(R)C(O)R, —N(R)SO₂N(R)₂, —N(R)SO₂R, —OC(O)N(R)₂, or optionally substituted $C_{1-6}$ aliphatic. In some embodiments, $R^1$ is optionally substituted $C_{1-6}$ aliphatic. In some embodiments, $R^1$ is $C_{1-4}$ alkyl. In some embodiments, $R^1$ is halogen. In some embodiments, $R^1$ is halogen substituted $C_{1-4}$ alkyl. In some embodiments, $R^1$ is —CF₃. In some embodiments, $R^1$ is —CN. In some embodiments, $R^1$ is methyl.

In some embodiments, p is at least 2, and two $R^1$ groups on adjacent carbon atoms are taken together with their intervening atoms to form an optionally substituted ring selected from phenyl, a 3-7 membered saturated or partially unsaturated monocyclic carbocyclic ring, a 7-10 membered saturated or partially unsaturated bicyclic carbocyclic ring, a 3-7 membered saturated or partially unsaturated monocyclic heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, an 8-10 membered bicyclic aryl ring, a 5-6 membered heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur. In some embodiments, two $R^1$ groups on adjacent carbon atoms are taken together with their intervening atoms to form an optionally substituted 3-7 membered saturated or partially unsaturated monocyclic carbocyclic ring. In some embodiments, two $R^1$ groups on adjacent carbon atoms are taken together with their intervening atoms to form a bicyclic ring having the formula:

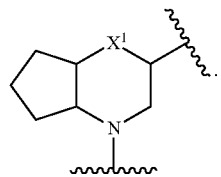

In certain embodiments, the bicyclic ring is further substituted with one, two, or three $R^1$ groups.

In some embodiments, p is at least 2, and two $R^1$ groups on non-adjacent carbon atoms are taken together with their intervening atoms to form an optionally substituted bridge of a bridged bicyclic group, wherein the bridge is a $C_{1-3}$ hydrocarbon chain wherein one methylene unit is optionally replaced by —NR—, —O—, —C(O)—, —OC(O)—, —C(O)O—, —S—S—, or —S—. In certain embodiments, two $R^1$ groups on non-adjacent carbon atoms are taken together with their intervening atoms to form an optionally substituted bridge of a bridged bicyclic group, wherein the bridge is a $C_{1-3}$ hydrocarbon chain. In some embodiments, two $R^1$ groups on non-adjacent carbon atoms are taken together with their intervening atoms to form an optionally substituted bridge having the formula:

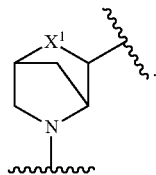

In certain embodiments, the bridged bicyclic group is further substituted with one, two, or three $R^1$ groups.

In some embodiments, p is at least 2, and two $R^1$ groups on the same carbon atom are taken together with their intervening atoms to form an optionally substituted spiro fused ring selected from a 3-7 membered saturated or partially unsaturated carbocyclic ring, or a 3-7 membered saturated or partially unsaturated monocyclic heterocyclic ring having 1-2 heteroatoms independently selected from nitrogen, oxygen, or sulfur. In some embodiments, two $R^1$ groups on the same carbon atom are taken together with their intervening atoms to form an optionally substituted spiro fused 3-7 membered saturated or partially unsaturated carbocyclic ring. In some embodiments, two $R^1$ groups on the same carbon atom are taken together with their intervening atoms to form an optionally substituted spiro fused ring having the formula:

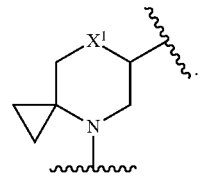

In certain embodiments, the spiro fused ring is further substituted with one, two, or three $R^1$ groups.

In some embodiments, each R is independently hydrogen or an optionally substituted group selected from $C_{1-6}$ aliphatic, phenyl, a 3-7 membered saturated or partially unsaturated carbocyclic ring, a 3-7 membered saturated or partially unsaturated monocyclic heterocyclic ring having 1-2 heteroatoms independently selected from nitrogen, oxygen, or sulfur, or a 5-6 membered heteroaryl ring having 1-3 heteroatoms independently selected from nitrogen, oxygen, or sulfur. In some embodiments, R is hydrogen. In some embodiments, R is optionally substituted $C_{1-6}$ aliphatic. In some embodiments, R is optionally substituted phenyl. In some embodiments, R is an optionally substituted 3-7 membered saturated or partially unsaturated carbocyclic ring. In some embodiments, R is an optionally substituted 3-7 membered saturated or partially unsaturated monocyclic heterocyclic ring having 1-2 heteroatoms independently selected from nitrogen, oxygen, or sulfur. In some embodiments, R is an optionally substituted 5-6 membered heteroaryl ring having 1-3 heteroatoms independently selected from nitrogen, oxygen, or sulfur.

In certain embodiments, a substituent on R is selected from —CN, —CF₃, —OH, —NH₂, or —CO₂H.

In some embodiments, each of $R^2$, $R^4$, and $R^8$ is independently R, —C(O)R, —CO₂R, —C(O)C(O)R, —C(O)CH₂C(O)R, —C(O)N(R)₂, —S(O)R, —S(O)₂R, or —S(O)₂N(R)₂. In some embodiments, each of $R^2$, $R^4$, and $R^8$ is hydrogen. In some embodiments, each of $R^2$, $R^4$, and $R^8$ is independently R.

In some embodiments, $R^2$ is R, —C(O)R, —CO₂R, —C(O)C(O)R, —C(O)CH₂C(O)R, —C(O)N(R)₂, —S(O)R, —S(O)$_2$R, or —S(O)$_2$N(R)$_2$. In some embodiments, R$^2$ is hydrogen or optionally substituted C$_{1-6}$ aliphatic. In some embodiments, R$^2$ is hydrogen. In other embodiments, R$^2$ is optionally substituted C$_{1-4}$ alkyl. In some embodiments, R$^2$ is optionally substituted phenyl. In some embodiments, R$^2$ is an optionally substituted 3-7 membered saturated or partially unsaturated carbocyclic ring. In some embodiments, R$^2$ is an optionally substituted 3-7 membered saturated or partially unsaturated monocyclic heterocyclic ring having 1-2 heteroatoms independently selected from nitrogen, oxygen, or sulfur. In some embodiments, R$^2$ is an optionally substituted 5-6 membered heteroaryl ring having 1-3 heteroatoms independently selected from nitrogen, oxygen, or sulfur.

In some embodiments, R$^x$ is hydrogen. In other embodiments, R$^x$ is optionally substituted C$_{1-6}$ aliphatic.

In some embodiments, R$^x$ and R$^2$ are taken together to form an optionally substituted spirocyclic heterocyclic ring selected from a 4-8 membered saturated or partially unsaturated monocyclic heterocyclic ring having 1-2 heteroatoms independently selected from nitrogen, oxygen, or sulfur, or a 7-10 membered saturated or partially unsaturated bicyclic heterocyclic ring having 1-3 heteroatoms independently selected from nitrogen, oxygen, or sulfur. In some embodiments, R$^x$ and R$^2$ are taken together to form an optionally substituted spirocyclic heterocyclic ring selected from a 4-8 membered saturated or partially unsaturated monocyclic heterocyclic ring having 1-2 heteroatoms independently selected from nitrogen, oxygen, or sulfur. In certain embodiments, R$^x$ and R$^2$ are taken together to form an optionally substituted spirocyclic heterocyclic ring selected from a 5-6 membered saturated or partially unsaturated monocyclic heterocyclic ring having 1-2 heteroatoms independently selected from nitrogen, oxygen, or sulfur. In certain embodiments, R$^x$ and R$^2$ are taken together to form an optionally substituted spirocyclic heterocyclic ring selected from a 5-6 membered saturated monocyclic heterocyclic ring having 1 nitrogen heteroatom.

In some embodiments, R$^1$ and R$^2$ are optionally taken together with their intervening atoms to form an optionally substituted ring selected from a 4-8 membered saturated or partially unsaturated monocyclic heterocyclic ring having 1-2 heteroatoms independently selected from nitrogen, oxygen, or sulfur, or a 7-10 membered saturated or partially unsaturated bicyclic heterocyclic ring having 1-3 heteroatoms independently selected from nitrogen, oxygen, or sulfur. In some embodiments, R$^1$ and R$^2$ are optionally taken together with their intervening atoms to form an optionally substituted five-membered saturated or partially unsaturated monocyclic heterocyclic ring having 1-2 heteroatoms independently selected from nitrogen, oxygen, or sulfur. In some embodiments, R$^1$ and R$^2$ are optionally taken together with their intervening atoms to form an optionally substituted six-membered saturated or partially unsaturated monocyclic heterocyclic ring having 1-2 heteroatoms independently selected from nitrogen, oxygen, or sulfur. In certain embodiments, such 5-6 membered monocyclic rings formed by R$^1$ and R$^2$ are substituted, and the substituents are taken together to form a seven-membered saturated or partially unsaturated monocyclic heterocyclic ring having 1-3 heteroatoms independently selected from nitrogen, oxygen, or sulfur, thereby forming a 6,5- or 6,6-fused bicyclic ring.

In some embodiments, R$^1$ and R$^2$ are optionally taken together with their intervening atoms to form an optionally substituted seven-membered saturated or partially unsaturated bicyclic heterocyclic ring having 1-3 heteroatoms independently selected from nitrogen, oxygen, or sulfur. In some embodiments, R$^1$ and R$^2$ are optionally taken together with their intervening atoms to form an optionally substituted eight-membered saturated or partially unsaturated bicyclic heterocyclic ring having 1-3 heteroatoms independently selected from nitrogen, oxygen, or sulfur. In some embodiments, R$^1$ and R$^2$ are optionally taken together with their intervening atoms to form an optionally substituted nine-membered saturated or partially unsaturated bicyclic heterocyclic ring having 1-3 heteroatoms independently selected from nitrogen, oxygen, or sulfur. In some embodiments, R$^1$ and R$^2$ are optionally taken together with their intervening atoms to form an optionally substituted ten-membered saturated or partially unsaturated bicyclic heterocyclic ring having 1-3 heteroatoms independently selected from nitrogen, oxygen, or sulfur.

In some embodiments, R$^2$ and R$^7$ are optionally taken together with their intervening atoms to form an optionally substituted ring selected from a 4-8 membered saturated or partially unsaturated monocyclic heterocyclic ring having 1-2 heteroatoms independently selected from nitrogen, oxygen, or sulfur, or a 7-10 membered saturated or partially unsaturated bicyclic heterocyclic ring having 1-3 heteroatoms independently selected from nitrogen, oxygen, or sulfur. In some embodiments, R$^2$ and R$^7$ are optionally taken together with their intervening atoms to form an optionally substituted five-membered saturated or partially unsaturated monocyclic heterocyclic ring having 1-2 heteroatoms independently selected from nitrogen, oxygen, or sulfur. In some embodiments, R$^2$ and R$^7$ are optionally taken together with their intervening atoms to form an optionally substituted six-membered saturated or partially unsaturated monocyclic heterocyclic ring having 1-2 heteroatoms independently selected from nitrogen, oxygen, or sulfur. In certain embodiments, such 5-6 membered monocyclic rings formed by R$^2$ and R$^7$ are substituted, and the substituents are taken together to form a seven-membered saturated or partially unsaturated monocyclic heterocyclic ring having 1-3 heteroatoms independently selected from nitrogen, oxygen, or sulfur, thereby forming a 6,5- or 6,6-fused bicyclic ring.

In some embodiments, R$^2$ and R$^7$ are optionally taken together with their intervening atoms to form an optionally substituted seven-membered saturated or partially unsaturated bicyclic heterocyclic ring having 1-3 heteroatoms independently selected from nitrogen, oxygen, or sulfur. In some embodiments, R$^2$ and R$^7$ are optionally taken together with their intervening atoms to form an optionally substituted eight-membered saturated or partially unsaturated bicyclic heterocyclic ring having 1-3 heteroatoms independently selected from nitrogen, oxygen, or sulfur. In some embodiments, R$^2$ and R$^7$ are optionally taken together with their intervening atoms to form an optionally substituted nine-membered saturated or partially unsaturated bicyclic heterocyclic ring having 1-3 heteroatoms independently selected from nitrogen, oxygen, or sulfur. In some embodiments, R$^2$ and R$^7$ are optionally taken together with their intervening atoms to form an optionally substituted ten-membered saturated or partially unsaturated bicyclic heterocyclic ring having 1-3 heteroatoms independently selected from nitrogen, oxygen, or sulfur.

In some embodiments, R$^2$ and R$^8$ are optionally taken together with their intervening atoms to form an optionally substituted ring selected from a 4-8 membered saturated or partially unsaturated monocyclic heterocyclic ring having 1-3 heteroatoms independently selected from nitrogen, oxygen, or sulfur, or a 7-10 membered saturated or partially unsaturated bicyclic heterocyclic ring having 1-3 heteroatoms independently selected from nitrogen, oxygen, or sulfur. In some embodiments, R$^2$ and R$^8$ are optionally taken together with their intervening atoms to form an optionally substituted 5-6 membered saturated or partially unsaturated monocyclic heterocyclic ring having 1-2 heteroatoms independently selected from nitrogen, oxygen, or sulfur. In some embodiments, $R^2$ and $R^8$ are optionally taken together with their intervening atoms to form an optionally substituted five-membered saturated or partially unsaturated monocyclic heterocyclic ring having 1-2 heteroatoms independently selected from nitrogen, oxygen, or sulfur. In some embodiments, $R^2$ and $R^8$ are optionally taken together with their intervening atoms to form an optionally substituted six-membered saturated or partially unsaturated monocyclic heterocyclic ring having 1-2 heteroatoms independently selected from nitrogen, oxygen, or sulfur. In certain embodiments, such 5-6 membered monocyclic rings formed by $R^2$ and $R^8$ are substituted, and the substituents are taken together to form a seven-membered saturated or partially unsaturated monocyclic heterocyclic ring having 1-3 heteroatoms independently selected from nitrogen, oxygen, or sulfur, thereby forming a 6,5- or 6,6-fused bicyclic ring.

In some embodiments, $R^2$ and $R^8$ are optionally taken together with their intervening atoms to form an optionally substituted seven-membered saturated or partially unsaturated bicyclic heterocyclic ring having 1-3 heteroatoms independently selected from nitrogen, oxygen, or sulfur. In some embodiments, $R^2$ and $R^8$ are optionally taken together with their intervening atoms to form an optionally substituted eight-membered saturated or partially unsaturated bicyclic heterocyclic ring having 1-3 heteroatoms independently selected from nitrogen, oxygen, or sulfur. In some embodiments, $R^2$ and $R^8$ are optionally taken together with their intervening atoms to form an optionally substituted nine-membered saturated or partially unsaturated bicyclic heterocyclic ring having 1-3 heteroatoms independently selected from nitrogen, oxygen, or sulfur. In some embodiments, $R^2$ and $R^8$ are optionally taken together with their intervening atoms to form an optionally substituted ten-membered saturated or partially unsaturated bicyclic heterocyclic ring having 1-3 heteroatoms independently selected from nitrogen, oxygen, or sulfur.

In some embodiments, each of $R^3$, $R^5$, $R^6$, $R^7$, and $R^9$ is independently R, halogen, —NO$_2$, —CN, —OR, —SR, —N(R)$_2$, —C(O)R, —CO$_2$R, —C(O)C(O)R, —C(O)CH$_2$C(O)R, —S(O)R, —S(O)$_2$R, —C(O)N(R)$_2$, —SO$_2$N(R)$_2$, —OC(O)R, —N(R)C(O)R, —N(R)N(R)$_2$, —N(R)C(=NR)N(R)$_2$, —C(=NR)N(R)$_2$, —C=NOR, —N(R)C(O)N(R)$_2$, —N(R)SO$_2$N(R)$_2$, —N(R)SO$_2$R, or —OC(O)N(R)$_2$. In some embodiments, each of $R^3$, $R^5$, $R^6$, $R^7$, and $R^9$ is hydrogen. In some embodiments, each of $R^3$, $R^5$, $R^6$, $R^7$, and $R^9$ is independently R.

In some embodiments, $R^3$ is R, halogen, —NO$_2$, —CN, —OR, —SR, —N(R)$_2$, —C(O)R, —CO$_2$R, —C(O)C(O)R, —C(O)CH$_2$C(O)R, —S(O)R, —S(O)$_2$R, —C(O)N(R)$_2$, —SO$_2$N(R)$_2$, —OC(O)R, —N(R)C(O)R, —N(R)N(R)$_2$, —N(R)C(=NR)N(R)$_2$, —C(=NR)N(R)$_2$, —C=NOR, —N(R)C(O)N(R)$_2$, —N(R)SO$_2$N(R)$_2$, —N(R)SO$_2$R, or —OC(O)N(R)$_2$. In some embodiments, $R^3$ is hydrogen or optionally substituted C$_{1-6}$ aliphatic. In some embodiments, $R^3$ is halogen, —CN, or optionally substituted C$_{1-6}$ alkyl. In some embodiments, $R^3$ is hydrogen. In other embodiments, $R^3$ is optionally substituted C$_{1-4}$ alkyl. In some embodiments, $R^3$ is optionally substituted phenyl. In some embodiments, $R^3$ is an optionally substituted 3-7 membered saturated or partially unsaturated carbocyclic ring. In some embodiments, $R^3$ is an optionally substituted 3-7 membered saturated or partially unsaturated monocyclic heterocyclic ring having 1-2 heteroatoms independently selected from nitrogen, oxygen, or sulfur. In some embodiments, $R^3$ is an optionally substituted 5-6 membered heteroaryl ring having 1-3 heteroatoms independently selected from nitrogen, oxygen, or sulfur.

In some embodiments, $R^4$ is R, —C(O)R, —CO$_2$R, —C(O)C(O)R, —C(O)CH$_2$C(O)R, —C(O)N(R)$_2$, —S(O)R, —S(O)$_2$R, or —S(O)$_2$N(R)$_2$. In some embodiments, $R^4$ is hydrogen, —C(O)R, or optionally substituted C$_{1-6}$ aliphatic. In some embodiments, $R^4$ is hydrogen or optionally substituted C$_{1-6}$ aliphatic. In some embodiments, $R^4$ is hydrogen. In other embodiments, $R^4$ is optionally substituted C$_{1-4}$ alkyl. In some embodiments, $R^4$ is optionally substituted phenyl. In some embodiments, $R^4$ is an optionally substituted 3-7 membered saturated or partially unsaturated carbocyclic ring. In some embodiments, $R^4$ is an optionally substituted 3-7 membered saturated or partially unsaturated monocyclic heterocyclic ring having 1-2 heteroatoms independently selected from nitrogen, oxygen, or sulfur. In some embodiments, $R^4$ is an optionally substituted 5-6 membered heteroaryl ring having 1-3 heteroatoms independently selected from nitrogen, oxygen, or sulfur.

In some embodiments, $R^3$ and $R^4$ are optionally taken together with their intervening atoms to form an optionally substituted ring selected from a 3-7 membered saturated or partially unsaturated monocyclic heterocyclic ring having 1-2 heteroatoms independently selected from nitrogen, oxygen, or sulfur, or a 7-10 membered saturated or partially unsaturated bicyclic heterocyclic ring having 1-3 heteroatoms independently selected from nitrogen, oxygen, or sulfur. In some embodiments, $R^3$ and $R^4$ are optionally taken together with their intervening atoms to form an optionally substituted ring selected from a 5-6 membered saturated or partially unsaturated monocyclic heterocyclic ring having 1-2 heteroatoms independently selected from nitrogen, oxygen, or sulfur. In some embodiments, $R^3$ and $R^4$ are optionally taken together with their intervening atoms to form an optionally substituted ring selected from pyrrole or pyrazole.

In some embodiments, $R^5$ is R, halogen, —NO$_2$, —CN, —OR, —SR, —N(R)$_2$, —C(O)R, —CO$_2$R, —C(O)C(O)R, —C(O)CH$_2$C(O)R, —S(O)R, —S(O)$_2$R, —C(O)N(R)$_2$, —SO$_2$N(R)$_2$, —OC(O)R, —N(R)C(O)R, —N(R)N(R)$_2$, —N(R)C(=NR)N(R)$_2$, —C(=NR)N(R)$_2$, —C=NOR, —N(R)C(O)N(R)$_2$, —N(R)SO$_2$N(R)$_2$, —N(R)SO$_2$R, or —OC(O)N(R)$_2$. In some embodiments, $R^5$ is hydrogen or optionally substituted C$_{1-6}$ aliphatic. In some embodiments, $R^5$ is propargyl. In some embodiments, $R^5$ is halogen. In some embodiments, $R^5$ is hydrogen, C$_{1-6}$ aliphatic, or —N(R)$_2$. In some embodiments, $R^5$ is halogen, —CN, or optionally substituted C$_{1-6}$ alkyl. In some embodiments, $R^5$ is hydrogen. In other embodiments, $R^5$ is optionally substituted C$_{1-4}$ alkyl. In some embodiments, $R^5$ is optionally substituted phenyl. In some embodiments, $R^5$ is an optionally substituted 3-7 membered saturated or partially unsaturated carbocyclic ring. In some embodiments, $R^5$ is an optionally substituted 3-7 membered saturated or partially unsaturated monocyclic heterocyclic ring having 1-2 heteroatoms independently selected from nitrogen, oxygen, or sulfur. In some embodiments, $R^5$ is an optionally substituted 5-6 membered heteroaryl ring having 1-3 heteroatoms independently selected from nitrogen, oxygen, or sulfur.

In some embodiments, $R^6$ is R, halogen, —NO$_2$, —CN, —OR, —SR, —N(R)$_2$, —C(O)R, —CO$_2$R, —C(O)C(O)R, —C(O)CH$_2$C(O)R, —S(O)R, —S(O)$_2$R, —C(O)N(R)$_2$, —SO$_2$N(R)$_2$, —OC(O)R, —N(R)C(O)R, —N(R)N(R)$_2$, —N(R)C(=NR)N(R)$_2$, —C(=NR)N(R)$_2$, —C=NOR, —N(R)C(O)N(R)$_2$, —N(R)SO$_2$N(R)$_2$, —N(R)SO$_2$R, or —OC(O)N(R)$_2$. In some embodiments, $R^6$ is hydrogen or optionally substituted C$_{1-6}$ aliphatic. In some embodiments, $R^6$ is halogen, —CN, or optionally substituted $C_{1-6}$ alkyl. In some embodiments, $R^6$ is hydrogen. In other embodiments, $R^6$ is optionally substituted $C_{1-4}$ alkyl. In some embodiments, $R^6$ is optionally substituted phenyl. In some embodiments, $R^6$ is an optionally substituted 3-7 membered saturated or partially unsaturated carbocyclic ring. In some embodiments, $R^6$ is an optionally substituted 3-7 membered saturated or partially unsaturated monocyclic heterocyclic ring having 1-2 heteroatoms independently selected from nitrogen, oxygen, or sulfur. In some embodiments, $R^6$ is an optionally substituted 5-6 membered heteroaryl ring having 1-3 heteroatoms independently selected from nitrogen, oxygen, or sulfur.

In some embodiments, $R^7$ is R, halogen, —NO$_2$, —CN, —OR, —SR, —N(R)$_2$, —C(O)R, —CO$_2$R, —C(O)C(O)R, —C(O)CH$_2$C(O)R, —S(O)R, —S(O)$_2$R, —C(O)N(R)$_2$, —SO$_2$N(R)$_2$, —OC(O)R, —N(R)C(O)R, —N(R)N(R)$_2$, —N(R)C(=NR)N(R)$_2$, —C(=NR)N(R)$_2$, —C=NOR, —N(R)C(O)N(R)$_2$, —N(R)SO$_2$N(R)$_2$, —N(R)SO$_2$R, or —OC(O)N(R)$_2$. In some embodiments, $R^7$ is hydrogen or optionally substituted $C_{1-6}$ aliphatic. In some embodiments, $R^7$ is halogen, —CN, or optionally substituted $C_{1-6}$ alkyl. In some embodiments, $R^7$ is hydrogen. In other embodiments, $R^7$ is optionally substituted $C_{1-4}$ alkyl. In some embodiments, $R^7$ is optionally substituted phenyl. In some embodiments, $R^7$ is an optionally substituted 3-7 membered saturated or partially unsaturated carbocyclic ring. In some embodiments, $R^7$ is an optionally substituted 3-7 membered saturated or partially unsaturated monocyclic heterocyclic ring having 1-2 heteroatoms independently selected from nitrogen, oxygen, or sulfur. In some embodiments, $R^7$ is an optionally substituted 5-6 membered heteroaryl ring having 1-3 heteroatoms independently selected from nitrogen, oxygen, or sulfur.

In certain embodiments, $X^1$ is —CR$^6$R$^7$— and $R^6$ and $R^7$ are independently hydrogen, substituted or unsubstituted phenyl, or substituted or unsubstituted $C_{1-4}$ alkyl. In some embodiments, $R^6$ and $R^7$ are independently hydrogen, unsubstituted phenyl, or $C_{1-4}$ unsubstituted alkyl. In some embodiments, $R^6$ and $R^7$ are hydrogen.

In some embodiments, $R^8$ is R, —C(O)R, —CO$_2$R, —C(O)C(O)R, —C(O)CH$_2$C(O)R, —C(O)N(R)$_2$, —S(O)R, —S(O)$_2$R, or —S(O)$_2$N(R)$_2$. In some embodiments, $R^8$ is hydrogen or optionally substituted $C_{1-6}$ aliphatic. In some embodiments, $R^8$ is hydrogen. In other embodiments, $R^8$ is optionally substituted $C_{1-4}$ alkyl. In some embodiments, $R^8$ is optionally substituted phenyl. In some embodiments, $R^8$ is an optionally substituted 3-7 membered saturated or partially unsaturated carbocyclic ring. In some embodiments, $R^8$ is an optionally substituted 3-7 membered saturated or partially unsaturated monocyclic heterocyclic ring having 1-2 heteroatoms independently selected from nitrogen, oxygen, or sulfur. In some embodiments, $R^8$ is an optionally substituted 5-6 membered heteroaryl ring having 1-3 heteroatoms independently selected from nitrogen, oxygen, or sulfur.

In some embodiments, $R^9$ is R, halogen, —NO$_2$, —CN, —OR, —SR, —N(R)$_2$, —C(O)R, —CO$_2$R, —C(O)C(O)R, —C(O)CH$_2$C(O)R, —S(O)R, —S(O)$_2$R, —C(O)N(R)$_2$, —SO$_2$N(R)$_2$, —OC(O)R, —N(R)C(O)R, —N(R)N(R)$_2$, —N(R)C(=NR)N(R)$_2$, —C(=NR)N(R)$_2$, —C=NOR, —N(R)C(O)N(R)$_2$, —N(R)SO$_2$N(R)$_2$, —N(R)SO$_2$R, or —OC(O)N(R)$_2$. In some embodiments, $R^9$ is hydrogen or optionally substituted $C_{1-6}$ aliphatic. In some embodiments, $R^9$ is halogen, —CN, or optionally substituted $C_{1-6}$ alkyl. In some embodiments, $R^9$ is hydrogen. In other embodiments, $R^9$ is optionally substituted $C_{1-4}$ alkyl. In some embodiments, $R^9$ is optionally substituted phenyl. In some embodiments, $R^9$ is an optionally substituted 3-7 membered saturated or partially unsaturated carbocyclic ring. In some embodiments, $R^9$ is an optionally substituted 3-7 membered saturated or partially unsaturated monocyclic heterocyclic ring having 1-2 heteroatoms independently selected from nitrogen, oxygen, or sulfur. In some embodiments, $R^9$ is an optionally substituted 5-6 membered heteroaryl ring having 1-3 heteroatoms independently selected from nitrogen, oxygen, or sulfur.

In certain embodiments, $X^1$ is —O—. In some embodiments, $X^1$ is —CR$^6$R$^7$—. In some embodiments, $X^1$ is —NR$^8$—. In some embodiments, when y is 0, $X^1$ is —CR$^6$R$^7$— or —NR$^8$—. In some embodiments, when z is 0, $X^1$ is —CR$^6$R$^7$— or —NR$^8$—. In some embodiments, when z is 0, $X^1$ is —CR$^6$R$^7$—. In some embodiments, when z is 1, $X^1$ is —CR$^6$R$^7$— or —NR$^8$—.

In some embodiments, $X^2$ is =CR$^9$—. In other embodiments, $X^2$ is =N—.

In some embodiments, Ring $A^1$ is an optionally substituted ring selected from phenyl, an 8-10 membered bicyclic aryl ring, a 5-6 membered heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur. In some embodiments, Ring $A^1$ is bicyclic. In some embodiments, Ring $A^1$ is monocyclic. In some embodiments, Ring $A^1$ is optionally substituted phenyl. In some embodiments, Ring $A^1$ is an optionally substituted 3-7 membered saturated or partially unsaturated monocyclic carbocyclic ring. In some embodiments, Ring $A^1$ is an optionally substituted 3-7 membered saturated or partially unsaturated monocyclic heterocyclic ring having 1-2 heteroatoms independently selected from nitrogen, oxygen, or sulfur. In some embodiments, Ring $A^1$ is an optionally substituted 7-10 membered saturated or partially unsaturated bicyclic heterocyclic ring having 1-3 heteroatoms independently selected from nitrogen, oxygen, or sulfur. In some embodiments, Ring $A^1$ is an optionally substituted 8-10 membered bicyclic aryl ring. In some embodiments, Ring $A^1$ is an optionally substituted 5-6 membered heteroaryl ring having 1-3 heteroatoms independently selected from nitrogen, oxygen, or sulfur. In some embodiments, Ring $A^1$ is an optionally substituted 8-10 membered bicyclic heteroaryl ring having 1-4 heteroatoms independently selected from nitrogen, oxygen, or sulfur.

In some embodiments, Ring $A^1$ is a substituted phenyl moiety. In certain embodiments, Ring $A^1$ is a phenyl moiety substituted with one or more substituents independently selected from halogen, —NO$_2$, —CN, —OR, —SR, —N(R)$_2$, —C(O)R, —CO$_2$R, —C(O)C(O)R, —C(O)CH$_2$C(O)R, —S(O)R, —S(O)$_2$R, —C(O)N(R)$_2$, —SO$_2$N(R)$_2$, —OC(O)R, —N(R)C(O)R, —N(R)N(R)$_2$, —N(R)C(=NR)N(R)$_2$, —C(=NR)N(R)$_2$, —C=NOR, —N(R)C(O)N(R)$_2$, —N(R)SO$_2$N(R)$_2$, —N(R)SO$_2$R, —OC(O)N(R)$_2$, or an optionally substituted group selected from $C_{1-12}$ aliphatic, phenyl, a 3-7 membered saturated or partially unsaturated monocyclic carbocyclic ring, a 7-10 membered saturated or partially unsaturated bicyclic carbocyclic ring, a 3-7 membered saturated or partially unsaturated heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, an 8-10 membered bicyclic aryl ring, a 5-6 membered heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur.

In certain embodiments, Ring $A^1$ is a phenyl moiety substituted with one or more substituents independently selected from halogen, —CN, —CF$_3$, —OH, —OR, —NH$_2$, —NR$_2$, —COOH, —SR, —S(O)R, —S(O)$_2$R, or an optionally substituted group selected from C$_{1-12}$ aliphatic, phenyl, a 3-7 membered saturated or partially unsaturated monocyclic carbocyclic ring, a 7-10 membered saturated or partially unsaturated bicyclic carbocyclic ring, a 3-7 membered saturated or partially unsaturated heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, an 8-10 membered bicyclic aryl ring, a 5-6 membered heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur. In some embodiments, substituents on Ring $A^1$ are selected from halogen, —CN, —CF$_3$, —OH, —NH$_2$, —N(R)$_2$, —COOH, —SR, —S(O)R, —S(O)$_2$R, —S(O)N(R)$_2$, —S(O)$_2$N(R)$_2$, or C$_{1-6}$ aliphatic.

In some embodiments, when Ring $A^1$ is a phenyl moiety substituted with one or more —S(O)R or —S(O)$_2$R groups, R is —CF$_3$ or —NR$_2$, In some embodiments, two substituents on Ring $A^1$ may be taken together with their intervening atoms to form an optionally substituted ring selected from phenyl, a 3-7 membered saturated or partially unsaturated monocyclic carbocyclic ring, a 7-10 membered saturated or partially unsaturated bicyclic carbocyclic ring, a 3-7 membered saturated or partially unsaturated heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, an 8-10 membered bicyclic aryl ring, a 5-6 membered heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur.

In some embodiments, Ring $A^1$ is selected from:

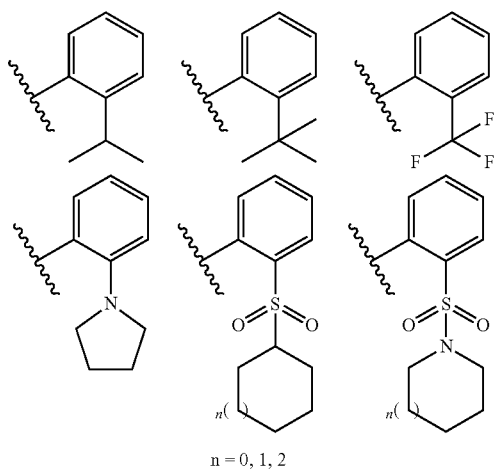

n = 0, 1, 2

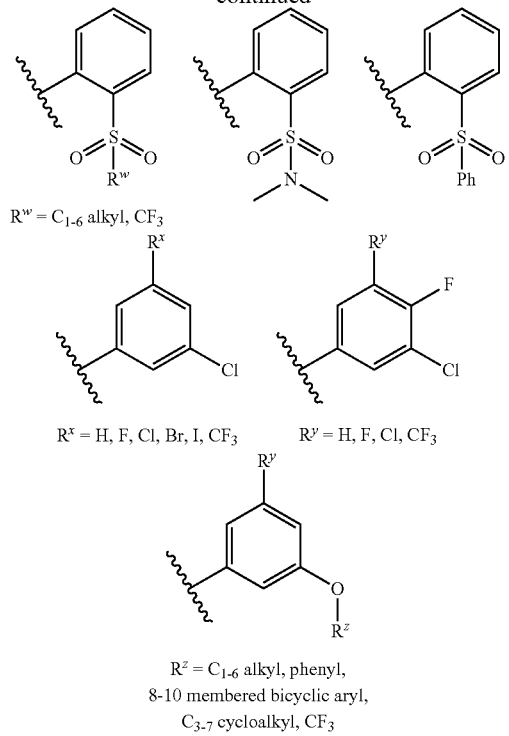

$R^w$ = C$_{1-6}$ alkyl, CF$_3$ $R^x$ = H, F, Cl, Br, I, CF$_3$ $R^y$ = H, F, Cl, CF$_3$ $R^z$ = C$_{1-6}$ alkyl, phenyl, 8-10 membered bicyclic aryl, C$_{3-7}$ cycloalkyl, CF$_3$ In some embodiments, Ring $A^1$ is

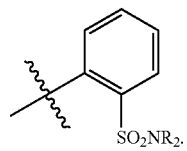

In certain embodiments, each R is an optionally substituted group selected from C$_{1-6}$ aliphatic, phenyl, or a 5-6 membered heteroaryl ring having 1-3 heteroatoms independently selected from nitrogen, oxygen, or sulfur. In some embodiments, two R groups on the same nitrogen are taken together with their intervening atoms to form an optionally substituted 3-7 membered saturated, partially unsaturated, or heteroaryl ring having 1-4 heteroatoms independently selected from nitrogen, oxygen, or sulfur. In some embodiments, two R groups on the same nitrogen are taken together with their intervening atoms to form an optionally substituted 5-6 membered saturated, partially unsaturated, or heteroaryl ring having 1-2 heteroatoms independently selected from nitrogen, oxygen, or sulfur. In some embodiments, wherein two R groups on the same nitrogen are taken together with their intervening atoms to form an optionally substituted group selected from piperidine or pyrrolidine.

In certain embodiments, L is a covalent bond. In other embodiments, L is an optionally substituted, bivalent C$_{1-8}$ saturated or unsaturated, straight or branched, hydrocarbon chain, wherein one, two, or three methylene units of L are optionally and independently replaced by -Cy-, —C(R)$_2$—, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, —C(=NR)—, —N=N—, or —C(=N$_2$)—. In some embodiments, L is an optionally substituted, bivalent $C_{1-4}$ saturated or unsaturated, straight or branched, hydrocarbon chain, wherein one, two, or three methylene units of L are optionally and independently replaced by -Cy-, —C(R)$_2$—, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, —C(=NR)—, —N=N—, or —C(=N$_2$)—. In some embodiments, L is an optionally substituted, bivalent $C_{1-4}$ saturated or unsaturated, straight or branched, hydrocarbon chain, wherein one methylene unit of L is replaced by -Cy-, —C(R)$_2$—, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, —C(=NR)—, —N=N—, or —C(=N$_2$)—. In some embodiments, L is an optionally substituted, bivalent $C_{1-4}$ saturated or unsaturated, straight or branched, hydrocarbon chain, wherein two methylene units of L are independently replaced by -Cy-, —C(R)$_2$—, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, —C(=NR)—, —N=N—, or —C(=N$_2$)—.

In certain embodiments, L is an optionally substituted bivalent $C_{1-4}$ saturated hydrocarbon chain, wherein one methylene unit of L is replaced by —C(O)— and one methylene unit of L is replaced by —N(R)—. In certain embodiments, L is an optionally substituted bivalent $C_{1-4}$ saturated hydrocarbon chain, wherein one methylene unit of L is replaced by —C(O)— and one methylene unit of L is replaced by —N(R)—, wherein R is hydrogen.

In some embodiments, one methylene unit of L is replaced by —C(R)$_2$—. In some embodiments, one methylene unit of L is replaced by —C(R)$_2$—, and each R is independently hydrogen or an optionally substituted group selected from $C_{1-6}$ aliphatic or 3-7 membered saturated carbocyclic. In some embodiments, one methylene unit of L is replaced by —C(R)$_2$—, and each R is hydrogen. In some embodiments, one methylene unit of L is replaced by —C(R)$_2$—, and each R is hydrogen or optionally substituted $C_{1-6}$ aliphatic. In some embodiments, one methylene unit of L is replaced by —C(R)$_2$—, and each R is hydrogen or optionally substituted 3-7 membered saturated carbocyclic. In some embodiments, one methylene unit of L is replaced by —C(R)$_2$—, and each R is independently hydrogen, a substituted $C_{1-6}$ aliphatic, or a substituted 3-7 membered saturated carbocyclic ring, wherein a substituent on R is selected from —CF$_3$ or —OH.

In some embodiments, L is —C(O)C(R)$_2$NR—. In some embodiments, L is selected from:

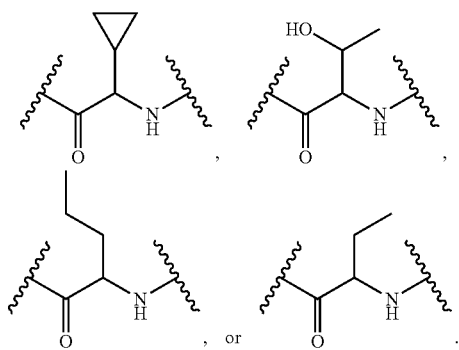

In some embodiments, L is selected from:

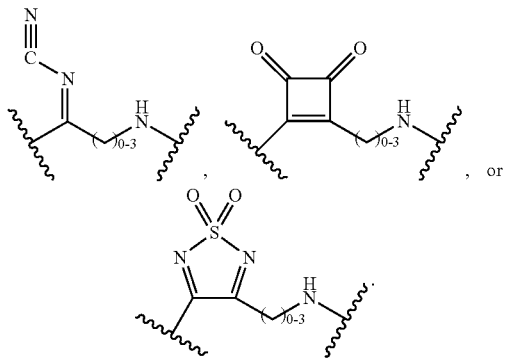

In some embodiments, one methylene unit of L is replaced by —C(R)$_2$—, and each R is optionally substituted with one or more groups selected from halogen, —CN, —CF$_3$, —OH, —NH$_2$, —COOH, or R$^\circ$.

In some embodiments, one methylene unit of L is replaced by -Cy-.

In certain embodiments, Cy is cycloalkylenyl. In certain embodiments, Cy is an optionally substituted phenylene. In certain embodiments, Cy is an optionally substituted 3-7 membered saturated or partially unsaturated carbocyclylene. In certain embodiments, Cy is an optionally substituted 3-7 membered saturated or partially unsaturated monocyclic heterocyclylene having 1-2 heteroatoms independently selected from nitrogen, oxygen, or sulfur. In certain embodiments, Cy is an optionally substituted 5-6 membered heteroarylene having 1-3 heteroatoms independently selected from nitrogen, oxygen. In some embodiments, Cy is

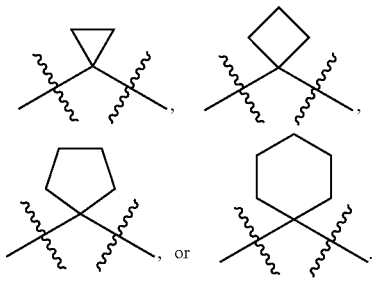

In certain embodiments, $X^2$ is =N—. In some embodiments, provided compounds are of formula I-a, I-a-i, or I-a-ii:

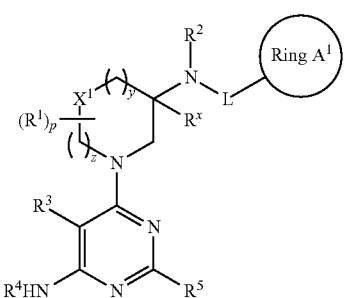

I-a

I-a-i

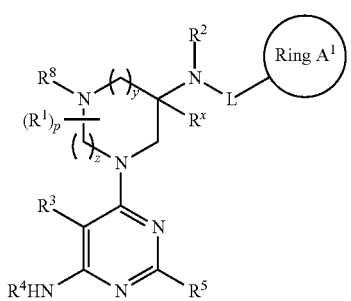

I-a-ii

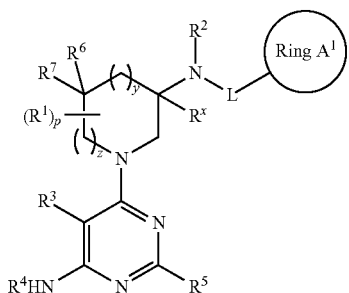

wherein each of $R^1$, $R^2$, $R^3$, $R^4$, $R^5$, $R^6$, $R^7$, $R^8$, $R^x$, L, Ring $A^1$, $X^1$, p, y, and z is as defined for formula I above and described in classes and subclasses herein.

In certain embodiments, $X^2$ is $=CR^9$—. In some embodiments, provided compounds are of formula I-b, I-b-i, or I-b-ii:

I-b

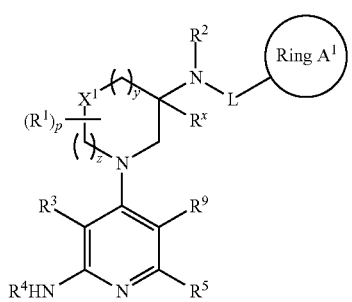

I-b-i

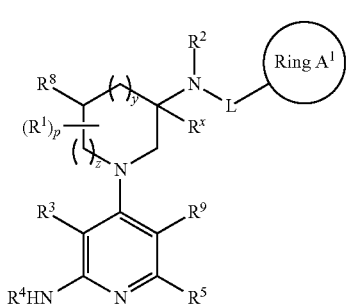

I-b-ii

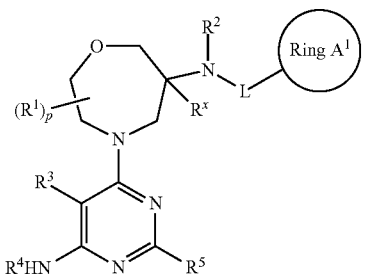

wherein each of $R^1$, $R^2$, $R^3$, $R^4$, $R^5$, $R^6$, $R^7$, $R^8$, $R^9$, $R^x$, L, Ring $A^1$, $X^1$, p, y, and z is as defined for formula I above and described in classes and subclasses herein.

In certain embodiments, y is 1, z is 2, and $X^1$ is —O—, thereby providing compounds of formula I-a-iii or I-b-iii:

I-a-iii

I-b-iii

wherein each of $R^1$, $R^2$, $R^3$, $R^4$, $R^5$, $R^9$, $R^x$, L, Ring $A^1$, and p is as defined for formula I above and described in classes and subclasses herein.

In certain embodiments, y is 0 and z is 2. In some embodiments, provided compounds are of formula I-a-iv, I-a-v, I-b-iv, or I-b-v:

I-a-iv

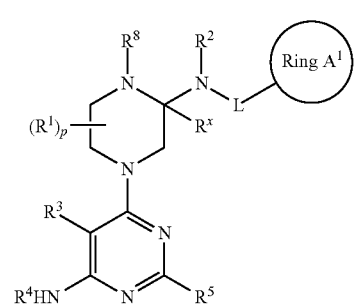

-continued
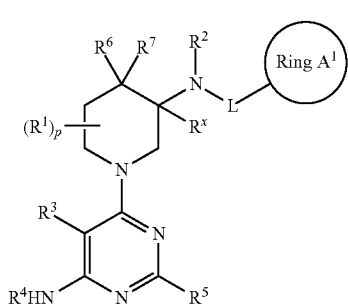
I-a-v
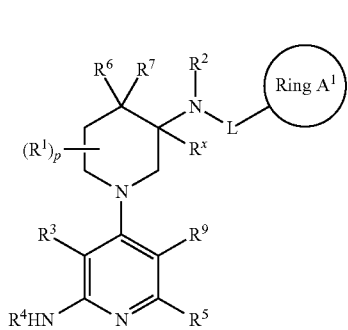
I-b-iv
I-b-v
wherein each of $R^1$, $R^2$, $R^3$, $R^4$, $R^5$, $R^6$, $R^7$, $R^8$, $R^9$, $R^x$, L, Ring $A^1$, and p is as defined for formula I above and described in classes and subclasses herein.
In some embodiments, a compound of the present invention includes particular stereoisomers of formula II-a, II-b, II-c, II-d, III-a, III-b, III-c, or III-d:
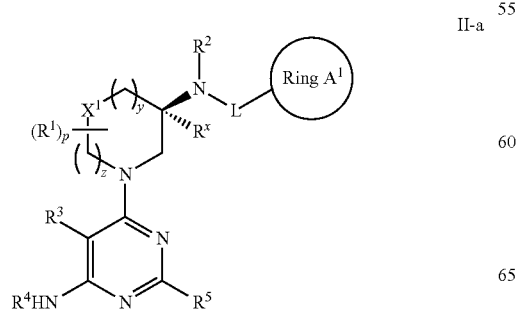
II-a
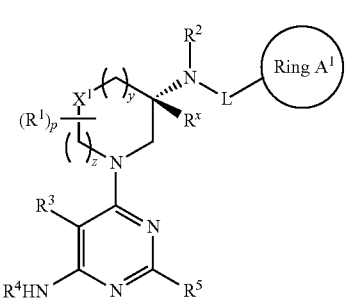
II-b
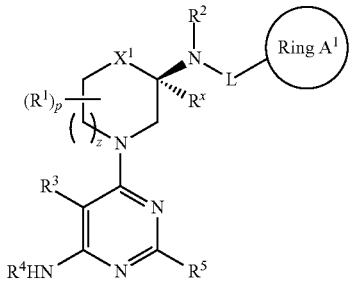
II-c
II-d
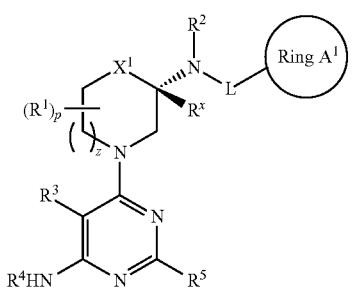
III-a
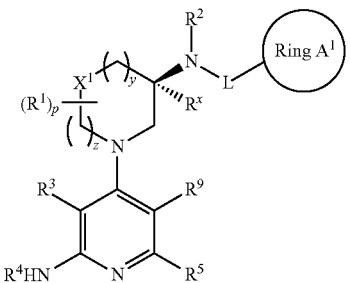
III-b
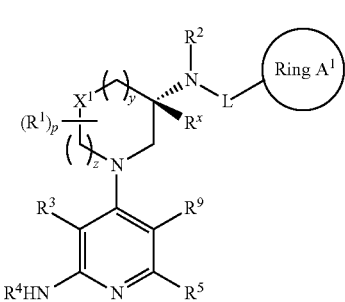

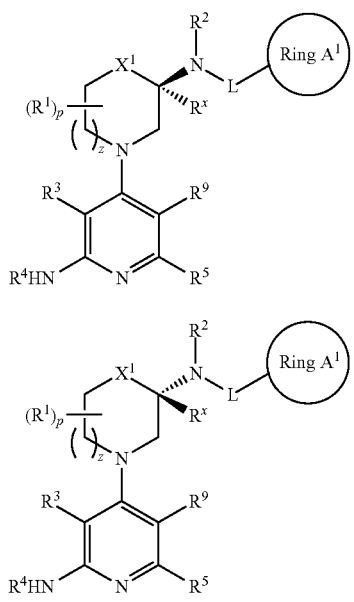

wherein each of $R^1$, $R^2$, $R^3$, $R^4$, $R^5$, $R^9$, $R^x$, L, $X^1$, Ring $A^1$, y, z, and p is as defined for formula I above and described in classes and subclasses herein.

In some embodiments, a Btk inhibitor is a racemic mixture or enriched in one or more stereoisomers. In some embodiments, a Btk inhibitor is a compound of Formula II-a. In some embodiments, a Btk inhibitor is a compound of Formula II-b. In some embodiments, a Btk inhibitor is a compound of Formula III-a. In some embodiments, a Btk inhibitor is a compound of Formula III-b.

As discussed above, in some embodiments, one methylene unit of L is replaced by —C(R)$_2$—. In some embodiments, a compound of the present invention is of formula IV-a, IV-b, IV-c, or IV-d:

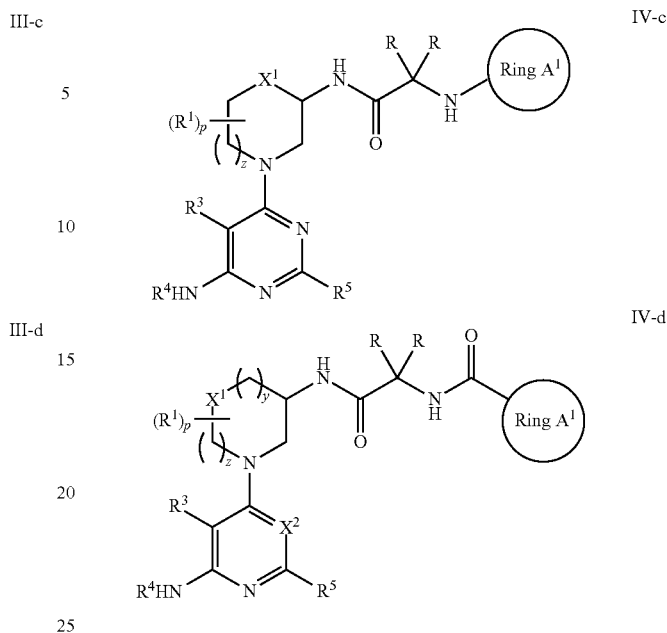

wherein each of R, $R^1$, $R^3$, $R^4$, $R^5$, $R^9$, $X^1$, $X^2$, Ring $A^1$, z, y, and p is as defined for formula I above and described in classes and subclasses herein.

In certain embodiments of formula IV-a, IV-b, IV-c, or IV-d, each R is independently hydrogen, unsubstituted $C_{1-6}$ alkyl, $C_{1-6}$ alkyl substituted —CF$_3$ or —OH, unsubstituted $C_{3-6}$ cycloalkyl, or unsubstituted 3-7 membered saturated or partially unsaturated monocyclic heterocyclic ring having 1-2 heteroatoms independently selected from nitrogen, oxygen, or sulfur.

In some embodiments, a compound of the present invention is of formula V, V-a, V-b, or V-c:

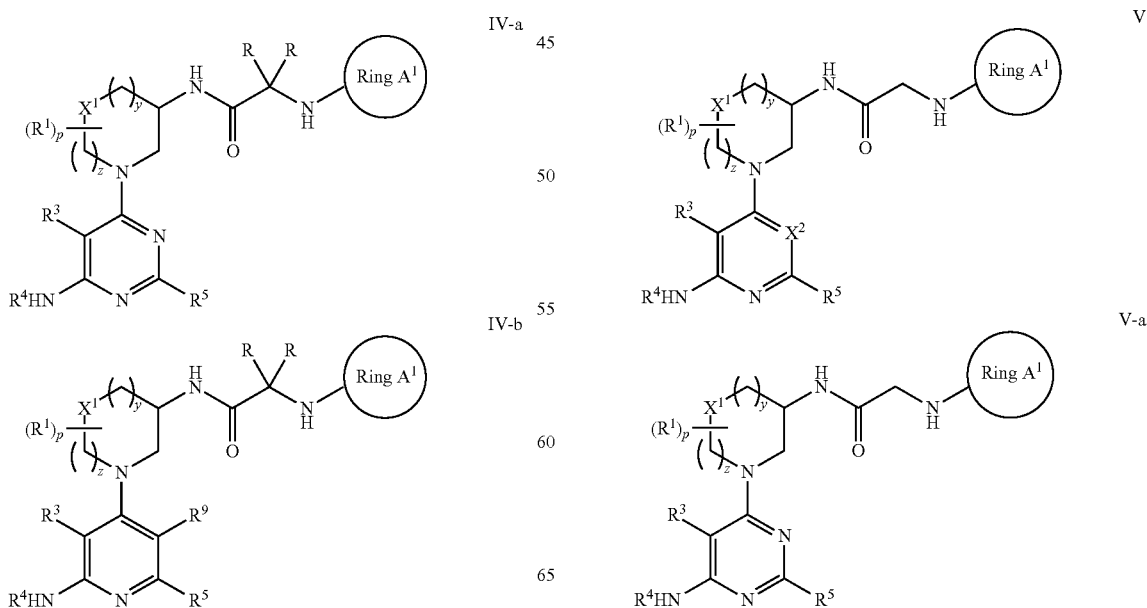

-continued

V-b

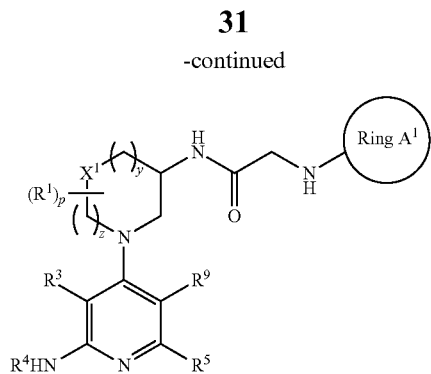

V-c

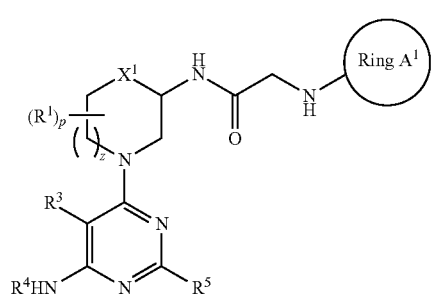

wherein each of $R^1$, $R^3$, $R^4$, $R^5$, $R^9$, $X^1$, $X^2$, Ring $A^1$, z, y, and p is as defined for formula I above and described in classes and subclasses herein.

In some embodiments, $R^2$ is taken together with $R^x$ to form an optionally substituted spirocyclic heterocyclyl ring selected from a 3 to 8-membered saturated or partially unsaturated monocyclic heterocyclic ring having 1 to 2 heteroatoms independently selected from nitrogen, oxygen, or sulfur. In certain embodiments, a compound of the present invention is of formula VI, VI-a, VI-b, of VI-c:

VI

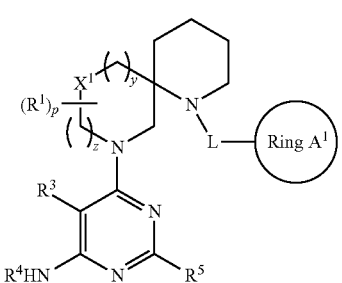

VI-a

-continued

VI-b

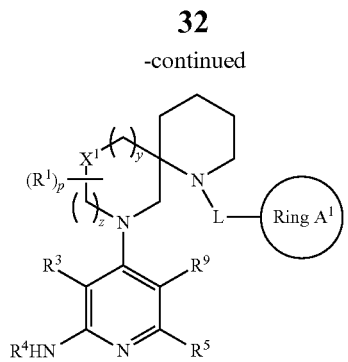

VI-c

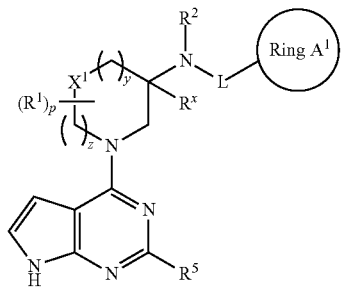

wherein each of $R^1$, $R^3$, $R^4$, $R^5$, $R^9$, $X^1$, L, Ring $A^1$, z, y, and p is as defined for formula I above and described in classes and subclasses herein, and wherein h is 0-4.

In some embodiments, h is 0. In some embodiments, h is 1. In some embodiments, h is 2. In some embodiments, h is 3. In some embodiments, h is 4.

In certain embodiments, $R^3$ and $R^4$ are taken together with their intervening atoms to form an optionally substituted group selected from a 4 to 7-membered saturated or partially unsaturated monocyclic heterocyclic ring having 1 to 2 heteroatoms independently selected from nitrogen, oxygen, or sulfur, or a 7 to 10-membered saturated or partially unsaturated bicyclic heterocyclic ring having 1 to 3 heteroatoms independently selected from nitrogen, oxygen, or sulfur. In some embodiments, $R^3$ and $R^4$ are taken together to form a substituted or unsubstituted pyrrole or substituted or unsubstituted pyrazole. In some embodiments, a compound of the present invention is of formula VII-a, VII-b, VIII-a, VIII-b, IX-a, or IX-b:

VII-a

-continued

VII-b
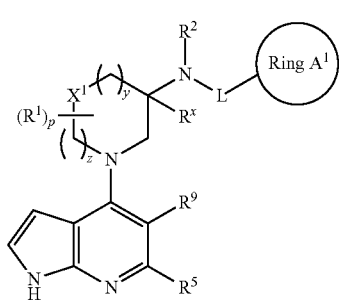

VIII-a
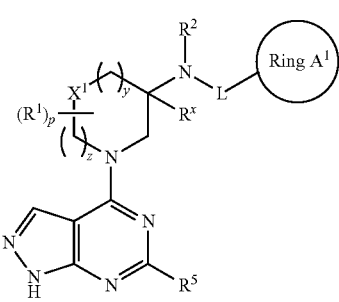

VIII-b
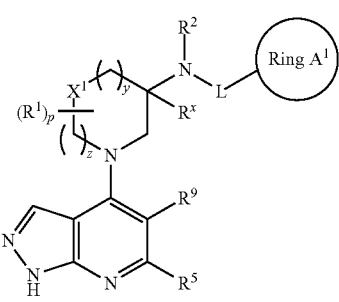

IX-a
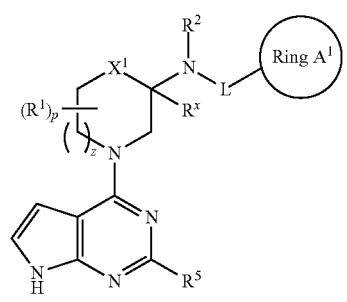

IX-b
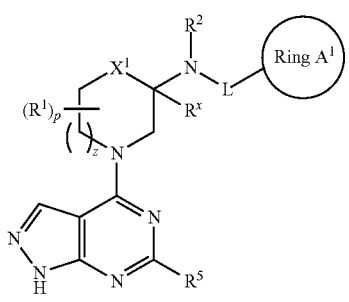

wherein each of $R^1$, $R^2$, $R^5$, $R^9$, $R^x$, $X^1$, L, Ring $A^1$, z, y, and p is as defined for formula I above and described in classes and subclasses herein.

In certain embodiments, $R^2$ and $R^7$ are taken together with their intervening atoms to form optionally substituted 4-8 membered saturated or partially unsaturated monocyclic heterocyclic ring having 1-2 heteroatoms independently selected from nitrogen, oxygen, or sulfur. In some embodiments, a provided compound is of formula X:

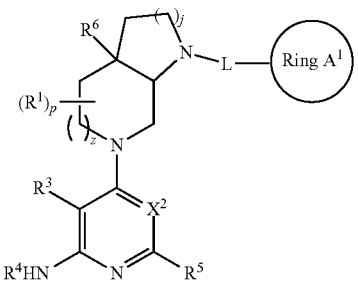
X wherein each of $R^1$, $R^2$, $R^3$, $R^4$, $R^5$, $R^6$, $R^x$, $X^2$, L, Ring $A^1$, z, and p is as defined for formula I above and described in classes and subclasses herein, and wherein j is 0-4.

In some embodiments, j is 0. In some embodiments, j is 1. In some embodiments, j is 2. In some embodiments, j is 3. In some embodiments, j is 4.

In certain embodiments, $R^2$ and $R^8$ are taken together with their intervening atoms to form optionally substituted 4-8 membered saturated or partially unsaturated monocyclic heterocyclic ring having 1-3 heteroatoms independently selected from nitrogen, oxygen, or sulfur. In some embodiments, a provided compound is of formula XI:

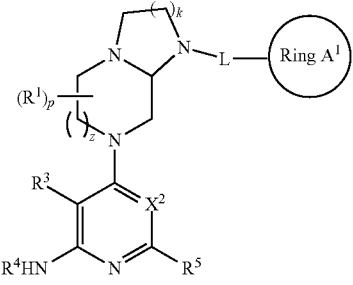
XI wherein each of $R^1$, $R^2$, $R^3$, $R^4$, $R^5$, $R^x$, $X^2$, L, Ring $A^1$, z, and p is as defined for formula I above and described in classes and subclasses herein, and wherein k is 0-4.

In some embodiments, k is 0. In some embodiments, k is 1. In some embodiments, k is 2. In some embodiments, k is 3. In some embodiments, k is 4.

In certain embodiments, a provided compound is a compound depicted in Table 1, below.

I. Exemplary Synthesis

Compounds of the invention are synthesized by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention. However, the discussion is not intended to define the scope of reactions or reaction sequences that are useful in preparing the compounds of the present invention.

Compounds of formula (I) can be prepared according to Scheme 1 using commercially available or synthesized substituted amine protected heterocycles such as 3-(tert-Butoxycarbonylamino)pyrrolidine, 3-(tert-Butoxycarbonylamino)piperidine or 3-(tert-Butoxycarbonylamino)azepane (Huang, P.; Wang, S, Zheng, H,; Fei, X. *Tetrahedron Lett.* 1997, 38, 271. Hu, X. E.; Kim, N. K.; Ledoussal, B. *Org. Lett.* 2002, 4, 4499. Kitas, E. A.; Galley, G.; Jakob-Roetne, R.; Flohr, A.; Wostl, A.; Mauser, H.; Alker, A. M.; Czech, C.; Ozmen, L.; David-Pierson, P.; Reinhardt, D. Jacobsen, H. *Bioorg. Med. Chem. Lett.* 2008, 18, 304. Burgey, C. S.; Paone, D. V.; Shaw, A. W.; Nguyen, D. N.; Deng, Z. J.; Williams, T. M.; Vacca, J. P.; Selnick, H. G.; Potteiger, C. M. PCT Int. Appl. (2006), 292 pp. WO 2006044504). The heterocyclic amine can be protected using the appropriate protecting group familiar to those skilled in the art. The exo-cyclic amino group can be substituted upon treated with a base such as sodium hydride or by other bases (e.g., DIEA, Et$_3$N, K$_2$CO$_3$, etc.) familiar to one skilled in the art and in a solvent such as DMF or other appropriate solvents to yield 1.3. The protected heterocyclic amine 1.4 can be de-protected to the amine which can be reacted with the substituted heteroaromatic such as pyridinyl and pyrimidyl moieties using DIEA or by other bases familiar to one skilled in the art and in a solvent such as DMF or another appropriate solvents to yield 1.6. Alternatively, the N-amination can be accomplished utilizing Buchwald coupling (Shafir, A. Buchwald, S. L. *J. Am. Chem. Soc.* 2006, 128, 8742. Mehrotra, M. M. et. al. *Bioorganic & Medicinal Chemistry Letters* 2002, 12, 1103). The exo-cyclic amine protecting group can be removed upon treatment with suitable conditions as described in Greene and Wuts, Protective Group in Organic Synthesis, 3rd edition, John Wiley & Sons, New York. The amine 1.7 can be reacted with the appropriate electrophile such as a substituted acid chloride, sulfonyl chloride, alkyl halide or carboxylic acid which can be activated using standard peptide coupling reagents such as EDCI/HOBt, PyBOP, HATU or BEM (Carpino, L. A. *J. Am. Chem. Soc.* 1993, 115, 4397. Carpino, L. A.; El-Faham, A. *J. Am. Chem. Soc.* 1995, 117, 5401. Li, P.; Xu, J. C. *J. Pept. Res.* 2001, 58, 129.) in the presence of a base such as DIEA or other bases familiar to one skilled in the art and in an appropriate solvent to yield 1.8. Alternatively and/or additionally, the exo-cyclic amine 1.7 can be reacted with chloroformate or chlorothioformate or o-, p-nitrophenylchloroformate or phenylchloroformate (or their thiocarbonyl equivalents), or diphenyl cyanocarbonimidate followed by displacement with the appropriate amine can also yield the corresponding urea, thiourea or cyanoguanidine. When synthesizing compounds containing the 1H-pyrazolo[3,4-d]pyrimidine moiety or other compounds reported within this invention which contain functional groups that are not compatible with electrophilic substitution, it will be necessary to do an additional step to remove the protecting group to afford compound I.

The groups "Lg", "Lg$^1$", and "Lg$^2$" in Schemes 1-3 are suitable leaving groups, i.e., groups that are subject to nucleophilic displacement. A "suitable leaving group" is a chemical group that is readily displaced by a desired incoming chemical moiety such as an amine. Suitable leaving groups are well known in the art, e.g., see, "Advanced Organic Chemistry," Jerry March, 5$^{th}$ Ed., pp. 351-357, John Wiley and Sons, N.Y. Such leaving groups include, but are not limited to, halogen, alkoxy, sulphonyloxy, optionally substituted alkylsulphonyloxy, optionally substituted alkenylsulfonyloxy, optionally substituted arylsulfonyloxy, acyl, and diazonium moieties. Examples of suitable leaving groups include chloro, iodo, bromo, fluoro, acetoxy, methoxy, methanesulfonyloxy (mesyloxy), tosyloxy, triflyloxy, nitro-phenylsulfonyloxy (nosyloxy), and bromo-phenylsulfonyloxy (brosyloxy).

The groups "Pg", "Pg$^1$", and "Pg$^2$" in Schemes 1-4 are suitable protecting groups, as defined above and described herein. One of ordinary skill will be familiar with a variety of protecting group and protecting group strategies that many be employed in the Schemes depicted below.

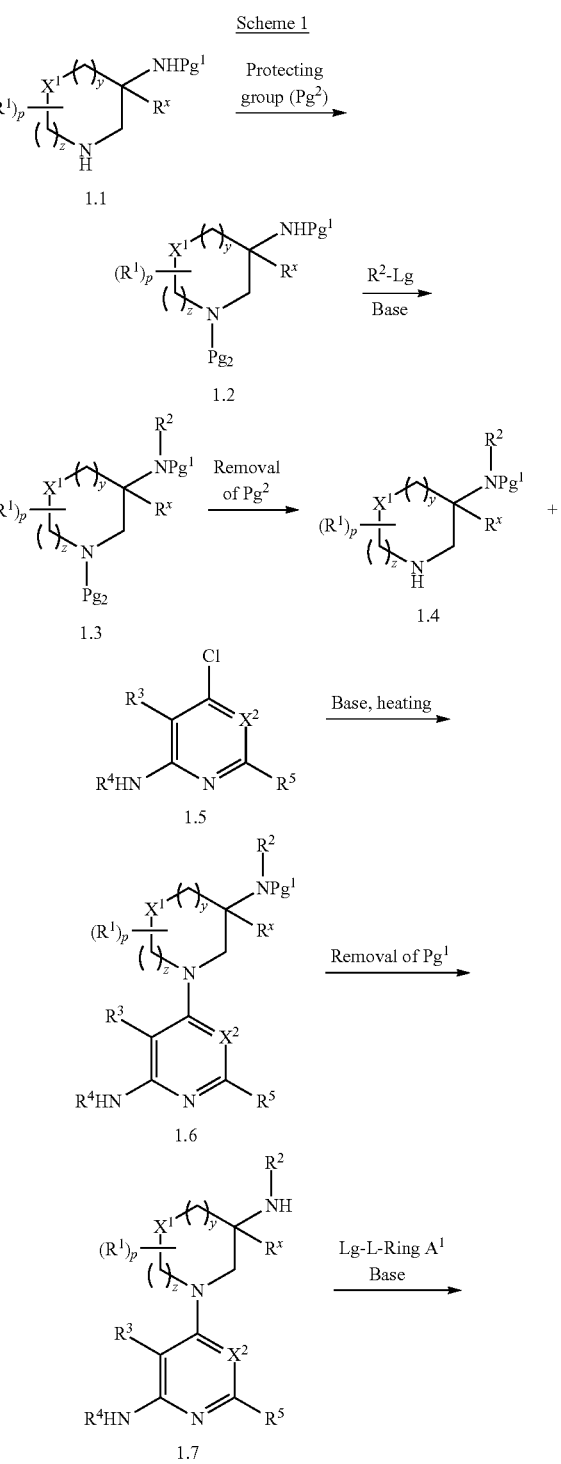

Scheme 1

-continued

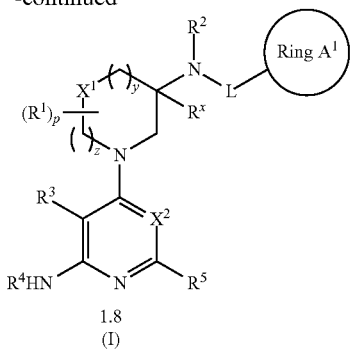

1.8
(I)

-continued

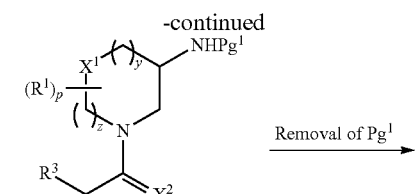

2.3

Removal of Pg¹ →

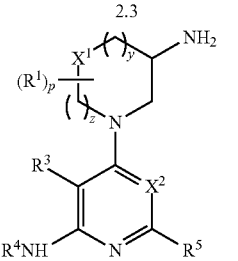

2.4

$\xrightarrow{\underset{\text{Base}}{\text{Lg}^1 \overset{O}{\underset{}{\parallel}} \text{Lg}^2}}$

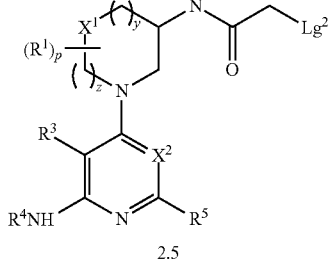

2.5

$\xrightarrow{\underset{\text{Base}}{\text{H}_2\text{N—Ring A}^1}}$

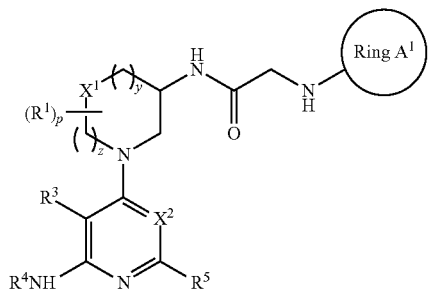

2.6
(V)

Alternatively and/or additionally, certain compounds of formula (I) can also be prepared according to Scheme 2 using commercially available substituted heterocycles such as pyrrolidine, piperidine or azepanes which can undergo N-animation with substituted heteroaromatic such as pyridinyl and pyrimidyl moities using DIEA or by other bases familiar to one skilled in the art and in a solvent such as DMF or another appropriate solvents to yield 2.3. The N-amination can also be accomplished utilizing Buchwald coupling (Shafir, A. Buchwald, S. L. *J. Am. Chem. Soc.* 2006, 128, 8742. Mehrotra, M. M. et. al. *Bioorganic & Medicinal Chemistry Letters* 2002, 12, 1103) to afford 2.3. The exo-cyclic amine protecting group can be removed upon treatment with suitable conditions as described in Greene and Wuts, Protective Group in Organic Synthesis, 3rd edition, John Wiley & Sons, New York to give compound 2.4. The amine can be substituted using the appropriate electrophile such as 2-chloroacetyl chloride in the presence of an organic base such as triethylamine or other suitable bases familiar to those skilled in the art and in a solvent such as dichloromethane or another appropriate solvent. Compound 2.5 can undergo nucleophilic displacement with various nucleophiles such as primary and secondary amines to yield compounds represented by structure 2.6. When synthesizing compounds containing the 1H-pyrazolo [3,4-d]pyrimidine moiety or other compounds reported within this invention which contain functional groups that are not compatible with electrophilic substitution it may be necessary to do an additional step to remove the protecting group to afford compound of formula V.

Scheme 2

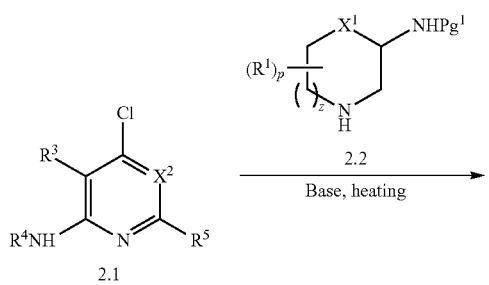

Compounds of formula (I) can be prepared via intermediates 2.4 which can be reacted with the appropriate electrophile such as a substituted or unsubstituted glycyl carboxamide as shown in Scheme 3. The protected amine compound 3.1 can be de-protected upon treatment with suitable conditions as described in Greene and Wuts, Protective Group in Organic Synthesis, 3rd edition, John Wiley & Sons, New York. The amine 3.2 can be reacted with the appropriate electrophile such as a substituted acid chloride, sulfonyl chloride, alkyl halide or carboxylic acid which can be activated using standard peptide coupling reagents such as EDCI/ HOBt, PyBOP, HATU or BEM (Carpino, L. A. *J. Am. Chem. Soc.* 1993, 115, 4397. Carpino, L. A.; El-Faham, A. *J. Am. Chem. Soc.* 1995, 117, 5401. Li, P.; Xu, J. C. *J. Pept. Res.* 2001, 58, 129.) in the presence of an organic base such as DIEA or other bases familiar to one skilled in the art and in an appropriate solvent to yield 3.3. When synthesizing compounds containing the 1H-pyrazolo[3,4-d]pyrimidine moiety or other compounds reported herein containing functional groups that are not compatible with electrophilic substitution it will be necessary to do an additional step to remove the protecting group to afford compound IV-d.

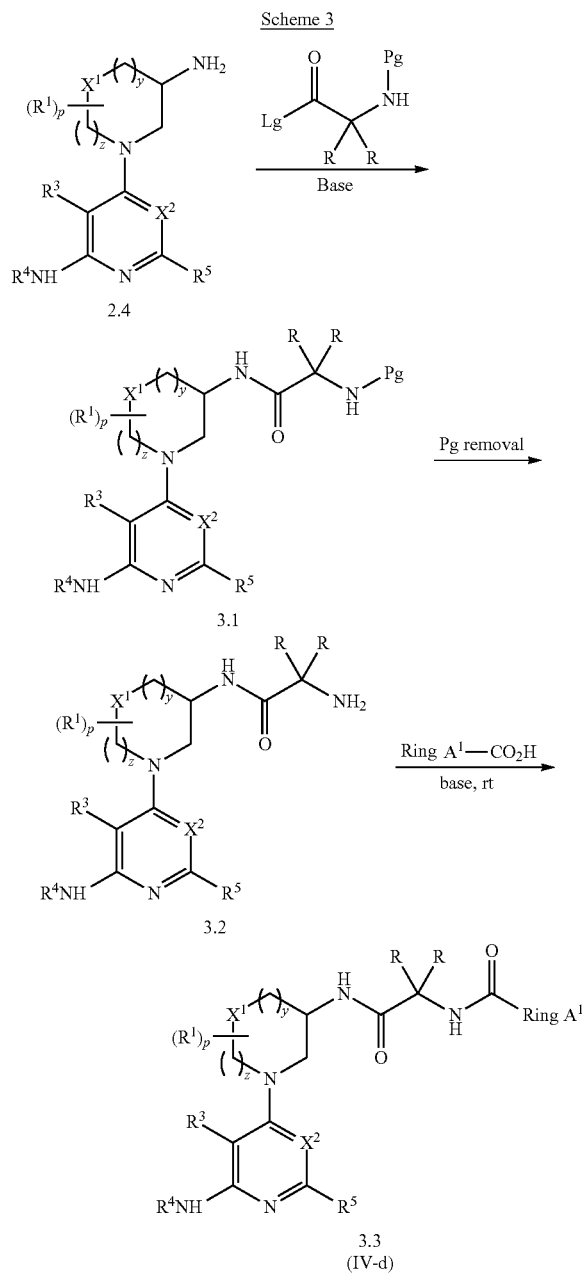

undergo N-amination upon treatment with a substituted heterocyclic amine in the presence of DIEA or by other bases familiar to one skilled in the art and in a solvent such as DMF or another appropriate solvent. The final step is the removal of the protecting group using suitable conditions to afford compounds of formula VIII-a.

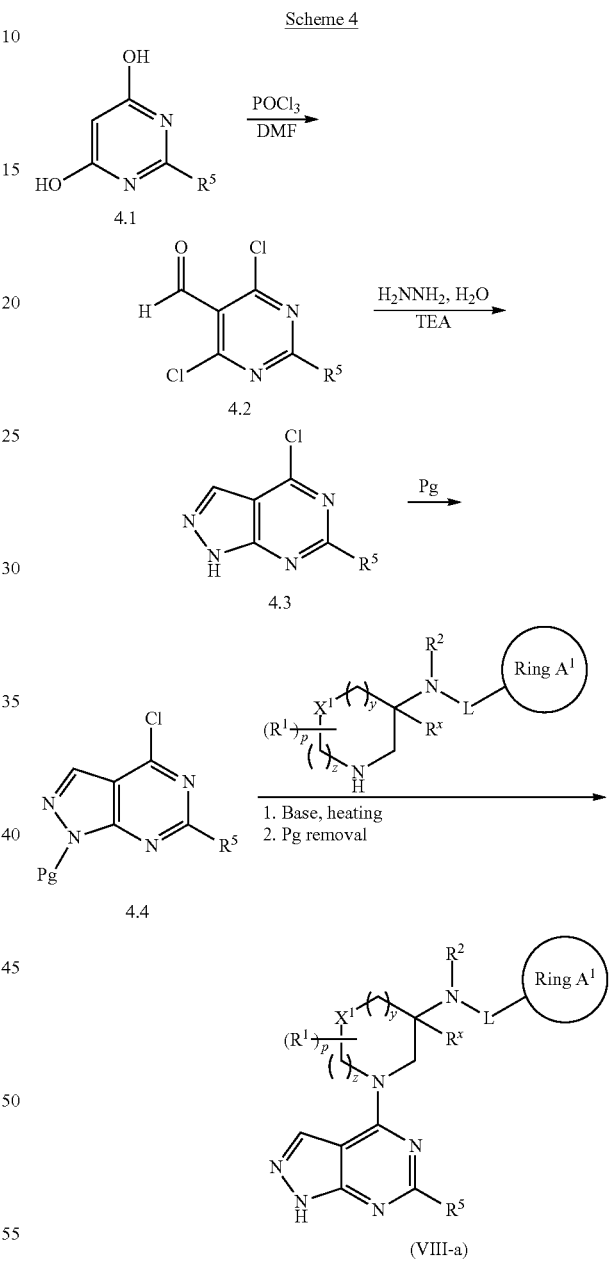

Compounds of formula (I) wherein $R^3$ and $R^4$ join together to form a heteroaryl (e.g. pyrazolo) can be prepared according to Scheme 4 using commercially available 4,6-dihydroxypyrimidine 4.1. The 4,6-dihydroxypyrimidine can be chlorinated and formylation under Vilsmeier conditions upon treatment with $POCl_3$ and DMF to afford the 5-formyl-6,3-dichloro-5-formylpyrimidine 4.2. The aldehyde 4.2 can be condensed with the hydrazine to afford the imine which can undergo intramolecular cyclization to give 4.3. The 4-chloro-1H-pyrazolo[3,4-d]pyrimidine intermediate can be protected upon treatment with suitable conditions as described in Greene and Wuts, Protective Group in Organic Synthesis, 3rd edition, John Wiley & Sons, New York to afford 4.4 and can then In certain embodiments, each of the aforementioned synthetic steps of Schemes 1-4 may be performed sequentially with isolation of each intermediate performed after each step. Alternatively, each of the steps as depicted in Schemes 1-4 above, may be performed in a manner whereby no isolation of each intermediate is performed. Furthermore, it will be readily apparent to the skilled artisan that additional steps may be performed to accomplish particular protection group and/or deprotection strategies.

Methods of Use

In certain embodiments, compounds of the present invention are for use in medicine. In some embodiments, compounds of the present invention are useful as kinase inhibitors. In certain embodiments, compounds of the present invention are selective inhibitors of Btk. Such methods include contacting a Btk with an effective amount of a Btk inhibitor. Therefore, the present invention further provides methods of inhibiting Btk enzymatic activity by contacting a Btk with a Btk inhibitor of the present invention.

Btk enzymatic activity, as used herein, refers to Btk kinase enzymatic activity. For example, where Btk enzymatic activity is decreased, PIP3 binding and/or phosphorylation of PLCγ is decreased. In some embodiments, the half maximal inhibitory concentration ($IC_{50}$) of the Btk inhibitor against Btk is less than 1 μM. In some embodiments, the $IC_{50}$ of the Btk inhibitor against Btk is less than 500 nM. In some embodiments, the $IC_{50}$ of the Btk inhibitor against Btk is less than 100 nM. In some embodiments, the $IC_{50}$ of the Btk inhibitor against Btk is less than 10 nM. In some embodiments, the $IC_{50}$ of the Btk inhibitor against Btk is less than 1 nM. In some embodiments, the $IC_{50}$ of the Btk inhibitor against Btk is from 0.1 nM to 10 μM. In some embodiments, the $IC_{50}$ of the Btk inhibitor against Btk is from 0.1 nM to 1 μM. In some embodiments, the $IC_{50}$ of the Btk inhibitor against Btk is from 0.1 nM to 100 nM. In some embodiments, the $IC_{50}$ of the Btk inhibitor against Btk is from 0.1 nM to 10 nM.

In certain embodiments, Btk inhibitors are useful for the treatment of diseases and disorders that may be alleviated by inhibiting (i.e., decreasing) Btk enzymatic activity. By "diseases" is meant diseases or disease symptoms. Thus, the present invention provides methods of treating autoimmune disorders, inflammatory disorders, and cancers in a subject in need thereof. Such methods include administering to a subject a therapeutically effective amount of a Btk inhibitor. The term "autoimmune disorders" includes diseases or disorders involving inappropriate immune response against native antigens, such as acute disseminated encephalomyelitis (ADEM), Addison's disease, alopecia areata, antiphospholipid antibody syndrome (APS), autoimmune hemolytic anemia, autoimmune hepatitis, bullous pemphigoid (BP), Coeliac disease, dermatomyositis, diabetes mellitus type 1, Goodpasture's syndrome, Graves' disease, Guillain-Barrésyndrome (GBS), Hashimoto's disease, idiopathic thrombocytopenic purpura, lupus erythematosus, mixed connective tissue disease, multiple sclerosis, myasthenia gravis, pemphigus vulgaris, pernicious anaemia, polymyositis, primary biliary cirrhosis, Sjögren's syndrome, temporal arteritis, and Wegener's granulomatosis. The term "inflammatory disorders" includes diseases or disorders involving acute or chronic inflammation such as allergies, asthma, prostatitis, glomerulonephritis, pelvic inflammatory disease (PID), inflammatory bowel disease (IBD, e.g., Crohn's disease, ulcerative colitis), reperfusion injury, rheumatoid arthritis, transplant rejection, and vasculitis. In some embodiments, the present invention provides methods of treating rheumatoid arthritis or lupus. The term "cancer" includes diseases or disorders involving abnormal cell growth and/or proliferation, such as glioma, thyroid carcinoma, breast carcinoma, lung cancer (e.g. small-cell lung carcinoma, non-small-cell lung carcinoma), gastric carcinoma, gastrointestinal stromal tumors, pancreatic carcinoma, bile duct carcinoma, ovarian carcinoma, endometrial carcinoma, prostate carcinoma, renal cell carcinoma, lymphoma (e.g., anaplastic large-cell lymphoma), leukemia (e.g. acute myeloid leukemia, T-cell leukemia, chronic lymphocytic leukemia), multiple myeloma, malignant mesothelioma, malignant melanoma, and colon cancer (e.g. microsatellite instability-high colorectal cancer). In certain embodiments, the present invention provides methods of treating leukemia or lymphoma.

The term "subject," as used herein, refers to a mammal to whom a pharmaceutical composition is administered. Exemplary subjects include humans, as well as veterinary and laboratory animals such as horses, pigs, cattle, dogs, cats, rabbits, rats, mice, and aquatic mammals.

Assays

To develop useful Btk inhibitors, candidate inhibitors capable of decreasing Btk enzymatic activity may be identified in vitro. The activity of the inhibitor compounds can be assayed utilizing methods known in the art and/or those methods presented herein.

Compounds that decrease Btk enzymatic activity may be identified and tested using biologically active Btk, either recombinant or naturally occurring. Btk can be found in native cells, isolated in vitro, or co-expressed or expressed in a cell. Measuring the reduction in the Btk enzymatic activity in the presence of an inhibitor relative to the activity in the absence of the inhibitor may be performed using a variety of methods known in the art, such as the BTK-POLYGAT-LS ASSAY described below in the Examples. Other methods for assaying the activity of Btk are known in the art. The selection of appropriate assay methods is well within the capabilities of those of skill in the art.

Once compounds are identified that are capable of reducing Btk enzymatic activity, the compounds may be further tested for their ability to selectively inhibit Btk relative to other enzymes. Inhibition by a compound of the invention is measured using standard in vitro or in vivo assays such as those well known in the art or as otherwise described herein.

Compounds may be further tested in cell models or animal models for their ability to cause a detectable changes in phenotype related to Btk activity. In addition to cell cultures, animal models may be used to test Btk inhibitors for their ability to treat autoimmune disorders, inflammatory disorders, or cancer in an animal model.

Pharmaceutical Compositions

In another aspect, the present invention provides pharmaceutical compositions comprising a Btk inhibitor compound of the invention or a Btk inhibitor compound in combination with a pharmaceutically acceptable excipient (e.g., carrier).

The pharmaceutical compositions include optical isomers, diastereomers, or pharmaceutically acceptable salts of the inhibitors disclosed herein. For example, in some embodiments, the pharmaceutical compositions include a compound of the present invention and citrate as a pharmaceutically acceptable salt. The Btk inhibitor included in the pharmaceutical composition may be covalently attached to a carrier moiety, as described above. Alternatively, the Btk inhibitor included in the pharmaceutical composition is not covalently linked to a carrier moiety.

A "pharmaceutically acceptable carrier," as used herein refers to pharmaceutical excipients, for example, pharmaceutically, physiologically, acceptable organic or inorganic carrier substances suitable for enteral or parenteral application that do not deleteriously react with the active agent. Suitable pharmaceutically acceptable carriers include water, salt solutions (such as Ringer's solution), alcohols, oils, gelatins, and carbohydrates such as lactose, amylose or starch, fatty acid esters, hydroxymethycellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention.

The compounds of the invention can be administered alone or can be coadministered to a subject. Coadministration is meant to include simultaneous or sequential administration of the compounds individually or in combination (more than one compound). The preparations can also be combined, when desired, with other active substances (e.g. to reduce metabolic degradation).

Formulations

Compounds of the present invention can be prepared and administered in a wide variety of oral, parenteral, and topical dosage forms. Thus, the compounds of the present invention can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable carrier or excipient and one or more compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances that may also act as diluents, flavoring agents, binders, preservatives, tablet disintegrating agents, or an encapsulating material.

In powders, the carrier is a finely divided solid in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. The compounds of the invention can also be incorporated into liposomes or administered via transdermal pumps or patches. Pharmaceutical admixtures suitable for use in the present invention include those described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions of the present invention may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920;

5,403,841; 5,212,162; and 4,861,760. The entire contents of these patents are incorporated herein by reference in their entirety for all purposes.

Effective Dosages

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat cancer, such compositions will contain an amount of active ingredient effective to achieve the desired result (e.g. decreasing the number of cancer cells in a subject).

The dosage and frequency (single or multiple doses) of compound administered can vary depending upon a variety of factors, including route of administration; size, age, sex, health, body weight, body mass index, and diet of the recipient; nature and extent of symptoms of the disease being treated (e.g., the disease responsive to Btk inhibition); presence of other diseases or other health-related problems; kind of concurrent treatment; and complications from any disease or treatment regimen. Other therapeutic regimens or agents can be used in conjunction with the methods and compounds of the invention.

For any compound described herein, the therapeutically effective amount can be initially determined from cell culture assays. Target concentrations will be those concentrations of active compound(s) that are capable of decreasing Btk enzymatic activity as measured, for example, using the methods described.

Therapeutically effective amounts for use in humans may be determined from animal models. For example, a dose for humans can be formulated to achieve a concentration that has been found to be effective in animals. The dosage in humans can be adjusted by monitoring Btk inhibition and adjusting the dosage upwards or downwards, as described above.

Dosages may be varied depending upon the requirements of the patient and the compound being employed. The dose administered to a patient, in the context of the present invention, should be sufficient to effect a beneficial therapeutic response in the patient over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached. In some embodiments, the dosage range is 0.001% to 10% w/v. In some embodiments, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

EXAMPLES

The examples below are meant to illustrate certain embodiments of the invention, and not to limit the scope of the invention. Abbreviations: AcCN=acetonitrile; BuOH=butanol; DCM=dichloromethane; DIEA, DIPEA=N,N-diisopropylethylamine; DMA=N,N-dimethylacetamide; DMAP=N,N-dimethylaminopyridine; DMF=N,N-dimethylformamide; DMSO=dimethylsulfoxide; EDC=N-(3-dimethylaminopropyl)-N'-ethylcarbodiimide hydrochloride; EtOAc=Ethyl Acetate; HOBt=1-hydroxybenzotriazole; HPLC=high pressure liquid chromatography; MS=mass-spectrometry; MsCl=methanesulfonylchloride; NMR=nuclear magnetic resonance; TFA=trifluoroacetic acid; THF=tetrahydrofuran; RT=room temperature; LC/MS=liquid chromatography mass spectroscopy; NCS=N-chlorosuccinimde; TMSI=trimethylsilylimidazole; NMM=N-methylmaleimide; IBCF=isobutylchloroformate; LDA=lithium diisopropylamide; Tf=triflate (trifluoromethanesulfonate); CDI=carbonyldiimidazole; DPPA=diphenylphosphoryl azide; HATU=2-(7-Aza-1H-benzotriazole-1-yl)-1,1,3,3-tetramethyluronium hexafluorophosphate; DME=dimethyl ether; Boc=tert-butoxycarbonyl; NBS=N-bromosuccinimide; EDCI=1-ethyl-3-(3-dimethylaminopropyl) carbodiimide; dppf=1,1'-bis(diphenylphosphino)ferrocene; SEM: 2-(trimethylsilyl)ethoxymethyl.

Starting materials for syntheses described herein are commercially available or can be synthesized by methods known in the art and/or described herein.

It will be appreciated that for compound preparations described herein, when reverse phase HPLC is used to purify a compound, a compound may exist as a mono-, di-, or tri-trifluoroacetic acid salt.

Example 1

Compounds useful in the methods and compositions described herein may be synthesized by a variety of routes, including the general synthetic routes described above in Schemes 1-4

Example 1

(N-(1-(7H-pyrrolo[2,3-d]pyrimidin-4-yl)piperidin-3-yl)-2

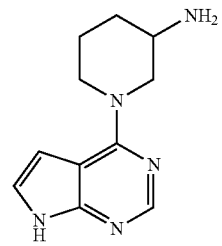 [SMILES: NC1CCCN(c2ncnc3[nH]ccc23)C1]

1-(7H-pyrrolo[2,3-d]pyrimidin-4-yl)piperidin-3-amine

To a solution of tert-butyl piperidin-3-ylcarbamate compound (5.0 g, 25 mmol) and 4-chloro-7H-pyrrolo[2,3-d]pyrimidine (3.75 g, 25 mmol) in DMF (50 mL) was added DIEA (4.2 mL, 3.1 g, 25 mmol) and the solution was stirred at 100° C. for 4 h. The reaction mixture was concentrated in vacuo and the residue was purified by column chromatography to give tert-butyl 1-(7H-pyrrolo[2,3-d]pyrimidin-4-yl)piperidin-3-ylcarbamate. To a solution of tert-butyl 1-(7H-pyrrolo[2,3-d]pyrimidin-4-yl)piperidin-3-ylcarbamate (6.3 g, 20 mmol) in dioxane (50 ml) was added 4.0 N HCl (50 mL, 200 mmol) and stirred at rt. After several hours, the reaction mixture was concentrated in vacuo to give compound 33.

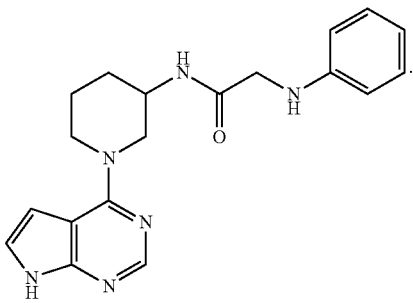

(N-(1-(7H-pyrrolo[2,3-d]pyrimidin-4-yl)piperidin-3-yl)-2-(phenylamino)acetamide

To a solution of 2-(phenylamino)acetic acid (37 mg, 0.25 mmol), EDCI (53 mg, 0.275 mmol), and HOBt (37 mg, 0.275 mmol) in DMF (1 mL) was DIEA (1.7 mL, 1.3 mg, 1.0 mmol) and 1-(7H-pyrrolo[2,3-d]pyrimidin-4-yl)piperidin-3-amine (54 mg, 0.25 mmol). The solution was stirred at rt for several hours, diluted with water and EtOAc (1:1, 10 mL). The organic phase was separated, washed with brine, dried (Na$_2$SO$_4$) and concentrated in vacuo to afford a residue which was purified by reverse phase chromatography C 18 column and 10% acetonitrile/water containing 0.1% TFA to afford example 2. $^1$H NMR (400 MHz, DMSO-d$_6$) δ 12.67 (s, 1H), 8.35 (s, 1H), 8.06 (d, J=6.8 Hz, 1H), 7.44 (s, 1H), 7.03~7.70 (m, 3H), 6.52~6.58 (m, 3H), 4.37 (d, J=12.7 Hz, 1H), 4.25 (d, J=12.2 Hz, 1H), 3.84 (s, 1H), 3.60 (m, 2H), 3.46 (m, 1H), 3.36 (m 1H), 1.87 (m, 2H), 1.61 (m, 2H). EIMS (m/z): calcd. for C$_{19}$H$_{22}$N$_6$O (M$^+$+1) 351.2. found 351.2.

Examples 2-15 are prepared according to Scheme 1 and Example 1 above.

Example 2

(N-(1-(7H-pyrrolo[2,3-d]pyrimidin-4-yl)piperidin-3-yl)-2-(3-phenylureido)acetamide)

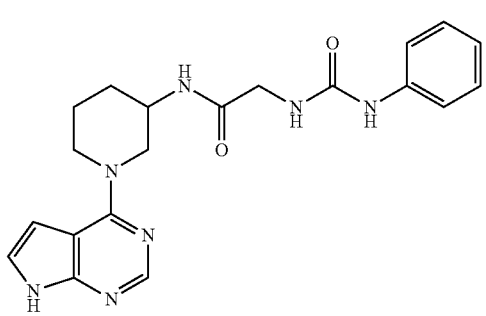 [SMILES: O=C(CNC(=O)Nc1ccccc1)NC1CCCN(c2ncnc3[nH]ccc23)C1]

The title compound of Example 2 was prepared in similar manner as described in Example 1 except 2-(phenylamino) acetic acid was substituted for 2-(3-phenylureido)acetic acid. $^1$H NMR (400 MHz, DMSO-d$_6$) δ 12.48 (s, 1H), 8.78 (m, 1H), 8.32 (s, 1H), 8.15 (d, J=6.4 Hz, 1H), 7.37 (d, J=8.3 Hz, 1H), 7.21 (t, J=7.3 Hz, 2H), 7.02 (s, 1H), 6.89 (t, J=7.1 Hz, 1H), 6.36 (m, 1H), 4.48 (d, J=13.2 Hz, 1H), 4.31 (d, J=10.3 Hz, 1H), 3.84 (m, 1H), 3.73 (m, 2H), 3.42 (m, 1H), 3.28 (m, 1H), 1.88~1.95 (m, 2H), 1.63 (m, 2H). EIMS (m/z): calcd. for C$_{20}$H$_{23}$N$_7$O$_2$ (M$^+$+1) 394.1. found 394.3.

Example 3

(N-(2-(1-(7H-pyrrolo[2,3-d]pyrimidin-4-yl)piperidin-3-ylamino)-2-oxoethyl)benzamide)

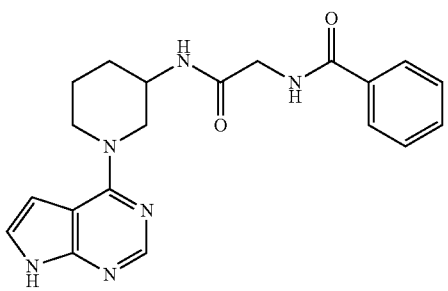 [SMILES: O=C(CNC(=O)c1ccccc1)NC1CCCN(c2ncnc3[nH]ccc23)C1]

The title compound of Example 3 was prepared in similar manner as described in Example 1 except 2-(phenylamino) acetic acid was substituted for 2-benzamidoacetic acid. $^1$H NMR (400 MHz, DMSO-d$_6$) δ 12.50 (s, 1H), 8.71 (m, 1H), 8.32 (s, 1H), 8.11 (d, J=6.4 Hz, 1H), 7.86 (d, J=7.3 Hz, 1H), 7.45~7.56 (m, 3H), 7.40 (s, 1H), 7.01 (s, 1H), 4.48 (d, J=11.7 Hz, 1H), 4.32 (d, J=11.7 Hz, 1H), 3.82~3.93 (m, 3H), 3.41 (m, 1H), 3.25~3.33 (m, 1H), 1.90~1.94 (m, 2H), 1.64 (m, 2H). EIMS (m/z): calcd. for C$_{20}$H$_{22}$N$_6$O$_2$ (M$^+$+1) 379.2. found 379.3.

Example 4

(N1-(1-(7H-pyrrolo[2,3-d]pyrimidin-4-yl)piperidin-3-yl)-N2

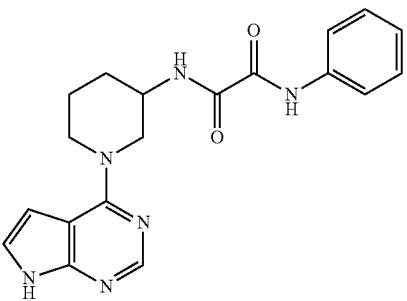

The title compound of Example 4 was prepared in similar manner as described in Example 1 except 2-(phenylamino) acetic acid was substituted for 2-oxo-2-(phenylamino)acetic acid. $^1$H NMR (400 MHz, DMSO-d$_6$) δ 12.24 (s, 1H), 10.70 (s, 1H), 9.05 (d, J=7.3 Hz, 1H), 8.27 (s, 1H), 7.82 (d, J=8.3 Hz, 2H), 7.33~7.37 (m, 3H), 7.13 (m, 1H), 6.897 (s, 1H), 4.57 (d, J=13.2 Hz, 1H), 4.48 (d, J=10.8 Hz, 1H), 8.34 (s, 1H), 7.99 (m, 1H), 7.45 (m, 1H), 7.32 (m, 4H), 7.22 (m, 1H), 7.02 (d, J=13.7 Hz, 1H), 3.90 (m, 1H), 3.30 (t, J=11.5 Hz, 1H), 3.21 (t, J=11.0 Hz, 1H), 1.95 (m, 1H), 1.85 (m, 2H), 1.63 (m, 1H). EIMS (m/z): calcd. for $C_{19}H_{20}N_6O_2$ (M$^+$+1) 365.2. found 365.2.

Example 5

(3R)—N-(1-(7H-pyrrolo[2,3-d]pyrimidin-4-yl)piperidin-3-yl)-3-hydroxy-3-phenylpropanamide

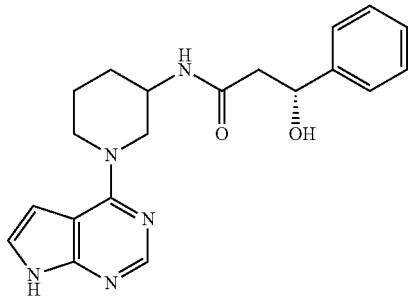

The title compound of Example 5 was prepared in similar manner as described in Example 1 except 2-(phenylamino) acetic acid was substituted for (R)-3-hydroxy-3-phenylpropanoic. $^1$H NMR (400 MHz, DMSO-d$_6$) δ 12.56 (s, 1H), 8.34 (s, 1H), 7.99 (m, 1H), 7.45 (m, 1H), 7.32 (m, 4H), 7.22 (m, 1H), 7.02 (d, J=13.7 Hz, 1H), 4.95 (m, 1H), 4.30~4.48 (m, 2H), 3.79 (m, 1H), 3.38 (m, 1H), 3.09~3.24 (m, 1H), 2.35 (m 1H), 1.83~1.90 (m, 2H), 1.54~1.60 (m, 2H). EIMS (m/z): calcd. for $C_{20}H_{23}N_5O_2$ (M$^+$+1) 366.2. found 366.0.

Example 6

(3S)—N-(1-(7H-pyrrolo[2,3-d]pyrimidin-4-yl)piperidin-3-yl)-3-hydroxy-3-phenylpropanamide

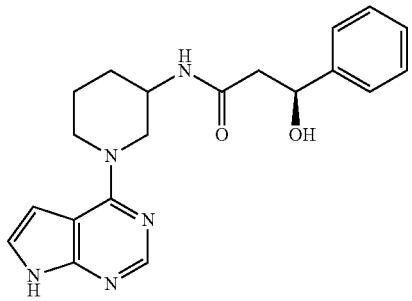

The title compound of Example 6 was prepared in similar manner as described in Example 1 except 2-(phenylamino) acetic acid was substituted for (S)-3-hydroxy-3-phenylpropanoic acid. $^1$H NMR (400 MHz, DMSO-d$_6$) δ 12.51 (s, 1H), 8.32 (s, 1H), 7.98 (m, 1H), 7.43 (m, 1H), 7.32 (m, 4H), 7.22 (m, 1H), 7.01 (d, J=13.7 Hz, 1H), 4.95 (m, 1H), 4.30~4.51 (m, 2H), 3.78 (m, 1H), 3.36 (m, 1H), 3.07~3.22 (m, 1H), 2.34 (m 1H), 1.83~1.90 (m, 2H), 1.54~1.60 (m, 2H) ppm. EIMS (m/z): calcd. for $C_{20}H_{23}N_5O_2$ (M$^+$+1) 366.2. found 366.0.

Example 7

(N-(1-(7H-pyrrolo[2,3-d]pyrimidin-4-yl)piperidin-3-yl)-3-phenylpropanamide)

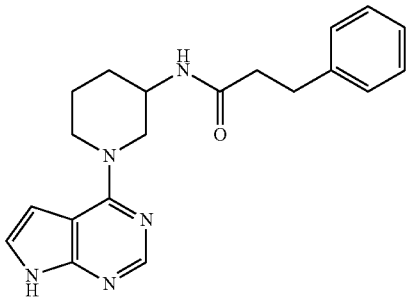

The title compound of Example 7 was prepared in similar manner as described in Example 1 except 2-(phenylamino) acetic acid was substituted for 3-phenylpropanoic acid. $^1$H NMR (400 MHz, DMSO-d$_6$) δ 12.49 (s, 1H), 8.32 (s, 1H), 7.99 (d, J=6.4 Hz, 1H), 7.43 (s, 1H), 7.23~7.26 (m, 2H), 7.13~7.18 (m, 3H), 6.99 (s, 1H), 4.39 (d, J=13.9 Hz, 1H), 4.26 (d, J=12.2 Hz, 1H), 3.79 (m, 1H), 3.41 (t, J=10.5 Hz, 1H), 3.22 (t, J=11.0 Hz, 1H), 2.78 (m, 2H), 2.37 (m, 2H), 1.88 (m, 2H), 1.54~1.62 (m, 2H) ppm. EIMS (m/z): calcd. for $C_{20}H_{23}N_5O_2$ (M$^+$+1) 351.2. found 351.0.

Example 8

(N-(1-(7H-pyrrolo[2,3-d]pyrimidin-4-yl)piperidin-3-yl)-2-phenoxyacetamide)

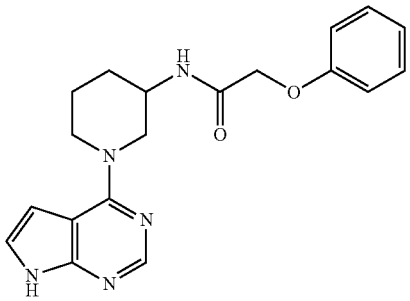

The title compound of Example 8 was prepared in similar manner as described in Example 1 except 2-(phenylamino) acetic acid was substituted for 2-phenoxyacetic acid. $^1$H NMR (400 MHz, DMSO-d$_6$) δ 12.48 (s, 1H), 8.32 (s, 1H), 8.20 (d, J=6.8 Hz, 1H), 7.40 (s, 1H), 7.28 (t, J=7.60 Hz, 2H), 6.91~6.96 (m, 3H), 4.49 (d, J=5.4 Hz, 2H), 4.45 (m, 1H), 4.32 (d, J=13.2 Hz, 1H), 3.90 (m, 1H), 3.37 (m, 2H), 1.73~1.91 (m, 2H), 1.61~1.70 (m, 2H) ppm. EIMS (m/z): calcd. for $C_{19}H_{21}N_5O_2$ (M⁺+1) 352.2. found 352.0.

Example 9

(3S)—N-(1-(7H-pyrrolo[2,3-d]pyrimidin-4-yl)piperidin-3-yl)-3-amino-3-phenylpropanamide

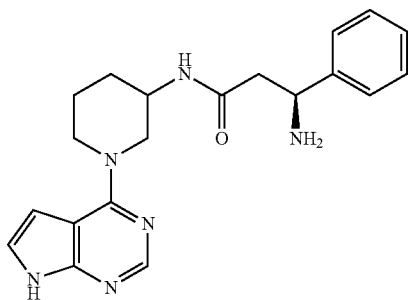

The title compound of Example 9 was prepared in similar manner as described in Example 1 except intermediate 2-(phenylamino)acetic acid was substituted for (S)-3-tert-butoxycarbonylamino-3-phenylpropionic acid. The Boc protected amine was treated with 4 N HCl in 1,4-dioxane (mL) for 2 h at rt. The reaction mixture was concentrated in vacuo to afford a solid which purified by reverse phase chromatography C18 column and 10% acetonitrile/water containing 0.1% TFA to afford the final product. EIMS (m/z): calcd. for $C_{20}H_{24}N_6O$ (M⁺+1) 365.2. found 365.4.

Example 10

(2S)—N-(1-(7H-pyrrolo[2,3-d]pyrimidin-4-yl)piperidin-3-yl)-2-amino-3-phenylpropanamide

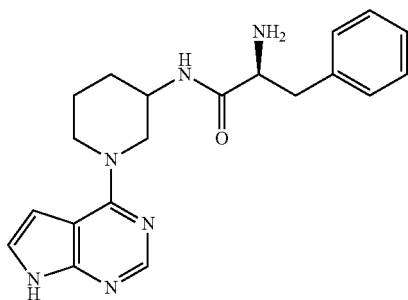 [SMILES: N[C@@H](Cc1ccccc1)C(=O)NC1CCCN(c2ncnc3[nH]ccc23)C1]

The title compound of Example 10 was prepared in similar manner as described in Example 1 except intermediate 2-(phenylamino)acetic acid was substituted for (R)-3-tert-butoxycarbonylamino-3-phenylpropionic acid. The Boc protected amine was treated with 4 N HCl in 1,4-dioxane (mL) for 2 h at rt. The reaction mixture was concentrated in vacuo to afford a solid which purified by reverse phase chromatography C18 column and 10% acetonitrile/water containing 0.1% TFA to afford the final product. EIMS (m/z): calcd. for $C_{20}H_{24}N_6O$ (M⁺+1) 365.2. found 365.4.

Example 11

((R)—N-(1-(7H-pyrrolo[2,3-d]pyrimidin-4-yl)piperidin-3-yl)-2

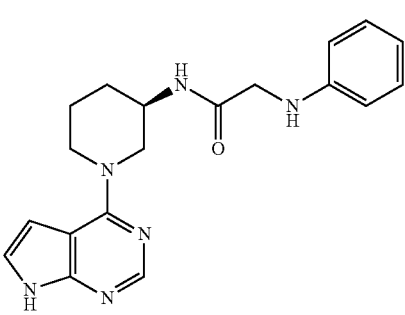

The title compound of Example 11 was prepared in similar manner as described in Example 1 except intermediate 1-(7H-pyrrolo[2,3-d]pyrimidin-4-yl)piperidin-3-amine was substituted for (R)-1-(7H-pyrrolo[2,3-d]pyrimidin-4-yl)piperidin-3-amine. ¹H NMR (400 MHz, DMSO-d₆) δ 12.56 (s, 1H), 8.33 (s, 1H), 8.05 (d, J=6.8 Hz, 1H), 7.42 (s, 1H), 7.05 (t, J=7.6 Hz, 2H), 6.98 (s, 1H), 6.51~6.57 (m, 3H), 4.40 (d, J=12.7 Hz, 1H), 4.26 (d, J=12.2 Hz, 1H), 3.87 (s, 1H), 3.64 (m, 2H), 3.45 (m, 1H), 3.33 (m 1H), 1.90 (m, 2H), 1.64 (m, 2H) ppm. EIMS (m/z): calcd. for $C_{19}H_{22}N_6O$ (M⁺+1) 351.2. found 351.2.

Example 12

(S)—N-(1-(7H-pyrrolo[2,3-d]pyrimidin-4-yl)piperidin-3-yl)-2-(phenylamino)acetamide

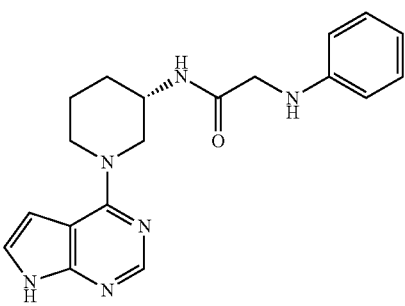

The title compound of Example 12 was prepared in similar manner as described in Example 1 except intermediate 1-(7H-pyrrolo[2,3-d]pyrimidin-4-yl)piperidin-3-amine was substituted for (S)-1-(7H-pyrrolo[2,3-d]pyrimidin-4-yl)piperidin-3-amine. ¹H NMR (400 MHz, DMSO-d₆) δ 12.63 (s, 1H), 8.34 (s, 1H), 8.06 (d, J=6.8 Hz, 1H), 7.43 (s, 1H), 7.00~7.06 (m, 3H), 6.51~6.57 (m, 3H), 4.40 (d, J=12.7 Hz, 1H), 4.25 (d, J=12.2 Hz, 1H), 3.87 (s, 1H), 3.64 (m, 2H), 3.45

(m, 1H), 3.35 (m 1H), 1.90 (m, 2H), 1.65 (m, 2H) ppm. EIMS (m/z): calcd. for $C_{10}H_{22}N_6O$ (M$^+$+1) 351.2. found 351.2.

Example 13

(N-(1-(7H-pyrrolo[2,3-d]pyrimidin-4-yl)piperidin-3-yl)-3

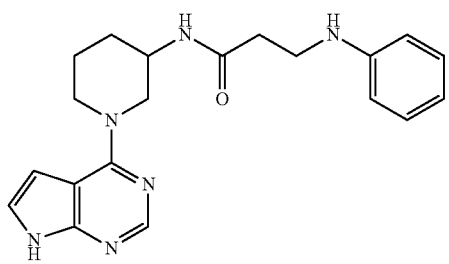 [SMILES: O=C(CCNc1ccccc1)NC1CCCN(c2ncnc3[nH]ccc23)C1]

The title compound of Example 13 was prepared in similar manner as described in Example 1 except 2-(phenylamino) acetic acid was substituted for 3-(phenylamino)propanoic acid. $^1$H NMR (400 MHz, DMSO-d$_6$) δ 12.65 (s, 1H), 8.35 (s, 1H), 8.09 (d, J=6.4 Hz, 1H), 7.45 (s, 1H), 7.05~7.12 (m, 3H), 6.60~6.62 (m, 3H), 4.39 (d, J=12.2 Hz, 1H), 4.20 (d, J=12.7 Hz, 1H), 3.83 (s, 1H), 3.53 (m, 1H), 3.39 (m, 1H), 3.14-3.27 (m, 2H), 2.33~2.37 (m, 2H), 1.91 (m, 2H), 1.59~1.63 (m, 2H) ppm. EIMS (m/z): calcd. for $C_{20}H_{24}N_6O$ (M$^+$+1) 365.2. found 365.0.

Example 14

(R)—N—((R)-1-(7H-pyrrolo[2,3-d]pyrimidin-4-yl)piperidin-3-yl)-1,2,3,4-tetrahydroquinoline-2-carboxamide

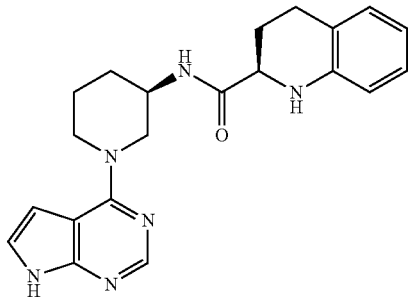 [SMILES: O=C(N[C@@H]1CCCN(c2ncnc3[nH]ccc23)C1)[C@H]1CCc2ccccc2N1]

The title compound of Example 14 was prepared in similar manner as described in Example 1 except 2-(phenylamino) acetic acid was substituted for (R)-1,2,3,4-tetrahydroquinoline-2-carboxylic acid. $^1$H NMR (400 MHz, DMSO-d$_6$) δ 12.56 (s, 1H), 8.31 (s, 1H), 7.84 (d, J=6.8 Hz, 1H), 7.43 (s, 1H), 6.98 (s, 1H), 6.86 (t, J=7.3 Hz, 1H), 6.79 (d, J=7.3 Hz, 1H), 6.54 (d, J=7.8 Hz, 1H), 6.44 (t, J=7.1 Hz, 1H), 4.39 (d, J=123.2 Hz, 1H), 4.25 (d, J=12.7 Hz, 1H), 3.81~3.87 (m, 2H), 3.34~3.46 (m, 2H), 2.56 (m, 1H), 2.44 (m, 1H), 1.63~1.95 (m, 7H) ppm. EIMS (m/z): calcd. for $C_{21}H_{24}N_6O$ (M$^+$+1) 377.2. found 377.2.

Example 15

(S)—N—((R)-1-(7H-pyrrolo[2,3-d]pyrimidin-4-yl)piperidin-3-yl)-1,2,3,4-tetrahydroquinoline-2-carboxamide

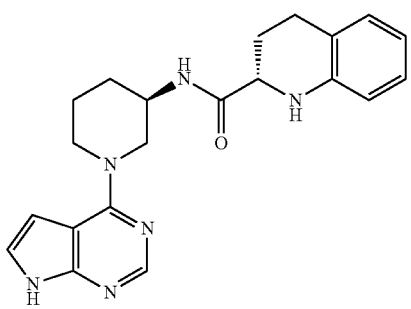 [SMILES: O=C(N[C@@H]1CCCN(c2ncnc3[nH]ccc23)C1)[C@@H]1CCc2ccccc2N1]

The title compound of Example 15 was prepared in similar manner as described in Example 1 except 2-(phenylamino) acetic acid was substituted for (S)-1,2,3,4-tetrahydroquinoline-2-carboxylic acid. $^1$H NMR (400 MHz, DMSO-d$_6$) δ 12.58 (s, 1H), 8.35 (s, 1H), 7.90 (d, J=6.4 Hz, 1H), 7.43 (s, 1H), 6.99 (s, 1H), 6.87 (t, J=7.1 Hz, 1H), 6.82 (d, J=6.8 Hz, 1H), 6.53 (d, J=6.8 Hz, 1H), 6.45 (t, J=7.1 Hz, 1H), 4.38 (d, J=13.2 Hz, 1H), 4.23 (d, J=13.2 Hz, 1H), 3.83 (m, 2H), 3.46 (m, 2H), 2.56 (m, 1H), 2.44 (m, 1H), 1.65-1.88 (m, 7H) ppm. EIMS (m/z): calcd. for $C_{21}H_{24}N_6O$ (M$^+$+1) 377.2. found 377.2.

Example 16

(N-(1-(7H-pyrrolo[2,3-d]pyrimidin-4-yl)piperidin-3-yl)-2-(methyl(phenyl)amino)acetamide)

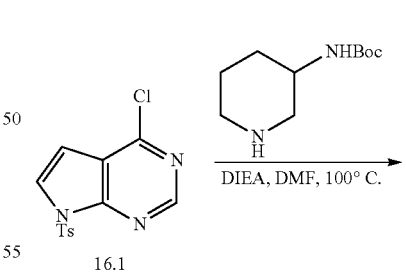

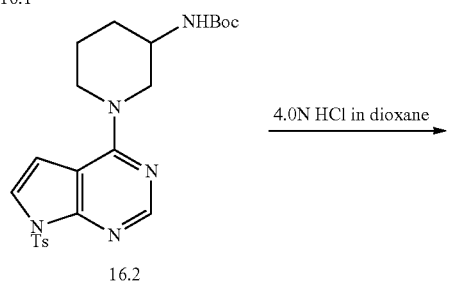

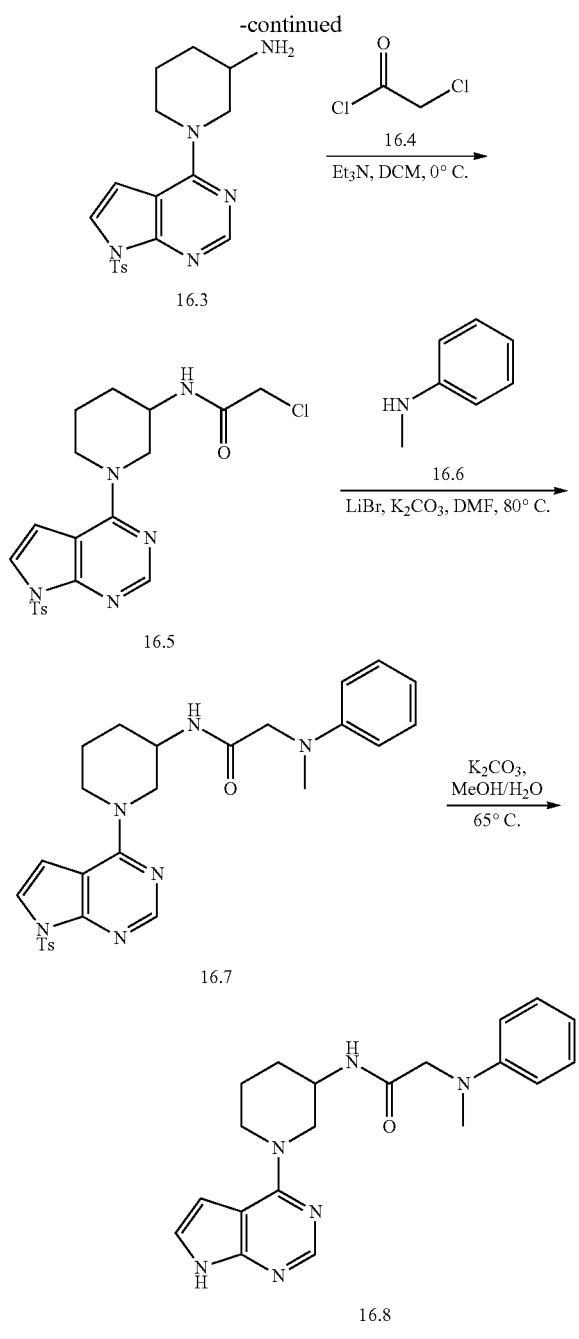

2-chloro-N-(1-(7-tosyl-7H-pyrrolo[2,3-d]pyrimidin-4-yl)piperidin-3-yl)acetamide. To a solution of compound 16.3 (7.4 g, 20 mmol), Et₃N (12.1 g, 16.8 mL, 120 mmol) in CH₂Cl₂ (200 mL) was added with α-chloroacetyl chloride 16.4 (2.4 g, 22 mmol) at 0° C. After stirring at rt for 1 h, the reaction mixture was diluted with CH₂Cl₂ (300 mL) and washed with sat. aq. NH₄Cl, sat. aq. NaHCO₃, and brine, and the organic layer was dried (Na₂SO₄) and concentrated in vacuo to afford a residue, which was purified by column chromatography (silica gel, 50% EtOAc in hexane) to afford compound 16.5.

2-(methyl(phenyl)amino)-N-(1-(7-tosyl-7H-pyrrolo[2,3-d]pyrimidin-4-yl)piperidin-3-yl)acetamide. A mixture of 16.6 (223 mg, 0.5 mmol), alkyl chloride 16.6 (107 mg, 1.0 mmol), LiBr (85 mg, 1.0 mmol), and K₂CO₃ (0.34, 2.5 mmol) in DMF (2.5 mL) was stirred at 80° C. for 12 h. The reaction mixture was concentrated in vacuo to afford a residue, which was purified by column chromatography (silica gel, 50% EtOAc in hexane) to give the desided product 16.7.

N-(1-(7H-pyrrolo[2,3-d]pyrimidin-4-yl)piperidin-3-yl)-2-(methyl(phenyl)amino)acetamide. A mixture of 16.7 (73 mg, 0.2 mmol) and K₂CO₃ (0.138 mg, 1.0 mmol) in MeOH (2 mL) and water (0.5 mL) was stirred at 65° C. for 5 h. The solvent was removed in vacuo and the residue diluted with water. The precipitate was isolated by filtration and purified by reverse phase chromatography C₁₈ column and 10% acetonitrile/water containing 0.1% TFA to afford example 16.8. ¹H NMR (400 MHz, DMSO-d₆) δ 12.48 (s, 1H), 8.31 (s, 1H), 8.02 (d, J=6.8 Hz, 1H), 7.39 (s, 1H), 7.12 (t, J=7.1 Hz, 2H), 6.91 (s, 1H), 6.59–6.63 (m, 3H), 4.36 (d, J=12.7 Hz, 1H), 4.23 (d, J=12.7 Hz, 1H), 3.83–3.94 (m, 3H), 3.46 (m, 1H), 3.36 (m, 1H), 2.95 (s, 3H), 1.89 (m, 2H), 1.64 (m, 2H) ppm. EIMS (m/z): calcd. for C₂₀H₂₄N₆O (M⁺+1) 365.2. found 365.0.

Examples 17-84 were prepared according to Scheme 2 and Example 16 above.

tert-Butyl 1-(7-tosyl-7H-pyrrolo[2,3-d]pyrimidin-4-yl)piperidin-3-ylcarbamate. To a mixture of 4-chloro-7-tosyl-7H-pyrrolo[2,3-d]pyrimidine (11.7 g, 25 mmol) and tert-butyl piperidin-3-ylcarbamate (5.0, 25 mmol) in DMF (50 mL) was added DIEA (3.2 g, 4.3 mL, 25 mmol) and the solution stirred was at 80° C. for 4 h. The reaction mixture was concentrated in vacuo and the residue purified by column chromatography to give compound 16.2.

1-(7-tosyl-7H-pyrrolo[2,3-d]pyrimidin-4-yl)piperidin-3-amine. A solution of Boc protected amine (9.4 g, 20 mmol) in 4.0 N HCl in dioxane (50 ml) was stirred at rt. After several hours, the reaction mixture was concentrated in vacuo to give 16.3 which used without any further purification.

Example 17

(N-(1-(7H-pyrrolo[2,3-d]pyrimidin-4-yl)piperidin-3-yl)-2-(2-tert-butylphenylamino)acetamide)

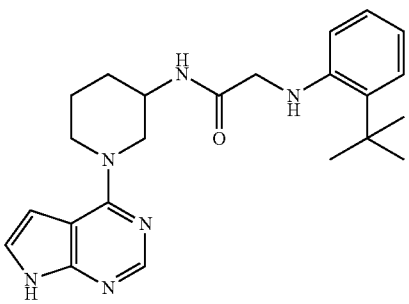 [SMILES: CC(C)(C)c1ccccc1NCC(=O)NC1CCCN(c2ncnc3[nH]ccc23)C1]

The title compound of Example 17 was prepared in similar manner as described in Example 16 except N-methylaniline was substituted for 2-tert-butylaniline. ¹H NMR (400 MHz, CD₃OD) δ 1.27 (s, 9H), 1.78 (m, 2H), 1.94 (m, 1H), 2.04 (d, J=14.18 Hz, 1H), 3.60 (m, 2H), 3.60 (m, 2H), 3.90 (s, 2H), 4.29 (d, J=12.72 Hz, 1H), 4.48 (d, J=13.69 Hz, 1H), 6.92 (d, J=7.83 Hz, 1H), 6.90 (s, 1H), 7.09 (m, 2H), 7.17 (m, 2H), 7.26 (s, 1H), 7.34 (d, 1H), 7.52 (s, 1H), 8.15 (s, 1H).

Example 18

(N-(1-(7H-pyrrolo[2,3-d]pyrimidin-4-yl)piperidin-3-yl)-2-(3-ten-butylphenylamino)acetamide)

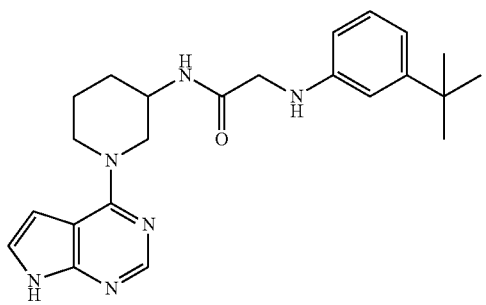 [SMILES: CC(C)(C)c1cccc(NCC(=O)NC2CCCN(c3ncnc4[nH]ccc34)C2)c1]

The title compound of Example 18 was prepared in similar manner as described in Example 16 except N-methylaniline was substituted for 3-tert-butylaniline. $^1$H NMR (MeOH, 400 MHz): δ 1.27 (s, 9H), 1.78 (m, 2H), 1.94 (m, 1H), 2.04 (d, J=14.18 Hz, 1H), 3.60 (m, 2H), 3.60 (m, 2H), 3.90 (s, 2H), 4.29 (d, J=12.72 Hz, 1H), 4.48 (d, J=13.69 Hz, 1H), 6.70 (d, J=7.83 Hz, 1H), 6.99 (s, 1H), 7.06 (m, 3H), 7.06 (s, 3H), 7.17 (t, J=7.83 Hz, 1H), 7.34 (s, 1H), 8.26 (s, 1H).

Example 19

(N-(1-(7H-pyrrolo[2,3-d]pyrimidin-4-yl)piperidin-3-yl)-2-(4-tert-butylphenylamino)acetamide)

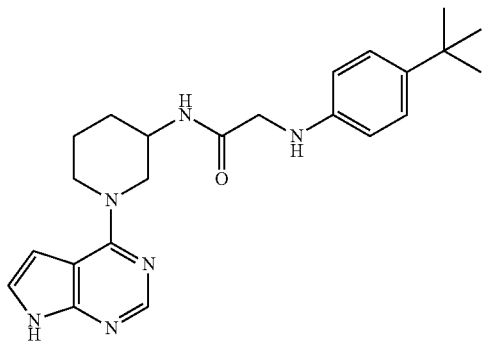 [SMILES: CC(C)(C)c1ccc(NCC(=O)NC2CCCN(c3ncnc4[nH]ccc34)C2)cc1]

The title compound of Example 19 was prepared in similar manner as described in Example 16 except N-methylaniline was substituted for 4-tert-butylaniline. $^1$H NMR (MeOH, 400 MHz): δ 1.26 (s, 9H), 1.78 (m, J=8.07, 8.07 Hz, 2H), 1.95 (m, 1H), 2.05 (m, J=12.23 Hz, 1H), 3.65 (m, 2H), 3.89 (s, 2H), 4.06 (m, 1H), 4.28 (d, J=12.72 Hz, 1H), 4.46 (d, J=13.21 Hz, 1H), 6.85 (d, J=8.31 Hz, 2H), 7.08 (s, 1H), 7.30 (d, J=7.83 Hz, 2H), 7.36 (s, 1H), 8.27 (s, 1H).

Example 20

(N-(1-(7H-pyrrolo[2,3-d]pyrimidin-4-yl)piperidin-3-yl)-2-(2-chlorophenylamino)acetamide)

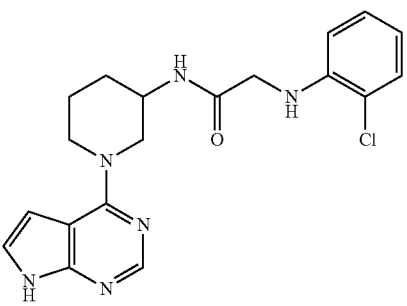

The title compound of Example 20 was prepared in similar manner as described in Example 16 except N-methylaniline was substituted for 2-chloroaniline. $^1$H NMR (400 MHz) δ 8.25 (s, 1H), 7.35 (d, 1H), 7.03 (s, 1H), 6.84-6.95 (m, 2H), 6.62 (m, 1H), 6.49 (t, 1H), 4.87 (d, 1H), 4.21 (d, 1H), 1.95 (m, 1H), 1.82 (m, 2H) ppm. EIMS (m/z): calcd. for $C_{19}H_{23}ClN_6O$ (M$^+$)+1 388.4.

Example 21

(N-(1-(7H-pyrrolo[2,3-d]pyrimidin-4-yl)piperidin-3-yl)-2-(3-chlorophenylamino)acetamide)

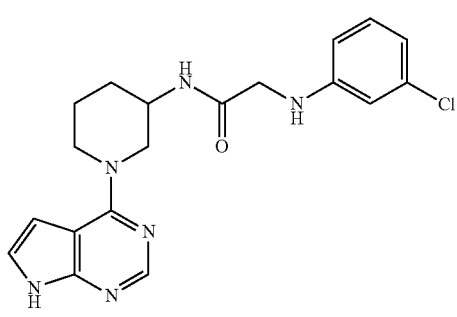 [SMILES: O=C(CNc1cccc(Cl)c1)NC1CCCN(c2ncnc3[nH]ccc23)C1]

The title compound of Example 21 was prepared in similar manner as described in Example 16 except N-methylaniline was substituted for 3-chloroaniline. $^1$H NMR (400 MHz, CD$_3$OD) δ 1.82 (m, 2H), 1.95 (m, 1H), 2.03 (m, 1H), 3.74 (m, 3H), 4.07 (m, 1H), 4.18 (m, J=13.69 Hz, 1H), 4.34 (d, J=13.21 Hz, 1H), 6.42 (d, J=8.31 Hz, 1H), 6.50 (s, 1H), 6.57 (d, J=7.83 Hz, 1H), 6.99 (m, 3H), 7.34 (s, 1H), 8.25 (s, 1H) ppm. EIMS (m/z): calcd. for $C_{19}H_{23}ClN_6O$ (M$^+$)+1 388.4.

Example 22

(N-(1-(7H-pyrrolo[2,3-d]pyrimidin-4-yl)piperidin-3-yl)-2-(4-chlorophenylamino)acetamide)

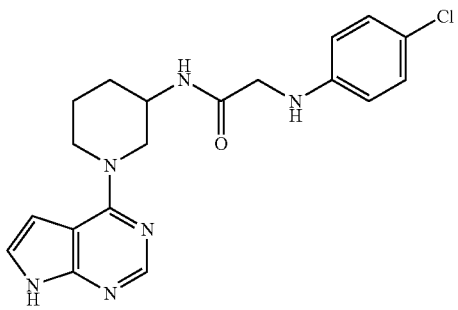 [SMILES: O=C(CNc1ccc(Cl)cc1)NC1CCCN(c2ncnc3[nH]ccc23)C1]

The title compound of Example 22 was prepared in similar manner as described in Example 16 except N-methylaniline was substituted for 4-chloroaniline. $^1$H NMR (400 MHz, CD$_3$OD): 1.80 (m, 2H), 1.93 (m, 1H), 2.02 (m, 1H), 3.77 (m, J=8.80 Hz, 1H), 4.05 (m, 1H), 4.16 (m, 1H), 4.30 (d, J=13.21 Hz, 1H), 6.45 (d, J=7.83 Hz, 2H), 6.97 (d, J=8.80 Hz, 3H), 6.97 (d, J=8.80 Hz, 2H), 7.34 (s, 1H), 8.24 (s, 1H) ppm. EIMS (m/z): calcd. for C$_{19}$H$_{23}$ClN$_6$O (M$^+$)+1 388.4.

Example 23

(N-(1-(7H-pyrrolo[2,3-d]pyrimidin-4-yl)piperidin-3-yl)-2-(2-fluorophenylamino)acetamide)

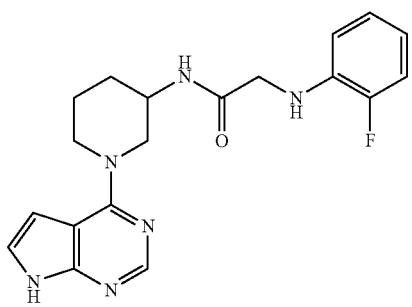 [SMILES: O=C(CNc1ccccc1F)NC1CCCN(c2ncnc3[nH]ccc23)C1]

The title compound of Example 23 was prepared in similar manner as described in Example 16 except N-methylaniline was substituted for 2-fluoroaniline. $^1$H NMR (400 MHz, CD$_3$OD) δ 8.25 (s, 1H), 7.35 (d, 1H), 7.03 (s, 1H), 6.84-6.95 (m, 2H), 6.62 (m, 1H), 6.49 (t, 1H), 4.87 (d, 1H), 4.21 (d, 1H), 0.06 (s, 1H), 3.98 (s, 1H), 3.73 (m, 3H), 3.63 (s, 1H), 2.35 (s, 1H), 2.01 (m, 1H), 1.95 (m, 1H), 1.82 (m, 2H) ppm. EIMS (m/z): calcd. for C$_{19}$H$_{23}$FN$_6$O (M$^+$)+1 370.4.

Example 24

(N-(1-(7H-pyrrolo[2,3-d]pyrimidin-4-yl)piperidin-3-yl)-2-(3-(trifluoromethyl)phenylamino)acetamide)

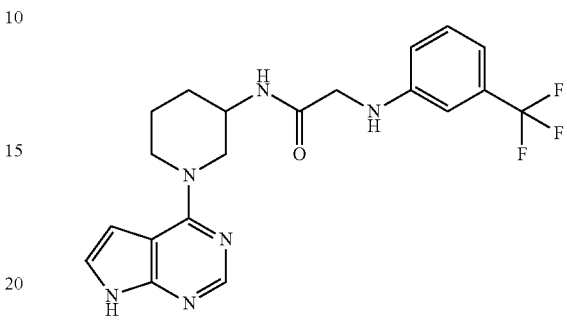

The title compound of Example 24 was prepared in similar manner as described in Example 16 except N-methylaniline was substituted for 3-trifluoromethylaniline. $^1$H NMR (400 MHz, CD$_3$OD) δ 8.26 (s, 1H), 7.34 (s, 1H), 7.22 (t, 1H), 7.03 (s, 1H), 6.89 (d, 1H), 6.79 (s, 1H), 6.74 (d, 1H), 4.45 (d, 1H), 4.28 (d, 1H), 4.06 (s, 1H), 3.81 (s, 2H), 3.62 (m, 2H), 2.05 (s, 1H), 1.97 (m, 1H), 1.80 (m, 12H). EIMS (m/z): calcd. for C$_{20}$H$_{23}$F$_3$N$_6$O (M$^+$)+1 420.4.

Example 25

(N-(1-(7H-pyrrolo[2,3-d]pyrimidin-4-yl)piperidin-3-yl)-2-(2,2-difluorobenzo[d][1,3]dioxol-4-ylamino)acetamide)

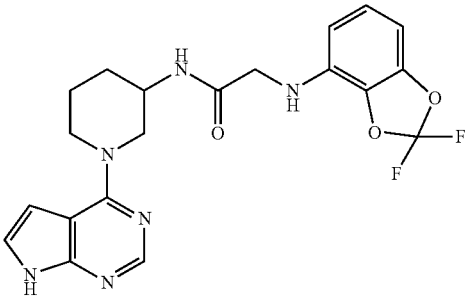 [SMILES: O=C(CNc1cccc2c1OC(F)(F)O2)NC1CCCN(c2ncnc3[nH]ccc23)C1]

The title compound of Example 25 was prepared in similar manner as described in Example 16 except N-methylaniline was substituted for 2,2-difluorobenzo[d][1,3]dioxol-4-amine. $^1$H NMR (400 MHz, CD$_3$OD): δ 8.25 (s, 1H), 7.33 (s, 1H), 7.03 (s, 1H), 6.87 (t, 1H), 6.48 (d, 1H), 6.35 (d, 1H), 4.45 (d, 1H), 4.27 (d, 1H), 4.06 (m, 1H), 3.87 (s, 2H), 3.63 (m, 2H), 2.01 (m, 2H), 1.80 (m, 2H). EIMS (m/z): calcd. for C$_{20}$H$_{22}$F$_2$N$_6$O$_3$ (M$^+$)+1 432.4.

Example 26

(N-(1-(7H-pyrrolo[2,3-d]pyrimidin-4-yl)piperidin-3-yl)-2-(3-sulfamoylphenylamino)acetamide)

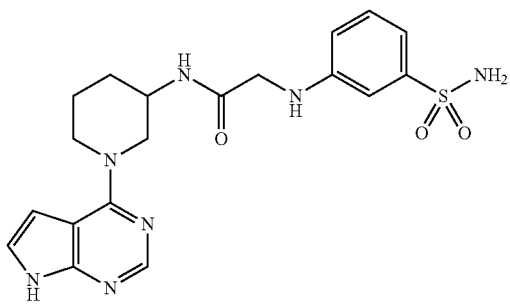 [SMILES: NS(=O)(=O)c1cccc(NCC(=O)NC2CCCN(c3ncnc4[nH]ccc34)C2)c1]

The title compound of Example 26 was prepared in similar manner as described in Example 16 except N-methylaniline was substituted for 3-aminobenzenesulfonamide. $^1$H NMR (400 MHz, CD$_3$OD) δ 8.25 (s, 1H), 7.33 (s, 1H), 7.21 (t, 1H), 7.14 (d, 1H), 37.03 (s, 2H), 6.73 (d, 1H), 4.43 (d, 1H), 4.26 (d, 1H), 4.06 (m, 1H), 3.64 (m, 2H), 2.01 (m, 2H). EIMS (m/z): calcd. for C$_{19}$H$_{25}$N$_7$O$_3$S (M$^+$)+1 431.5.

Example 27

(N-(1-(7H-pyrrolo[2,3-d]pyrimidin-4-yl)piperidin-3-yl)-2-(2,3-dichlorophenylamino)acetamide)

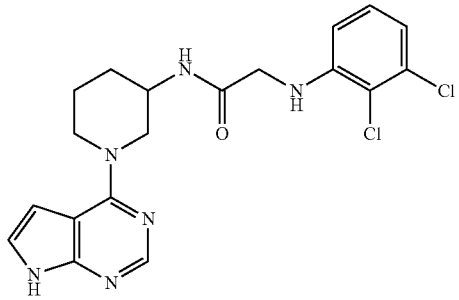 [SMILES: O=C(CNc1cccc(Cl)c1Cl)NC1CCCN(c2ncnc3[nH]ccc23)C1]

The title compound of Example 27 was prepared in similar manner as described in Example 16 except N-methylaniline was substituted for 2,3-dichloroaniline. $^1$H NMR (400 MHz, CD$_3$OD) δ 8.26 (s, 1H), 7.35 (d, 1H), 7.00 (m, 2H), 6.77 (d, 1H), 6.42 (d, 1H), 4.35 (d, 1H), 4.17 (d, 1H), 4.08 (s, 1H), 3.86 (s, 2H), 3.78 (m, 2H), 3.31 (s, 2H), 2.06 (m, 1H), 1.97 (m, 1H), 1.83 (m, 2H). EIMS (m/z): calcd. for C$_{19}$H$_{22}$Cl$_2$N$_6$O (M$^+$)+1 420.3.

Example 28

(N-(1-(7H-pyrrolo[2,3-d]pyrimidin-4-yl)piperidin-3-yl)-2-(3-(methylsulfonyl)phenylamino)acetamide)

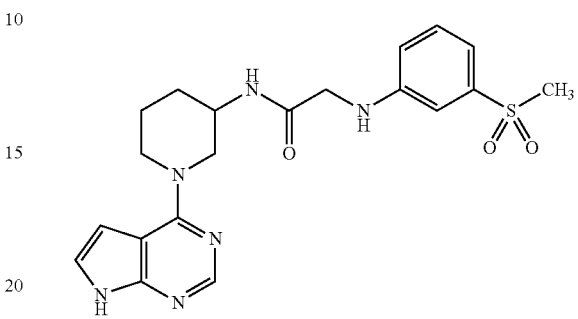

The title compound of Example 28 was prepared in similar manner as described in Example 16 except N-methylaniline was substituted for 3-(methylsulfonyl)aniline. $^1$H NMR (400 MHz, CD$_3$OD) δ 6.69 (s, 1H), 5.74 (t, 2H), 5.60 (d, 1H), 5.48 (s, 2H), 5.29 (d, 1H), 2.87 (d, 1H), 2.70 (d, 1H), 2.49 (s, 1H), 2.28 (s, 2H), 2.07 (m, 2H), 1.74 (s, 5H), 1.48 (s, 3H), 0.45 (m, 2H), 0.25 (m, 2H). EIMS (m/z): calcd. for C$_{20}$H$_{26}$N$_6$O$_3$S (M$^+$)+1 430.5.

Example 29

(N-(1-(7H-pyrrolo[2,3-d]pyrimidin-4-yl)piperidin-3-yl)-2-(3-fluorophenylamino)acetamide)

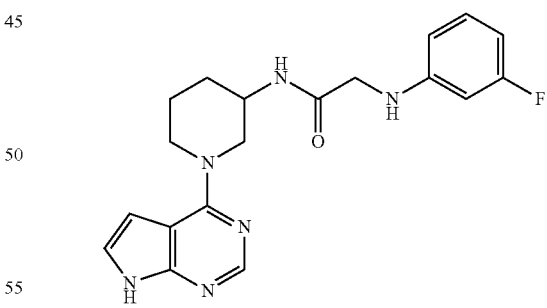

The title compound of Example 29 was prepared in similar manner as described in Example 16 except N-methylaniline was substituted for 3-fluoroaniline. $^1$H NMR (400 MHz, CD$_3$OD) δ 8.26 (s, 1H), 7.35 (d, 1H), 7.02 (m, 2H), 6.82 (d, 2H), 6.21 (d, 1H), 4.35 (d, H), 4.20 (d, 1H), 4.07 (s, 1H), 3.75 (s, 4H), 2.06 (m, 1H), 1.94 (m, 1H), 1.82 (m, 2H). EIMS (m/z): calcd. for C$_{19}$H$_{23}$FN$_6$O (M$^+$)+1 370.4.

Example 30

(N-(1-(7H-pyrrolo[2,3-d]pyrimidin-4-yl)piperidin-3-yl)-2-(2,6-diethylphenylamino)acetamide)

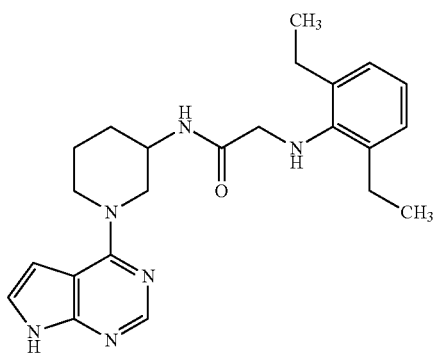 [SMILES: CCc1cccc(CC)c1NCC(=O)NC1CCCN(c2ncnc3[nH]ccc23)C1]

The title compound of Example 30 was prepared in similar manner as described in Example 16 except N-methylaniline was substituted for 2,6-diethylaniline. $^1$H NMR (400 MHz, CD$_3$OD): δ 8.30 (s, 1H), 7.39 (d, 1H), 7.13 (d, 2H), 7.05 (t, 3H), 4.57 (d, 1H), 4.33 (d, 1H), 4.11 (s, 1H), 3.68 (m, 3H), 2.66 (m, 4H), 2.15 (m, 1H), 2.03 (s, 1H), 1.84 (t, 2H), 1.22 (m, 5H). EIMS (m/z): calcd. for C$_{23}$H$_{32}$N$_6$O (M$^+$)+1 408.5.

Example 31

(N-(1-(7H-pyrrolo[2,3-d]pyrimidin-4-yl)piperidin-3-yl)-2-(m-tolylamino)acetamide)

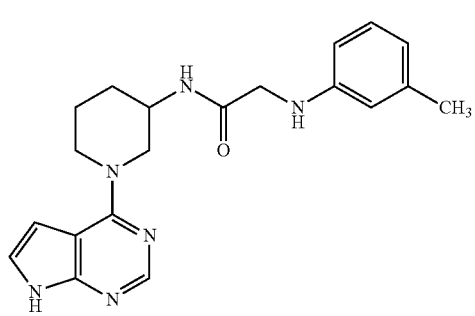 [SMILES: Cc1cccc(NCC(=O)NC2CCCN(c3ncnc4[nH]ccc34)C2)c1]

The title compound of Example 31 was prepared in similar manner as described in Example 16 except N-methylaniline was substituted for 3-methylaniline. $^1$H NMR (400 MHz, CD$_3$OD): δ 8.25 (s, 1H), 7.36 (s, 1H), 7.03 (s, 1H), 6.96 (t, 1H), 6.17 (t, 3H), 4.87 (d, 1H), 24.20 (d, 1H), 4.08 (s, 1H), 3.76 (m, 3H), 2.21 (s, 2H), 2.04 (s, 1H), 1.93 (m, 1H), 1.81 (m, 2H). EIMS (m/z): calcd. for C$_{20}$H$_{26}$N$_6$O (M$^+$)+1 366.2.

Example 32

(N-(1-(7H-pyrrolo[2,3-d]pyrimidin-4-yl)piperidin-3-yl)-2-(3-methoxyphenylamino)acetamide)

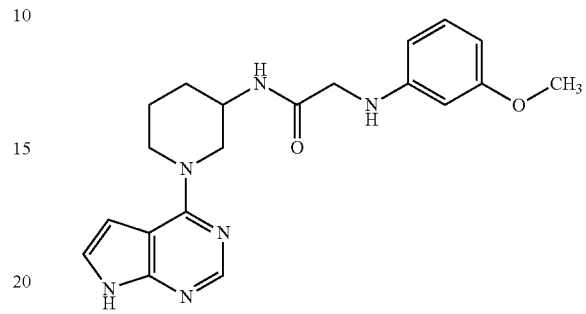

The title compound of Example 32 was prepared in similar manner as described in Example 16 except N-methylaniline was substituted for 3-methoxyaniline. $^1$H NMR (400 MHz, CD$_3$OD): δ 8.24 (s, 1H), 7.35 (s, 1H), 7.01 (s, 1H), 6.95 (t, 1H), 6.24 (d, 1H), 6.12 (m, 2H), 4.32 (d, 1H), 4.15 (d, 1H), 4.07 (s, 1H), 3.75 (m, 1H), 3.69 (s, 2H), 3.30 (s, 1H), 2.03 (m, 1H), 1.92 (m, 1H), 1.81 (m, 2H). EIMS (m/z): calcd. for C$_{20}$H$_{26}$N$_6$O$_2$ (M$^+$)+1 382.5.

Example 33

(N-(1-(7H-pyrrolo[2,3-d]pyrimidin-4-yl)piperidin-3-yl)-2-(4-fluorophenylamino)acetamide)

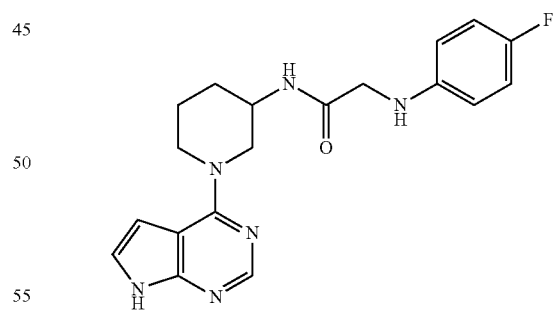

The title compound of Example 33 was prepared in similar manner as described in Example 16 except N-methylaniline was substituted for 4-fluoroaniline. $^1$H NMR (CD$_3$OD, 400 MHz): δ 8.25 (s, 1H), 7.35 (s, 1H), 7.02 (s, 1H), 6.8 (t, 2H), 6.54 (m, 2H), 4.85 (d, 1H), 4.20 (d, 1H), 4.06 (s, 1H), 3.72 (m, 3H), 2.02 (m, 1H), 1.93 (m, 1H), 1.81 (m, 2H). EIMS (m/z): calcd. for C$_{19}$H$_{23}$FN$_6$O$_2$ (M$^+$)+1 370.4.

Example 34

(N-(1-(7H-pyrrolo[2,3-d]pyrimidin-4-yl)piperidin-3-yl)-2-(3-cyanophenylamino)acetamide)

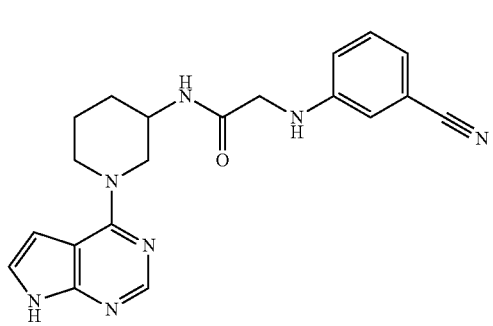 [SMILES: N#Cc1cccc(NCC(=O)NC2CCCN(c3ncnc4[nH]ccc34)C2)c1]

The title compound of Example 34 was prepared in similar manner as described in Example 16 except N-methylaniline was substituted for 3-aminobenzonitrile. $^1$H NMR (400 MHz, CD$_3$OD) δ 8.25 (s, 1H), 7.32 (d, 1H), 7.20 (t, 1H), 7.01 (s, 1H), 6.91 (d, 1H), 6.81 (d, 1H), 6.76 (s, 1H), 4.41 (d, 1H), 4.23 (d, 1H), 4.05 (s, 1H), 3.78 (s, 2H), 3.67 (m, 1H), 2.05 (m, 1H), 1.96 (m, 1H), 1.79 (m, 2H). EIMS (m/z): calcd. for C$_{20}$H$_{23}$N$_7$O (M$^+$)+1 377.4.

Example 35

(N-(1-(7H-pyrrolo[2,3-d]pyrimidin-4-yl)piperidin-3-yl)-2-(2,5-dichlorophenylamino)acetamide)

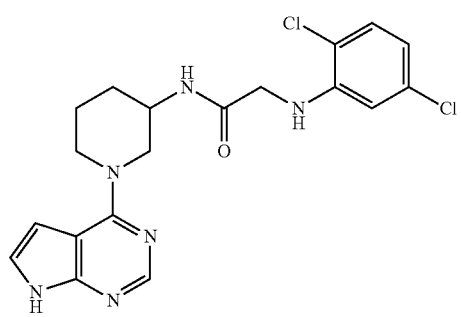

The title compound of Example 35 was prepared in similar manner as described in Example 16 except N-methylaniline was substituted for 2,5-dichloroaniline. $^1$H NMR (400 MHz, CD$_3$OD) δ 8.24 (s, 1H), 7.33 (s, 1H), 7.15 (d, 1H), 7.00 (s, 1H), 6.58 (d, 1H), 6.48 (s, 1H), 4.37 (d, 1H), 4.18 (d, 1H), 4.07 (s, 1H), 3.82 (s, 2H), 3.75 (m, 2H), 2.06 (m, 1H), 1.98 (m, 1H), 1.83 (m, 2H). EIMS (m/z): calcd. for C$_{19}$H$_{22}$Cl$_2$N$_6$O (M$^+$)+1 421.3.

Example 36

(N-(1-(7H-pyrrolo[2,3-d]pyrimidin-4-yl)piperidin-3-yl)-2-(3-(trifluoromethoxy)phenylamino)acetamide)

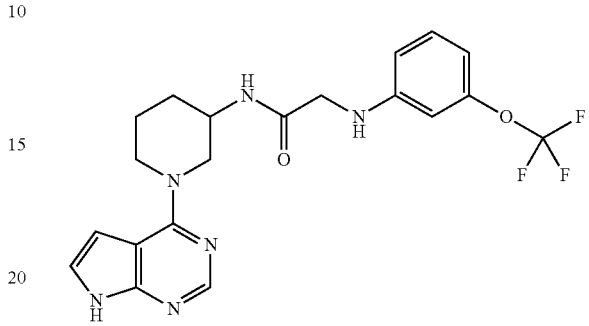

The title compound of Example 36 was prepared in similar manner as described in Example 16 except N-methylaniline was substituted for 3-(trifluoromethoxy)aniline. $^1$H NMR (400 MHz, CD$_3$OD) δ 8.27 (s, 1H), 7.35 (s, 1H), 7.12 (t, 1H), 7.05 (s, 1H), 6.50 (d, 2H), 6.41 (s, 1H), 4.45 (d, 1H), 4.28 (d, 1H), 4.06 (s, 1H), 3.77 (s, 2H), 3.62 (m, 2H), 2.05 (m, 1H), 1.97 (m, 1H), 1.81 (m, 2H). EIMS (m/z): calcd. for C$_{20}$H$_{23}$F$_3$N$_6$O$_2$ (M$^+$)+1 436.4.

Example 37

(N-(1-(7H-pyrrolo[2,3-d]pyrimidin-4-yl)piperidin-3-yl)-2-(2-methoxyphenylamino)acetamide)

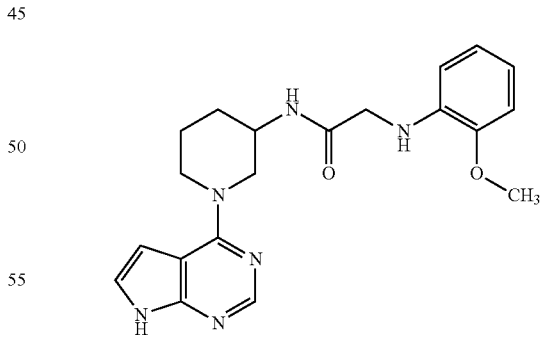

The title compound of Example 37 was prepared in similar manner as described in Example 16 except N-methylaniline was substituted for 2-(methoxy)aniline. $^1$H NMR (400 MHz, CD$_3$OD) δ 8.21 (s, 1H), 7.34 (s, 1H), 7.01 (s, 1H), 6.80 (s, 1H), 6.67 (s, 2H), 6.37 (s, 1H), 4.32 (d, 1H), 4.18 (d, 1H), 4.06 (s, 1H), 3.83 (s, 3H), 3.74 (m, 3H), 2.02 (m, 1H), 1.93 (m, 1H), 1.80 (m, 2H). EIMS (m/z): calcd. for C$_{20}$H$_{26}$N$_6$O$_2$ (M$^+$)+1 382.5.

Example 38

(N-(1-(7H-pyrrolo[2,3-d]pyrimidin-4-yl)piperidin-3-yl)-2-(3-isopropylphenylamino)acetamide)

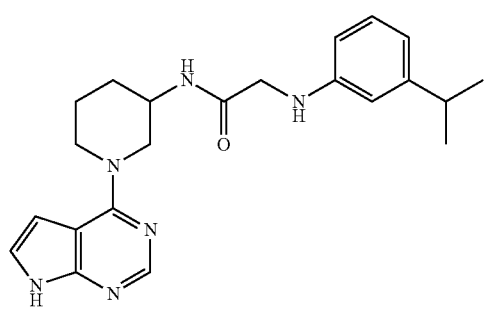 [SMILES: CC(C)c1cccc(NCC(=O)NC2CCCN(c3ncnc4[nH]ccc34)C2)c1]

The title compound of Example 38 was prepared in similar manner as described in Example 16 except N-methylaniline was substituted for 3-isopropylaniline. $^1$H NMR (400 MHz, CD$_3$OD) δ 8.26 (s, 1H), 7.69 (d, 1H), 7.36 (s, 1H), 7.21 (d, 1H), 7.05 (s, 2H), 6.55 (d, 2H), 6.41 (s, 1H), 4.44 (d, 1H), 4.25 (s, 1H), 4.06 (s, 1H), 3.65 (m, 2H), 2.77 (m, 1H), 2.35 (s, 1H), 2.03 (m, 1H), 1.94 (m, 1H), 1.79 (m, 2H), 1.19 (d, 5H). EIMS (m/z): calcd. for C$_{22}$H$_{30}$N$_6$O$_2$ (M$^+$)+1 394.3.

Example 39

(N-(1-(7H-pyrrolo[2,3-d]pyrimidin-4-yl)piperidin-3-yl)-2-(biphenyl-3-ylamino-)acetamide)

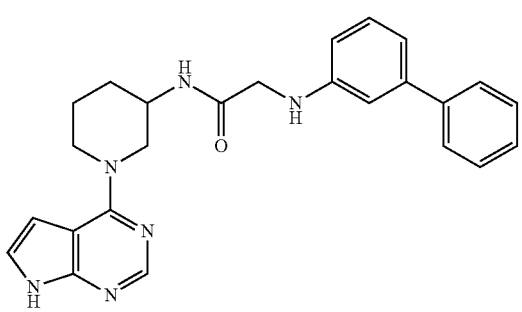 [SMILES: O=C(CNc1cccc(-c2ccccc2)c1)NC1CCCN(c2ncnc3[nH]ccc23)C1]

The title compound of Example 39 was prepared in similar manner as described in Example 16 except N-methylaniline was substituted for biphenyl-3-amine. $^1$H NMR (400 MHz, CD$_3$OD) δ 8.21 (s, 1H), 7.52 (d, 2H), 7.38 (t, 2H), 7.29 (m, 2H), 7.15 (t, 1H), 6.93 (m, 2H), 6.81 (s, 1H), 6.53 (d, 1H), 4.35 (d, 1H), 4.20 (d, 1H), 4.08 (s, 1H), 3.85 (s, 2H), 3.66 (t, 2H), 2.02 (m, 1H), 1.92 (m, 1H), 1.80 (m, 2H). EIMS (m/z): calcd. for C$_{25}$H$_{28}$N$_6$O (M$^+$)+1 428.5.

Example 40

(N-(1-(7H-pyrrolo[2,3-d]pyrimidin-4-yl)piperidin-3-yl)-2-(3-bromophenylamino)acetamide)

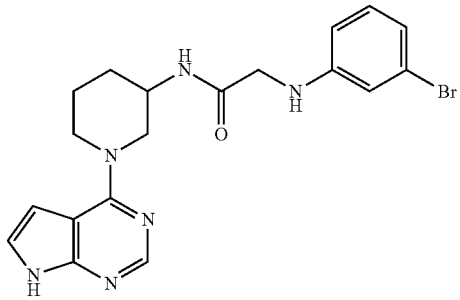 [SMILES: O=C(CNc1cccc(Br)c1)NC1CCCN(c2ncnc3[nH]ccc23)C1]

The title compound of Example 40 was prepared in similar manner as described in Example 16 except N-methylaniline was substituted for 3-bromoaniline. $^1$H NMR (400 MHz, CD$_3$OD) δ 8.25 (s, 1H), 7.34 (s, 1H), 7.01 (s, 1H), 6.92 (t, 1H), 6.71 (d, 1H), 6.71 (d, 1H), 6.66 (s, 1H), 6.45 (d, 1H), 4.35 (d, 1H), 4.20 (d, 1H), 4.06 (s, 1H), 3.71 (s, 4H), 2.03 (m, 1H), 1.95 (m, 1H), 1.82 (m, 2H). EIMS (m/z): calcd. for C$_{19}$H$_{23}$BrN$_6$O (M$^+$)+1 431.3.

Example 41

(N-(1-(7H-pyrrolo[2,3-d]pyrimidin-4-yl)piperidin-3-yl)-2-(5,6,7,8-tetrahydronaphthalen-1-ylamino)acetamide)

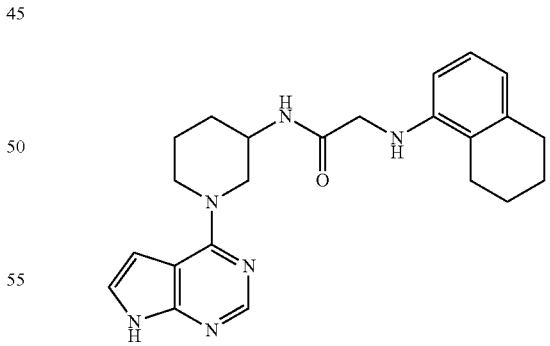

The title compound of Example 41 was prepared in similar manner as described in Example 16 except N-methylaniline was substituted for 5,6,7,8-tetrahydronaphthalen-1-amine. $^1$H NMR (400 MHz, CD$_3$OD): δ 8.21 (s, 1H), 7.34 (s, 1H), 7.00 (s, 1H), 6.82 (t, 1H), 6.41 (d, 1H), 6.14 (d, 1H), 4.30 (d, 1H), 4.09 (m, 2H), 3.76 (m, 4H), 2.66 (m, 2H), 2.43 (s, 2H), 2.02 (m, 1H), 1.85 (m, 5H), 1.71 (s, 3H). EIMS (m/z): calcd. for C$_{23}$H$_{30}$N$_6$O (M$^+$)+1 406.5.

Example 42

(N-(1-(7H-pyrrolo[2,3-d]pyrimidin-4-yl)piperidin-3-yl)-2-(3-phenoxyphenylamino)acetamide)

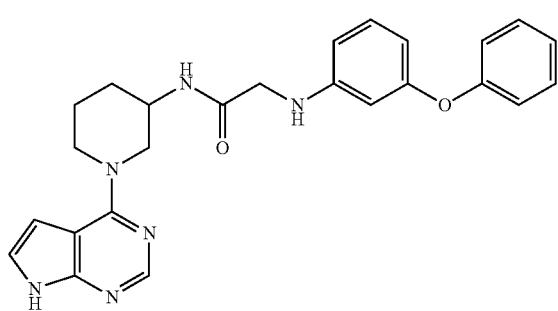 [SMILES: O=C(CNc1cccc(Oc2ccccc2)c1)NC1CCCN(c2ncnc3[nH]ccc23)C1]

The title compound of Example 42 was prepared in similar manner as described in Example 16 except N-methylaniline was substituted for 3-phenoxyaniline. $^1$H NMR (400 MHz, CD$_3$OD) δ 8.24 (s, 1H), 7.33 (s, 1H), 7.26 (t, 2H), 7.01 (m, 4H), 6.91 (m, 2H), 6.29 (m, 3H), 6.16 (s, 1H), 4.35 (d, 1H), 4.23 (d, 1H), 4.02 (s, 1H), 3.70 (s, 3H), 1.96 (m, 2H), 1.77 (s, 2H). EIMS (m/z): calcd. for C$_{25}$H$_{28}$N$_6$O (M$^+$)+1 444.5.

Example 43

(3-(2-(1-(7H-pyrrolo[2,3-d]pyrimidin-4-yl)piperidin-3-ylamino)-2-oxoethylamino)-N,N-dimethylbenzamide)

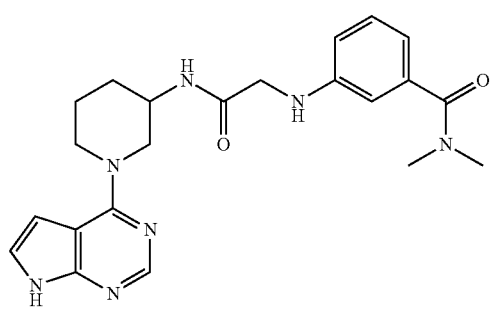 [SMILES: CN(C)C(=O)c1cccc(NCC(=O)NC2CCCN(c3ncnc4[nH]ccc34)C2)c1]

The title compound of Example 43 was prepared in similar manner as described in Example 16 except N-methylaniline was substituted for 3-amino-N,N-dimethylbenzamide. $^1$H NMR (400 MHz, CD$_3$OD) δ 8.23 (s, 1H), 7.35 (s, 1H), 7.12 (t, 1H), 7.04 (s, 1H), 6.66 (d, 1H), 6.59 (d, 1H), 6.55 (s, 1H), 4.40 (d, 1H), 4.25 (d, 1H), 4.05 (m, 1H), 3.76 (s, 2H), 3.63 (m, 2H), 3.06 (s, 3H), 2.96 (s, 3H), 2.03 (m, 1H), 1.94 (m, 1H), 1.79 (m, 2H) ppm. EIMS (m/z): calcd. for C$_{22}$H$_{29}$N$_7$O$_2$ (M$^+$)+1 423.5.

Example 44

(N-(1-(7H-pyrrolo[2,3-d]pyrimidin-4-yl)piperidin-3-yl)-2-(3-chloro-4-fluorophenylamino)acetamide)

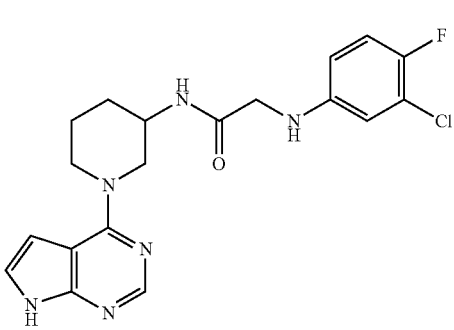 [SMILES: O=C(CNc1ccc(F)c(Cl)c1)NC1CCCN(c2ncnc3[nH]ccc23)C1]

The title compound of Example 44 was prepared in similar manner as described in Example 16 except N-methylaniline was substituted for 3-chloro-4-fluoroaniline. $^1$H NMR (400 MHz, CD$_3$OD) δ 8.27 (s, 1H), 7.34 (s, 1H), 7.01 (s, 1H), 6.90 (t, 1H), 6.56 (t, 1H), 6.43 (m, 1H), 4.36 (d, 1H), 4.19 (d, 1H), 4.07 (s, 1H), 3.72 (s, 2H), 3.63 (m, 5H), 2.04 (m, 1H), 1.96 (m, 1H), 1.82 (m, 2H). EIMS (m/z): calcd. for C$_{19}$H$_{22}$ClFN$_6$O (M$^+$)+1 404.9.

Example 45

(N-(1-(7H-pyrrolo[2,3-d]pyrimidin-4-yl)piperidin-3-yl)-2-(2,3-dihydro-1H-inden-4-ylamino)acetamide)

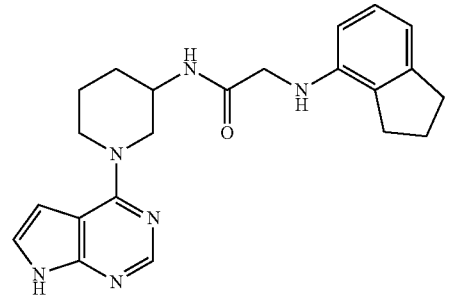 [SMILES: O=C(CNc1cccc2c1CCC2)NC1CCCN(c2ncnc3[nH]ccc23)C1]

The title compound of Example 45 was prepared in similar manner as described in Example 16 except N-methylaniline was substituted for 2,3-dihydro-1H-inden-4-amine. $^1$H NMR (400 MHz, CD$_3$OD) δ 8.20 (s, 1H), 7.34 (s, 1H), 7.00 (s, 1H), 6.84 (t, 1H), 6.58 (d, 1H), 6.16 (d, 1H), 4.29 (d, 1H), 4.12 (d, 2H), 3.77 (s, 4H), 2.84 (t, 2H), 2.69 (t, 2H), 2.04 (t, 3H), 1.91 (m, 1H), 1.79 (m, 2H). EIMS (m/z): calcd. for C$_{22}$H$_{28}$N$_6$O (M$^+$)+1 392.5.

Example 46

(N-(1-(7H-pyrrolo[2,3-d]pyrimidin-4-yl)piperidin-3-yl)-2-(naphthalen-1-ylamino)acetamide)

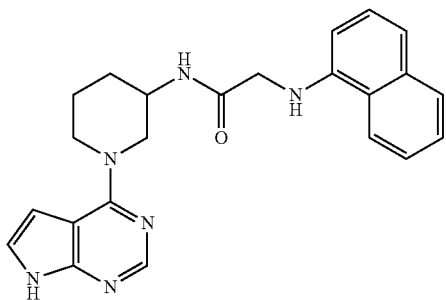

The title compound of Example 46 was prepared in similar manner as described in Example 16 except N-methylaniline was substituted for naphthalen-1-amine. $^1$H NMR (400 MHz, CD$_3$OD) δ 8.09 (s, 1H), 7.92 (d, 1H), 7.73 (d, 1H), 7.43 (m, 2H), 7.27 (s, 1H), 7.13 (s, 2H), 6.89 (s, 1H), 6.33 (s, 1H), 4.16 (m, 2H), 3.95 (m, 4H), 3.84 (m, 2H), 2.02 (m, 1H), 1.88 (m, 2H), 1.77 (m, 1H). EIMS (m/z): calcd. for C$_{23}$H$_{26}$N$_6$O (M$^+$)+1 402.5.

Example 47

(N-(1-(7H-pyrrolo[2,3-d]pyrimidin-4-yl)piperidin-3-yl)-2-(3-chloro-2-fluorophenylamino)acetamide)

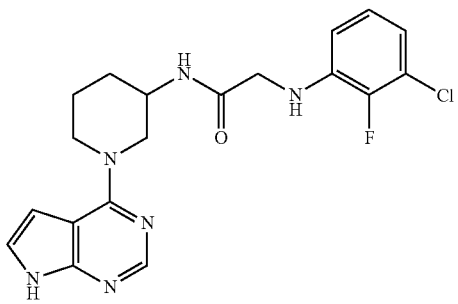

The title compound of Example 47 was prepared in similar manner as described in Example 16 except N-methylaniline was substituted for 3-chloro-2-fluoroaniline. $^1$H NMR (400 MHz, CD$_3$OD) δ 8.24 (s, 1H), 7.35 (s, 1H), 6.99 (s, 1H), 6.85 (t, 1H), 6.66 (d, 1H), 6.26 (d, 1H), 4.30 (d, 1H), 4.09 (m, 2H), 3.80 (m, 2H), 2.18 (s, 3H), 2.03 (m, 1H), 1.87 (m, 1H), 1.82 (m, 2H). EIMS (m/z): calcd. for C$_{19}$H$_{22}$ClFN$_6$O (M$^+$)+1 404.9.

Example 48

(N-(1-(7H-pyrrolo[2,3-d]pyrimidin-4-yl)piperidin-3-yl)-2-(3,5-dichlorophenylamino)acetamide)

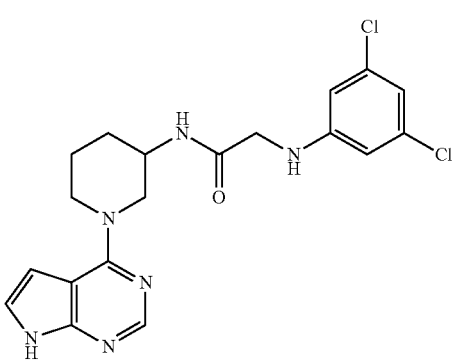

The title compound of Example 48 was prepared in similar manner as described in Example 16 except N-methylaniline was substituted for 3,5-dichloroaniline. $^1$H NMR (400 MHz, CD$_3$OD) δ 8.28 (s, 1H), 7.34 (s, 1H), 7.01 (s, 1H), 6.57 (s, 1H), 6.45 (s, 2H), 4.36 (d, 1H), 4.21 (d, 1H), 4.07 (s, 1H), 3.76 (m, 5H), 2.01 (m, 2H), 1.83 (m, 2H). EIMS (m/z): calcd. for C$_{19}$H$_{22}$O$_2$N$_6$O (M$^+$)+1 421.3.

Example 49

(N-(1-(7H-pyrrolo[2,3-d]pyrimidin-4-yl)piperidin-3-yl)-2-(3-chloro-5-fluorophenylamino)acetamide)

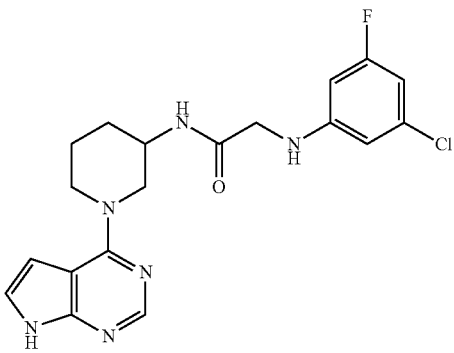

The title compound of Example 49 was prepared in similar manner as described in Example 16 except N-methylaniline was substituted for 3-chloro-5-fluoroaniline. $^1$H NMR (400 MHz, CD$_3$OD) δ 8.24 (s, 1H), 7.34 (s, 1H), 7.14 (t, 1H), 7.03 (m, 3H), 6.69 (d, 1H), 4.40 (d, 1H), 4.23 (d, 1H), 4.07 (s, 1H), 3.80 (s, 2H), 3.66 (m, 2H), 2.88 (s, 2H), 1.80 (m, 1H). EIMS (m/z): calcd. for C$_{19}$H$_{22}$ClFN$_6$O (M$^+$)+1 404.9.

Example 50

(N-(1-(7H-pyrrolo[2,3-d]pyrimidin-4-yl)piperidin-3-yl)-2-(3-isopropoxyphenylamino)acetamide)

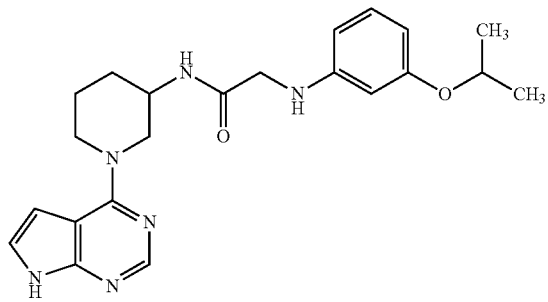 [SMILES: CC(C)Oc1cccc(NCC(=O)NC2CCCN(c3ncnc4[nH]ccc34)C2)c1]

The title compound of Example 50 was prepared in similar manner as described in Example 16 except N-methylaniline was substituted for 3-isopropoxyaniline. $^1$H NMR (400 MHz, CD$_3$OD) δ 8.25 (s, 1H), 7.36 (s, 1H), 7.04 (s, 1H), 6.95 (s, 1H), 6.26 (s, 1H), 6.14 (d, 2H), 4.49 (m, 1H), 4.40 (d, 1H), 4.23 (d, 1H), 4.07 (s, 1H), 3.71 (m, 3H), 2.01 (m, 2H), 1.80 (m, 2H), 1.26 (s, 6H). EIMS (m/z): calcd. for C$_{22}$H$_{30}$N$_6$O$_2$ (M$^+$)+1 410.5.

Example 51

(N-(1-(7H-pyrrolo[2,3-d]pyrimidin-4-yl)piperidin-3-yl)-2-(5-chloro-2-fluorophenylamino)acetamide)

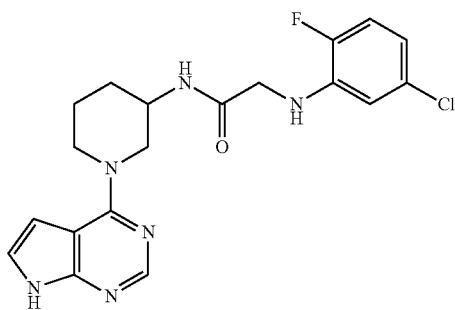

The title compound of Example 51 was prepared in similar manner as described in Example 16 except N-methylaniline was substituted for 3-chloro-6-fluoroaniline. $^1$H NMR (400 MHz, CD$_3$OD) δ 8.27 (s, 1H), 7.34 (s, 1H), 7.03 (s, 1H), 6.91 (t, 1H), 6.52 (m, 2H), 4.40 (d, 1H), 4.24 (d, 1H), 4.08 (s, 1H), 3.81 (s, 2H), 3.71 (m, 2H), 2.05 (m, 2H), 1.84 (m, 2H). EIMS (m/z): calcd. for C$_{19}$H$_{22}$ClFN$_6$O (M$^+$)+1 404.9.

Example 52

(N-(1-(7H-pyrrolo[2,3-d]pyrimidin-4-yl)piperidin-3-yl)-2-(3-chloro-2-methylphenylamino)acetamide)

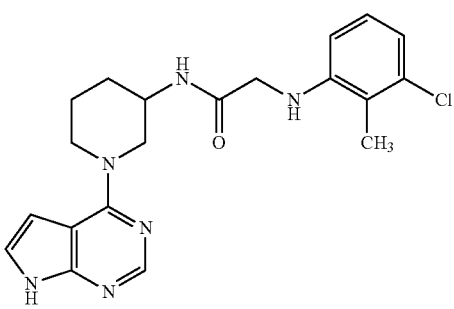 [SMILES: Cc1c(Cl)cccc1NCC(=O)NC1CCCN(c2ncnc3[nH]ccc23)C1]

The title compound of Example 52 was prepared in similar manner as described in Example 16 except N-methylaniline was substituted for 3-chloro-2-methylaniline. $^1$H NMR (400 MHz, CD$_3$OD) δ 8.06 (s, 1H), 7.09 (s, 1H), 6.88 (t, 1H), 6.67 (d, 1H), 6.57 (s, 1H), 6.62 (d, 1H), 4.02 (m, 3H), 3.77 (m, 4H), 2.12 (s, 3H), 1.90 (m, 1H), 1.79 (m, 2H), 1.64 (m, H), 1.29 (m, 1H). EIMS (m/z): calcd. for C$_{20}$H$_{25}$ClN$_6$O (M$^+$)+1 400.9.

Example 53

(N-(1-(7H-pyrrolo[2,3-d]pyrimidin-4-yl)piperidin-3-yl)-2-(3-chloro-2-methoxyphenylamino)acetamide)

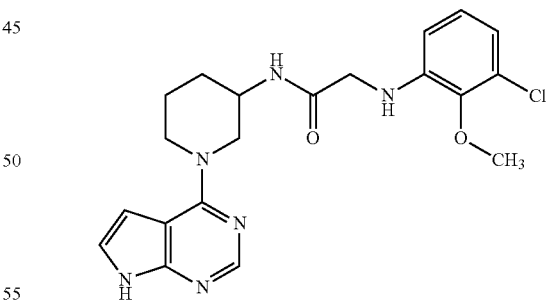

The title compound of Example 53 was prepared in similar manner as described in Example 16 except N-methylaniline was substituted for 3-chloro-2-methoxyaniline. $^1$H NMR (400 MHz, CD$_3$OD) δ 8.07 (s, 1H), 7.08 (s, 1H), 6.79 (m, 1H), 6.61 (m, 2H), 6.33 (m, 1H), 4.08 (m, 3H), 3.76 (m, 5H), 3.68 (s, 4H), 1.96 (m, 1H), 1.77 (s, 2H), 1.66 (s, 2H). EIMS (m/z): calcd. for C$_{20}$H$_{25}$ClN$_6$O$_2$ (M$^+$)+1 416.9.

Example 54

(N-(1-(7H-pyrrolo[2,3-d]pyrimidin-4-yl)piperidin-3-yl)-2-(1-oxoisoindolin-4-ylamino)acetamide)

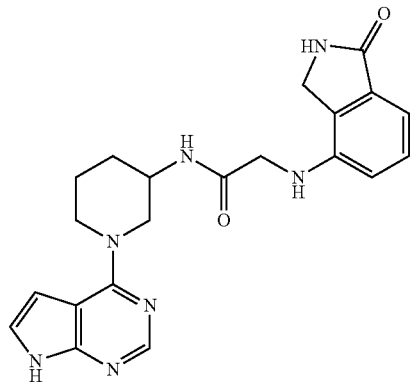 [SMILES: O=C(CNc1cccc2c1CNC2=O)NC1CCCN(c2ncnc3[nH]ccc23)C1]

The title compound of Example 54 was prepared in similar manner as described in Example 16 except N-methylaniline was substituted for 4-aminoisoindolin-1-one. $^1$H NMR (400 MHz, CD$_3$OD) δ 8.23 (s, 1H), 7.70 (d, 1H), 7.33 (s, 1H), 7.21 (t, 2H), 7.10 (d, 1H), 6.99 (s, 1H), 6.58 (d, 1H), 4.35 (m, 1H), 4.18 (d, 1H), 3.89 (s, 2H), 3.70 (m, 2H), 2.36 (s, 1H), 2.02 (m, 2H), 1.81 (m, 1H). EIMS (m/z): calcd. for C$_{21}$H$_{25}$N$_7$O$_2$ (M$^+$)+1 407.5.

Example 55

(N-(1-(7H-pyrrolo[2,3-d]pyrimidin-4-yl)piperidin-3-yl)-2-(3-ethynylphenylamino)acetamide)

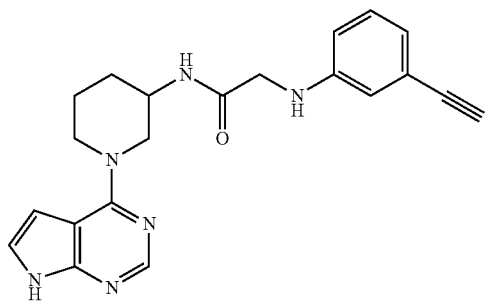 [SMILES: C#Cc1cccc(NCC(=O)NC2CCCN(c3ncnc4[nH]ccc34)C2)c1]

The title compound of Example 55 was prepared in similar manner as described in Example 16 except N-methylaniline was substituted for 3-ethynylaniline. $^1$H NMR (400 MHz, DMSO-d$_6$) δ 1.4-1.6 (m, 2H), 1.7-1.8 (m, 1H), 1.8-1.9 (m, 1H), 3.03 (t, J=10 Hz, 1H), 3.13 (t, J=11 Hz, 1H), 3.61 (s, 2H), 3.72 (s, 1H), 4.35 (d, J=13 Hz, 1H), 4.42 (d, J=13 Hz, 1H), 6.08 (s, 1H), 6.5-6.6 (m, 4H), 7.02 (t, J=8 Hz, 1H), 7.11 (s, 1H), 7.96 (d, J=7 Hz, 1H), 8.06 (s, 1H), 11.64 (s, 1H). EIMS (+) MS m/z=375 (M+1).

Example 56

(N-(1-(7H-pyrrolo[2,3-d]pyrimidin-4-yl)piperidin-3-yl)-2-(3-(pyrrolidin-1-yl)phenylamino)acetamide)

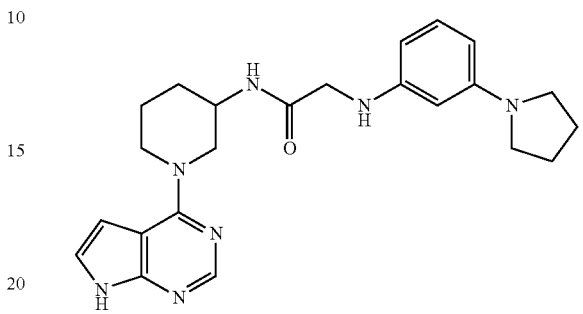

The title compound of Example 56 was prepared in similar manner as described in Example 16 except N-methylaniline was substituted for 3-(pyrrolidin-1-yl)aniline. $^1$H NMR (400 MHz, DMSO-d$_6$) δ 1.5-1.7 (m, 2H), 1.7-1.9 (m, 6H), 3.0-3.2 (m, 5H), 3.3-3.5 (m, 1H), 3.4-3.5 (m, 1H), 3.68 (d, J=9 Hz, 1H), 3.88 (m, 1H), 4.18 (d, J=12 Hz, 1H), 4.34 (d, J=12 Hz, 1H), 6.39 (d, J=8 Hz, 1H), 6.60 (t, J=7 Hz, 1H), 6.8-6.9 (m, 2H), 7.0-7.1 (m, 1H), 7.3-7.5 (m, 1H), 8.11 (d, J=7 Hz, 1H), 8.31 (s, 1H), 12.57 (s, 1H). EIMS (+) MS m/z=420 (M+1).

Example 57

(N-(1-(7H-pyrrolo[2,3-d]pyrimidin-4-yl)piperidin-3-yl)-2-(3-ten-butyl-1-methyl-1H-pyrazol-5-ylamino)acetamide)

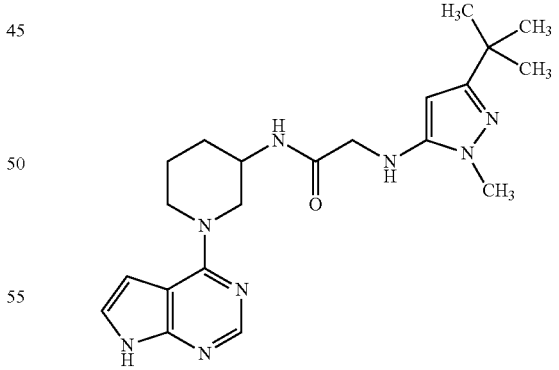

The title compound of Example 57 was prepared in similar manner as described in Example 16 except N-methylaniline was substituted for 3-tert-butyl-1-methyl-1H-pyrazol-5-amine. $^1$H NMR (400 MHz, CD$_3$OD) δ 1.18 (s, 9H), 1.6-1.7 (m, 1H), 1.7-1.8 (m, 2H), 1.9-2.0 (m, 1H), 3.31 (s, 2H), 3.47 (s, 3H), 3.6-3.7 (m, 2H), 3.9-4.1 (m, 1H), 4.1-4.2 (m, 1H), 4.22 (d, J=14 Hz, 1H), 5.22 (s, 1H), 6.64 (s, 1H), 7.11 (s, 1H), 8.11 (s, 1H). EIMS (+) MS m/z=411 (M+1).

Example 58

(N-(1-(7H-pyrrolo[2,3-d]pyrimidin-4-yl)piperidin-3-yl)-2-(1-tert-butyl-3-methyl-1H-pyrazol-5-ylamino)acetamide)

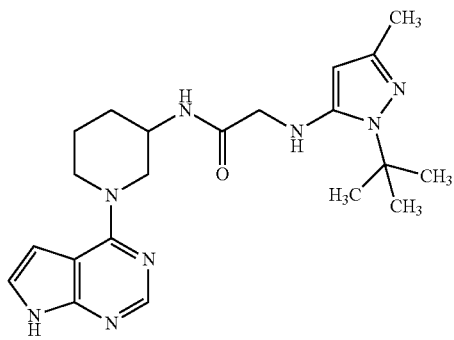 [SMILES: Cc1cc(NCC(=O)NC2CCCN(c3ncnc4[nH]ccc34)C2)n(C(C)(C)C)n1]

The title compound of Example 58 was prepared in similar manner as described in Example 16 except N-methylaniline was substituted for 1-tert-butyl-3-methyl-1H-pyrazol-5-amine. $^1$H NMR (400 MHz, CD$_3$OD) δ 1.43 (s, 9H), 1.4-1.5 (m, 2H), 1.6-1.7 (m, 1H), 1.8-1.9 (m, 1H), 1.91 (s, 2H), 2.24 (s, 2H), 3.1-3.2 (m, 1H), 3.49 (t, J=5 Hz, 2H), 3.6-3.8 (m, 1H), 4.23 (d, J=12 Hz, 1H), 4.36 (d, J=12 Hz, 1H), 5.72 (s, 1H), 6.57 (s, 1H), 7.06 (d, J=8 Hz, 1H), 7.43 (d, J=8 Hz, 1H), 7.84 (d, J=8 Hz, 1H), 8.07 (s, 1H), 11.63 (s, 1H). EIMS (+) MS m/z=411 (M+1).

Example 59

(N-(1-(7H-pyrrolo[2,3-d]pyrimidin-4-yl)piperidin-3-yl)-2-(pyridin-3-ylamino)acetamide)

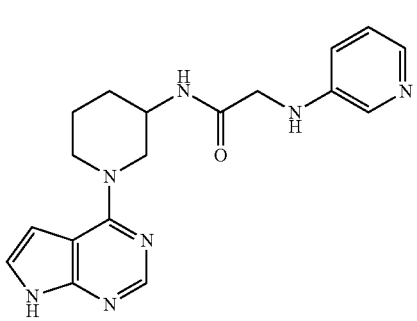 [SMILES: O=C(CNc1cccnc1)NC1CCCN(c2ncnc3[nH]ccc23)C1]

The title compound of Example 59 was prepared in similar manner as described in Example 16 except N-methylaniline was substituted for pyridin-3-amine. $^1$H NMR (400 MHz, DMSO-d$_6$) δ 1.8-2.0 (m, 2H), 3.33 (t, J=9 Hz, 1H), 3.49 (s, 1H), 3.80 (s, 1H), 4.25 (d, J=12 Hz, 2H), 4.43 (d, J=12 Hz, 2H), 4.84 (d, J=16 Hz, 2H), 6.78 (d, J=6 Hz, 2H), 6.87 (s, 1H), 7.37 (s, 1H), 7.98 (d, J=6 Hz, 2H), 8.32 (s, 1H), 12.55 (s, 1H). EIMS (+) MS m/z=352 (M+1).

Example 60

(N-(1-(N-(1-(7H-pyrrolo[2,3-d]pyrimidin-4-yl)piperidin-3-yl)-2-(3-(1-methyl-1H-pyrazol-3-yl)phenylamino)acetamide)

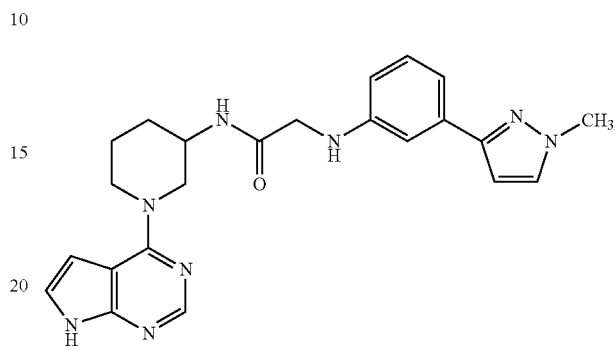

The title compound of Example 60 was prepared in similar manner as described in Example 16 except N-methylaniline was substituted for 3-(1-methyl-1H-pyrazol-3-yl)aniline. $^1$H NMR (400 MHz, DMSO-d$_6$) δ 1.5-1.6 (m, 2H), 1.8-1.9 (m, 2H), 3.1-3.6 (m, 5H), 3.65 (s, 2H), 3.80 (s, 3H), 4.23 (d, J=12 Hz, 1H), 4.36 (d, J=12 Hz, 1H), 6.44 (s, 1H), 6.60 (s, 1H), 6.97 (s, 2H), 7.03 (s, 1H), 7.84 (s, 1H), 7.64 (s, 1H), 8.08 (s, 1H), 8.27 (s, 1H), 12.48 (s, 1H). EIMS (+) MS m/z=431 (M+1).

Example 61

(N-(1-(7H-pyrrolo[2,3-d]pyrimidin-4-yl)piperidin-3-yl)-2-(3-(dimethylamino)phenylamino)acetamide)

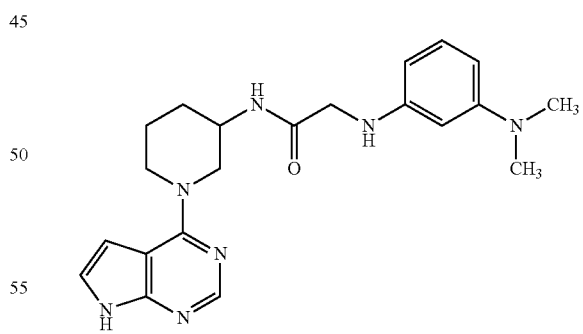

The title compound of Example 61 was prepared in similar manner as described in Example 16 except N-methylaniline was substituted for N1,N1-dimethylbenzene-1,3-diamine. $^1$H NMR (400 MHz, CD$_3$OD) δ 0.8-1.0 (m, 2H), 1.1-1.3 (m, 2H), 2.36 (s, 6H), 2.6-2.8 (m, 2H), 2.98 (d, J=6 Hz, 1H), 3.1-3.3 (m, 1H), 3.49 (d, J=12 Hz, 1H), 3.69 (d, J=12 Hz, 1H), 5.92 (s, 1H), 6.13 (s, 1H), 6.35 (d, J=8 Hz, 1H), 6.41 (s, 1H), 6.49 (s, 1H), 6.83 (d, J=8 Hz, 1H), 7.42 (s, 1H). EIMS (+) MS m/z=494 (M+1).

Example 62

(N-(1-(7H-pyrrolo[2,3-d]pyrimidin-4-yl)piperidin-3-yl)-2-(3,4-difluorophenylamino)acetamide)

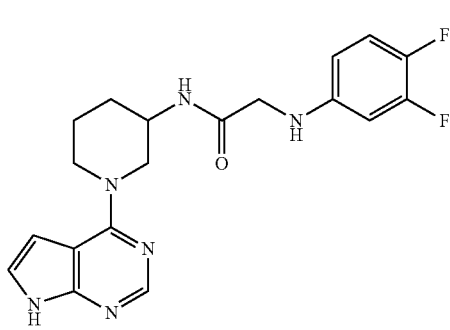 [SMILES: O=C(CNc1ccc(F)c(F)c1)NC1CCCN(c2ncnc3[nH]ccc23)C1]

The title compound of Example 62 was prepared in similar manner as described in Example 16 except N-methylaniline was substituted for 3,4-difluoroaniline. $^1$H NMR (400 MHz, DMSO-$d_6$) δ1.6-1.7 (m, 2H), 1.8-1.9 (m, 2H), 3.3-3.5 (m, 2H), 3.59 (d, J=6 Hz, 2H), 3.8-3.9 (m, 1H), 4.20 (d, J=13 Hz, 1H), 4.35 (d, J=13 Hz, 1H), 6.24 (s, 1H), 6.43 (s, 1H), 6.93 (s, 1H), 7.05 (s, 1H), 7.37 (s, 1H), 8.06 (s, 1H), 8.29 (s, 1H), 12.53 (s, 1H). EIMS (+) MS m/z=487 (M+1).

Example 63

(N-(1-(7H-pyrrolo[2,3-d]pyrimidin-4-yl)piperidin-3-yl)-2-(3-fluoro-5-(trifluoromethyl)phenylamino)acetamide)

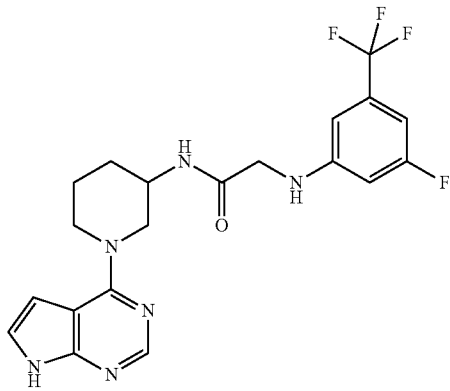 [SMILES: O=C(CNc1cc(F)cc(C(F)(F)F)c1)NC1CCCN(c2ncnc3[nH]ccc23)C1]

The title compound of Example 63 was prepared in similar manner as described in Example 16 except N-methylaniline was substituted for 3-fluoro-5-trifluoromethylaniline. $^1$H NMR (400 MHz, DMSO-$d_6$) δ 1.5-1.6 (m, 2H), 1.8-2.0 (m, 2H), 3.2-3.6 (m, 5H), 4.26 (d, J=13 Hz, 1H), 4.37 (d, J=13 Hz, 1H), 6.53 (d, J=12 Hz, 1H), 6.61 (d, J=12 Hz, 1H), 6.67 (s, 1H), 6.88 (s, 1H), 7.32 (s, 1H), 8.16 (s, 1H), 8.27 (s, 1H), 12.39 (s, 1H). ES (+) EIMS m/z=437 (M+1).

Example 64

(N-(1-(7H-pyrrolo[2,3-d]pyrimidin-4-yl)piperidin-3-yl)-2-(2-methyl-3-(trifluoromethyl)phenylamino)acetamide)

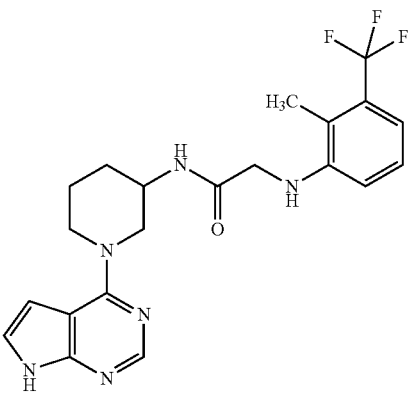 [SMILES: Cc1c(NCC(=O)NC2CCCN(c3ncnc4[nH]ccc34)C2)cccc1C(F)(F)F]

The title compound of Example 64 was prepared in similar manner as described in Example 16 except N-methylaniline was substituted for 2-methyl-3-trifluoromethylaniline. $^1$H NMR (400 MHz, DMSO-$d_6$) δ 1.5-1.6 (m, 2H), 1.8-2.0 (m, 2H), 2.15 (s, 3H), 3.2-3.6 (m, 5H), 4.26 (d, J=13 Hz, 1H), 4.37 (d, J=13 Hz, 1H), 6.65 (d, J=8 Hz, 1H), 6.87 (d, J=8 Hz, 1H), 6.90 (s, 1H), 7.09 (t, J=8 Hz, 1H), 7.36 (s, 1H), 8.06 (s, 1H), 8.27 (s, 1H), 12.47 (s, 1H) ppm. ES (+) MS m/z=433 (M+1).

Example 65

(N-(1-(7H-pyrrolo[2,3-d]pyrimidin-4-yl)piperidin-3-yl)-2-(4-methyl-3-(trifluoromethyl)phenylamino)acetamide)

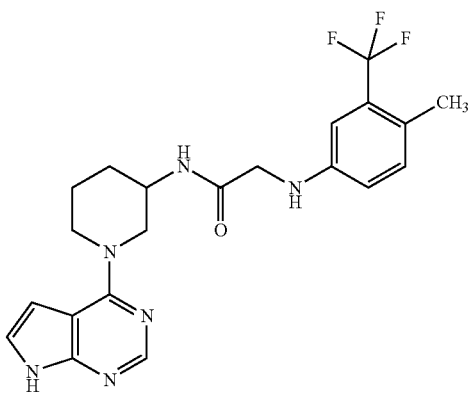 [SMILES: Cc1ccc(NCC(=O)NC2CCCN(c3ncnc4[nH]ccc34)C2)cc1C(F)(F)F]

The title compound of Example 65 was prepared in similar manner as described in Example 16 except N-methylaniline was substituted for 4-methyl-3-trifluoromethylaniline. $^1$H NMR (400 MHz, DMSO-$d_6$) δ 1.5-1.7 (m, 2H), 1.8-1.9 (m, 2H), 2.21 (s, 3H), 3.3-3.4 (m, 2H), 3.5-3.8 (m, 3H), 4.26 (d, J=13 Hz, 1H), 4.37 (d, J=13 Hz, 1H), 6.62 (d, J=8 Hz, 1H), 6.79 (s, 1H), 6.91 (s, 1H), 7.03 (d, J=8 Hz, 1H), 7.35 (s, 1H), 8.09 (s, 1H), 8.30 (s, 1H), 12.51 (s, 1H). ES (+) MS m/z=433 (M+1).

Example 66

(N-(1-(7H-pyrrolo[2,3-d]pyrimidin-4-yl)piperidin-3-yl)-2-(2-cyanophenylamino)acetamide)

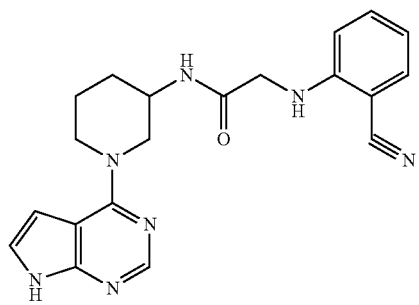 [SMILES: N#Cc1ccccc1NCC(=O)NC1CCCN(c2ncnc3[nH]ccc23)C1]

The title compound of Example 66 was prepared in similar manner as described in Example 16 except N-methylaniline was substituted for 2-aminobenzonitrile. $^1$H NMR (400 MHz, DMSO-$d_6$) δ 1.5-1.7 (m, 2H), 1.8-1.9 (m, 2H), 3.3-3.8 (m, 5H), 4.26 (d, J=13 Hz, 1H), 4.37 (d, J=13 Hz, 1H), 6.17 (s, 1H), 6.49 (d, J=8 Hz, 1H), 6.63 (t, J=7 Hz, 1H), 6.85 (s, 1H), 7.3-7.4 (m, 2H), 7.44 (d, J=7 Hz, 1H), 8.15 (d, J=7 Hz, 1H), 8.24 (s, 1H), 12.37 (s, 1H). ES (+) MS m/z=476 (M+1).

Example 67

(N-(1-(7H-pyrrolo[2,3-d]pyrimidin-4-yl)piperidin-3-yl)-2-(2,4-difluorophenylamino)acetamide)

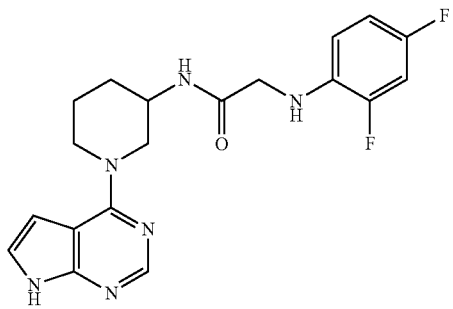 [SMILES: O=C(CNc1ccc(F)cc1F)NC1CCCN(c2ncnc3[nH]ccc23)C1]

The title compound of Example 67 was prepared in similar manner as described in Example 16 except N-methylaniline was substituted for 4,2-difluoroaniline. $^1$H NMR (400 MHz, DMSO-$d_6$) δ 1.5-1.7 (m, 2H), 1.7-2.0 (m, 2H), 3.31 (t, J=10 Hz, 1H), 3.43 (t, J=10 Hz, 1H), 3.69 (d, J=6 Hz, 2H), 3.7-3.9 (m, 1H), 4.23 (d, J=13 Hz, 1H), 4.37 (d, J=13 Hz, 1H), 6.2-6.3 (m, 1H), 6.8-7.0 (m, 2H), 7.37 (s, 1H), 6.13 (d, J=6 Hz, 1H), 8.30 (s, 1H), 12.55 (s, 1H). ES (+) MS m/z=487 (M+1).

Example 68

(N-(1-(7H-pyrrolo[2,3-d]pyrimidin-4-yl)piperidin-3-yl)-2-(3,5-difluorophenylamino)acetamide)

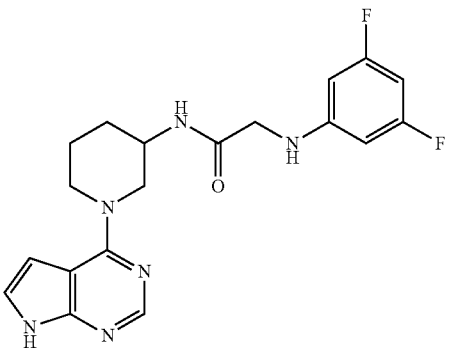 [SMILES: O=C(CNc1cc(F)cc(F)c1)NC1CCCN(c2ncnc3[nH]ccc23)C1]

The title compound of Example 68 was prepared in similar manner as described in Example 16 except N-methylaniline was substituted for 3,5-difluoroaniline. $^1$H NMR (400 MHz, DMSO-$d_6$) δ 1.5-1.7 (m, 2H), 1.7-2.0 (m, 2H), 3.29 (t, J=10 Hz, 1H), 3.41 (t, J=11 Hz, 1H), 3.65 (d, J=8 Hz, 2H), 3.7-3.8 (m, 1H), 4.23 (d, J=12 Hz, 1H), 4.37 (d, J=12 Hz, 1H), 6.14 (d, J=11 Hz, 1H), 6.19 (t, J=9 Hz, 1H), 6.90 (s, 1H), 7.34 (s, 1H), 8.13 (d, J=6 Hz, 1H), 8.27 (s, 1H), 12.43 (s, 1H). ES (+) MS m/z=487 (M+1).

Example 69

(N-(1-(7H-pyrrolo[2,3-d]pyrimidin-4-yl)piperidin-3-yl)-2-(2-fluoro-5-(trifluoromethyl)phenylamino)acetamide)

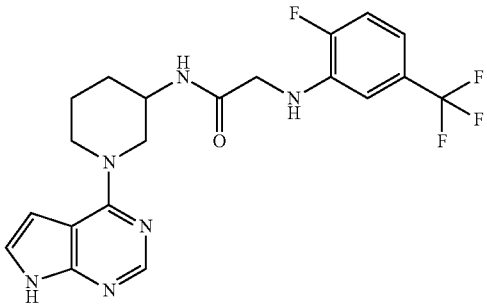 [SMILES: O=C(CNc1cc(C(F)(F)F)ccc1F)NC1CCCN(c2ncnc3[nH]ccc23)C1]

The title compound of Example 69 was prepared in similar manner as described in Example 16 except N-methylaniline was substituted for 2-fluoro-5-trifluoromethylaniline. $^1$H NMR (400 MHz, DMSO-$d_6$) δ 1.5-1.7 (m, 2H), 1.8-1.9 (m, 2H), 3.28 (t, J=10 Hz, 1H), 3.40 (t, J=11 Hz, 1H), 3.77 (d, J=8 Hz, 2H), 3.8-3.9 (m, 1H), 4.26 (d, J=12 Hz, 1H), 4.38 (d, J=12 Hz, 1H), 6.75 (d, J=8 Hz, 1H), 6.8-6.9 (m, 1H), 7.20 (d, J=9 Hz, 1H), 7.36 (s, 1H), 8.20 (d, J=7 Hz, 1H), 8.31 (s, 1H), 12.55 (s, 1H). ES (+) MS m/z=437 (M+1).

Example 70

(N-(1-(7H-pyrrolo[2,3-d]pyrimidin-4-yl)piperidin-3-yl)-2-(2-fluoro-3-(trifluoromethyl)phenylamino)acetamide)

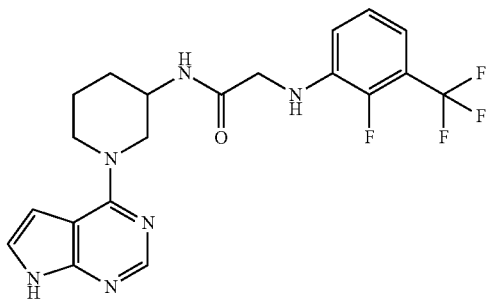 [SMILES: O=C(CNc1cccc(C(F)(F)F)c1F)NC1CCCN(c2ncnc3[nH]ccc23)C1]

The title compound of Example 70 was prepared in similar manner as described in Example 16 except N-methylaniline was substituted for 2-fluoro-3-trifluoromethylaniline. $^1$H NMR (400 MHz, DMSO-d-6) δ 1.5-1.7 (m, 2H), 1.8-1.9 (m, 2H), 3.29 (t, J=10 Hz, 1H), 3.40 (t, J=11 Hz, 1H), 3.77 (d, J=6 Hz, 2H), 3.8-3.9 (m, 1H), 4.26 (d, J=12 Hz, 1H), 4.38 (d, J=13 Hz, 1H), 6.7-6.8 (m, 3H), 6.90 (s, 1H), 7.07 (t, J=8 Hz, 1H), 7.37 (s, 1H), 8.13 (d, J=7 Hz, 1H), 8.29 (s, 1H), 12.47 (s, 1H). ES (+) MS m/z=437 (M+1).

Example 71

(N-(1-(7H-pyrrolo[2,3-d]pyrimidin-4-yl)piperidin-3-yl)-2-(2,3-difluorophenylamino)acetamide)

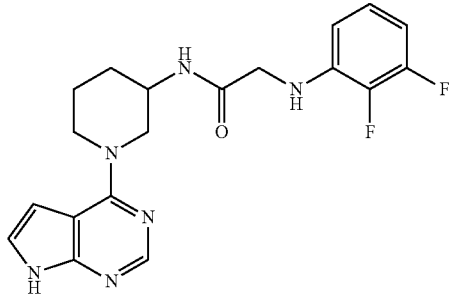 [SMILES: O=C(CNc1cccc(F)c1F)NC1CCCN(c2ncnc3[nH]ccc23)C1]

The title compound of Example 71 was prepared in similar manner as described in Example 16 except N-methylaniline was substituted for 2,3-difluoroaniline. $^1$H NMR (400 MHz, DMSO-d$_6$) δ 1.5-1.7 (m, 2H), 1.8-1.9 (m, 2H), 3.29 (t, J=10 Hz, 1H), 3.40 (t, J=11 Hz, 1H), 3.69 (d, J=5 Hz, 2H), 3.81 (s, 1H), 4.22 (d, J=13 Hz, 1H), 4.35 (d, J=13 Hz, 1H), 6.29 (t, J=8 Hz, 1H), 6.50 (q, J=9 Hz, 1H), 6.85 (q, J=7 Hz, 1H), 6.89 (s, 1H), 7.36 (s, 1H), 8.08 (d, J=7 Hz, 1H), 8.27 (s, 1H), 12.46 (s, 1H). ES (+) MS m/z=387 (M+1).

Example 72

(N-(1-(7H-pyrrolo[2,3-d]pyrimidin-4-yl)piperidin-3-yl)-2

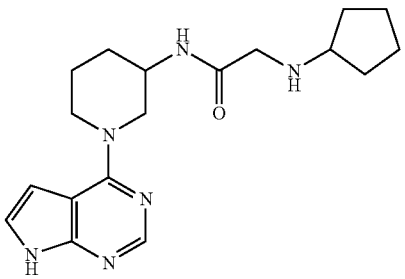 [SMILES: O=C(CNC1CCCC1)NC1CCCN(c2ncnc3[nH]ccc23)C1]

The title compound of Example 72 was prepared in similar manner as described in Example 16 except N-methylaniline was substituted for cyclopentanamine. $^1$H NMR (400 MHz, CD$_3$OD) δ 1.1-15 (m, 2H), 1.4-1.5 (m, 2H), 1.5-1.7 (m, 6H), 1.7-1.9 (m, 1H), 2.0-2.2 (m, 1H), 2.87 (t, J=6 Hz, 1H), 3.16 (s, 2H), 3.7-3.8 (m, 2H), 3.9-4.1 (m, 2H), 4.20 (d, J=13 Hz, 2H), 6.70 (d, J=3 Hz, 1H), 7.12 (d, J=2 Hz, 1H), 8.20 (S, 1H). ES (+) MS m/z=443 (M+1).

Example 73

(N-(1-(7H-pyrrolo[2,3-d]pyrimidin-4-yl)piperidin-3-yl)-2-(4-cyano-3-(trifluoromethyl)phenylamino)acetamide)

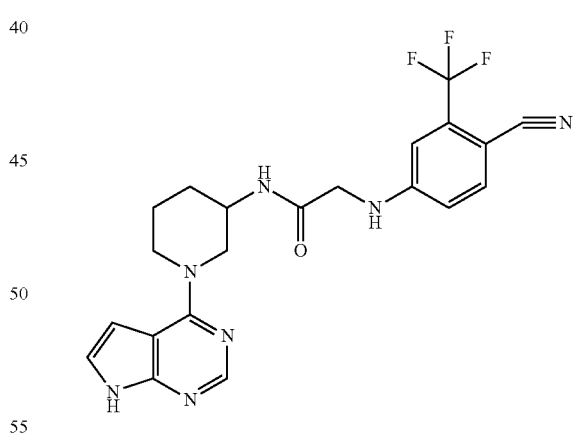

The title compound of Example 73 was prepared in similar manner as described in Example 16 except N-methylaniline was substituted for 4-amino-2-(trifluoromethyl)benzonitrile. $^1$H NMR (400 MHz, CD$_3$OD) δ 1.6-1.8 (m, 2H), 2.0-2.2 (m, 2H), 3.44 (s, 1H), 3.5-3.7 (m, 1H), 3.9 (s, 1H), 4.0-4.1 (m, 1H), 4.3-4.6 (m, 3H), 6.77 (d, J=9 Hz, 1H), 6.99 (s, 1H), 7.06 (s, 1H), 7.34 (s, 1H), 7.58 (d, J=9 Hz, 2H), 8.29 (d, J=6 Hz, 1H). ES (+) MS m/z=444 (M+1).

Example 74

(N-(1-(7H-pyrrolo[2,3-d]pyrimidin-4-yl)piperidin-3-yl)-2-(4-fluoro-3-(trifluoromethyl)phenylamino)acetamide)

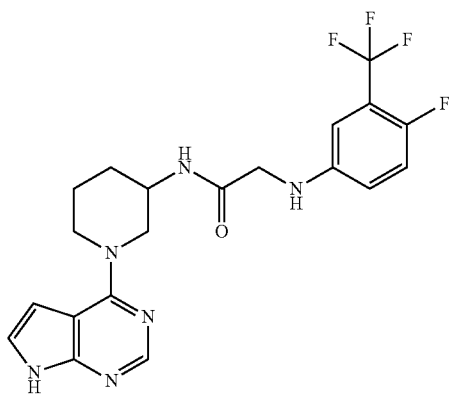 [SMILES: O=C(CNc1ccc(F)c(C(F)(F)F)c1)NC1CCCN(c2ncnc3[nH]ccc23)C1]

The title compound of Example 74 was prepared in similar manner as described in Example 16 except N-methylaniline was substituted for 4-fluoro-3-trifluoromethylaniline. $^1$H NMR (400 MHz, CD$_3$OD) δ 1.6-1.9 (m, 2H), 2.0-2.1 (m, 2H), 3.4-3.7 (m, 2H), 3.78 (s, 1H), 4.06 (s, 1H), 4.29 (d, J=13 Hz, 1H), 4.47 (d, J=13 Hz, 1H), 6.7-6.8 (m, 1H), 7.0-7.1 (m, 1H), 7.1-7.2 (m, 2H), 7.34 (s, 1H), 8.26 (s, 1H). ES (+) MS m/z=437 (M+1).

Example 75

(2-(1H-indazol-7-ylamino)-N-(1-(7H-pyrrolo[2,3-d]pyrimidin-4

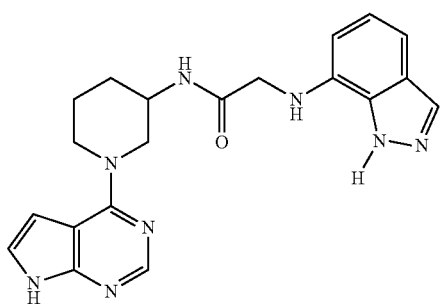 [SMILES: O=C(CNc1cccc2cn[nH]c12)NC1CCCN(c2ncnc3[nH]ccc23)C1]

The title compound of Example 75 was prepared in similar manner as described in Example 16 except N-methylaniline was substituted for 1H-indazol-7-amine. $^1$H NMR (400 MHz, CD$_3$OD) δ 1.5-1.97 (m, 3H), 1.8-2.0 (m, 1H), 3.5-3.6 (m, 2H), 3.90 (s, 2H), 4.0-4.1 (m, 2H), 4.17 (d, J=13 Hz, 1H), 5.95 (d, J=7 Hz, 1H), 6.57 (s, 1H), 6.80 (d, J=8 Hz, 1H), 7.0-7.1 (m, 2H), 8.03 (d, J=4 Hz, 1H). ES (+) MS m/z=391 (M+1).

Example 76

(2-(1H-indazol-4-ylamino)-N-(1-(7H-pyrrolo[2,3-d]pyrimidin-4-yl)piperidin-3-yl)acetamide)

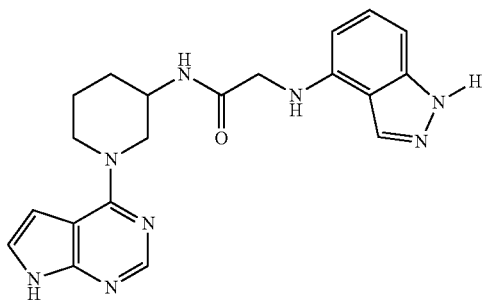 [SMILES: O=C(CNc1cccc2[nH]ncc12)NC1CCCN(c2ncnc3[nH]ccc23)C1]

The title compound of Example 76 was prepared in similar manner as described in Example 16 except N-methylaniline was substituted for 1H-indazol-4-amine. $^1$H NMR (400 MHz, CD$_3$OD) δ 1.5-1.97 (m, 3H), 1.8-2.0 (m, 1H), 3.5-3.6 (m, 2H), 3.93 (s, 2H), 4.0-4.1 (m, 2H), 4.25 (d, J=13 Hz, 1H), 6.30 (s, 1H), 6.59 (s, 1H), 6.90 (t, J=8 Hz, 1H), 7.04 (s, 1H), 7.09 (d, J=8 Hz, 1H), 7.94 (s, 1H), 8.02 (s, 1H). ES (+) MS m/z=391 (M+1).

Example 77

(2-(3-(1H-pyrazol-1-yl)phenylamino)-N-(1-(7H-pyrrolo[2,3-d]pyrimidin-4-yl)piperidin-3-yl)acetamide)

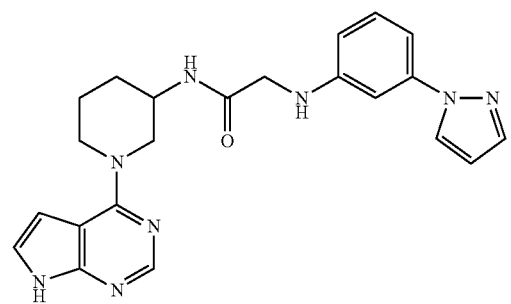 [SMILES: O=C(CNc1cccc(-n2cccn2)c1)NC1CCCN(c2ncnc3[nH]ccc23)C1]

The title compound of Example 77 was prepared in similar manner as described in Example 16 except N-methylaniline was substituted for 2-(1H-pyrazol-1-yl)aniline. $^1$H NMR (400 MHz, DMSO-d$_6$) δ 1.5-1.7 (m, 2H), 1.9-2.0 (m, 2H), 3.30 (t, J=10 Hz, 1H), 3.40 (t, J=11 Hz, 1H), 3.69 (d, J=6 Hz, 2H), 3.8-3.9 (m, 1H), 4.23 (d, J=14 Hz, 1H), 4.39 (d, J=14 Hz, 1H), 6.45 (s, 2H), 6.9-7.0 (m, 2H), 7.00 (s, 1H), 7.11 (d, J=8 Hz, 1H), 7.37 (s, 1H), 7.63 (s, 1H), 8.12 (d, J=7 Hz, 1H), 8.80 (s, 2H), 12.57 (s, 1H). ES (+) MS m/z=417 (M+1).

Example 78

(N-(1-(7H-pyrrolo[2,3-d]pyrimidin-4-yl)piperidin-3-yl)-2-(1-methyl-1H-indazol-4-ylamino)acetamide)

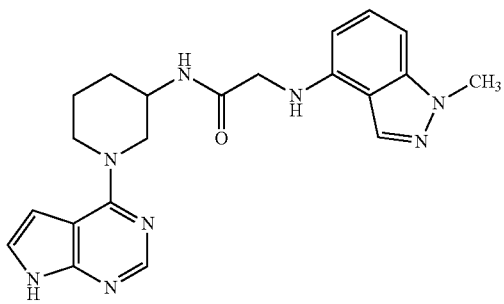 [SMILES: Cn1ncc2c(NCC(=O)NC3CCCN(c4ncnc5[nH]ccc45)C3)cccc21]

The title compound of Example 78 was prepared in similar manner as described in Example 16 except N-methylaniline was substituted for 1-methyl-1H-indazol-4-amine. $^1$H NMR (400 MHz, DMSO-$d_6$) δ 1.5-1.7 (m, 2H), 1.9-2.0 (m, 2H), 3.32 (t, J=10 Hz, 1H), 3.40 (t, J=11 Hz, 1H), 3.78 (d, J=6 Hz, 2H), 3.8-3.9 (m, 1H), 3.90 (s, 3H), 4.22 (d, J=12 Hz, 1H), 4.37 (d, J=13 Hz, 1H), 5.88 (d, J=8 Hz, 1H), 6.70 (d, J=8 Hz, 1H), 6.94 (s, 1H), 7.01 (t, J=7 Hz, 1H), 7.37 (s, 1H), 8.0-8.1 (m, 2H), 8.29 (s, 1H), 12.56 (s, 1H). ES (+) MS m/z=405 (M+1).

Example 79

(N-(1-(7H-pyrrolo[2,3-d]pyrimidin-4-yl)piperidin-3-yl)-2-(1-phenyl-1H-pyrazol-3-ylamino)acetamide)

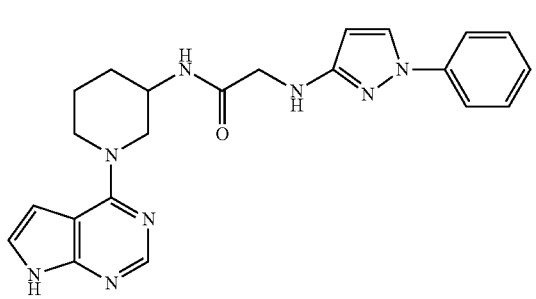 [SMILES: O=C(CNc1ccn(-c2ccccc2)n1)NC1CCCN(c2ncnc3[nH]ccc23)C1]

The title compound of Example 79 was prepared in similar manner as described in Example 16 except N-methylaniline was substituted for 1-phenyl-1H-pyrazol-3-amine. $^1$H NMR (400 MHz, DMSO-$d_6$) δ 1.5-1.7 (m, 2H), 1.9-2.0 (m, 2H), 3.32 (t, J=10 Hz, 1H), 3.40 (t, J=11 Hz, 1H), 3.78 (d, J=6 Hz, 2H), 3.8-3.9 (m, 1H), 4.22 (d, J=12 Hz, 1H), 4.37 (d, J=13 Hz, 1H), 5.79 (s, 1H), 6.98 (s, 1H), 7.07 (t, J=7 Hz, 1H), 7.3-7.4 (m, 3H), 7.60 (d, J=8 Hz, 2H), 8.03 (d, J=7 Hz, 1H), 8.12 (s, 1H), 8.31 (s, 1H), 12.62 (s, 1H). ES (+) MS m/z=417 (M+1).

Example 80

(N-(1-(7H-pyrrolo[2,3-d]pyrimidin-4-yl)piperidin-3-yl)-2-(1-methyl-1H-pyrazol-3-ylamino)acetamide)

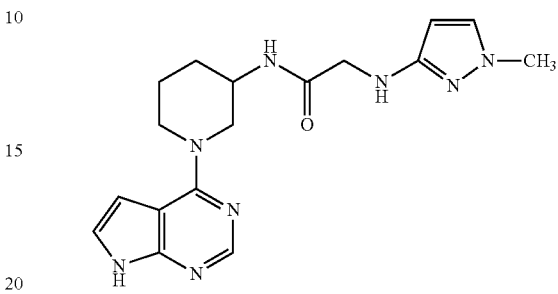

The title compound of Example 80 was prepared in similar manner as described in Example 16 except N-methylaniline was substituted for 1-methyl-1H-pyrazol-3-amine. $^1$H NMR (400 MHz, DMSO-$d_6$) δ 1.5-1.7 (m, 2H), 1.9-2.0 (m, 2H), 3.32 (t, J=10 Hz, 1H), 3.40 (t, J=11 Hz, 1H), 3.58 (s, 3H), 3.78 (d, J=6 Hz, 2H), 3.8-3.9 (m, 1H), 4.22 (d, J=12 Hz, 1H), 4.37 (d, J=13 Hz, 1H), 5.47 (s, 1H), 7.02 (s, 1H), 7.4-7.5 (m, 2H), 7.80 (d, J=7 Hz, 1H), 8.85 (s, 1H), 12.72 (s, 1H). ES (+) MS m/z=355 (M+1).

Example 81

(N-(1-(7H-pyrrolo[2,3-d]pyrimidin-4-yl)piperidin-3-yl)-2-(quinolin-8-ylamino)acetamide)

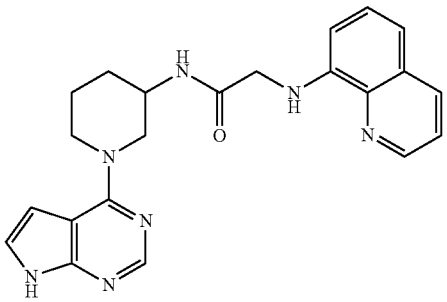 [SMILES: O=C(CNc1cccc2cccnc12)NC1CCCN(c2ncnc3[nH]ccc23)C1]

The title compound of Example 82 was prepared in similar manner as described in Example 16 except N-methylaniline was substituted for quinolin-8-amine. $^1$H NMR (400 MHz, DMSO-$d_6$) δ 1.4-1.6 (m, 2H), 1.7-1.8 (m, 1H), 1.8-1.9 (m, 1H), 3.09 (t, J=11 Hz, 1H), 3.18 (t, J=11 Hz, 1H), 3.7-3.9 (m, 3H), 4.35 (d, J=13 Hz, 1H), 4.46 (d, J=13 Hz, 1H), 6.48 (d, J=7 Hz, 1H), 6.62 (s, 1H), 7.08 (d, J=8 Hz, 1H), 7.13 (s, 1H), 7.32 (t, J=8 Hz, 1H), 7.49 (s, 1H), 8.06 (s, 1H), 8.19 (d, J=8 Hz, 1H), 8.74 (s, 1H), 11.62 (s, 1H). ES (+) MS m/z=402 (M+1).

Example 82

(N-(1-(7H-pyrrolo[2,3-d]pyrimidin-4-yl)piperidin-3-yl)-2-(3-(trifluoromethylthio)phenylamino)acetamide)

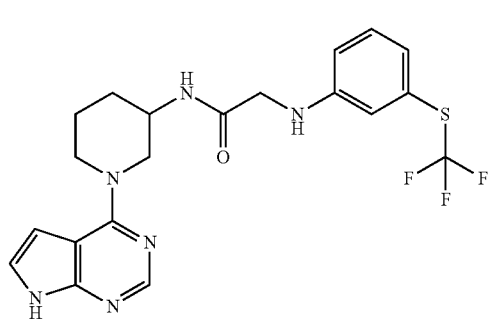 [SMILES: O=C(CNc1cccc(SC(F)(F)F)c1)NC1CCCN(c2ncnc3[nH]ccc23)C1]

The title compound of Example 82 was prepared in similar manner as described in Example 16 except N-methylaniline was substituted for 3-(trifluoromethylthio)aniline. $^1$H NMR (400 MHz, DMSO-$d_6$) δ 1.4-1.6 (m, 2H), 1.7-1.8 (m, 1H), 1.8-1.9 (m, 1H), 3.07 (t, J=10 Hz, 1H), 3.18 (t, J=11 Hz, 1H), 3.6-3.7 (m, 2H), 3.7-3.8 (m, 1H), 4.33 (d, J=13 Hz, 1H), 4.41 (d, J=13 Hz, 1H), 6.36 (s, 1H), 6.58 (s, 1H), 6.71 (d, J=8 Hz, 1H), 6.9-6.9 (m, 2H), 7.11 (s, 1H), 7.17 (t, J=7 Hz, 1H), 8.02 (d, J=7 Hz, 1H), 8.07 (s, 1H), 11.63 (s, 1H). ES (+) MS m/z=451 (M+1).

Example 83

(N-(1-(7H-pyrrolo[2,3-d]pyrimidin-4-yl)piperidin-3-yl)-2-(3-morpholinophenylamino)acetamide)

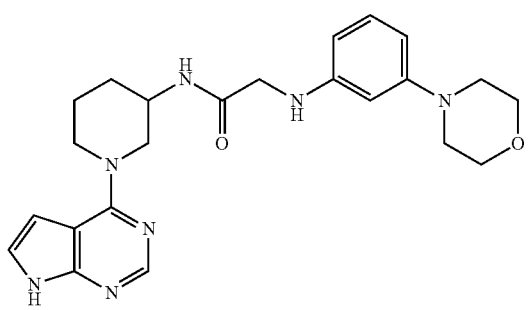 [SMILES: O=C(CNc1cccc(N2CCOCC2)c1)NC1CCCN(c2ncnc3[nH]ccc23)C1]

The title compound of Example 83 was prepared in similar manner as described in Example 16 except N-methylaniline was substituted for 3-morpholinoaniline. $^1$H NMR (400 MHz, CD$_3$OD) δ 1.4-1.6 (m, 2H), 1.7-1.8 (m, 1H), 18-1.9 (m, 1H), 2.97 (s, 4H), 3.1-3.3 (m, 2H), 3.68 (s, 2H), 3.70 (s, 4H), 3.75 (s, 1H), 4.30 (d, J=14 Hz, 1H), 4.39 (d, J=13 Hz, 1H), 6.00 (d, J=8 Hz, 1H), 6.08 (s, 1H), 6.17 (d, J=8 Hz, 1H), 6.57 (s, 1H), 6.88 (t, J=8 Hz, 1H), 7.09 (s, 1H), 7.86 (d, J=7 Hz, 1H), 8.06 (s, 1H). ES (+) MS m/z=436 (M+1).

Example 84

(N-(1-(7H-pyrrolo[2,3-d]pyrimidin-4-yl)piperidin-3-yl)-2-(2,3-dimethylphenylamino)acetamide)

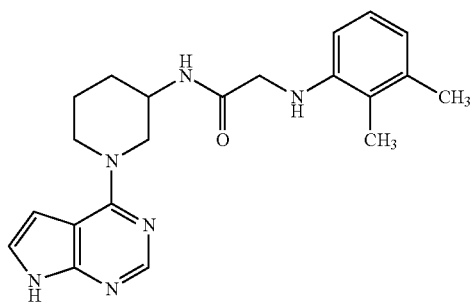 [SMILES: Cc1cccc(NCC(=O)NC2CCCN(c3ncnc4[nH]ccc34)C2)c1C]

The title compound of Example 82 was prepared in similar manner as described in Example 16 except N-methylaniline was substituted for 2,3-dimethylaniline. $^1$H NMR (400 MHz, DMSO-$d_6$) δ 1.4-1.6 (m, 2H), 1.7-1.9 (m, 2H), 1.97 (s, 3H), 2.15 (s, 3H), 3.11 (t, J=10 Hz, 1H), 3.20 (t, J=10 Hz, 1H), 3.63 (s, 2H), 3.74 (s, 1H), 4.29 (d, J=12 Hz, 1H), 4.87 (d, J=13 Hz, 1H), 6.18 (d, J=8 Hz, 1H), 6.44 (d, J=7 Hz, 1H), 6.58 (s, 1H), 6.83 (t, J=8 Hz, 1H), 7.13 (s, 1H), 7.87 (d, J=6 Hz, 1H), 8.07 (s, 1H), 11.64 (s, 1H). ES (+) MS m/z=379 (M+1).

Example 85

(N-(1-(7H-pyrrolo[2,3-d]pyrimidin-4-yl)piperidin-3-yl)-N-methyl-2-(phenylamino)acetamide)

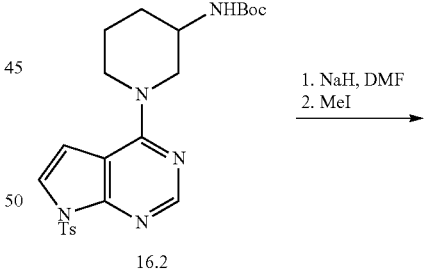

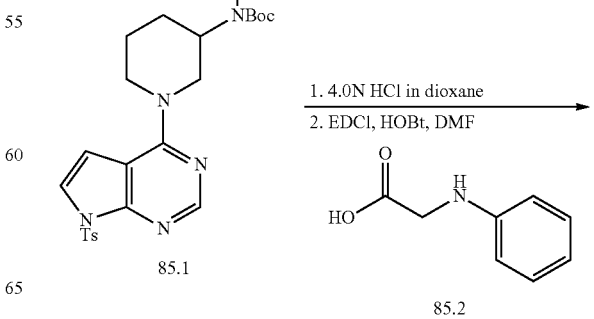

-continued

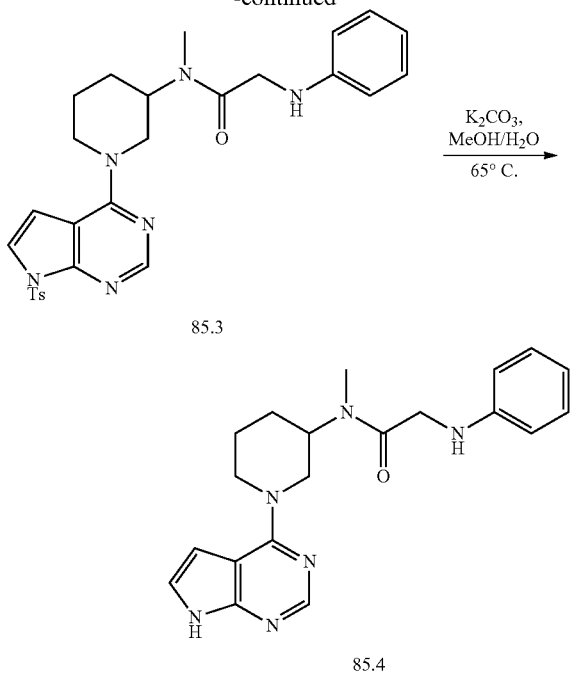

residue, which was purified by column chromatography (gradient EtOAc in hexane) to afford 85.3 which was used without further purification.

(N-(1-(7H-pyrrolo[2,3-d]pyrimidin-4-yl)piperidin-3-yl)-N-methyl-2-(phenylamino)acetamide). A mixture of N-methyl-2-(phenylamino)-N-(1-(7-tosyl-7H-pyrrolo[2,3-d]pyrimidin-4-yl)piperidin-3-yl)acetamide (77 mg, 0.15 mmol), $K_2CO_3$ (103 mg, 0.75 mmol), MeOH (2 mL) and water (0.5 mL) was stirred at 65° C. overnight. The reaction mixture was concentrated in vacuo. The residue was taken up in EtOAc and washed with water and separated, and the organic phase was concentrated in vacuo. The crude material was purified by reverse phase chromatography $C_{18}$ column and 10% acetonitrile/water containing 0.1% TFA to afford the title final product. $^1$H NMR (400 MHz, DMSO-$d_6$) δ 12.52 (s, 1H), 8.33 (s, 1H), 7.40 (s, 1H), 7.07~7.11 (m, 2H), 6.86 (m, 1H), 6.69 (d, J=7.8 Hz, 1H), 6.55~6.62 (m, 2H), 4.40~4.57 (m, 2H), 3.94 (m, 3H), 3.16~3.52 (m, 2H), 3.00 (s, 3H), 2.87 (s, 1H), 1.88~2.00 (m, 2H), 1.64~1.77 (m, 2H) ppm. EIMS (m/z): calcd. for $C_{20}H_{24}N_6O$ ($M^+$+1) 365.2. found 365.0.

Example 86

(N-(1-(7H-pyrrolo[2,3-d]pyrimidin-4-yl)piperidin-3-yl)-N-benzyl-2-(phenylamino)acetamide)

tert-Butyl methyl(1-(7-tosyl-7H-pyrrolo[2,3-d]pyrimidin-4-yl)piperidin-3-yl)carbamate. The tert-butyl 1-(7-tosyl-7H-pyrrolo[2,3-d]pyrimidin-4-yl)piperidin-3-ylcarbamate intermediate (0.28 g, 0.6 mmol) synthesized from the corresponding 4-chloro-7-tosyl-7H-pyrrolo[2,3-d]pyrimidine and tert-butyl piperidin-3-ylcarbamate in a similar fashion as described in example 155 was dissolved in DMF (3 mL) was added NaH (26 mg, 0.66 mmol), and the reaction mixture was stirred at rt for 30 min. The solution was treated with MeI (0.1 g, 46 uL, 0.72 mmol) and allowed to stir at rt for 30 min. The reaction was quenched by adding several drops of sat. aq. $NH_4Cl$ and then concentrated in vacuo to afford a residue. The residue was suspended in sat. aq. $NaHCO_3$ (20 mL) and extracted with $CH_2Cl_2$ (3×20 mL). The organic phases were combined, dried ($Na_2SO_4$), and concentrated in vacuo to afford a residue, which was purified by column chromatography (silica gel, gradient EtOAc in hexane) to afford 85.1 which was used without further purification.
Note: The tert-butyl 1-(7-tosyl-7H-pyrrolo[2,3-d]pyrimidin-4-yl)piperidin-3-ylcarbamate intermediate was synthesized from the corresponding 4-chloro-7-tosyl-7H-pyrrolo[2,3-d]pyrimidine and tert-butyl piperidin-3-ylcarbamate in a similar fashion as described in example 155.

N-methyl-2-(phenylamino)-N-(1-(7-tosyl-7H-pyrrolo[2,3-d]pyrimidin-4-yl)piperidin-3-yl)acetamide. A solution of tert-butyl methyl(1-(7-tosyl-7H-pyrrolo[2,3-d]pyrimidin-4-yl)piperidin-3-yl)carbamate (0.2 g, 0.4 mmol) in 4.0 N HCl in dioxane (4 mL) was stirred at rt for 6 h. The reaction mixture was concentrated in vacuo to afford the amine, which was used without further purification. To a solution of EDCI (68 mg, 0.44 mmol), HOBt (59 mg, 0.44 mmol), and DIEA (23 mg, 29 uL, 3.0 mmol) in DMF (2 mL) was added 2-(Phenylamino)acetic acid (60 mg, 0.4 mmol). The solution was stirred at rt for 4 h and concentrated in vacuo to afford a

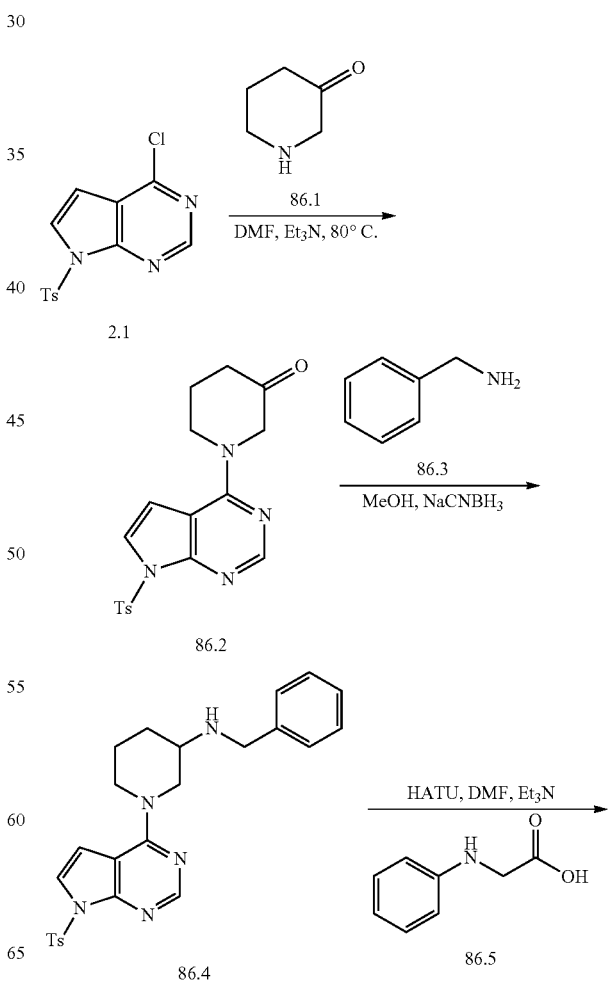

-continued

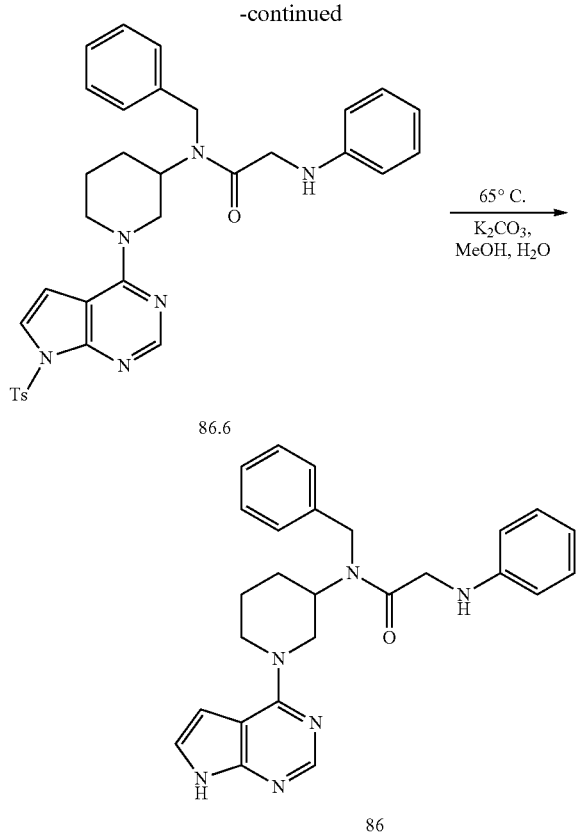

86.6

86

1-(7-tosyl-7H-pyrrolo[2,3-d]pyrimidin-4-yl)piperidin-3-one. A mixture of 4-chloro-7-(toluene-4-sulfonyl)-7H-pyrrolo[2,3-d]pyrimidine (100 mg, 0.32 mmol) (synthesized as describe by Cox, P. J.; Majid, T.; Amendola, S.; Deprets, S. D.; Edlin, C.; Pedgrift, B.; Halley, F.; Edwards, M.; Baudoin, B., Mclay, L; Aldous, D. J. PCT Int. Appl. (2003), 66 pp. WO 2003000695), piperidin-3-one (32 mg, 0.32 mmol) and Et$_3$N (90 µL, 0.64 mmol) in DMF (4 mL) was heated at 80° C. for 16 h. The reaction mixture was diluted with water and extracted with EtOAc. The organic phase was washed with aq. citric acid and aq. NaHCO$_3$, dried (Na$_2$SO$_4$), filtered and concentrated in vacuo to afford a residue which was purified by chromatography (silica gel, gradient EtOAc in hexanes) to afford 86.2.

N-benzyl-1-(7-tosyl-7H-pyrrolo[2,3-d]pyrimidin-4-yl)piperidin-3-amine. To a solution of 1-(7-tosyl-7H-pyrrolo[2,3-d]pyrimidin-4-yl)piperidin-3-one (75 mg, 0.2 mmol) and benzylamine (25 µL, 0.22 mmol) in MeOH (3 mL) was added AcOH (20 µL, 0.4 mmol) and NaBH$_3$CN (32 mg, 0.5 mmol). The solution was stirred at rt for 16 hr after which time the solvent was removed in vacuo to afford a residue which was diluted with water and extracted with EtOAc. The organic phase was separated, washed with aq. NaHCO$_3$ and water, dried (Na$_2$SO$_4$) and concentrated in vacuo to afford a residue which was purified by column chromatography (silica gel, gradient EtOAc in hexanes). EIMS (m/z): calcd. for C$_{25}$H$_{27}$N$_5$O$_2$S (M$^+$+1) 462.2. found 462.2.

N-benzyl-2-(phenylamino)-N-(1-(7-tosyl-7H-pyrrolo[2,3-d]pyrimidin-4-yl)piperidin-3-yl)acetamide. To a solution of N-phenylglycine (29 mg, 0.2 mmol), HATU (75 mg, 0.2 mmol), Et$_3$N (50 µL, 0.4 mmol) in DMF (3 mL) was added N-benzyl-1-(7-tosyl-7H-pyrrolo[2,3-d]pyrimidin-4-yl)piperidin-3-amine (90 mg, 0.2 mmol). After stirring at rt for 4 h, the solution was diluted with EtOAc and washed with water, aq. citric acid and aq. NaHCO$_3$. The organic phase was dried (Na$_2$SO$_4$), filtered and concentrated in vacuo to afford a residue which was purified by column chromatography (silica gel, gradient EtOAc in hexanes) to afford the title compound.

(N-(1-(7H-pyrrolo[2,3-d]pyrimidin-4-yl)piperidin-3-yl)-N-benzyl-2-(phenylamino)acetamide). A solution of N-benzyl-2-(phenylamino)-N-(1-(7-tosyl-7H-pyrrolo[2,3-d]pyrimidin-4-yl)piperidin-3-yl)acetamide (65 mg, 0.11 mmol) and K$_2$CO$_3$ (76 mg, 0.55 mmol in MeOH (3 mL) and water (1 mL) was heated to 65° C. The solution was concentrated to afford a residue which was dissolved in water and EtOAc. The organic phase was collected, washed with water and aq. NaHCO$_3$, separated, dried (Na$_2$SO$_4$) and concentrated in vacuo to afford a residue which was purified by reversed phase chromatography yielding 25 mg, 52% yield. $^1$H NMR (400 MHz, DMSO-d$_6$) δ 8.13 (d, J=12.05 Hz, 1H), 7.41 (d, J=7.28 Hz, 1H), 7.24-7.38 (m, 2H), 7.22-7.24 (m, 1H), 7.13-7.21 (m, 2H), 7.00-7.13 (m, 2H), 6.65 (d, J=8.03 Hz, 2H), 6.42-6.61 (m, 2H), 5.62-5.69 (m, 1H), 4.49-4.72 (m, 2H), 4.19-4.29 (m, 2H), 3.87-4.06 (m, 2H), 2.96-3.20 (m, 2H), 2.80-2.95 (m, 1H), 1.81 (br. s., 2H), 1.42-1.68 (m, 1H). EIMS (m/z): calcd. for C$_{26}$H$_{28}$N$_6$O (M$^+$+1) 441.2. found (M$^+$+1)= 441.3.

Examples 87-89 were prepared according to Example 86 above.

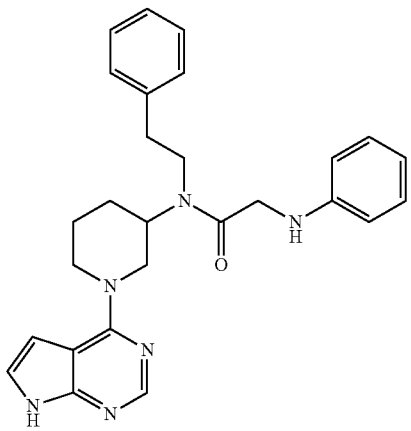 [SMILES: O=C(CNc1ccccc1)N(CCc1ccccc1)C1CCCN(c2ncnc3[nH]ccc23)C1]

Example 87

(N-(1-(7H-pyrrolo[2,3-d]pyrimidin-4-yl)piperidin-3-yl)-N-phenethyl-2-(phenylamino)acetamide)

Compound 87 was prepared according to the procedure of Scheme 4 using phenethylamine in place of benzylamine. $^1$H NMR (400 MHz, DMSO-d$_6$) δ 8.12 (d, J=12.04 Hz, 1H), 7.23-7.38 (m, 5H), 7.00-7.13 (m, 2H), 6.89-6.97 (ddd, J=7.65, 7.78, 15.18 Hz, 3H), 6.41-6.68 (m, 2H), 5.54-5.73 (m, 1H), 4.52-4.82 (m, 2H), 3.94 (dd, J=5.15, 16.94 Hz, 2H), 3.53-3.75 (m, 2H), 2.97-3.20 (m, 2H), 1.71-1.95 (m, 4H), 1.44-1.67 (m, 2H). EIMS (m/z): calcd. for C$_{27}$H$_{30}$N$_6$O (M$^+$+1) 455.2. found (M$^+$+1)=455.3.

Example 88

(N-(1-(7H-pyrrolo[2,3-d]pyrimidin-4-yl)piperidin-3-yl)-N-(cyclohexylmethyl)-2-(phenylamino)acetamide)

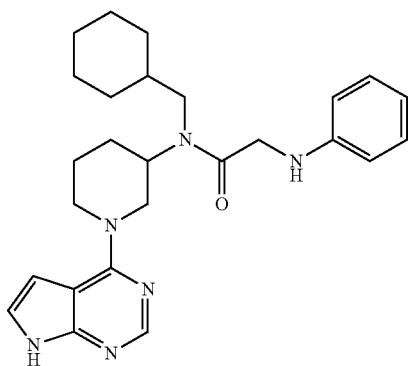 [SMILES: O=C(CNc1ccccc1)N(CC1CCCCC1)C1CCCN(c2ncnc3[nH]ccc23)C1]

The title compound was prepared according to the above procedure using cyclohexylmethylamine in place of benzylamine. $^1$H NMR (400 MHz, DMSO-$d_6$) δ 8.13 (d, J=12.05 Hz, 1H), 7.23-7.38 (m, 2H), 6.89-6.97 (ddd, J=7.68, 7.76, 15.15 Hz, 3H), 6.42-6.61 (m, 2H), 6.26 (br.s., 1H), 3.94 (dd, J=5.15, 16.94 Hz, 2H), 3.53-3.75 (m, 2H), 2.96-3.20 (m, 4H), 2.80-2.95 (m, 4H), 1.71-1.95 (m, 4H), 1.41-1.69 (m, 8H). EIMS (m/z): calcd. for $C_{26}H_{34}N_6O$ ($M^+$+1) 447.4. found ($M^+$+1)=447.4.

Example 89

(N-(1-(7H-pyrrolo[2,3-d]pyrimidin-4-yl)piperidin-3-yl)-N-(2-(dimethylamino)ethyl)-2-(phenylamino)acetamide)

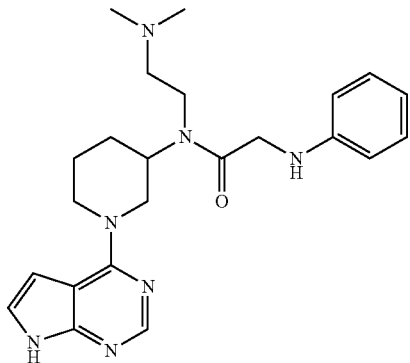 [SMILES: CN(C)CCN(C(=O)CNc1ccccc1)C1CCCN(c2ncnc3[nH]ccc23)C1]

The title compound was prepared according to the above procedure using N,N-dimethyl-1,2-ethanediamine in place of benzylamine. $^1$H NMR (400 MHz, DMSO-$d_6$) δ 8.11 (d, J=12.03 Hz, 1H), 7.22-7.40 (m, 2H), 6.90-6.99 (ddd, J=7.63, 7.75, 15.20 Hz, 3H), 6.24 (br.s., 1H), 3.97 (dd, J=5.15, 16.94 Hz, 2H), 3.53-3.75 (m, 4H), 2.96-3.20 (m, 4H), 2.26 (s, 4H), 1.71-1.95 (m, 3H), 1.42-1.68 (m, 4H). EIMS (m/z): calcd. for $C_{23}H_{31}N_7O$ ($M^+$+1) 422.4. found ($M^+$+1)=422.4.

Example 92

(N-(2-(1-(7H-pyrrolo[2,3-d]pyrimidin-4-yl)piperidin-3-ylamino)-2-oxoethyl)-2-chlorobenzamide)

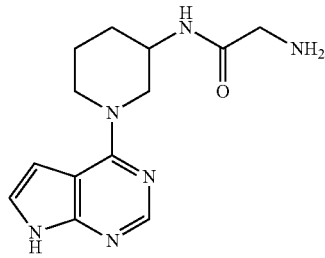 [SMILES: NCC(=O)NC1CCCN(c2ncnc3[nH]ccc23)C1]

N-(1-(7H-pyrrolo[2,3-d]pyrimidin-4-yl)piperidin-3-yl)-2-aminoacetamide

To a solution of 2-(tert-butoxycarbonylamino)acetic acid (0.7 g, 4 mmol), HATU (1.5 g, 4 mmol), Et$_3$N (1.1 mL, 4 mmol) in DMF (60 mL) was added N-benzyl-1-(7-tosyl-7H-pyrrolo[2,3-d]pyrimidin-4-yl)piperidin-3-amine (1.8 g, 40 mmol). After stirring at RT for 4 h, the solution was diluted with EtOAc and washed with water, aq. citric acid and aq. NaHCO$_3$. The organic phase was dried (Na$_2$SO$_4$), filtered and concentrated in vacuo to afford a residue which was purified by column chromatography (silica gel, gradient EtOAc in hexanes) to a solid. The Boc protected amine was dissolved in 1,4-dioxane (10 mL) and treated with 4 N HCl (10 equiv.) at rt for 5 h. The solvent was concentrated in vacuo to afford N-(1-(7H-pyrrolo[2,3-d]pyrimidin-4-yl)piperidin-3-yl)-2-aminoacetamide as a solid which was used without any additional purification.

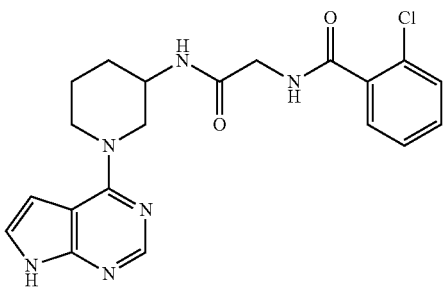 [SMILES: O=C(CNC(=O)c1ccccc1Cl)NC1CCCN(c2ncnc3[nH]ccc23)C1]

(N-(2-(1-(7H-pyrrolo[2,3-d]pyrimidin-4-yl)piperidin-3-ylamino)-2-oxoethyl)-2-chlorobenzamide)

To a solution of N-(1-(7H-pyrrolo[2,3-d]pyrimidin-4-yl)piperidin-3-yl)-2-aminoacetamide (0.25 mmol) in DMF (3 mL) can be added 2-chlorobenzoic acid (0.25 mmol), HOBt (0.25 mmol), EDCI (0.25 mmol), and DIEA (0.50 mmol) in DMF (3 mL). The reaction mixture can be stirred at RT overnight. The reaction mixture can be concentrated in vacuo and the residue purified by reverse phase chromatography C$_{18}$ column and 10% acetonitrile/water containing 0.1% TFA to afford the title compound 92. $^1$H NMR (400 MHz, CD$_3$OD) δ 8.29 (s, 1H), 7.55 (d, 1H), 7.47 (s, 2H), 7.37 (m, 2H), 6.62 (m, 1H), 7.12 (d, 1H), 4.54 (d, 1H), 4.30 (d, 1H), 4.08 (m, 1H), 4.00 (s, 2H), 3.75-3.65 (m, 2H), 2.15-2.04 (m, 2H), 1.82 (m, 2H). EIMS (m/z): calcd. for $C_{19}H_{23}ClN_6O_2$ ($M^+$)+1 414.4.

Examples 93-99 were prepared according to the method outlined in example 92 above.

Example 93

(N-(2-(1-(7H-pyrrolo[2,3-d]pyrimidin-4-yl)piperi-din-3-ylamino)-2-oxoethyl)-3-chlorobenzamide)

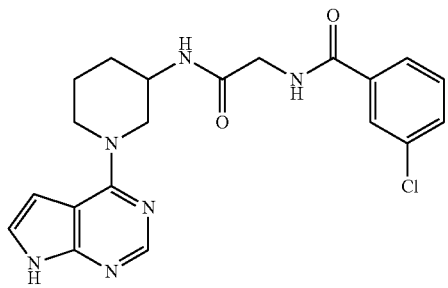 [SMILES: O=C(CNC(=O)c1cccc(Cl)c1)NC1CCCN(c2ncnc3[nH]ccc23)C1]

The title compound of Example 93 was prepared in similar manner as described in Example 92 except 2-chlorobenzoic acid was substituted for 3-chlorobenzoic acid. $^1$H NMR (400 MHz, CD$_3$OD) δ 8.27 (s, 1H), 7.85 (s, 1H), 7.77 (d, 2H), 7.75 (d, 1H), 7.56 (d, 1H), 7.47 (m, 2H), 7.34 (s, 1H), 7.10 (d, 1H), 4.54 (d, 1H), 4.30 (d, 1H), 4.31 (m, 1H), 4.01 (d, 2H), 3.75-3.65 (m, 2H), 2.15-2.04 (m, 2H), 1.82 (m, 2H). EIMS (m/z): calcd. for C$_{19}$H$_{23}$ClN$_6$O$_2$ (M$^+$)+1 414.4.

Example 94

(N-(2-(1-(7H-pyrrolo[2,3-d]pyrimidin-4-yl)piperi-din-3-ylamino)-2-oxoethyl)-4-chlorobenzamide)

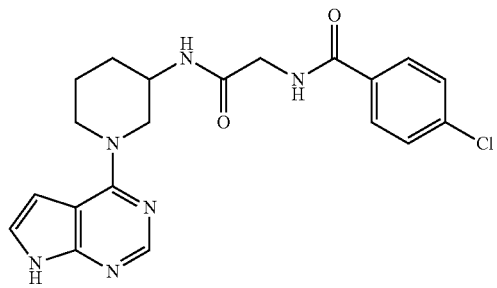 [SMILES: O=C(CNC(=O)c1ccc(Cl)cc1)NC1CCCN(c2ncnc3[nH]ccc23)C1]

The title compound of Example 94 was prepared in similar manner as described in Example 92 except 2-chlorobenzoic acid was substituted for 4-chlorobenzoic acid. $^1$H NMR (400 MHz, CD$_3$OD) δ 8.27 (s, 1H), 7.84 (d, 2H), 7.50 (d, 2H), 7.34 (s, 1H), 7.10 (s, 1H), 4.54 (d, 1H), 4.30 (d, 1H), 4.31 (m, 1H), 4.01 (d, 2H), 3.75-3.65 (m, 2H), 2.15-2.04 (m, 2H), 1.82 (m, 2H). EIMS (m/z): calcd. for C$_{19}$H$_{23}$ClN$_6$O$_2$ (M$^+$)+1 414.4.

Example 95

(N-(2-(1-(7H-pyrrolo[2,3-d]pyrimidin-4-yl)piperi-din-3-ylamino)-2-oxoethyl)-4-tert-butylbenzamide)

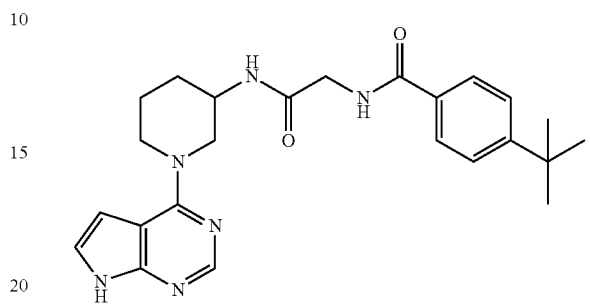

The title compound of Example 95 was prepared in similar manner as described in Example 92 except 2-chlorobenzoic acid was substituted for 4-tert-butylbenzoic acid. $^1$H NMR (400 MHz, CD$_3$OD) δ 8.27 (s, 1H), 7.78 (d, 2H), 7.51 (d, 2H), 7.34 (s, 1H), 7.10 (s, 1H), 4.54 (d, 1H), 4.30 (d, 1H), 4.31 (m, 1H), 4.01 (d, 2H), 3.75-3.65 (m, 2H), 2.15-2.04 (m, 2H), 1.82 (m, 2H). EIMS (m/z): calcd. for C$_{24}$H$_{30}$N$_6$O$_2$ (M$^+$)+1 435.4.

Example 96

(N-(1-(7H-pyrrolo[2,3-d]pyrimidin-4-yl)piperidin-3-yl)-2-(2-phenylacetamido)acetamide)

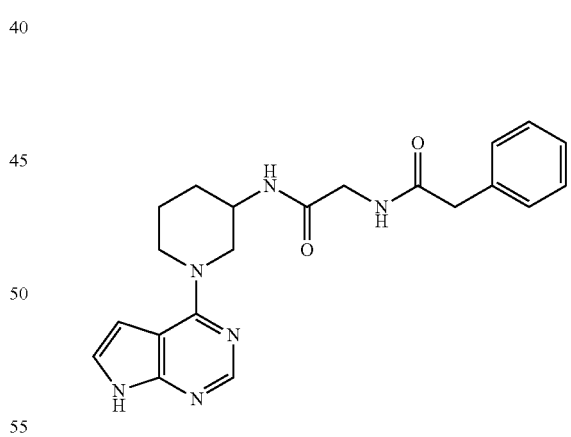

The title compound of Example 96 was prepared in similar manner as described in Example 92 except 2-chlorobenzoic acid was substituted for 2-phenylacetic acid. $^1$H NMR (400 MHz, CD$_3$OD) δ 8.17 (s, 1H), 7.26-7.22 (m, 6H), 7.15 (s, 1H), 7.01 (s, 1H), 4.42 (d, 1H), 4.25 (d, 1H), 3.95 (m, 1H), 3.72 (d, 2H), 4.00 (s, 2H), 3.48 (d, 2H), 3.51-3.42 (m, 2H), 2.05-1.89 (m, 2H), 1.71-1.65 (m, 2H). EIMS (m/z): calcd. for C$_{21}$H$_{24}$N$_6$O$_2$ (M$^+$)+1 394.5.

Example 97

(N-(2-(1-(7H-pyrrolo[2,3-d]pyrimidin-4-yl)piperidin-3-ylamino)-2-oxoethyl)-1-naphthamide)

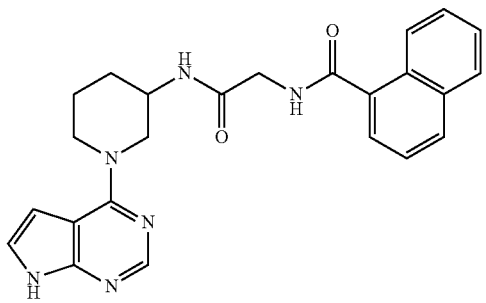 [SMILES: O=C(CNC(=O)c1cccc2ccccc12)NC1CCCN(c2ncnc3[nH]ccc23)C1]

The title compound of Example 97 was prepared in similar manner as described in Example 92 except 2-chlorobenzoic acid was substituted for 1-naphthoic acid. $^1$H NMR (400 MHz, CD$_3$OD) δ 8.32 (d, 1H), 8.26 (s, 1H), 7.98 (d, 1H), 7.90 (s, 1H), 7.71 (d, 2H), 7.53-7.62 (m, 3H), 7.33 (s, 1H), 7.12 (s, 1H), 4.55 (d, 1H), 4.33 (d, 1H), 4.09 (s, 2H), 3.71-3.63 (m, 2H), 2.14-2.03 (m, 2H), 1.84-1.80 (m, 2H). EIMS (m/z): calcd. for C$_{24}$H$_{24}$N$_6$O$_2$(M+1) 429.6.

Example 98

(N-(2-(1-(7H-pyrrolo[2,3-d]pyrimidin-4-yl)piperidin-3-ylamino)-2

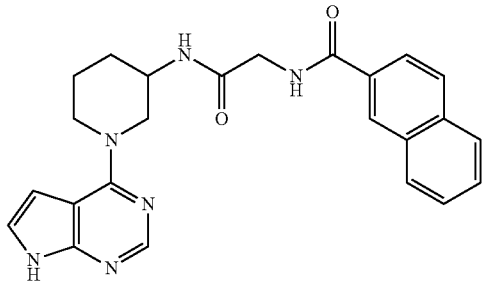 [SMILES: O=C(CNC(=O)c1ccc2ccccc2c1)NC1CCCN(c2ncnc3[nH]ccc23)C1]

The title compound of Example 98 was prepared in similar manner as described in Example 92 except 2-chlorobenzoic acid was substituted for 2-naphthoic acid. $^1$H NMR (400 MHz, CD$_3$OD) δ 8.41 (s, 1H), 8.27 (s, 1H), 8.00-7.90 (m, 6H), 7.60 (m, 2H), 7.32 (s, 1H), 7.12 (s, 1H), 4.55 (d, 1H), 4.33 (d, 1H), 4.07 (d, 2H), 3.71-3.63 (m, 2H), 2.14-2.03 (m, 2H), 1.84-1.80 (m, 2H). EIMS (m/z): calcd. for C$_{24}$H$_{24}$N$_6$O$_2$ (M+1) 429.6.

Example 99

(N-(2-(1-(7H-pyrrolo[2,3-d]pyrimidin-4-yl)piperidin-3-ylamino)-2-oxoethyl)cyclohexanecarboxamide)

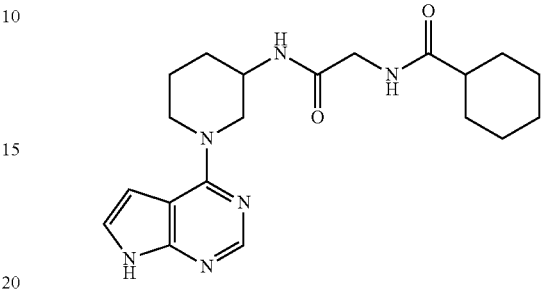

The title compound of Example 98 was prepared in similar manner as described in Example 92 except 2-chlorobenzoic acid was substituted for cyclohexanecarboxylic acid. $^1$H NMR (400 MHz, CD$_3$OD) δ 8.30 (s, 1H), 7.37 (s, 1H), 7.10 (s, 1H), 4.51 (d, 1H), 4.34 (d, 1H), 4.02 (s, 2H), 3.78 (d, 2H), 3.67-3.57 (m, 2H), 2.25-2.20 (m, 1H), 2.05-1.89 (m, 2H), 1.82-1.79 (m, 8H), 1.71-1.68 (m, 2H), 1.14-1.26 (m, 4H). EIMS (m/z): calcd. for C$_{20}$H$_{28}$N$_6$O$_2$ (M+1) 386.5.

Example 100

(R)—N—((R)-1-(7H-pyrrolo[2,3-d]pyrimidin-4-yl)piperidin-3-yl)-2-(phenylamino)propanamide

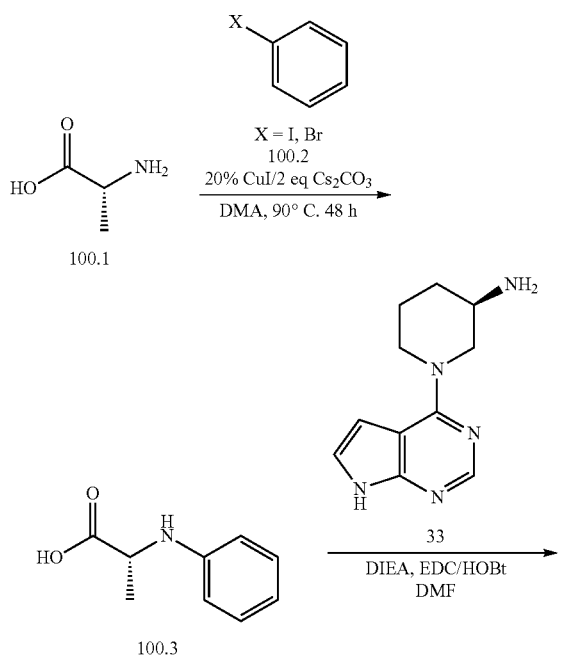

101
-continued

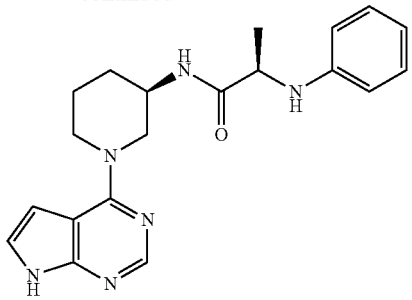

100

(R)-2-(phenylamino)propanoic acid

A solution of (R)-2-aminopropanoic acid (89 mg, 1 mmol), iodobenzene (203 mg, 1.0 mmol), Cs$_2$CO$_3$ (0.65 g, 2 mmol), and CuI (7 mg, 0.04 mmol) in DMF (2 mL) can be heated at 90° C. for 12 h under an atmosphere of nitrogen. The solution can be cooled to rt and diluted with EtOAc-water (2:1, 15 mL) and adjusted to pH 3-5 by added concentrated HCl. The organic layer can be separated, washed with brine, dried (Na$_2$SO$_4$), filtered, and concentrated in vacuo to afford the title intermediate as an oil, which can be used without further purification.

((R)—N—((R)-1-(7H-pyrrolo[2,3-d]pyrimidin-4-yl)piperidin-3-yl)-2-(phenylamino)propanamide). To a solution of (R)-2-(phenylamino)propanoic acid (49 mg, 0.3 mmol) and (R)-1-(7H-pyrrolo[2,3-d]pyrimidin-4-yl)piperidin-3-amine (65 mg, 0.3 mmol) in DMF (2 mL) was added DIEA (116 mg, 156 uL, 0.9 mmol), EDCI (50 mg, 0.33 mmol), and HOBt (44 mg, 0.33 mmol). The resulting solution was then stirred at rt for 1 h. The solvent was removed in vacuo to afford a residue, which was purified by reverse phase chromatography C$_{18}$ column and 10% acetonitrile/water containing 0.1% TFA to afford the title compound. $^1$H NMR (400 MHz, CD$_3$OD) δ 1.39 (d, J=6.85 Hz, 3H), 1.73 (m, 3H), 1.96 (d, J=6.36 Hz, 1H), 3.58 (m, 2H), 3.77 (d, J=6.85 Hz, 1H), 3.95 (s, 1H), 4.10 (m, 2H), 6.53 (d, J=7.83 Hz, 2H), 6.62 (m, 2H), 7.04 (t, J=7.34 Hz, 2H), 7.10 (s, 1H), 8.05 (s, 1H). EIMS (m/z): 364 (M+1).

Examples 101-132 were prepared according to the method outlined in example 100 above.

Example 101

(2R)—N-(1-(7H-pyrrolo[2,3-d]pyrimidin-4-yl)piperidin-3-yl)-2-(phenylamino)propanamide

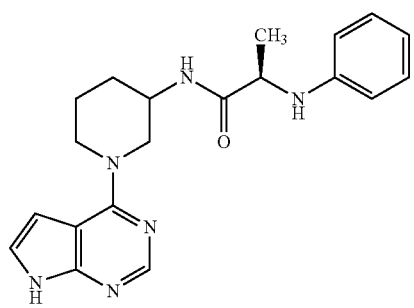 [SMILES: C[C@@H](Nc1ccccc1)C(=O)NC1CCCN(c2ncnc3[nH]ccc23)C1]

The title compound of Example 101 was prepared in similar manner as described in Example 100 except (R)-1-(7H-pyrrolo[2,3-d]pyrimidin-4-yl)piperidin-3-amine was substituted for 1-(7H-pyrrolo[2,3-d]pyrimidin-4-yl)piperidin-3-amine. $^1$H NMR (400 MHz, CD$_3$OD) δ 1.40 (d, J=7.34 Hz, 3H), 1.77 (s, 2H), 2.01 (m, 2H), 3.68 (d, J=9.29 Hz, 2H), 3.84 (m, 1H), 3.99 (d, J=22.01 Hz, 1H), 4.22 (m, 2H), 6.60 (m, 2H), 6.69 (t, J=7.09 Hz, 1H), 6.97 (d, J=10.76 Hz, 1H), 7.05 (m, 2H), 7.34 (d, J=18.10 Hz, 1H), 8.23 (d, J=11.74 Hz, 1H). EIMS (m/z): 364 (M+1).

Example 102

(2S)—N-(1-(7H-pyrrolo[2,3-d]pyrimidin-4-yl)piperidin-3-yl)-2-(phenylamino)propanamide

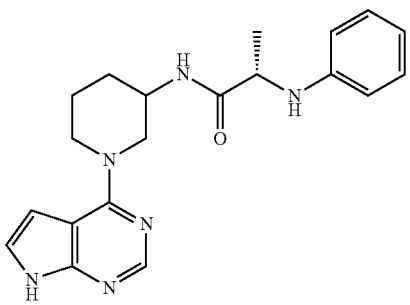 [SMILES: C[C@H](Nc1ccccc1)C(=O)NC1CCCN(c2ncnc3[nH]ccc23)C1]

The title compound of Example 102 was prepared in similar manner as described in Example 100 except (R)-2-aminopropanoic acid was substituted for (S)-2-aminopropanoic acid. $^1$H NMR (400 MHz, CD$_3$OD) δ 1.41 (d, J=6.85 Hz, 3H), 1.78 (m, 2H), 1.94 (m, 2H), 3.71 (m, 2H), 3.81 (m, 1H), 4.04 (m, 1H), 4.28 (m, 2H), 6.52 (m, 2H), 6.63 (t, J=7.34 Hz, 1H), 7.00 (m, 3H), 7.35 (d, J=20.54 Hz, 1H), 8.23 (d, J=12.23 Hz, 1H). EIMS (m/z): 364 (M+1).

Example 103

(R)—N—((R)-1-(7H-pyrrolo[2,3-d]pyrimidin-4-yl)piperidin-3-yl)-3-methyl-2-(phenylamino)butanamide

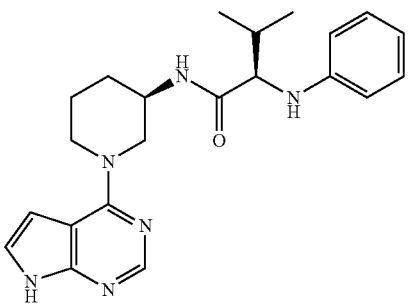 [SMILES: CC(C)[C@@H](Nc1ccccc1)C(=O)N[C@@H]1CCCN(c2ncnc3[nH]ccc23)C1]

The title compound of Example 103 was prepared in similar manner as described in Example 100 except (R)-2-aminopropanoic acid was substituted for (R)-3-methyl-2-aminobutanoic acid. $^1$H NMR (400 MHz, CD$_3$OD) δ 0.20 (s, 2H), 0.36 (s, 1H), 0.51 (d, J=20.05 Hz, 2H), 2.00 (m, 1H), 2.10 (s, 1H), 2.46 (s, 1H), 2.61 (d, J=13.69 Hz, 1H), 2.73 (d, J=13.21 Hz, 1H), 5.03 (m, 3H), 5.44 (m, 3H), 5.80 (s, 1H), 6.64 (s, 1H). EIMS (m/z): 393 (M+1).

Example 104

(R)—N—((R)-1-(7H-pyrrolo[2,3-d]pyrimidin-4-yl)piperidin-3-yl)-3-phenyl-2-(phenylamino)propanamide

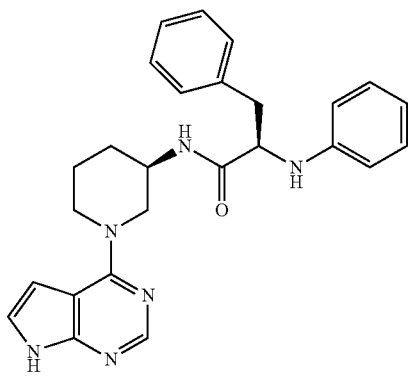 [SMILES: O=C(N[C@@H]1CCCN(c2ncnc3[nH]ccc23)C1)[C@@H](Cc1ccccc1)Nc1ccccc1]

The title compound of Example 104 was prepared in similar manner as described in Example 100 except (R)-2-aminopropanoic acid was substituted for (R)-3-phenyl-2-aminopropanoic acid. $^1$H NMR (400 MHz, CD$_3$OD) δ 1.67 (m, 2H), 1.87 (d, J=13.69 Hz, 1H), 1.96 (d, J=8.31 Hz, 1H), 3.08 (d, J=6.85 Hz, 2H), 3.56 (t, J=10.52 Hz, 1H), 3.94 (s, 1H), 4.09 (t, J=7.09 Hz, 2H), 4.21 (d, J=12.23 Hz, 2H), 6.59 (d, J=7.83 Hz, 1H), 6.66 (t, J=6.85 Hz, 1H), 6.97 (d, J=2.93 Hz, 1H), 7.04 (t, J=7.58 Hz, 2H), 7.20 (s, 1H), 7.27 (d, J=3.42 Hz, 5H), 7.39 (s, 1H), 8.23 (s, 1H). EIMS (m/z): 440 (M+1).

Example 105

(R)—N—((R)-1-(7H-pyrrolo[2,3-d]pyrimidin-4-yl)piperidin-3-yl)-4-methyl-2-(phenylamino)pentanamide

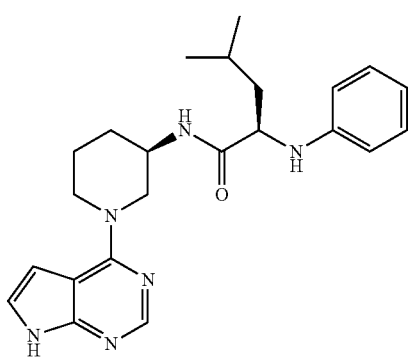 [SMILES: CC(C)C[C@@H](Nc1ccccc1)C(=O)N[C@@H]1CCCN(c2ncnc3[nH]ccc23)C1]

The title compound of Example 105 was prepared in similar manner as described in Example 100 except (R)-2-aminopropanoic acid was substituted for (R)-4-methyl-2-aminopentanoic acid. $^1$H NMR (400 MHz, CD$_3$OD) δ 0.89 (dd, J=28.37, 6.36 Hz, 6H), 1.57 (s, 2H), 1.72 (m, 3H), 1.97 (m, 2H), 3.75 (m, 3H), 4.03 (m, 2H), 4.18 (d, J=13.21 Hz, 1H), 6.58 (d, J=7.83 Hz, 1H), 6.67 (t, J=7.34 Hz, 1H), 6.94 (s, 1H), 7.03 (t, J=7.34 Hz, 3H), 7.35 (s, 1H), 8.20 (s, 1H). EIMS (m/z): 407 (M+1).

Example 106

(R)—N—((R)-1-(7H-pyrrolo[2,3-d]pyrimidin-4-yl)piperidin-3-yl)-2-phenyl-2-(phenylamino)acetamide

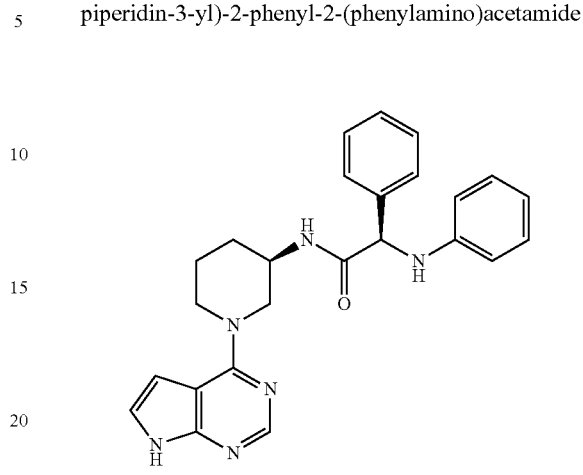

The title compound of Example 106 was prepared in similar manner as described in Example 100 except (R)-2-aminopropanoic acid was substituted for (R)-2-phenyl-2-aminoacetic acid. $^1$H NMR (400 MHz, CD$_3$OD) δ 1.64 (dd, J=8.56, 3.18 Hz, 1H), 1.77 (dd, J=20.05, 8.31 Hz, 3H), 1.97 (d, J=6.85 Hz, 1H), 3.49 (dd, J=12.96, 7.58 Hz, 1H), 3.59 (m, 1H), 3.95 (s, 1H), 4.08 (t, J=11.98 Hz, 2H), 6.54 (m, 1H), 6.63 (m, 3H), 7.05 (m, 3H), 7.27 (d, J=5.87 Hz, 3H), 7.41 (d, J=6.85 Hz, 2H), 8.03 (s, 1H). EIMS (m/z): 427 (M+1).

Example 107

(R)—N—((R)-1-(7H-pyrrolo[2,3-d]pyrimidin-4-yl)piperidin-3-yl)-2-cyclopropyl-2-(phenylamino)acetamide

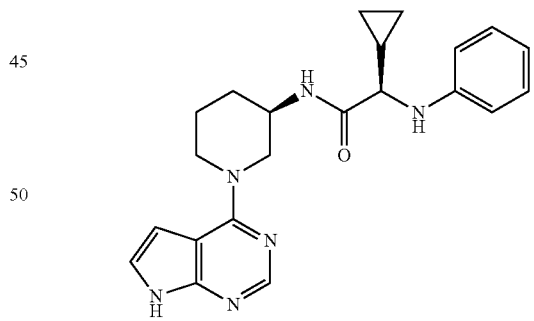

The title compound of Example 107 was prepared in similar manner as described in Example 100 except (R)-2-aminopropanoic acid was substituted for (R)-2-cyclopropyl-2-aminoacetic acid. $^1$H NMR (400 MHz, CD$_3$OD) δ 0.35 (dd, J=9.29, 4.89 Hz, 1H), 0.49 (m, 2H), 0.64 (d, J=4.40 Hz, 1H), 1.14 (m, 1H), 1.75 (m, 2H), 1.97 (m, 2H), 3.14 (d, J=8.80 Hz, 1H), 3.67 (m, 2H), 4.00 (s, 1H), 4.15 (d, J=13.21 Hz, 1H), 4.29 (d, J=13.21 Hz, 1H), 6.71 (d, J=7.83 Hz, 2H), 6.80 (t, J=7.34 Hz, 1H), 6.99 (d, J=2.93 Hz, 1H), 7.11 (t, J=7.58 Hz, 2H), 7.36 (d, J=2.93 Hz, 1H), 8.23 (s, 1H). EIMS (m/z): 391 (M+1).

Example 108

(R)—N—((R)-1-(7H-pyrrolo[2,3-d]pyrimidin-4-yl)piperidin-3-yl)-3,3-dimethyl-2-(phenylamino)butanamide

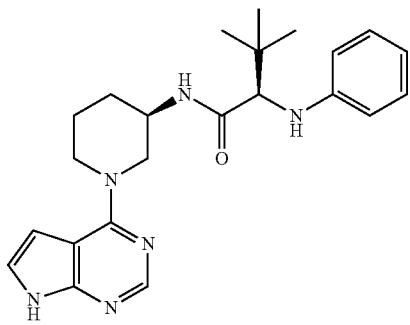 [SMILES: CC(C)(C)[C@@H](Nc1ccccc1)C(=O)N[C@@H]1CCCN(c2ncnc3[nH]ccc23)C1]

The title compound of Example 108 was prepared in similar manner as described in Example 100 except (R)-2-aminopropanoic acid was substituted for (R)-3,3-dimethyl-2-aminobutanoic acid. ¹H NMR (400 MHz, CD₃OD) δ 1.04 (d, J=22.99 Hz, 9H), 1.77 (m, 2H), 1.99 (m, 2H), 3.50 (dd, J=12.47, 9.05 Hz, 1H), 3.61 (m, 2H), 4.01 (s, 1H), 4.25 (d, J=13.21 Hz, 1H), 4.37 (d, J=13.21 Hz, 1H), 6.64 (d, J=7.83 Hz, 3H), 7.04 (m, 3H), 7.38 (s, 1H), 8.24 (s, 1H). EIMS (m/z): 407 (M+1).

Example 109

(R)—N—((R)-1-(7H-pyrrolo[2,3-d]pyrimidin-4-yl)piperidin-3-yl)-2-cyclohexyl-2-(phenylamino)acetamide

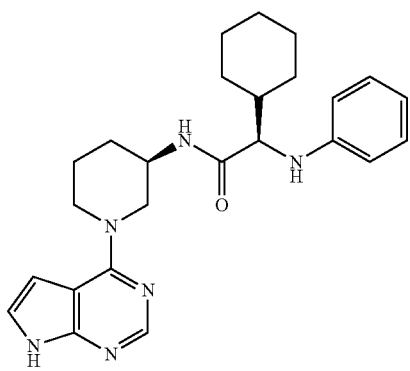 [SMILES: O=C(N[C@@H]1CCCN(c2ncnc3[nH]ccc23)C1)[C@H](Nc1ccccc1)C1CCCCC1]

The title compound of Example 109 was prepared in similar manner as described in Example 100 except (R)-2-aminopropanoic acid was substituted for (R)-2-cyclohexyl-2-aminoacetic acid. ¹H NMR (400 MHz, CD₃OD) δ 1.19 (m, 5H), 1.70 (m, 7H), 1.96 (m, 3H), 3.64 (m, 2H), 3.73 (m, 1H), 4.01 (s, 1H), 4.14 (d, J=13.21 Hz, 1H), 4.26 (d, J=13.21 Hz, 1H), 6.64 (m, 3H), 6.97 (d, J=2.45 Hz, 1H), 7.04 (t, J=7.34 Hz, 2H), 7.37 (d, J=2.93 Hz, 1H). EIMS (m/z): 433 (M+1).

Example 110

(2R,3R)—N—((R)-1-(7H-pyrrolo[2,3-d]pyrimidin-4-yl)piperidin-3-yl)-3-hydroxy-2-(phenylamino)butanamide

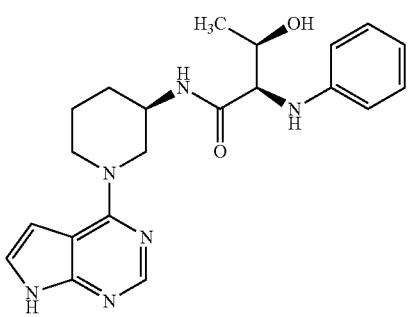 [SMILES: C[C@@H](O)[C@@H](Nc1ccccc1)C(=O)N[C@@H]1CCCN(c2ncnc3[nH]ccc23)C1]

The title compound of Example 110 was prepared in similar manner as described in Example 100 except (R)-2-aminopropanoic acid was substituted for (2R,3R)-3-hydroxy-2-aminobutanoic acid. ¹H NMR (400 MHz, CD₃OD) δ 0.26 (d, J=6.36 Hz, 3H), 0.74 (m, 3H), 0.98 (d, J=6.36 Hz, 1H), 2.52 (m, 2H), 2.77 (d, J=4.40 Hz, 1H), 2.99 (s, 1H), 3.18 (m, 2H), 5.65 (m, 4H), 6.10 (m, 3H), 7.06 (s, 1H). EIMS (m/z): 395 (M+1).

Example 111

(2R,3S)—N—((R)-1-(7H-pyrrolo[2,3-d]pyrimidin-4-yl)piperidin-3-yl)-3-hydroxy-2-(phenylamino)butanamide

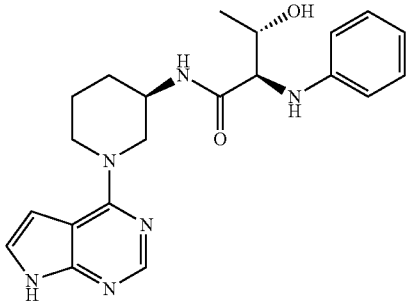 [SMILES: C[C@H](O)[C@@H](Nc1ccccc1)C(=O)N[C@@H]1CCCN(c2ncnc3[nH]ccc23)C1]

The title compound of Example 111 was prepared in similar manner as described in Example 100 except (R)-2-aminopropanoic acid was substituted for (2R,3S)-3-hydroxy-2-aminobutanoic acid. ¹H NMR (400 MHz, CD₃OD) δ 1.23 (d, J=6.36 Hz, 3H), 1.73 (d, J=5.87 Hz, 2H), 1.88 (s, 1H), 1.96 (d, J=10.27 Hz, 1H), 3.71 (m, 3H), 4.01 (s, 1H), 4.10 (d, J=13.21 Hz, 1H), 4.17 (m, 1H), 4.25 (d, J=13.21 Hz, 1H), 6.71 (d, J=7.83 Hz, 2H), 6.79 (t, J=7.34 Hz, 1H), 6.94 (s, 1H), 7.10 (t, J=7.34 Hz, 2H), 7.33 (s, 1H), 8.21 (s, 1H). EIMS (m/z): 395 (M+1).

Example 112

(R)—N—((R)-1-(7H-pyrrolo[2,3-d]pyrimidin-4-yl) piperidin-3-yl)-2-(3-chlorophenylamino)-3-methylbutanamide

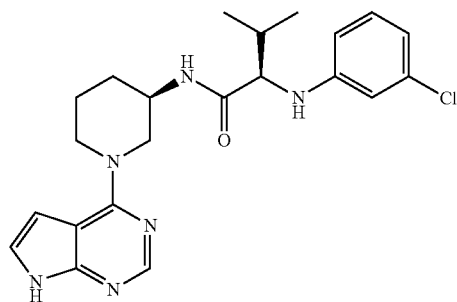

The title compound of Example 112 was prepared in similar manner as described in Example 100 except (R)-2-aminopropanoic acid was substituted for (R)-3-methyl-2-aminobutanoic acid. $^1$H NMR (400 MHz, CD$_3$OD) δ 1.01 (dd, J=17.36, 6.60 Hz, 6H), 1.77 (m, 2H), 1.96 (s, 1H), 2.05 (m, 2H), 3.54 (m, 2H), 3.63 (d, J=10.27 Hz, 1H), 4.02 (s, 1H), 4.20 (d, J=12.72 Hz, 1H), 4.31 (d, J=12.72 Hz, 1H), 6.46 (d, J=8.31 Hz, 1H), 6.53 (d, J=7.83 Hz, 1H), 6.57 (s, 1H), 6.94 (m, 3H), 7.32 (s, 1H), 8.22 (s, 1H) ppm. EIMS (m/z): 427 (M+1).

Example 113

(R)—N—((R)-1-(7H-pyrrolo[2,3-d]pyrimidin-4-yl) piperidin-3-yl)-2-(3,5-dichlorophenylamino)-3-hydroxy-3-methylbutanamide

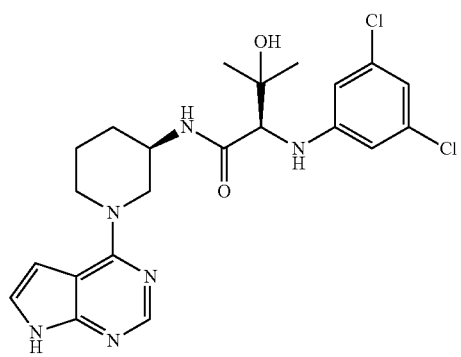 [SMILES: CC(C)(O)[C@@H](Nc1cc(Cl)cc(Cl)c1)C(=O)N[C@@H]1CCCN(c2ncnc3[nH]ccc23)C1]

The title compound of Example 113 was prepared in similar manner as described in Example 100 except (R)-2-aminopropanoic acid was substituted for (R)-3-hydroxy-3-methyl-2-aminobutanoic acid. $^1$H NMR (300 MHz, MeOD) δ 8.17 (s, 1H), 8.12 (s, 1H), 7.24 (d, J=3.78 Hz, 1H), 7.14 (d, J=3.40 Hz, 1H), 6.91 (d, J=3.40 Hz, 1H), 6.78 (d, J=3.78 Hz, 1H), 6.47 (s, 1H), 6.43 (d, J=1.51 Hz, 2H), 6.35 (d, J=1.89 Hz, 3H), 4.26 (dd, J=3.21, 13.41 Hz, 1H), 4.02-4.18 (m, 2H), 3.81-4.02 (m, 5H), 3.58-3.72 (m, 6H), 1.62-1.82 (m, 5H), 1.21 (s, 6H). EIMS (m/z): calcd. for C$_{22}$H$_{26}$C$_{12}$FN$_6$O$_2$ (M+H) 477. found 477.

Example 114

(R)—N—((R)-1-(7H-pyrrolo[2,3-d]pyrimidin-4-yl) piperidin-3-yl)-2-(phenylamino)butanamide

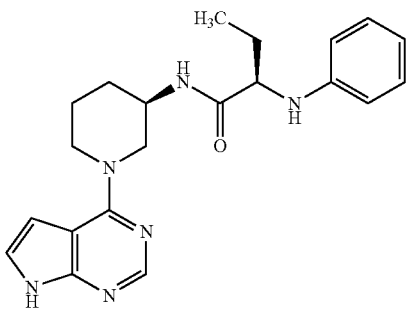 [SMILES: CC[C@@H](Nc1ccccc1)C(=O)N[C@@H]1CCCN(c2ncnc3[nH]ccc23)C1]

The title compound of Example 114 was prepared in similar manner as described in Example 100 except (R)-2-aminopropanoic acid was substituted for (R)-2-aminobutanoic acid. $^1$H NMR (400 MHz, CD$_3$OD) δ 0.99 (t, J=6.85 Hz, 3H), 1.78 (m, 4H), 1.90 (m, 1H), 2.02 (s, 1H), 3.63 (m, 3H), 4.00 (s, 1H), 4.11 (s, 1H), 4.26 (d, J=13.21 Hz, 1H), 6.54 (d, J=7.34 Hz, 2H), 6.62 (s, 1H), 6.99 (m, 3H), 7.34 (s, 1H), 8.19 (s, 1H). EIMS (m/z): calcd. for C$_{21}$H$_{26}$N$_6$O (M+H) 379. found 379 (M+H).

Example 115

(2R,3S)—N—((R)-1-(7H-pyrrolo[2,3-d]pyrimidin-4-yl)piperidin-3-yl)-3-methyl-2-(phenylamino)pentanamide

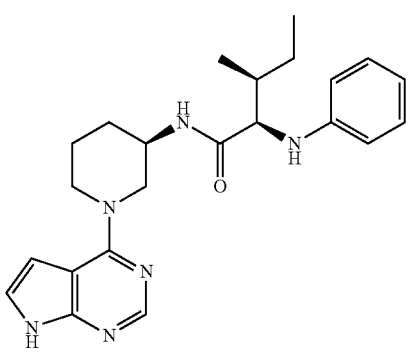 [SMILES: CC[C@H](C)[C@@H](Nc1ccccc1)C(=O)N[C@@H]1CCCN(c2ncnc3[nH]ccc23)C1]

The title compound of Example 115 was prepared in similar manner as described in Example 100 except (R)-2-aminopropanoic acid was substituted for (2R,3S)-3-methyl-2-aminopentanoic acid. $^1$H NMR (400 MHz, CD$_3$OD) δ 0.75 (m, 3H), 0.85 (t, J=6.85 Hz, 3H), 1.15 (d, J=6.85 Hz, 1H), 1.33 (m, 1H), 1.63 (s, 2H), 1.85 (m, 3H), 3.56 (m, 3H), 3.87 (d, J=26.41 Hz, 2H), 4.09 (m, 1H), 6.46 (m, 3H), 6.84 (m, 3H), 7.19 (d, J=22.01 Hz, 1H), 8.07 (d, J=13.21 Hz, 1H). EIMS (m/z): 407 (M+1).

Example 116

(R)—N—((R)-1-(7H-pyrrolo[2,3-d]pyrimidin-4-yl)piperidin-3-yl)-4-(methylsulfonyl)-2-(phenylamino)butanamide

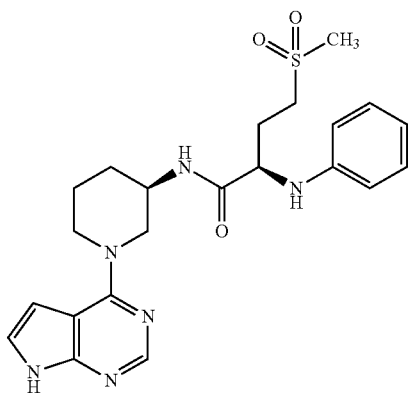 [SMILES: CS(=O)(=O)CC[C@@H](Nc1ccccc1)C(=O)N[C@@H]1CCCN(c2ncnc3[nH]ccc23)C1]

The title compound of Example 116 was prepared in similar manner as described in Example 100 except (R)-2-aminopropanoic acid was substituted for (R)-4-(methylsulfonyl)-2-aminobutanoic acid. ¹H NMR (400 MHz, CD₃OD) δ 1.81 (m, 3H), 1.96 (m, 1H), 2.09 (d, J=10.27 Hz, 2H), 2.19 (m, 1H), 2.97 (m, 3H), 3.23 (m, 1H), 3.84 (m, 2H), 3.98 (dd, J=7.58, 4.16 Hz, 1H), 4.05 (s, 2H), 4.21 (d, J=13.69 Hz, 1H), 6.57 (d, J=8.31 Hz, 2H), 6.64 (t, J=6.85 Hz, 1H), 7.03 (m, 3H), 7.37 (s, 1H), 8.25 (s, 1H). EIMS (m/z): 457 (M+1).

Example 117

(2R,3R)—N—((R)-1-(7H-pyrrolo[2,3-d]pyrimidin-4-yl)piperidin-3-yl)-3-methyl-2-(phenylamino)pentanamide

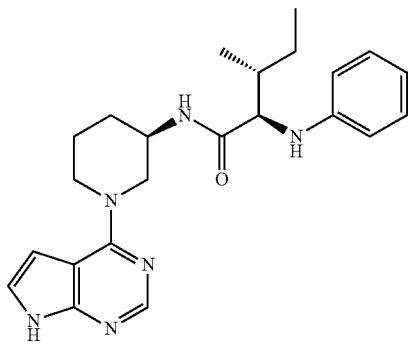 [SMILES: CC[C@@H](C)[C@@H](Nc1ccccc1)C(=O)N[C@@H]1CCCN(c2ncnc3[nH]ccc23)C1]

The title compound of Example 117 was prepared in similar manner as described in Example 100 except (R)-2-aminopropanoic acid was substituted for (2R,3R)-2-amino-3-methylpentanoic acid. ¹H NMR (400 MHz, CD₃OD) δ 0.94 (t, J=7.34 Hz, 3H), 0.99 (d, J=6.85 Hz, 3H), 1.30 (m, 1H), 1.65 (m, 1H), 1.78 (d, J=4.40 Hz, 2H), 1.87 (m, 1H), 1.96 (m, 1H), 2.05 (s, 1H), 3.63 (m, 3H), 4.04 (s, 2H), 4.19 (d, J=11.74 Hz, 1H), 4.31 (d, J=12.72 Hz, 1H), 6.62 (m, 3H), 7.02 (m, 3H), 7.38 (d, J=2.93 Hz, 1H), 8.22 (s, 1H). EIMS (m/z): 407 (M+1).

Example 118

(R)—N—((R)-1-(7H-pyrrolo[2,3-d]pyrimidin-4-yl)piperidin-3-yl)-2-(3-chloro-5-fluorophenylamino)-2-cyclopropylacetamide

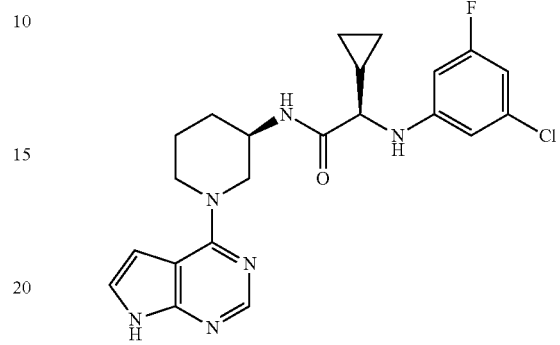

The title compound of Example 118 was prepared in similar manner as described in Example 107 except iodobenzene was substituted for 1-chloro-3-fluoro-5-iodobenzene. ¹H NMR (400 MHz, CD₃OD) δ 0.38 (d, J=4.40 Hz, 1H), 0.49 (m, 2H), 0.64 (d, J=5.38 Hz, 1H), 1.12 (d, J=4.89 Hz, 1H), 1.82 (t, J=8.56 Hz, 2H), 2.02 (s, 1H), 2.09 (d, J=13.69 Hz, 1H), 3.06 (d, J=8.31 Hz, 1H), 3.61 (dd, J=12.23, 9.29 Hz, 1H), 3.72 (d, J=8.80 Hz, 1H), 4.06 (s, 1H), 4.22 (s, 1H), 4.37 (d, J=13.21 Hz, 1H), 6.18 (d, J=11.25 Hz, 1H), 6.35 (m, 2H), 7.01 (s, 1H), 7.37 (s, 1H), 8.27 (s, 1H). EIMS (m/z): 443 (M+1).

Example 119

(R)—N—((R)-1-(7H-pyrrolo[2,3-d]pyrimidin-4-yl)piperidin-3-yl)-2-(3-chlorophenylamino)-2-cyclopropylacetamide

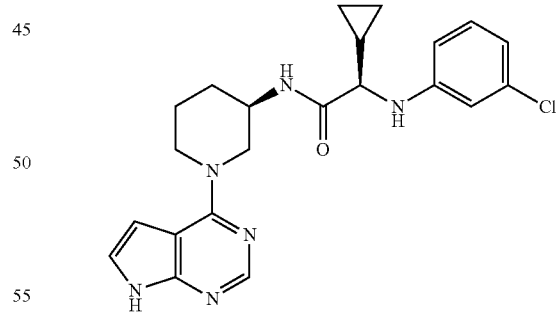

The title compound of Example 119 was prepared in similar manner as described in Example 107 except iodobenzene that was substituted for 1-chloro-3-iodobenzene. ¹H NMR (400 MHz, CD₃OD) δ 0.36 (m, 1H), 0.49 (s, 2H), 0.61 (s, 1H), 1.11 (d, J=4.40 Hz, 1H), 1.82 (m, 2H), 1.99 (s, 1H), 2.08 (d, J=7.83 Hz, 1H), 3.05 (d, J=8.31 Hz, 1H), 3.59 (dd, J=12.23, 9.29 Hz, 1H), 3.68 (d, J=9.78 Hz, 1H), 4.05 (s, 1H), 4.21 (d, J=12.23 Hz, 1H), 4.34 (d, J=13.21 Hz, 1H), 6.43 (d, J=8.31 Hz, 1H), 6.55 (m, 2H), 6.97 (m, 2H), 7.37 (s, 1H), 8.25 (s, 1H). EIMS (m/z): 425 (M+1);

Example 120

(R)—N—((R)-1-(7H-pyrrolo[2,3-d]pyrimidin-4-yl)piperidin-3-yl)-2-cyclopropyl-2-(3,5-difluorophenylamino)acetamide

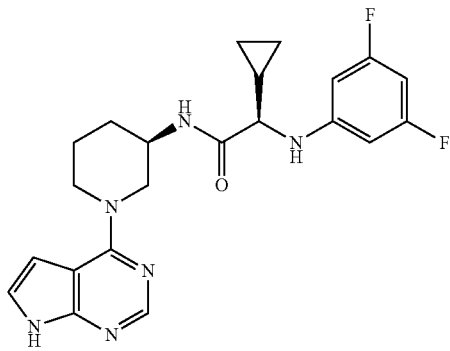 [SMILES: O=C(N[C@@H]1CCCN(c2ncnc3[nH]ccc23)C1)[C@H](Nc1cc(F)cc(F)c1)C1CC1]

The title compound of Example 120 was prepared in similar manner as described in Example 107 except iodobenzene that was substituted for 1-bromo-3,5-difluorobenzene. $^1$H NMR (400 MHz, CD$_3$OD) δ 0.36 (d, J=3.91 Hz, 1H), 0.48 (d, J=5.87 Hz, 2H), 0.62 (s, 1H), 1.10 (s, 1H), 1.82 (m, 2H), 2.10 (s, 2H), 3.05 (d, J=8.80 Hz, 1H), 3.62 (m, 1H), 3.73 (m, 1H), 4.03 (s, 1H), 4.19 (s, 1H), 4.35 (d, J=13.69 Hz, 1H), 6.07 (d, J=8.31 Hz, 3H), 6.99 (s, 1H), 7.36 (s, 1H), 8.25 (s, 1H). EIMS (m/z): 426 (M+1).

Example 121

(R)—N—((R)-1-(7H-pyrrolo[2,3-d]pyrimidin-4-yl)piperidin-3-yl)-2-cyclopropyl-2-(3-fluoro-5-(trifluoromethyl)phenylamino)acetamide

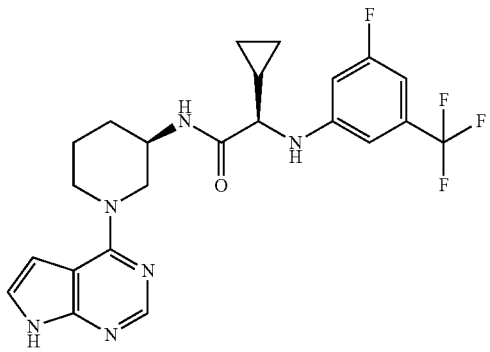 [SMILES: O=C(N[C@@H]1CCCN(c2ncnc3[nH]ccc23)C1)[C@H](Nc1cc(F)cc(C(F)(F)F)c1)C1CC1]

The title compound of Example 121 was prepared in similar manner as described in Example 107 except iodobenzene that was substituted for 1-bromo-3-fluoro-5-trifluoromethylbenzene. $^1$H NMR (400 MHz, CD$_3$OD) δ 0.38 (m, 1H), 0.47 (s, 2H), 0.63 (s, 1H), 1.14 (d, J=3.91 Hz, 1H), 1.81 (t, J=8.31 Hz, 2H), 2.06 (d, J=32.28 Hz, 2H), 3.12 (d, J=8.80 Hz, 1H), 3.57 (m, 1H), 3.67 (m, 1H), 4.04 (s, 1H), 4.27 (d, J=12.23 Hz, 1H), 4.42 (d, J=13.21 Hz, 1H), 6.45 (d, J=11.25 Hz, 1H), 6.56 (d, J=8.80 Hz, 1H), 6.65 (s, 1H), 7.02 (s, 1H), 7.36 (s, 1H), 8.27 (s, 1H). EIMS (m/z): 476 (M+1).

Example 122

(R)—N—((R)-1-(7H-pyrrolo[2,3-d]pyrimidin-4-yl)piperidin-3-yl)-5-methyl-2-(phenylamino)hexanamide

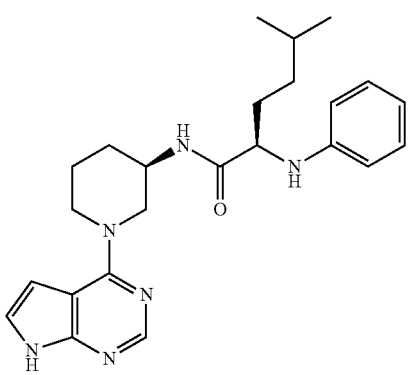 [SMILES: CC(C)CC[C@@H](Nc1ccccc1)C(=O)N[C@@H]1CCCN(c2ncnc3[nH]ccc23)C1]

The title compound of Example 122 was prepared in similar manner as described in Example 100 except (R)-2-aminopropanoic acid that was substituted for (R)-2-amino-5-methylhexanoic acid. $^1$H NMR (400 MHz, CD$_3$OD) δ 0.88 (t, J=5.87 Hz, 6H), 1.26 (m, 1H), 1.37 (m, 1H), 1.53 (m, 1H), 1.73 (m, 4H), 1.93 (s, 1H), 2.05 (t, J=9.78 Hz, 1H), 4.03 (s, 1H), 4.10 (d, J=10.76 Hz, 1H), 4.24 (d, J=13.21 Hz, 1H), 6.56 (d, J=7.34 Hz, 1H), 6.64 (t, J=7.09 Hz, 1H), 7.01 (m, 2H), 7.37 (s, 1H), 8.22 (s, 1H). EIMS (m/z): 420 (M+1).

Example 123

(N—((R)-1-(7H-pyrrolo[2,3-d]pyrimidin-4-yl)piperidin-3-yl)-4,4,4-trifluoro-2-(phenylamino)butanamide)

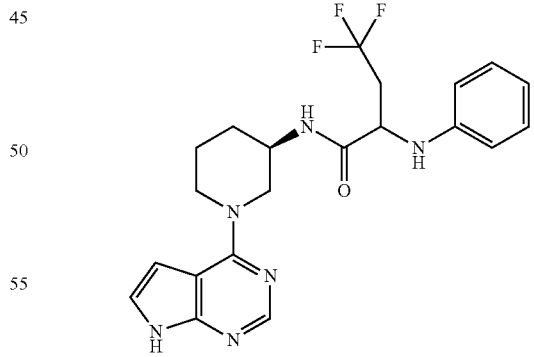

The title compound of Example 123 was prepared in similar manner as described in Example 100 except (R)-2-aminopropanoic acid that was substituted for 2-amino-4,4,4-trifluorobutanoic acid. $^1$H NMR (400 MHz, CD$_3$OD) δ 1.81 (m, 2H), 1.99 (m, 2H), 2.60 (m, 1H), 2.76 (m, 1H), 3.72 (m, 2H), 3.99 (dd, J=9.05, 4.65 Hz, 1H), 4.17 (m, 2H), 4.33 (d, J=13.21 Hz, 1H), 6.62 (m, 3H), 7.01 (m, 3H), 7.32 (d, J=26.90 Hz, 1H), 8.23 (d, J=7.34 Hz, 1H). EIMS (m/z): 433 (M+1);

Example 124

(R)—N—((R)-1-(7H-pyrrolo[2,3-d]pyrimidin-4-yl)piperidin-3-yl)-2-(3-chloro-5-fluorophenylamino)-3,3-dimethylbutanamide

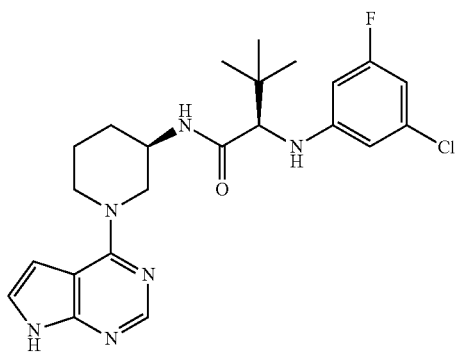 [SMILES: CC(C)(C)[C@@H](Nc1cc(F)cc(Cl)c1)C(=O)N[C@@H]1CCCN(c2ncnc3[nH]ccc23)C1]

The title compound of Example 124 was prepared in similar manner as described in Example 118 except (R)-2-amino-2-cyclopropylacetic acid that was substituted for 1 (R)-2-amino-3,3-dimethylbutanoic acid. $^1$H NMR (400 MHz, CD$_3$OD) δ 1.05 (s, 9H), 1.80 (t, J=8.80 Hz, 2H), 2.04 (m, 2H), 3.53 (dd, J=12.23, 9.29 Hz, 1H), 3.63 (m, 2H), 4.03 (s, 1H), 4.31 (d, J=12.72 Hz, 1H), 4.44 (d, J=13.21 Hz, 1H), 6.34 (m, 1H), 6.51 (s, 1H), 7.03 (s, 1H), 7.37 (s, 1H), 8.15 (d, J=6.36 Hz, 1H), 8.28 (s, 1H) ppm. EIMS (m/z): 459 (M+1).

Example 125

(R)—N—((R)-1-(7H-pyrrolo[2,3-d]pyrimidin-4-yl)piperidin-3-yl)-2-cyclopropyl-2-(3,5-dichlorophenylamino)acetamide

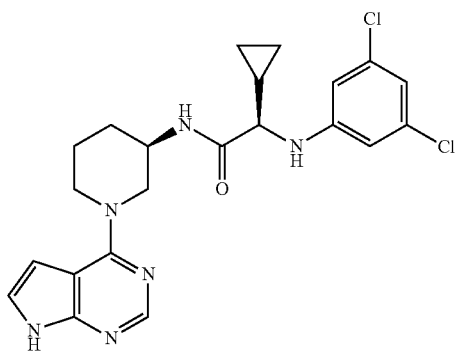

The title compound of Example 125 was prepared in similar manner as described in Example 107 except iodobenzene that was substituted for 1-bromo-3,5-dichlorobenzene. $^1$H NMR (400 MHz, CD$_3$OD) δ 0.38 (m, 1H), 0.50 (m, 2H), 0.64 (d, J=4.89 Hz, 1H), 1.12 (s, 1H), 1.84 (m, 2H), 2.07 (d, J=34.24 Hz, 2H), 3.07 (d, J=8.80 Hz, 1H), 3.59 (dd, J=12.47, 9.54 Hz, 1H), 3.70 (m, 1H), 4.07 (s, 1H), 4.24 (s, 1H), 4.39 (d, J=13.21 Hz, 1H), 6.48 (s, 2H), 6.59 (s, 1H), 7.02 (s, 1H), 7.37 (s, 1H), 8.28 (s, 1H). EIMS (m/z): 460 (M+1).

Example 126

(R)—N-(1-(7H-pyrrolo[2,3-d]pyrimidin-4-yl)piperidin-3-yl)-1-(phenylamino)cyclopropanecarboxamide

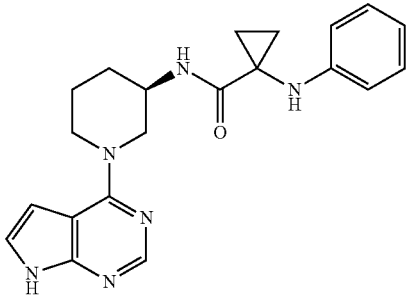 [SMILES: O=C(N[C@@H]1CCCN(c2ncnc3[nH]ccc23)C1)C1(Nc2ccccc2)CC1]

The title compound of Example 126 was prepared in similar manner as described in Example 100 except (R)-2-aminopropanoic acid that was substituted for 1 1-aminocyclopropanecarboxylic acid. $^1$H NMR (400 MHz, DMSO-d$_6$) δ 12.47 (s, 1H), 8.29 (s, 1H), 7.64 (d, J=7.3 Hz, 1H), 7.41 (s, 1H), 7.00 (t, J=7.3 Hz, 1H), 6.85 (s, 1H), 6.55 (t, J=7.3 Hz, 1H), 6.49 (d, J=7.8 Hz, 2H), 6.26 (br s, 1H), 4.22 (d, J=11.7 Hz, 1H), 4.14 (d, J=13.2 Hz, 1H), 3.85 (s, 1H), 3.42 (m, 2H), 1.65~1.78 (m, 4H), 1.37 (m, 2H), 0.87 (m, 2H). EIMS (m/z): calcd. for C$_{21}$H$_{24}$N$_6$O (M$^+$+1) 377.20. found 377.25

Example 127

(R)—N-(1-(7H-pyrrolo[2,3-d]pyrimidin-4-yl)piperidin-3-yl)-1-(phenylamino)cyclopentanecarboxamide

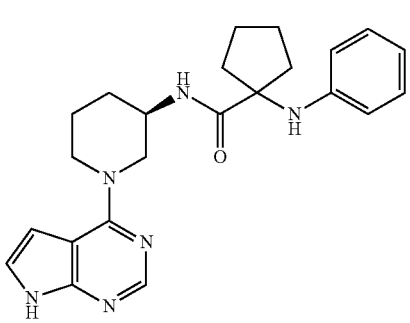 [SMILES: O=C(N[C@@H]1CCCN(c2ncnc3[nH]ccc23)C1)C1(Nc2ccccc2)CCCC1]

The title compound of Example 126 was prepared in similar manner as described in Example 100 except (R)-2-aminopropanoic acid that was substituted for 1-aminocyclopentanecarboxylic acid. $^1$H NMR (400 MHz, DMSO-d$_6$) δ 12.25 (s, 1H), 8.31 (s, 1H), 7.68 (d, J=7.3 Hz, 1H), 7.44 (s, 1H), 7.00 (t, J=7.3 Hz, 1H), 6.85 (s, 1H), 6.54 (t, J=7.1 Hz, 1H), 6.45 (d, J=7.8 Hz, 2H), 5.80 (br s, 1H), 4.24 (m, 2H), 3.82 (m, 1H), 3.21~3.33 (m, 2H), 2.11 (m, 2H), 1.56~1.76 (m, 10H). EIMS (m/z): calcd. for C$_{23}$H$_{28}$N$_6$O (M$^+$+1) 405.23. found 405.25

Example 128

(R)-N-(1-(7H-pyrrolo[2,3-d]pyrimidin-4-yl)piperidin-3-yl)-2-methyl-2-(phenylamino)propanamide

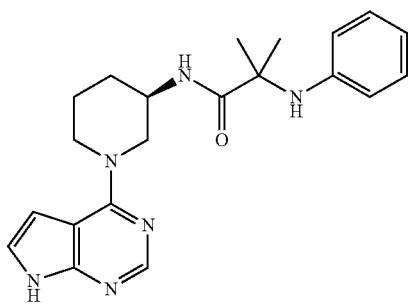 [SMILES: CC(C)(Nc1ccccc1)C(=O)N[C@@H]1CCCN(c2ncnc3[nH]ccc23)C1]

The title compound of Example 126 was prepared in similar manner as described in Example 100 except 2-amino-2-methylpropanoic acid that was substituted for 1-aminocyclopentanecarboxylic acid. $^1$H NMR (400 MHz, DMSO-$d_6$) δ 12.56 (s, 1H), 8.33 (s, 1H), 7.80 (d, J=7.3 Hz, 1H), 7.46 (s, 1H), 7.05 (t, J=7.3 Hz, 1H), 6.90 (s, 1H), 6.62 (m, 1H), 6.52 (m, 2H), 4.27~4.37 (m, 2H), 3.84 (m, 1H), 3.21~3.31 (m, 2H), 1.78 (m, 2H), 1.60 (m, 2H), 1.35 (s, 3H), 1.34 (s, 3H). EIMS (m/z): calcd. for $C_{21}H_{26}N_6O$ (M$^+$+1) 379.22. found 379.00.

Example 129

(R)—N—((R)-1-(1H-pyrazolo[3,4-d]pyrimidin-4-yl)piperidin-3-yl)-2-(3-chloro-5-fluorophenylamino)butanamide

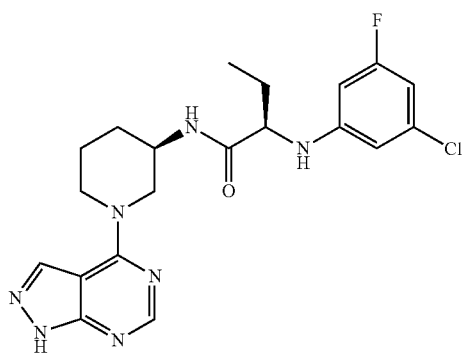

The title compound of Example 129 was prepared in similar manner as described in Example 139 except (R)-2-(3-chloro-5-fluorophenylamino)-2-cyclopropylacetic acid was substituted for (R)-2-(3-chloro-5-fluorophenylamino)butanoic acid. $^1$H NMR (400 MHz, CD$_3$OD) 13.7 (br.s., 1H), 9.13 (br.s., 1H), 8.27 (d, J=12.05 Hz, 1H), 8.14 (br.s., 1H), 7.55 (s, 1H), 7.26-7.34 (m, 1H), 6.55-6.67 (m, 1H), 6.42-6.49 (m, 1H), 3.45-3.52 (m, 1H), 2.55-2.89 (m, 4H), 1.97-2.22 (m, 2H), 1.79-1.89 (m, 2H), 1.77 (m, 2H), 0.90 (t, J=4.11, 8.06 Hz, 3H). EIMS (m/z): calcd. for $C_{20}H_{23}ClFN_7O$ (M+1H) 432.30. found 432.30.

Example 130

(R)—N—((R)-1-(1H-pyrazolo[3,4-d]pyrimidin-4-yl)piperidin-3-yl)-2-(3,5-dichlorophenylamino)butanamide

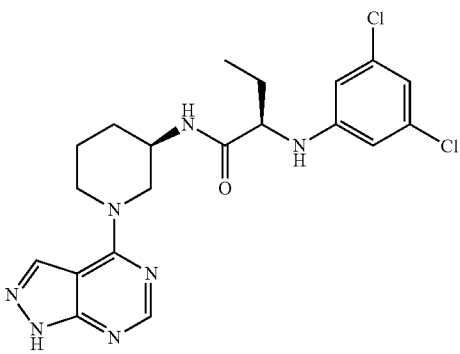 [SMILES: CC[C@@H](Nc1cc(F)cc(Cl)c1)C(=O)N[C@@H]1CCCN(c2ncnc3[nH]ncc23)C1]

The title compound of Example 130 was prepared in similar manner as described in Example 139 except (R)-2-(3-chloro-5-fluorophenylamino)-2-cyclopropylacetic acid was substituted for (R)-2-(3,5-dichlorophenylamino)butanoic acid. $^1$H NMR (400 MHz, MeOD) 13.5 (br.s., 1H), 9.17 (br.s., 1H), 8.29 (d, J=12.05 Hz, 1H), 8.14 (br.s., 1H), 7.55 (s, 1H), 7.16-7.22 (m, 1H), 6.49-6.55 (m, 1H), 6.38-6.44 (m, 1H), 3.43-3.51 (m, 1H), 2.56-2.95 (m, 4H), 1.97-2.22 (m, 2H), 1.79-1.89 (m, 2H), 1.69-1.77 (m, 2H), 1.10-0.90 (t, J=4.14, 8.08 Hz, 3H). EIMS (m/z): calcd. for $C_{20}H_{23}Cl_2N_7O$ (M+1H) 448.20. found 448.20.

Example 131

(R)—N—((R)-1-(1H-pyrazolo[3,4-d]pyrimidin-4-yl)piperidin-3-yl)-2-(3-chlorophenylamino)butanamide

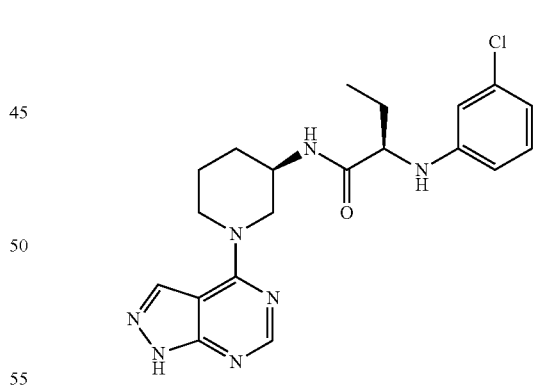

The title compound of Example 131 was prepared in similar manner as described in Example 139 except (R)-2-(3-chloro-5-fluorophenylamino)-2-cyclopropylacetic acid was substituted for (R)-2-(3-chlorophenylamino)butanoic acid. $^1$H NMR (400 MHz, CD$_3$OD) δ 13.4 (br.s., 1H), 9.19 (br.s., 1H), 8.39 (d, J=12.05 Hz, 1H), 8.17 (br.s., 1H), 7.48 (s, 1H), 7.28-7.37 (m, 1H), 7.14-7.22 (m, 1H), 6.49-6.57 (m, 1H), 6.38-6.46 (m, 1H), 3.42-3.51 (m, 1H), 2.58-2.95 (m, 4H), 1.97-2.24 (m, 2H), 1.79-1.89 (m, 2H), 1.69-1.78 (m, 2H), 1.11-0.91 (t, J=4.15, 8.04 Hz, 3H). EIMS (m/z): calcd. for $C_{20}H_{24}ClN_7O$ (M+1H) 414.17. found 414.3.

Example 132

(R)—N—((R)-1-(7H-pyrrolo[2,3-d]pyrimidin-4-yl)piperidin-3-yl)-3-cyclopropyl-2-(3,5-dichlorophenylamino)propanamide

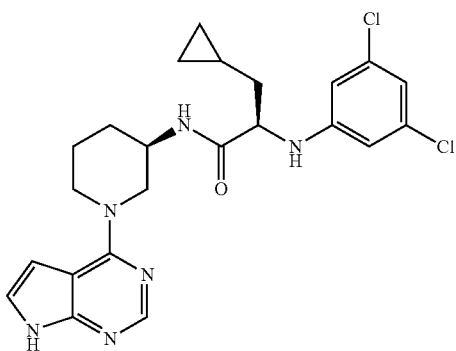 [SMILES: O=C(N[C@@H]1CCCN(c2ncnc3[nH]ccc23)C1)[C@@H](CC1CC1)Nc1cc(Cl)cc(Cl)c1]

The title compound of Example 132 was prepared in similar manner as described in Example 139 except (R)-2-(3-chloro-5-fluorophenylamino)-2-cyclopropylacetic acid was substituted for (R)-3-cyclopropyl-2-(3,5-dichlorophenylamino)propanoic acid. $^1$H NMR (400 MHz, DMSO-d$_6$) δ 11.65 (br. s., 1H), 8.23 (d, J=7.28 Hz, 1H), 8.03-8.17 (m, 1H), 7.04-7.14 (m, 1H), 6.58-6.67 (m, 3H), 6.40-6.58 (m, 2H), 4.37-4.59 (m, 2H), 3.89 (q, J=7.61 Hz, 1H), 3.63-3.80 (m, 1H), 3.30 (s, 1H), 3.13 (t, J=10.54 Hz, 1H), 3.03 (dd, J=9.79, 12.80 Hz, 1H), 1.71-1.92 (m, 2H), 1.32-1.61 (m, 3H), 0.67-0.89 (m, 1H), 0.30-0.53 (m, 2H), 0.04-0.21 (m, 2H). EIMS (m/z): calcd. for C$_{23}$H$_{26}$Cl$_2$N$_6$O (M+1H) 473.4. found 474.4.

Example 133

(N—((R)-1-(7H-pyrrolo[2,3-d]pyrimidin-4-yl)piperidin-3-yl)-2-(3,5-dichlorophenylamino)-2-(oxetan-3-yl)acetamide

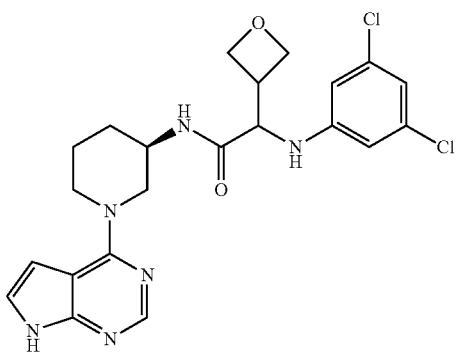 [SMILES: O=C(N[C@@H]1CCCN(c2ncnc3[nH]ccc23)C1)C(Nc1cc(Cl)cc(Cl)c1)C1COC1]

Oxetan-3-one. Pyridine (162 g, 2.05 mol) was added dropwise to a 10° C. solution of CrO$_3$ (100 g, 1.02 mol) in CH$_2$Cl$_2$ (2.4 L). Reaction mixture was stirred at RT for 1 h to obtain Collin's reagent. The reaction mixture was cooled to 5° C., and a mixture of oxetan-3-ol (13 g, 0.18 mol) in CH$_2$Cl$_2$ (300 mL) was added dropwise over 20 min. The resulting reaction mixture was stirred at 5° C. for 30 min. After the consumption of the starting material (monitored by GC), the reaction mixture was filtered through a plug of silica gel. The solvent was evaporated under reduced pressure to afford 7.2 g crude oxetan-3-one in pyridine (150 mL) as brown oil. The crude material was directly taken to the next step without purification.

(Methyl 2-(benzyloxycarbonylamino)-2-(oxetan-3-ylidene)acetate). To a –70° C. stirred solution of N-benzyloxy carbonyl-(phosphono glycine trimethylester) (34.4 g 0.104 mol) under N$_2$ was added tetra methyl guanidine (12.6 mL, 0.1 mol). The reaction mixture was further stirred at –70° C. under N$_2$ for 1 h. Oxetan-3-one (7.2 g, 0.1 mol) was added to the reaction mixture at –70° C., and the resulting reaction mixture was stirred at RT. After consumption of starting material (by TLC), the reaction mixture was diluted with EtOAc (200 mL) and filtered, and the solid residue was washed with EtOAc (2×300 mL). The combined organic layers were washed with 1% citric acid (2×300 mL) and brine solution (300 mL), dried over Na$_2$SO$_4$, and filtered, and the solvent was removed under reduced pressure. The crude material was purified with flash chromatography (20% EtOAc/Hexane) to afford the title intermediate (10 g, 37%) as an off-white solid. $^1$H-NMR: (200 MHz, CDCl$_3$): δ 7.39 (s, 5H), 6.78 (bs, 1H), 5.39-5.48 (m, 4H), 5.12 (s, 2H), 3.8 (s, 3H). [TLC system: 30% EtOAc/Hexane, R$_f$ 0.4].

Methyl 2-amino-2-(oxetan-3-yl)acetate. To a stirred solution of (methyl 2-(benzyloxycarbonylamino)-2-(oxetan-3-ylidene)acetate) (5 g, 0.0179 mol) in MeOH:CH$_2$Cl$_2$ (1:1, 800 mL) was added 10% Pd(OH)$_2$ (526 mg). The reaction mixture was stirred under H$_2$ (40 psi) at RT for 2 h. After consumption of starting material (by TLC), the reaction mixture was filtered through a pad of Celite®. The filtrate was concentrated under reduced pressure, and the residue was purified by flash chromatography [3-5% MeOH-DCM] to afford the title intermediate (1.16 g, 44.6%) as a brown liquid. $^1$H-NMR: (200 MHz, CDCl$_3$): δ 4.74-4.82 (m, 2H), 4.54-4.67 (m, 2H), 3.87-3.76 (m, 3H), 3.72 (s, 3H), 3.18-3.23 (m, 1H). [TLC system: 10% MeOH/DCM, R$_E$ 0.3].

(2-Amino-2-(oxetan-3-yl)acetic acid). To a stirred solution of methyl 2-amino-2-(oxetan-3-yl)acetate (1.2 g, 8.27 mmol) in H$_2$O (12 mL) was added TEA (6 mL, 43.4 mmol) at 0° C., and the resulting mixture was stirred 4 h at rt. After complete consumption of starting material (by TLC), volatile solvents were evaporated under reduced pressure to afford the crude compound. The crude material was washed with hexane and co-evaporated with CCl$_4$ to afford the title intermediate (600 mg, 35.2%) as a white powder. $^1$H NMR: (500 MHz, D$_2$O): δ 4.78-4.72 (m, 3H), 4.62 (m, 1H), 3.98 (d, J=12.0 Hz, 1H), 3.43-3.38 (m, 1H). Mass: 132.1 [M$^+$+1]. [TLC system: n.BuO:AcOH:H$_2$O 4:1:1, Rf, 0.4].

(N—((R)-1-(7H-pyrrolo[2,3-d]pyrimidin-4-yl)piperidin-3-yl)-2-(3,5-dichlorophenylamino)-2-(oxetan-3-yl)acetamide). To a solution of 2-amino-2-(oxetan-3-yl)acetic acid (0.3 mmol) and (R)-1-(7H-pyrrolo[2,3-d]pyrimidin-4-yl)piperidin-3-amine (0.3 mmol) in DMF (2 mL) was added DIEA (0.9 mmol), EDCI (0.33 mmol), and HOBt (0.33 mmol). The resulting solution was then stirred at rt for 1 h. The solvent was removed in vacuo to afford a residue, which was purified by reverse phase chromatography C$_{18}$ column and 10% acetonitrile/water containing 0.1% TFA to afford the title compound. $^1$H NMR (400 MHz, MeOD) δ 8.08 (s, 1H), 7.03 (d, J=3.51 Hz, 1H), 6.55 (d, J=3.51 Hz, 1H), 6.41 (t, J=1.76 Hz, 1H), 6.37 (d, J=1.76 Hz, 1H), 4.64-4.69 (m, 1H), 4.54-4.60 (m, 1H), 4.42 (t, J=6.27 Hz, 1H), 4.07 (d, J=9.29 Hz, 1H), 3.71-3.97 (m, 3H), 1.83-1.93 (m, 1H), 1.76 (br. s., 1H), 1.62 (br. s., 1H). EIMS (m/z): calcd. for C$_{22}$H$_{24}$Cl$_2$N$_6$O$_2$(M+1H) 475. found 475.

Example 134

(R)—N—((R)-1-(6-amino-5-cyanopyrimidin-4-yl)piperidin-3-yl)-2-(3-chloro-5-fluorophenylamino)-2-cyclopropylacetamide

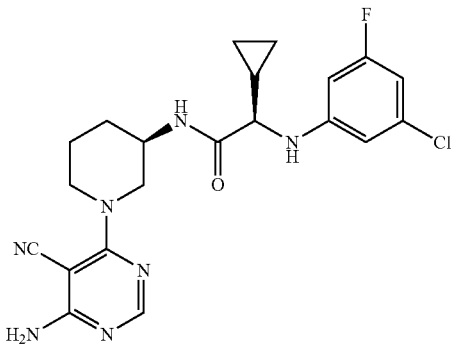 [SMILES: N#Cc1c(N)ncnc1N1CCC[C@@H](NC(=O)[C@H](Nc2cc(F)cc(Cl)c2)C2CC2)C1]

(R)-2-(3-chloro-5-fluorophenylamino)-2-cyclopropylacetic acid. A solution of amino acid (R)-2-amino-2-cyclopropylacetic acid (1 mmol), 1-bromo-3-chloro-5-fluorobenzene (1 mmol), $Cs_2CO_3$ (2 mmol), and CuI (0.04 mmol) in DMF (2 mL) can be heated at 90° C. for 12 h under an atmosphere of nitrogen. The solution can be cooled to rt, diluted with EtOAc-water (2:1, 15 mL), and adjusted to a pH 3-5 with 1 N HCl. The organic layer can be separated, washed with brine, dried ($Na_2SO_4$), and concentrated in vacuo to afford the title intermediate as an oil, which can be used without further purification.

(R)-tert-butyl 3-((R)-2-(3-chloro-5-fluorophenylamino)-2-cyclopropylacetamido)piperidine-1-carboxylate. To a solution of (R)-2-(3-chloro-5-fluorophenylamino)-2-cyclopropylacetic acid (0.3 mmol) and (R)-tert-butyl 3-aminopiperidine-1-carboxylate (0.3 mmol) in DMF (2 mL) can be added DIEA (0.9 mmol), EDCI (0.33 mmol), and HOBt (0.33 mmol). The resulting solution can then be stirred at RT for 1 h. The solvent can be removed in vacuo to afford a residue, which can be purified by column chromatography (silica gel, gradient EtOAc in hexane) to afford the title intermediate.

((R)—N—((R)-1-(6-amino-5-cyanopyrimidin-4-yl)piperidin-3-yl)-2-(3-chloro-5-fluorophenylamino)-2-cyclopropylacetamide) To a solution of (R)-tert-butyl 3-((R)-2-(3-chloro-5-fluorophenylamino)-2-cyclopropylacetamido)piperidine-1-carboxylate (0.3 mmol) in 1,4-dioxane (1 mL) can be added 4 N HCl in dioxane (2 mL). The solution can be stirred for 1 h with the solvent concentrated in vacuo to afford a solid, which can be used without further purification. The solid can be dissolved in DMF (4 mL), treated with DIEA (6 mmol) and 4-amino-6-chloropyrimidine-5-carbonitrile (1 mmol), and heated to 100° C. for 4 h. The solution can be cooled to RT, diluted with water, and extracted with EtOAc, and the organic phase can be dried ($Na_2SO_4$), filtered, and concentrated in vacuo to afford an oil, which can be purified by reverse phase chromatography $C_{18}$ column and 10% acetonitrile/water containing 0.1% TFA to afford the title compound. $^1$H NMR (400 MHz, $CD_3OD$) δ 0.37 (d, J=3.91 Hz, 1H), 0.55 (m, 2H), 0.63 (m, 1H), 1.15 (m, 1H), 1.77 (t, J=7.58 Hz, 2H), 1.99 (d, J=26.90 Hz, 2H), 3.05 (d, J=8.80 Hz, 1H), 3.75 (dd, J=12.47, 7.09 Hz, 2H), 3.98 (s, 1H), 4.16 (m, 2H), 6.18 (d, J=11.74 Hz, 1H), 6.37 (d, J=14.18 Hz, 2H), 8.11 (s, 1H). EIMS (m/z): 444 (M+1).

Example 135

(R)-2-(3-chloro-5-fluorophenylamino)-2-cyclopropyl-N—((R)-1-(7-oxo-5,6,7,8-tetrahydropyrido[2,3-d]pyrimidin-4-yl)piperidin-3-yl)acetamide

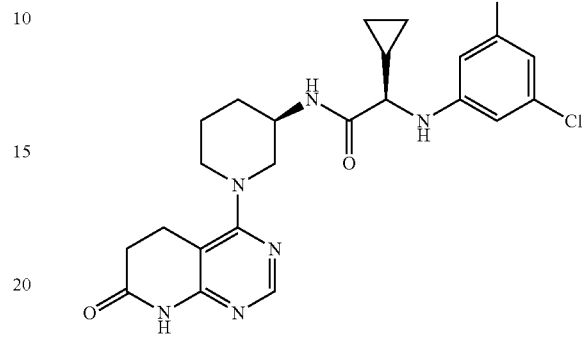

The title compound of Example 135 was prepared in similar manner as described in Example 134 except 4-amino-6-chloropyrimidine-5-carbonitrile was substituted for 4-chloro-5,6-dihydropyrido[2,3-d]pyrimidin-7(8H)-one. $^1$H NMR (400 MHz, $CD_3OD$) δ 0.38 (d, J=3.91 Hz, 1H), 0.58 (m, 3H), 0.64 (m, 1H), 1.14 (d, J=3.91 Hz, 1H), 1.74 (d, J=6.85 Hz, 2H), 1.94 (m, 2H), 2.60 (m, 2H), 2.88 (t, J=7.09 Hz, 2H), 3.04 (d, J=8.80 Hz, 1H), 3.17 (dd, J=12.47, 8.07 Hz, 1H), 3.67 (m, 2H), 4.01 (s, 1H), 6.20 (d, J=11.25 Hz, 1H), 6.36 (d, J=14.18 Hz, 2H), 8.30 (s, 1H). EIMS (m/z): 473 (M+1).

Example 136

(R)-2-(3-chloro-5-fluorophenylamino)-2-cyclopropyl-N—((R)-1-(7-methyl-7H-pyrrolo[2,3-d]pyrimidin-4-yl)piperidin-3-yl)acetamide

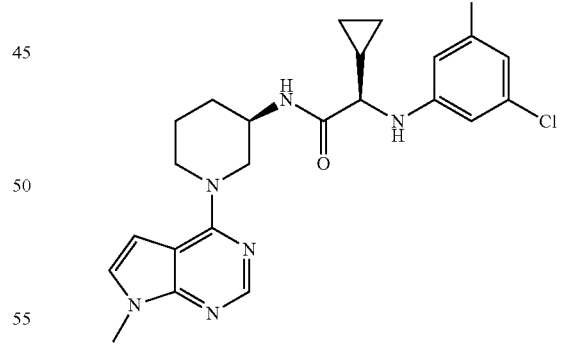

The title compound of Example 136 was prepared in similar manner as described in Example 134 except 4-amino-6-chloropyrimidine-5-carbonitrile was substituted for 4-chloro-7-methyl-7H-pyrrolo[2,3-d]pyrimidine. $^1$H NMR (400 MHz, $CD_3OD$) δ 0.37 (s, 1H), 0.50 (m, 2H), 0.64 (s, 1H), 1.13 (d, J=5.38 Hz, 1H), 1.82 (m, 2H), 2.08 (m, 2H), 3.06 (d, J=8.80 Hz, 1H), 3.56 (dd, J=12.72, 8.80 Hz, 1H), 3.68 (d, J=8.80 Hz, 1H), 3.89 (s, 3H), 4.07 (m, 2H), 4.30 (d, J=13.69 Hz, 1H), 6.17 (d, J=11.74 Hz, 1H), 6.35 (m, 2H), 7.02 (d, J=12.23 Hz, 1H), 7.41 (s, 1H), 8.27 (s, 1H). EIMS (m/z): 458 (M+1).

Example 137

(R)-2-(3-chloro-5-fluorophenylamino)-2-cyclopropyl-N—((R)-1-(1-methyl-1H-pyrazolo[3,4-d]pyrimidin-4-yl)piperidin-3-yl)acetamide

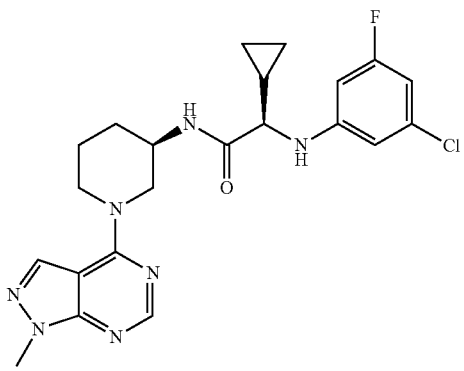 [SMILES: Cn1ncc2c(N3CCC[C@@H](NC(=O)[C@H](Nc4cc(F)cc(Cl)c4)C4CC4)C3)ncnc21]

The title compound of Example 137 was prepared in similar manner as described in Example 134 except 4-amino-6-chloropyrimidine-5-carbonitrile was substituted for 4-chloro-1-methyl-1H-pyrazolo[3,4-d]pyrimidine. $^1$H NMR (400 MHz, CDCl$_3$) δ 8.36 (br. s., 1H), 8.23-8.34 (m, 1H), 6.31-6.50 (m, 2H), 6.20 (d, J=1.76 Hz, 1H), 4.30 (br. s., 1H), 4.16-4.26 (m, 1H), 3.95-4.10 (m, 4H), 3.57-3.82 (m, 3H), 3.07 (br. s., 1H), 2.08 (br. s., 2H), 1.81 (br. s., 2H), 1.10 (br. s., 1H), 0.28-0.72 (m, 4H). EIMS (m/z): calcd. for C$_{22}$H$_{25}$ClFN$_7$O (M+1H) 457. found 457.

Example 138

(R)-2-(3-chloro-5-fluorophenylamino)-2-cyclopropyl-N—((R)-1-(5-fluoro-7H-pyrrolo[2,3-d]pyrimidin-4-yl)piperidin-3-yl)acetamide

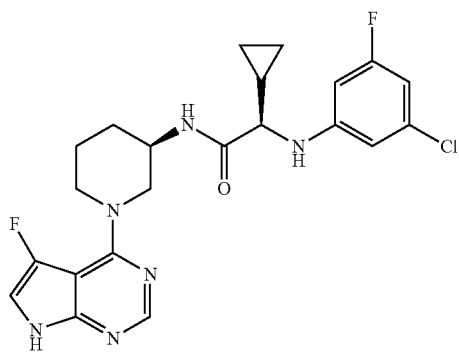 [SMILES: O=C(N[C@@H]1CCCN(c2ncnc3[nH]cc(F)c23)C1)[C@H](Nc1cc(F)cc(Cl)c1)C1CC1]

The title compound of Example 138 was prepared in similar manner as described in Example 134 except 4-amino-6-chloropyrimidine-5-carbonitrile was substituted for 4-Chloro-5-fluoro-7H-pyrrolo[2,3-d]pyrimidine. The 4-Chloro-5-fluoro-7H-pyrrolo[2,3-d]pyrimidine was synthesized as reported by Wang, X.; Seth, P. P.; Ranken, R.; Swayze, E. E; Migawa M. T. Synthesis and Biological Activity of 5-Fluorotubercidiny. *Nucleosides, Nucleotides Nucleic Acids* 2004, 23, 161. $^1$H NMR (400 MHz, CD$_3$OD) δ 8.21 (s, 3H), 7.22 (d, J=2.26 Hz, 3H), 6.34 (t, J=1.63 Hz, 3H), 6.28-6.30 (m, 1H), 6.25-6.27 (m, 1H), 6.15 (t, J=2.13 Hz, 1H), 6.12 (t, J=2.13 Hz, 1H), 3.98-4.11 (m, 9H), 3.66-3.77 (m, 6H), 3.03 (d, J=8.78 Hz, 3H), 2.65 (s, 1H), 1.95-2.12 (m, 6H), 1.77-1.86 (m, 6H), 1.04-1.17 (m, 3H), 0.56-0.68 (m, 3H), 0.46-0.55 (m, 6H), 0.31-0.41 (m, 3H). EIMS (m/z): calcd. for C$_{22}$H$_{23}$ClF$_2$N$_6$O (M+1H) 461. found 461.

Example 138.1

(R)-2-(3-chloro-5-fluorophenylamino)-N—((R)-1-(5-cyano-1H-pyrrolo[2,3-b]pyridin-4-yl)piperidin-3-yl)-2-cyclopropylacetamide

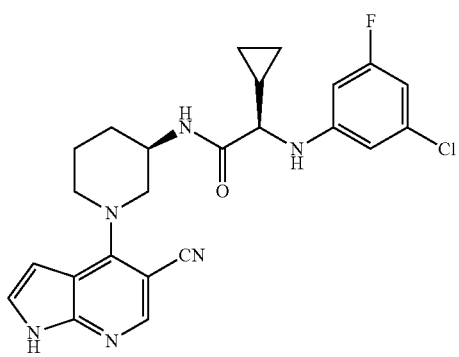 [SMILES: N#Cc1cnc2[nH]ccc2c1N1CCC[C@@H](NC(=O)[C@H](Nc2cc(F)cc(Cl)c2)C2CC2)C1]

The title compound of Example 138.1 was prepared in similar manner as described in Example 134 except 4-amino-6-chloropyrimidine-5-carbonitrile was substituted for 4-chloro-1H-pyrrolo[2,3-b]pyridine-5-carbonitrile. $^1$H NMR (400 MHz, CD$_3$OD) δ 0.36 (s, 1H), 0.58 (m, 5H), 1.14 (d, J=6.85 Hz, 1H), 1.82 (m, 1H), 2.08 (s, 1H), 2.97 (d, J=8.80 Hz, 1H), 3.11 (d, J=8.80 Hz, 1H), 3.58 (dd, J=11.74, 7.83 Hz, 1H), 3.81 (d, J=16.63 Hz, 1H), 4.07 (d, J=12.72 Hz, 1H), 4.17 (s, 1H), 6.11 (d, J=11.25 Hz, 1H), 6.24 (m, 1H), 6.40 (s, 1H), 6.87 (s, 1H), 7.36 (s, 1H), 8.33 (s, 1H). EIMS (m/z): 467 (M+1).

Example 139

(R)—N—((R)-1-(1H-pyrazolo[3,4-d]pyrimidin-4-yl)piperidin-3-yl)-2-(3-chloro-5-fluorophenylamino)-2-cyclopropylacetamide

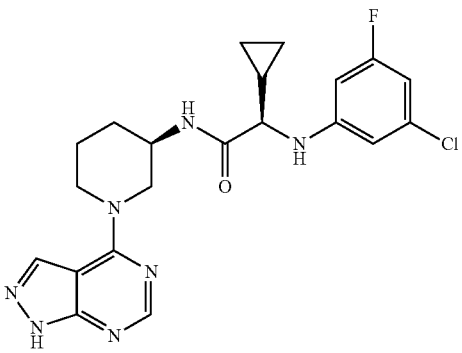 [SMILES: O=C(N[C@@H]1CCCN(c2ncnc3[nH]ncc23)C1)[C@H](Nc1cc(F)cc(Cl)c1)C1CC1]

4,6-dichloropyrimidine-5-carbaldehyde. Dry DMF (1.3 L, 16.5 mol) was added dropwise to POCl$_3$ (4 L, 42.9 mol) at 10~20° C. with stirring. After the addition was completed, the slurry was further stirred at rt for 5 min. Pyrimidine-4,6-diol (1 Kg, 8.9 mol) was slowly added to the mixture. The resulting mixture was heated to reflux, stirred for 3 h, then slowly poured into crushed ice with stirring. The reaction mixture was stirred for another 5 min and then extracted with EtOAc (3×3 L). The organic layers were combined and adjusted to pH 8 with saturated aqueous $Na_2CO_3$. After washing with brine, the organic layer was dried over $Na_2SO_4$, filtered, and concentrated to dryness under vacuum to give crude title intermediate (800 g, 53.3%) as a yellow solid.

4-chloro-1H-pyrazolo[3,4-d]pyrimidine. Hydrazine hydrate (11.5 mL, 23.7 mmol) was slowly added to a solution of 4,6-dichloro-pyrimidine-5-carbaldehyde (40.0 g, 22.6 mmol) and triethylamine (30 mL, 22 mmol) in 1,4-dioxane (600 mL) with cooling to maintain an internal temperature below 20° C. After the addition was completed, the reaction was warmed to rt. After 1 hr, the reaction was filtered. The solvent was removed in vacuo to afford the title intermediate (29 g, 83%) as a light yellow solid. $^1$H NMR (400 MHz, DMSO-$d_6$) δ14.52 (br. s, 1H), 8.83 (s, 1H), 8.45 (s, 1H). MS m/z 155 [M+1]$^+$.

4-chloro-1-((2-(trimethylsilyl)ethoxy)methyl)-1H-pyrazolo[3,4-d]pyrimidine. Diisopropylethylamine (35 mL, 0.20 mol) was added to a solution of 4-chloro-1H-pyrazolo[3,4-d]pyrimidine (25 g, 0.16 mol) and [β-(trimethylsilyl)ethoxy]methyl chloride (36 mL, 0.20 mol) in THF (200 mL, 2 mol) and DMF (100 mL, 1 mol) at −20° C. After 1 h, the reaction mixture was warmed to rt. The reaction mixture was diluted with $CH_2Cl_2$, washed with 0.5 N HCl, and concentrated under reduced pressure. The residue was purified by flash chromatography using hexane/EtOAc ($SiO_2$, 100/0 to 0/100) to afford the title intermediate (26 g, 56%) as a clear oil. $^1$H NMR (400 MHz, CDCl$_3$) 8.84, (s, 1H), 8.24 (s, 1H), 5.86, (s, 2H), 3.68 (m, 2H), 0.95 (m, 2H), 0.03 (s, 9H). MS m/z 285 [M+1]$^+$.

((R)—N—((R)-1-(1H-pyrazolo[3,4-d]pyrimidin-4-yl)piperidin-3-yl)-2-(3-chloro-5-fluorophenylamino)-2-cyclopropylacetamide). The (R)-2-(3-chloro-5-fluorophenylamino)-2-cyclopropyl-N—((R)-piperidin-3-yl)acetamide (1 mmol) prepared in a similar fashion as described for example 134 was dissolved in 1-butanol (4 mL) to which was added DIEA (6 mmol) and 4-chloro-1-((2-(trimethylsilyl)ethoxy)methyl)-1H-pyrazolo[3,4-d]pyrimidine (1 mmol). The reaction mixture was heated to 80° C. and stirred for 4 h. The solution was cooled to rt, diluted with water, and extracted with EtOAc. The organic phase was dried ($Na_2SO_4$), filtered, and concentrated in vacuo to afford an oil, which was purified by column chromatography (silica gel, gradient EtOAc in hexane) to afford the SEM protected compound. A solution of SEM protected compound (0.3 mmol) in EtOH (3 mL) was treated 4 N HCl in dioxane (2 mL). The solution was heated at reflux for 2 h, and the solvent was concentrated in vacuo to afford a solid, which was purified by reverse phase chromatography $C_{18}$ column and 10% acetonitrile/water containing 0.1% TFA to afford the title compound. $^1$H NMR (300 MHz, CDCl$_3$) δ 8.83 (br. s., 2H), 8.44 (s, 2H), 8.15 (br. s., 1H), 6.37-6.40 (m, 2H), 6.32-6.37 (m, 2H), 6.15-6.23 (m, 2H), 4.42 (br. s., 2H), 4.04 (d, J=3.59 Hz, 2H), 3.87 (dd, J=9.06, 13.03 Hz, 2H), 3.70-3.80 (m, 1H), 3.09 (d, J=8.69 Hz, 2H), 1.96-2.18 (m, 4H), 1.76-1.93 (m, 4H), 1.03-1.16 (m, 2H), 0.56-0.69 (m, 2H), 0.42-0.51 (m, 3H), 0.38 (dd, J=4.72, 9.82 Hz, 2H). EIMS (m/z): calcd. for $C_{21}H_{23}ClFN_7O$ (M+H) 444. found 444.

Examples 140-146 were prepared according to Example 139 above.

Example 140

(R)—N-(1-(6-amino-5-chloropyrimidin-4-yl)piperidin-3-yl)-2-(3,5-dichlorophenylamino)acetamide

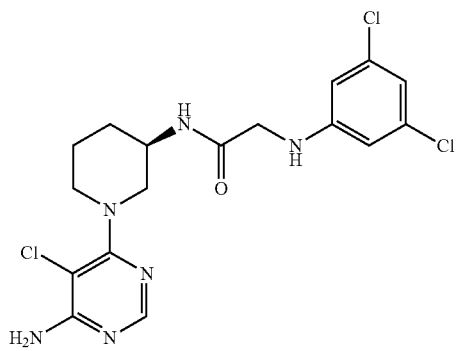 [SMILES: Nc1ncnc(N2CCC[C@@H](NC(=O)CNc3cc(Cl)cc(Cl)c3)C2)c1Cl]

The title compound of Example 140 was prepared in similar manner as described in Example 134 except the key intermediate (R)-tert-butyl 3-((R)-2-(3-chloro-5-fluorophenylamino)-2-cyclopropylacetamido)piperidine-1-carboxylate was replaced with (R)-tert-butyl 3-(2-(3,5-dichlorophenylamino)acetamido)piperidine-1-carboxylate and the 4-amino-6-chloropyrimidine-5-carbonitrile was substituted for 5,6-dichloropyrimidin-4-amine. $^1$H NMR (300 MHz, CD$_3$OD) δ 7.91 (s, 1H), 6.51-6.63 (m, 1H), 6.34 (d, J=1.51 Hz, 2H), 3.93-4.10 (m, 1H), 3.47-3.57 (m, 3H), 3.20-3.31 (m, 2H), 2.76-3.01 (m, 1H), 1.72-1.85 (m, 2H), 1.54-1.67 (m, 2H). EIMS (m/z): calcd. for $C_{17}H_{19}Cl_3N_6O$ (M+1H) 431. found 431.

Example 141

(R)—N-(1-(6-acetamidopyrimidin-4-yl)piperidin-3-yl)-2-(3,5-dichlorophenylamino)acetamide

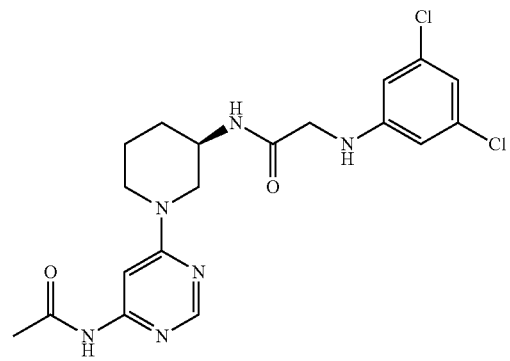 [SMILES: CC(=O)Nc1cc(N2CCC[C@@H](NC(=O)CNc3cc(Cl)cc(Cl)c3)C2)ncn1]

The title compound of Example 141 was prepared in similar manner as described in Example 134 except the key intermediate (R)-tert-butyl 3-((R)-2-(3-chloro-5-fluorophenylamino)-2-cyclopropylacetamido)piperidine-1-carboxylate was replaced with (R)-tert-butyl 3-(2-(3,5-dichlorophenylamino)acetamido)piperidine-1-carboxylate and the 4-amino-6-chloropyrimidine-5-carbonitrile was substituted for N-(6-chloropyrimidin-4-yl)acetamide. $^1$H NMR (400 MHz, DMSO-$d_6$) δ 10.32 (s, 1H), 8.17 (s, 1H), 7.96 (d, J=7.78 Hz, 1H), 6.56 (t, J=1.88 Hz, 1H), 6.47 (d, J=1.76 Hz, 2H), 4.02 (br. s., 1H), 3.79 (br. s., 1H), 3.61 (d, J=9.29 Hz, 3H), 2.84-3.17 (m, 2H), 2.00 (s, 3H), 1.75 (br. s., 2H), 1.33-1.57 (m, 2H). EIMS (m/z): calcd. for $C_{19}H_{22}Cl_2N_6O_2$ (M+1H) 437. found 437.

Example 142

(R)-2-(3,5-dichlorophenylamino)-N-(1-(6-(isopropylamino)pyrimidin-4-yl)piperidin-3-yl)acetamide

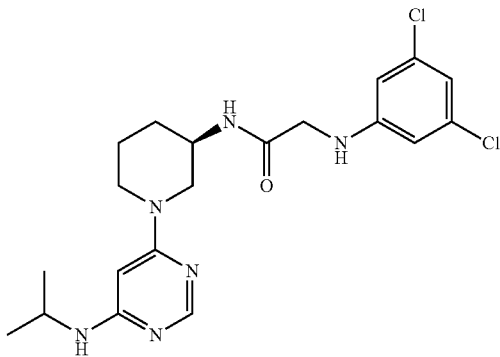 [SMILES: CC(C)Nc1cc(N2CCC[C@@H](NC(=O)CNc3cc(Cl)cc(Cl)c3)C2)ncn1]

The title compound of Example 142 was prepared in similar manner as described in Example 134 except the key intermediate (R)-tert-butyl 3-((R)-2-(3-chloro-5-fluorophenylamino)-2-cyclopropylacetamido)piperidine-1-carboxylate was replaced with (R)-tert-butyl 3-(2-(3,5-dichlorophenylamino)acetamido)piperidine-1-carboxylate and the 4-amino-6-chloropyrimidine-5-carbonitrile was substituted for 6-chloro-N-isopropylpyrimidin-4-amine. $^1$H NMR (300 MHz, CD$_3$OD) δ 8.08 (s, 1H), 6.63 (t, J=1.89 Hz, 2H), 6.48 (d, J=1.89 Hz, 3H), 5.72 (s, 1H), 3.78-4.05 (m, 5H), 3.42-3.60 (m, 3H), 1.90-2.08 (m, 2H), 1.80 (td, J=3.59, 8.97 Hz, 3H), 1.65 (td, J=3.21, 8.03 Hz, 2H), 1.13-1.39 (m, 13H). EIMS (m/z): calcd. for $C_{20}H_{26}O_2N_6O$ (M+1H) 437. found 437.

Example 143

(R)-2-(3,5-dichlorophenylamino)-N-(1-(6-(ethylamino)pyrimidin-4-yl)piperidin-3-yl)acetamide

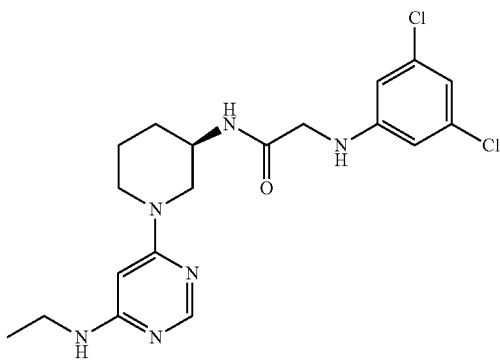 [SMILES: CCNc1cc(N2CCC[C@@H](NC(=O)CNc3cc(Cl)cc(Cl)c3)C2)ncn1]

The title compound of Example 143 was prepared in similar manner as described in Example 134 except the key intermediate (R)-tert-butyl 3-((R)-2-(3-chloro-5-fluorophenylamino)-2-cyclopropylacetamido)piperidine-1-carboxylate was replaced with (R)-tert-butyl 3-(2-(3,5-dichlorophenylamino)acetamido)piperidine-1-carboxylate and the 4-amino-6-chloropyrimidine-5-carbonitrile was substituted for 6-chloro-N-ethylpyrimidin-4-amine. $^1$H NMR (300 MHz, CD$_3$OD) δ 8.08 (s, 1H), 6.63 (t, J=1.70 Hz, 1H), 6.48 (d, J=1.89 Hz, 2H), 5.70 (s, 1H), 3.89-4.03 (m, 2H), 3.74 (s, 2H), 3.55 (d, J=7.55 Hz, 2H), 1.91-2.03 (m, 1H), 1.76-1.87 (m, 2H), 1.65 (dt, J=4.20, 8.59 Hz, 1H), 1.26 (t, J=7.18 Hz, 3H). EIMS (m/z): calcd. for $C_{19}H_{24}Cl_2N_6O$ (M+1H) 423. found 423.

Example 144

(R)-2-(3,5-dichlorophenylamino)-N-(1-(6-(methylamino)pyrimidin-4-yl)piperidin-3-yl)acetamide

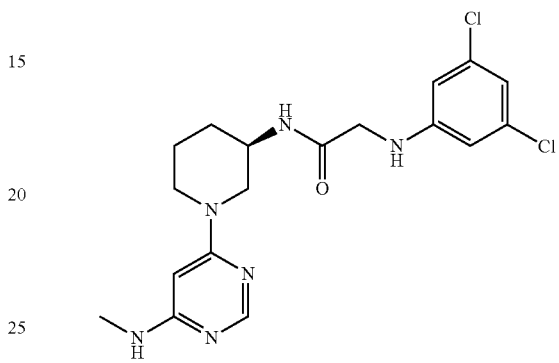

The title compound of Example 144 was prepared in similar manner as described in Example 134 except the key intermediate (R)-tert-butyl 3-((R)-2-(3-chloro-5-fluorophenylamino)-2-cyclopropylacetamido)piperidine-1-carboxylate was replaced with (R)-tert-butyl 3-(2-(3,5-dichlorophenylamino)acetamido)piperidine-1-carboxylate and the 4-amino-6-chloropyrimidine-5-carbonitrile was substituted for 6-chloro-N-methylpyrimidin-4-amine. $^1$H NMR (300 MHz, CD$_3$OD) δ 8.08 (s, 1H), 6.63 (s, 1H), 6.48 (d, J=1.51 Hz, 2H), 5.69 (s, 1H), 3.91 (dd, J=3.78, 7.55 Hz, 3H), 3.74 (s, 2H), 3.50-3.67 (m, 2H), 2.90 (s, 3H), 1.96 (dt, J=4.53, 9.06 Hz, 1H), 1.73-1.88 (m, 2H), 1.57-1.73 (m, 1H). EIMS (m/z): calcd. for $C_{18}H_{22}Cl_2N_6O$ (M+1H) 409. found 409.

Example 145

(R)—N-(1-(6-aminopyrimidin-4-yl)piperidin-3-yl)-2-(3,5-dichlorophenylamino)acetamide

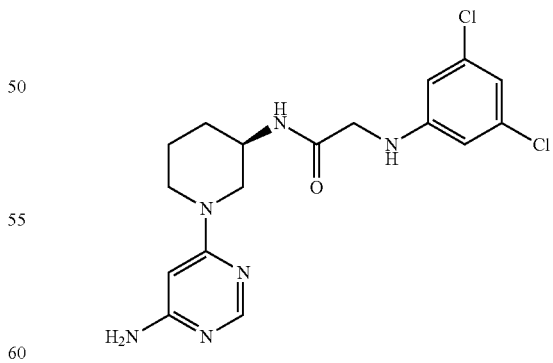

The title compound of Example 145 was prepared in similar manner as described in Example 134 except the key intermediate (R)-tert-butyl 3-((R)-2-(3-chloro-5-fluorophenylamino)-2-cyclopropylacetamido)piperidine-1-carboxylate was replaced with (R)-tert-butyl 3-(2-(3,5-dichlorophenylamino)acetamido)piperidine-1-carboxylate and the 4-amino-6-chloropyrimidine-5-carbonitrile was substituted for 6-chloropyrimidin-4-amine. $^1$H NMR (400 MHz, DMSO-$d_6$) δ 8.18 (s, 1H), 8.00 (d, J=7.28 Hz, 1H), 7.50 (br. s., 2H), 6.54-6.70 (m, 1H), 6.47 (d, J=1.76 Hz, 3H), 3.98 (br. s., 1H), 3.84 (br. s., 1H), 3.55-3.71 (m, 6H), 3.06 (dd, J=8.91, 12.93 Hz, 2H), 1.76 (br. s., 3H), 1.38-1.60 (m, 3H). EIMS (m/z): calcd. for $C_{17}H_{20}Cl_2N_6O$ (M+1H) 395. found 395.

Example 146

(R)-2-(3,5-dichlorophenylamino)-N-(1-(6-oxo-6,7-dihydro-5H-pyrrolo[2,3-d]pyrimidin-4-yl)piperidin-3-yl)acetamide

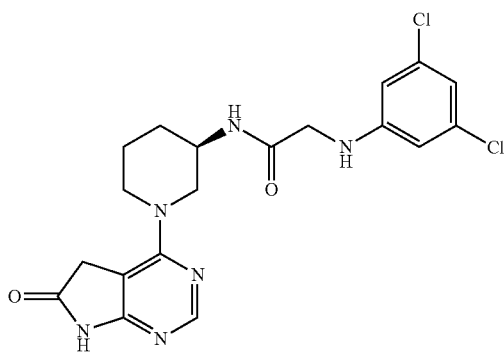 [SMILES: O=C1Cc2c(ncnc2N2CCC[C@@H](NC(=O)CNc3cc(Cl)cc(Cl)c3)C2)N1]

The title compound of Example 146 was prepared in similar manner as described in Example 134 except the key intermediate (R)-tert-butyl 3-((R)-2-(3-chloro-5-fluorophenylamino)-2-cyclopropylacetamido)piperidine-1-carboxylate was replaced with (R)-tert-butyl 3-(2-(3,5-dichlorophenylamino)acetamido)piperidine-1-carboxylate and the 4-amino-6-chloropyrimidine-5-carbonitrile was substituted for 4-chloro-5H-pyrrolo[2,3-d]pyrimidin-6(7H)-one. $^1$H NMR (300 MHz, DMSO-$d_6$) δ 10.99 (s, 1H), 8.17 (s, 1H), 8.03 (d, J=7.18 Hz, 1H), 6.62 (t, J=1.70 Hz, 1H), 6.54 (d, J=1.89 Hz, 2H), 4.13 (d, J=12.46 Hz, 3H), 3.69 (dd, J=11.33, 15.86 Hz, 10H), 2.84-3.22 (m, 2H), 1.82 (d, J=3.40 Hz, 1H), 1.66-1.76 (m, 1H), 1.43-1.63 (m, 2H). EIMS (m/z): calcd. for $C_{19}H_{20}Cl_2N_6O$ (M+1H) 435. found 435.

Example 147

(R)-2-(3-Chloro-5-fluorophenylamino)-2-cyclopropyl-N-((3R,5S)-5-methyl-1-(1H-pyrazolo[3,4-d]pyrimidin-4-yl)piperidin-3-yl)acetamide tert-Butyl 5-methylpyridin-3-ylcarbamate. A solution of 5-methyl-pyridin-3-ylamine (250 mg, 2.31 mmol) and di-tert-butyldicarbonate (505 mg, 2.31 mmol) in THF (5 mL) was stirred at rt for 4 h. The reaction mixture was concentrated in vacuo to afford a residue, which was suspended in EtOAc and washed with aq. NaHCO$_3$ and water. The organic phase was collected, dried (Na$_2$SO$_4$), filtered, and concentrated in vacuo to give an oil, which was purified by column chromatography (silica gel, gradient EtOAc in hexanes) to yield the title intermediate.

tert-Butyl (3R,5S)-5-methylpiperidin-3-ylcarbamate. A Parr bottle was charged with tert-butyl 5-methylpyridin-3-ylcarbamate (365 mg, 1.75 mmol) and AcOH (10 mL, 0.17 mol). Nitrogen was bubbled through the mixture for several minutes with stirring before 5% Pt/C (365 mg, 0.027 mol) was added, and the bottle was placed under an atmosphere of hydrogen (60 psi) for 24 h. The mixture was filtered and the solvent concentrated in vacuo to afford the title intermediate as an oil, which was used without further purification.

tert-Butyl (3R,5S)-5-methyl-1-(1-((2-(trimethylsilyl)ethoxy)methyl)-1H-pyrazolo[3,4-d]pyrimidin-4-yl)piperidin-3-ylcarbamate. A mixture of tert-butyl (3R,5S)-5-methylpiperidin-3-ylcarbamate (150 mg, 0.7 mmol), 4-chloro-1-((2-(trimethylsilyl)ethoxy)methyl)-1H-pyrazolo[3,4-d]pyrimidine (200 mg, 0.7 mmol) and Et$_3$N (195 µL, 1.4 mmol) in DMF (5 mL) was heated at 80° C. for 16 h. The solution was cooled, diluted with water, extracted with EtOAc, washed with aq. citric acid and aq. NaHCO$_3$, dried (Na$_2$SO$_4$), filtered, and concentrated in vacuo to afford a residue, which was purified by column chromatography (silica gel, gradient EtOAc in hexanes).

(3R,5S)-5-Methyl-1-(1H-pyrazolo[3,4-d]pyrimidin-4-yl)piperidin-3-amine-5. A solution of tert-butyl (3R,5S)-5-methyl-1-(1-((2-(trimethylsilyl)ethoxy)methyl)-1H-pyrazolo[3,4-d]pyrimidin-4-yl)piperidin-3-ylcarbamate (75 mg, 0.16 mmol) and 12N HCl (0.5 mL, 6 mmol) in EtOH (1.5 mL) was heated to reflux for 4 h. The reaction mixture was concentrated in vacuo, and the residue was dissolved in CH$_2$Cl$_2$ (3 mL) and MeOH (1 mL), treated with a polymer supported carbonate resin, filtered, and concentrated in vacuo to afford a residue, which was used without further purification.

((R)-2-(3-Chloro-5-fluorophenylamino)-2-cyclopropyl-N-43R,5S)-5-methyl-1-(1H-pyrazolo[3,4-d]pyrimidin-4-yl)piperidin-3-yl)acetamide). A mixture of (R)-2-(3-chloro-5-fluorophenylamino)-2-cyclopropylacetic acid (21 mg, 0.086 mmol) and 1-hydroxybenzotriazole (12 mg, 0.086 mmol) in DMF (5 mL) was treated with EDCI (17 mg, 0.086 mmol), (3R,5S)-5-methyl-1-(1H-pyrazolo[3,4-d]pyrimidin-4-yl)piperidin-3-amine (20 mg, 0.086 mmol), and Et$_3$N (40 µL, 0.26 mmol). After 16 h, the reaction mixture was diluted with water, and the organics were extracted into EtOAc, washed with aq. citric acid, aq. NaHCO$_3$, dried (Na$_2$SO$_4$), filtered, and concentrated in vacuo to afford a residue, which was purified by reversed phase chromatography. $^1$H NMR (400 MHz, CD$_3$OD) δ 8.87 (br. s., 2H), 8.47 (s, 2H), 8.28 (br. s., 2H), 6.34-6.47 (m, 4H), 6.27 (d, J=11.29 Hz, 2H), 3.94 (dd, J=4.77, 10.79 Hz, 2H), 3.08-3.19 (m, 3H), 2.66 (s, 2H), 2.01-2.22 (m, 2H), 1.90 (br. s., 2H), 1.35-1.55 (m, 2H), 1.21 (tt, J=4.11, 8.06 Hz, 3H), 1.01-1.15 (m, 6H), 0.51-0.79 (m, 7H), 0.43 (dq, 2H). (M$^+$+1)=458.30. EIMS (m/z): calcd. for $C_{22}H_{25}ClFN_7O$ (M+1H) 458.18. found 458.30.

Example 148

(R)-2-(3-chloro-5-fluorophenylamino)-2-cyclopropyl-N-((3R,6S)-6-methyl-1-(1H-pyrazolo[3,4-d]pyrimidin-4-yl)piperidin-3-yl)acetamide

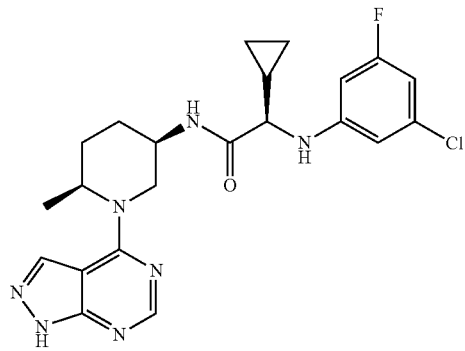 [SMILES: C[C@H]1CC[C@@H](NC(=O)[C@H](Nc2cc(F)cc(Cl)c2)C2CC2)CN1c1ncnc2[nH]ncc12]

The title compound was synthesized according to Example 147 above using 6-methyl-pyridin-3-ylamine in place of 5-methyl-pyridin-3-ylamine. ¹H NMR (400 MHz, CD₃OD) δ 8.63 (br. s., 1H), 8.30 (br. s., 2H), 6.10-6.31 (m, 3H), 5.95 (d, J=11.04 Hz, 3H), 4.15 (br. s., 2H), 4.03 (br. s., 1H), 2.93 (d, J=8.78 Hz, 2H), 2.56 (s, 3H), 1.95-2.30 (m, 5H), 1.66 (d, J=11.04 Hz, 5H), 1.33 (d, J=4.27 Hz, 7H), 0.43 (br. s., 3H), 0.22 (dd, 4H). EIMS (m/z): calcd. for C₂₂H₂₅ClFN₇O (M+1H) 458.18. found 458.30.

Example 149

(R)-2-(3-chloro-5-fluorophenylamino)-2-cyclopropyl-N-(4-phenyl-1-(1H-pyrazolo[3,4-d]pyrimidin-4-yl)piperidin-3-yl)acetamide

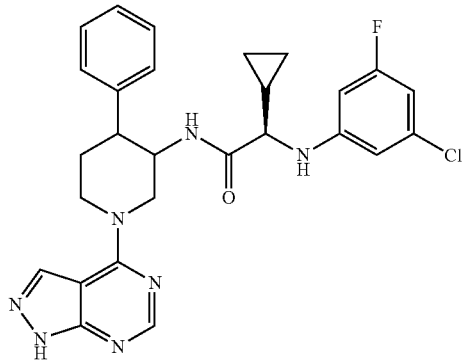 [SMILES: O=C(NC1CN(c2ncnc3[nH]ncc23)CCC1c1ccccc1)[C@H](Nc1cc(F)cc(Cl)c1)C1CC1]

The title compound was synthesized according to Example 147 above using tert-butyl 4-phenylpiperidine-1-carboxylate in place of tert-butyl 5-methylpiperidin-3-ylcarbamate. ¹H NMR (400 MHz, CD₃OD) δ 8.77-8.99 (m, 2H), 8.53 (s, 2H), 8.06 (dd, J=7.66, 15.69 Hz, 2H), 6.93-7.38 (m, 7H), 6.29-6.47 (m, 2H), 6.24 (s, 1H), 5.97-6.20 (m, 2H), 4.25-4.38 (m, 1H), 4.19 (td, J=3.64, 7.22 Hz, 1H), 3.03-3.19 (m, 3H), 2.83-3.01 (m, 3H), 2.66 (s, 1H), 2.15 (d, J=13.05 Hz, 2H), 1.94 (br. s., 2H), 0.39-0.58 (m, 2H), 0.15-0.37 (m, 2H). EIMS (m/z): calcd. for C₂₇H₂₇ClFN₇O (M+1H) 520.19. found 520.30.

Example 150

(R)-2-(3-chloro-5-fluorophenylamino)-2-cyclopropyl-N-((3R,4S)-4-methyl-1-(1H-pyrazolo[3,4-d]pyrimidin-4-yl)piperidin-3-yl)acetamide

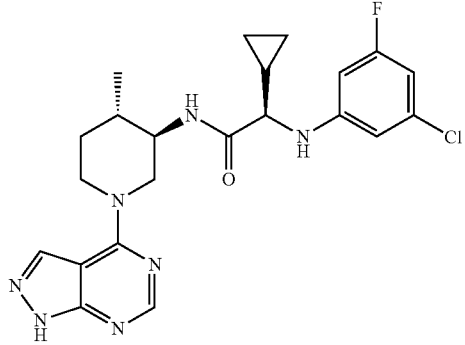 [SMILES: C[C@H]1CCN(c2ncnc3[nH]ncc23)C[C@@H]1NC(=O)[C@H](Nc1cc(F)cc(Cl)c1)C1CC1]

The title compound was synthesized according to Example 147 above using tert-butyl (4S,3R) 4-methylpiperidin-3-ylcarbamate in place of tert-butyl 5-methylpiperidin-3-ylcarbamate. ¹H NMR (400 MHz, CD₃OD) δ 8.66 (d, J=19.83 Hz, 1H), 8.35 (s, 1H), 8.19 (br. s., 1H), 6.27-6.35 (m, 2H), 6.18 (tt, J=2.16, 11.01 Hz, 1H), 3.43-3.59 (m, 1H), 2.99-3.06 (m, 1H), 1.89-1.98 (m, 1H), 1.84 (br. s., 1H), 1.35 (br. s., 1H), 1.06-1.17 (m, 1H), 0.97 (d, J=6.53 Hz, 1H), 0.84 (d, J=6.53 Hz, 1H), 0.45-0.66 (m, 3H), 0.29-0.39 (m, 1H). EIMS (m/z): calcd. for C₂₂H₂₅ClFN₇O (M+1H) 458.18. found 458.30.

Example 151

(R)-2-(3-chloro-5-fluorophenylamino)-2-cyclopropyl-N-((3R,4R)-4-methyl-1-(1H-pyrazolo[3,4-d]pyrimidin-4-yl)piperidin-3-yl)acetamide

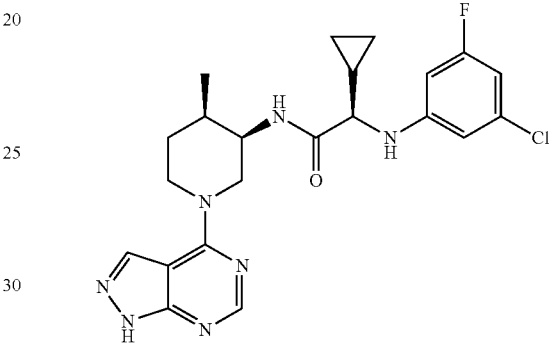

The title compound was synthesized according to Example 147 above using tert-butyl (4R,3R) 4-methylpiperidin-3-ylcarbamate in place of tert-butyl 5-methylpiperidin-3-ylcarbamate. ¹H NMR (400 MHz, MeOD) δ 8.30 (br. s., 1H), 7.62 (br. s., 1H), 7.48 (d, J=8.53 Hz, 1H), 6.15-6.20 (m, 2H), 5.99 (dt, J=2.20, 11.42 Hz, 1H), 4.16 (br. s., 1H), 4.04 (br. s., 1H), 2.90-3.00 (m, 2H), 2.09-2.19 (m, 2H), 1.75 (br. s., 2H), 1.57-1.70 (m, 2H), 0.92 (dd, J=7.03, 17.32 Hz, 8H), 0.46-0.55 (m, 1H), 0.38 (d, J=4.77 Hz, 3H), 0.10-0.25 (m, 2H). EIMS (m/z): calcd. for C₂₂H₂₅ClFN₇O (M+1H) 458.18. found 458.30.

Example 152

(R)-2-cyclopropyl-2-(3,5-dichlorophenylamino)-N-((3R,4S)-4-methyl-1-(1H-pyrazolo[3,4-d]pyrimidin-4-yl)piperidin-3-yl)acetamide

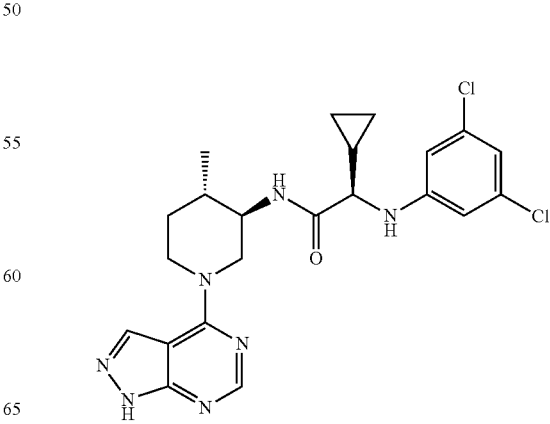

The title compound was synthesized according to Example 147 above using tert-butyl (4S,3R) 4-methyl-piperidin-3-yl carbamate in place of tert-butyl 5-methylpiperidin-3-ylcarbamate. $^1$H NMR (400 MHz, MeOD) δ 8.45 (d, J=1.25 Hz, 1H), 6.59-6.62 (m, 1H), 6.53 (d, J=1.76 Hz, 1H), 6.51 (d, J=1.76 Hz, 1H), 3.52-3.69 (m, 2H), 3.04-3.15 (m, 2H), 1.83-2.10 (m, 3H), 1.47 (br. s., 1H), 1.15-1.29 (m, 1H), 1.06 (d, J=6.53 Hz, 1H), 0.93 (d, J=6.53 Hz, 2H), 0.55-0.75 (m, 3H), 0.37-0.46 (m, 1H). EIMS (m/z): calcd. for $C_{22}H_{25}Cl_2N_7O$ (M+1H) 474.18. found 474.20.

Example 153

(R)-2-(3,5-dichlorophenylamino)-N-43R,4S)-4-methyl-1-(1H-pyrazolo[3,4-d]pyrimidin-4-yl)piperidin-3-yl)pentanamide

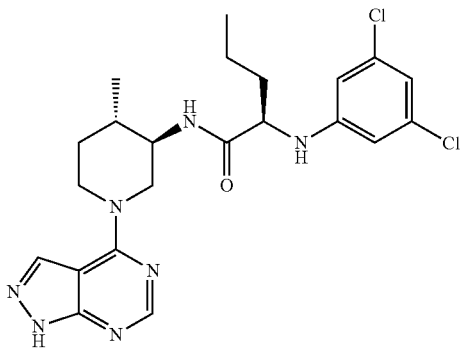 [SMILES: CCC[C@@H](Nc1cc(Cl)cc(Cl)c1)C(=O)N[C@H]1CN(c2ncnc3[nH]ncc23)CC[C@@H]1C]

The title compound was synthesized according to Example 147 above using tert-butyl (4S,3R) 4-methylpiperidin-3-yl-carbamate in place of tert-butyl 5-methylpiperidin-3-ylcarbamate. $^1$H NMR (400 MHz, MeOD) δ 8.51 (br. s., 1H), 6.68 (q, J=1.84 Hz, 1H), 6.64 (d, J=1.76 Hz, 1H), 6.61 (d, J=1.76 Hz, 1H), 3.86 (br. s., 1H), 3.59-3.73 (m, 1H), 2.09 (br. s., 1H), 1.93-2.02 (m, 1H), 1.81-1.91 (m, 2H), 1.47-1.69 (m, 3H), 1.03-1.13 (m, 4H), 0.97 (d, J=6.53 Hz, 2H). EIMS (m/z): calcd. for $C_{22}H_{27}Cl_2N_7O$ (M+1H) 476.4. found 476.3.

Example 154

(R)-2-(3-chloro-5-fluorophenylamino)-N-43R,4S)-4-methyl-1-(1H-pyrazolo[3,4-d]pyrimidin-4-yl)piperidin-3-yl)butanamide

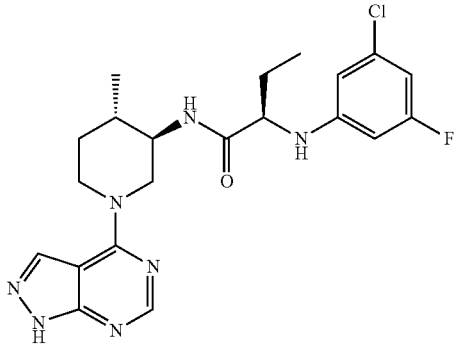 [SMILES: CC[C@@H](Nc1cc(F)cc(Cl)c1)C(=O)N[C@H]1CN(c2ncnc3[nH]ncc23)CC[C@@H]1C]

The title compound was synthesized according to Example 147 above using tert-butyl (4S,3R) 4-methylpiperidin-3-yl-carbamate in place of tert-butyl 5-methylpiperidin-3-ylcarbamate. $^1$H NMR (300 MHz, CHLOROFORM-d) δ 12.71 (br. s., 1H), 12.40 (s, 1H), 12.28 (d, J=12.46 Hz, 1H), 10.31-10.45 (m, 2H), 10.20-10.31 (m, 1H), 7.65-7.76 (m, 1H), 7.45-7.65 (m, 2H), 5.73-6.06 (m, 4H), 5.42 (d, J=11.33 Hz, 1H), 4.96-5.09 (m, 5H), 4.87 (d, J=6.42 Hz, 2H). EIMS (m/z): calcd. for $C_{22}H_{27}Cl_2N_7O$ (M+1H) 446.2. found 446.3.

Example 155

(Z)-1-(1-(7H-pyrrolo[2,3-d]pyrimidin-4-yl)piperidin-3-yl)-3-(2-chlorophenyl)-2-cyanoguanidine

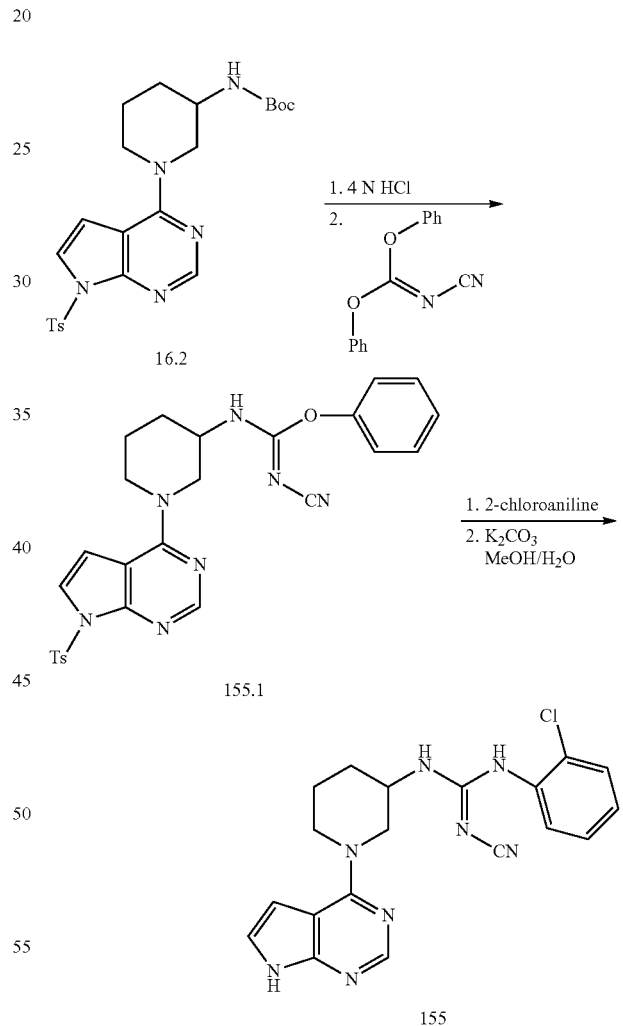

Phenyl N'-cyano-N-(1-(7-tosyl-7H-pyrrolo[2,3-d]pyrimidin-4-yl)piperidin-3-yl)carbamimidate. To a solution tert-butyl 1-(7-tosyl-7H-pyrrolo[2,3-d]pyrimidin-4-yl)piperidin-3-ylcarbamate (6.3 g, 20 mmol) in dioxane (50 ml) was added 4.0 N HCl (50 mL, 200 mmol) and stirred at rt. After several hours, the reaction mixture was concentrated in vacuo to give the deprotected amine. A solution of 1-(7-tosyl-7H-pyrrolo

[2,3-d]pyrimidin-4-yl)piperidin-3-amine (580 mg, 1.29 mmol) and diphenyl cyanocarbonimidate (370 mg, 1.5 mmol) in DMF (20 mL) was heated at 65 C for 16 h. the reaction mixture was cooled to rt and diluted with EtOAc and water (1:2, 200 mL). The organic phase was separated washed subsequently with sat. NaHCO$_3$ brine, water, dried (Na$_2$SO$_4$) and concentrated in vacuo to afford 155.

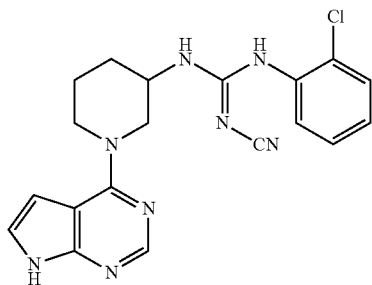 [SMILES: N#C/N=C(\Nc1ccccc1Cl)NC1CCCN(c2ncnc3[nH]ccc23)C1]

((Z)-1-(1-(7H-pyrrolo[2,3-d]pyrimidin-4-yl)piperidin-3-yl)-3-(2-chlorophenyl)-2-cyanoguanidine). To a solution of phenyl N'-cyano-N-(1-(7-tosyl-7H-pyrrolo[2,3-d]pyrimidin-4-yl)piperidin-3-yl)carbamimidate (48 mg, 0.087 mmol) in DMF (2 mL) was added ortho-chloroaniline (28 mg, 0.22 mmol) and the solution was heated in a microwave to 180° C. for 20 min. The solution was diluted with EtOAc and water (1:2, 20 mL). The organic phase was separated washed subsequently with sat. NaHCO$_3$, 1 N HCl, water and dried (Na$_2$SO$_4$) and concentrated in vacuo to afford a solid. To a solution of 1-(2-chlorophenyl)-2-cyano-3-(1-(7-tosyl-7H-pyrrolo[2,3-d]pyrimidin-4-yl)piperidin-3-yl)guanidine was dissolved in water/MeOH (1:4, 2.5 mL) was added K$_2$CO$_3$ (60 mg, 0.44 mmol) and heated to 65° C. for 3 h. The solution was concentrated in vacuo to afford a solid which was purified by reverse phase chromatography C18 column and 10% acetonitrile/water 0.1% TFA to afford example 115. $^1$H NMR (d$^6$-DMSO, 400 MHz): δ 12.38 (br. s., 1H), 9.01 (s, 1H), 8.25 (s, 1H), 7.39-7.54 (m, 2H), 7.15-7.40 (m, 7H), 7.07 (br. s., 1H), 6.79 (br. s., 1H), 4.37 (br. s., 1H), 4.22 (br. s., 1H), 3.74-3.96 (m, 1H), 3.38 (dd, J=9.29, 13.05 Hz, 2H), 1.90 (br. s., 1H), 1.76 (br. s., 1H), 1.40-1.72 (m, 2H).

Examples 156-160 were prepared according to Example 155 above.

Example 156

(Z)-1-(1-(7H-pyrrolo[2,3-d]pyrimidin-4-yl)piperidin-3-yl)-3-(3-chlorophenyl)-2-cyanoguanidine

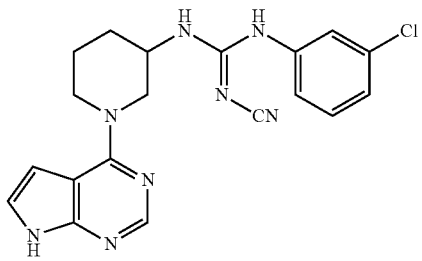 [SMILES: N#C/N=C(\Nc1cccc(Cl)c1)NC1CCCN(c2ncnc3[nH]ccc23)C1]

The title compound of Example 156 was prepared in similar manner as described in Example 155 except 2-chloroaniline was substituted for 3-chloroaniline. $^1$H NMR (400 MHz, DMSO-d$_6$): δ 12.46 (br. s., 1H), 9.32 (br. s., 1H), 8.32 (s, 1H), 7.53 (d, J=7.53 Hz, 1H), 7.40 (d, J=2.76 Hz, 1H), 7.21-7.35 (m, 2H), 7.08-7.21 (m, 2H), 6.89 (d, J=1.51 Hz, 1H), 4.42 (d, J=13.30 Hz, 1H), 4.24 (br. s., 1H), 3.86-4.05 (m, 1H), 3.37-3.67 (m, 2H), 1.92-2.11 (m, 1H), 1.85 (br. s., 1H), 1.73 (d, J=14.05 Hz, 2H).

Example 157

(Z)-1-(1-(7H-pyrrolo[2,3-d]pyrimidin-4-yl)piperidin-3-yl)-3-(4-chlorophenyl)-2-cyanoguanidine

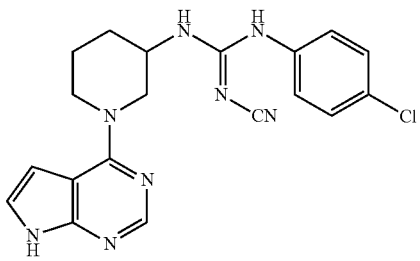 [SMILES: N#C/N=C(\Nc1ccc(Cl)cc1)NC1CCCN(c2ncnc3[nH]ccc23)C1]

The title compound of Example 157 was prepared in similar manner as described in Example 155 except 2-chloroaniline was substituted for 4-chloroaniline. $^1$H NMR (d$^6$-DMSO 400 MHz): δ 12.32 (br. s., 1H), 9.18 (s, 1H), 8.24 (s, 1H), 7.22-7.42 (m, 3H), 7.12 (d, J=9.04 Hz, 2H), 6.80 (br. s., 1H), 4.34 (br. s., 1H), 4.19 (br. s., 1H), 3.88 (br. s., 1H), 3.26-3.52 (m, 2H), 1.91 (d, J=4.02 Hz, 1H), 1.77 (br. s., 1H), 1.40-1.71 (m, 2H).

Example 158

(Z)-1-(1-(7H-pyrrolo[2,3-d]pyrimidin-4-yl)piperidin-3-yl)-2-cyano-3-(3-(trifluoromethyl)phenyl)guanidine

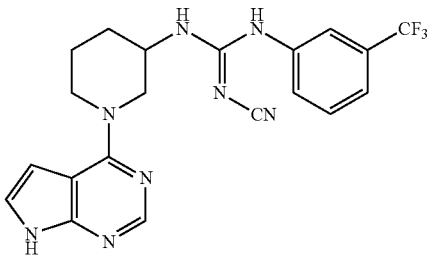 [SMILES: N#C/N=C(\Nc1cccc(C(F)(F)F)c1)NC1CCCN(c2ncnc3[nH]ccc23)C1]

The title compound of Example 158 was prepared in similar manner as described in Example 155 except 2-chloroaniline was substituted for 3-(trifluoromethyl)aniline. $^1$H NMR (d$^6$-DMSO, 400 MHz): δ 12.44 (br. s., 1H), 9.44 (br. s., 1H), 8.32 (s, 1H), 7.33-7.66 (m, 6H), 6.89 (br. s., 1H), 4.45 (d, J=10.04 Hz, 1H), 4.26 (br. s., 1H), 3.51 (dd, J=9.04, 12.80 Hz, 2H), 1.94-2.06 (m, 1H), 1.85 (br. s., 1H), 1.73 (d, J=12.55 Hz, 2H).

Example 159

(Z)-1-(1-(7H-pyrrolo[2,3-d]pyrimidin-4-yl)piperidin-3-yl)-2-cyano-3-(4-(trifluoromethyl)phenyl)guanidine

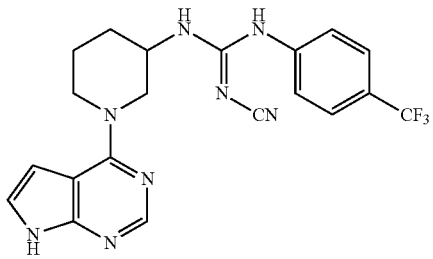 [SMILES: N#C/N=C(\Nc1ccc(C(F)(F)F)cc1)NC1CCCN(c2ncnc3[nH]ccc23)C1]

The title compound of Example 159 was prepared in similar manner as described in Example 155 except 2-chloroaniline was substituted for 4-(trifluoromethyl)aniline. $^1$H NMR (d$^6$-DMSO, 400 MHz): δ 12.08 (br. s., 1H), 9.74-10.05 (m, 1H), 9.48 (br. s., 1H), 8.31-8.45 (m, 1H), 8.26 (s, 1H), 7.44-7.77 (m, 2H), 7.15-7.34 (m, 2H), 6.57 (d, J=8.28 Hz, 1H), 4.49 (br. s., 1H), 4.36 (br. s., 1H), 4.21-4.32 (m, 1H), 3.84 (br. s., 1H), 3.31-3.43 (m, 1H), 1.83 (br. s., 2H), 1.57 (br. s., 1H).

Example 160

(Z)-1-(1-(7H-pyrrolo[2,3-d]pyrimidin-4-yl)piperidin-3-yl)-3-(4-tert-butylphenyl)-2-cyanoguanidine

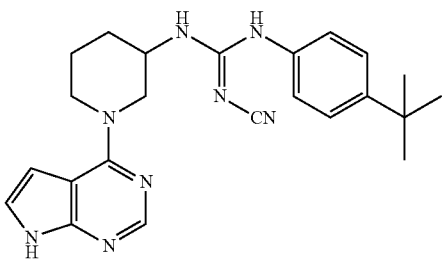 [SMILES: CC(C)(C)c1ccc(N/C(=N\C#N)NC2CCCN(c3ncnc4[nH]ccc34)C2)cc1]

The title compound of Example 158 was prepared in similar manner as described in Example 155 except 2-chloroaniline was substituted for 4-tert-butylaniline. $^1$H NMR (d$^6$-DMSO, 400 MHz): δ 12.32 (br. s., 1H), 9.02 (s, 1H), 8.21 (s, 1H), 7.32 (d, J=2.76 Hz, 1H), 7.17-7.28 (m, 2H), 7.09 (d, J=7.78 Hz, 1H), 7.03 (d, J=8.53 Hz, 2H), 6.80 (br. s., 1H), 4.30 (d, J=3.26 Hz, 1H), 4.16 (br. s., 1H), 3.80-3.97 (m, 1H), 3.46 (dd, J=8.91, 13.18 Hz, 1H), 3.26-3.41 (m, 1H), 2.43 (dt, J=1.79, 3.70 Hz, 12H), 1.91 (d, J=6.02 Hz, 1H), 1.62-1.84 (m, 2H), 1.45-1.61 (m, 1H).

Example 161

In vitro BTK kinase assay: BTK-POLYGAT-LS ASSAY. The purpose of the BTK in vitro assay is to determine compound potency against BTK through the measurement of IC$_{50}$. Compound inhibition is measured after monitoring the amount of phosphorylation of a fluorescein-labeled polyGAT peptide (Invitrogen PV3611) in the presence of active BTK enzyme (Upstate 14-552), ATP, and inhibitor. The BTK kinase reaction was done in a black 96 well plate (costar 3694). A 24 μL aliquot of a ATP/peptide master mix (final concentration; ATP 10 μM, polyGAT 100 nM) in kinase buffer (10 mM Tris-HCl pH 7.5, 10 mM MgCl$_2$, 200 μM Na3VO4, 5 mM DTT, 0.01% Triton X-100, and 0.2 mg/ml Casein) is added to each well. Next, 1 μL of a 4-fold, 40× compound titration in 100% DMSO solvent is added, followed by adding 15 μL of BTK enzyme mix in 1× kinase buffer (with a final concentration of 0.25 nM). The assay is incubated for 30 minutes before being stopped with 28 μL of a 50 mM EDTA solution. Five μL of the kinase reaction is transferred to a low volume white 384 well plate (Corning 3674) and 5 μL of a 2× detection buffer (Invitrogen PV3574, with 4 nM Tb-PY20 antibody, Invitrogen PV3552) is added. The plate is covered and incubated for 45 minutes at room temperature. Time resolved fluorescence (TRF) on Molecular Devices M5 (332 nm excitation; 488 nm emission; 518 nm fluorescein emission) is measured. IC$_{50}$ values are calculated using a four parameter fit with 100% enzyme activity determined from the DMSO control and 0% activity from the EDTA control.

Example 162

Protocol for Human B Cell Stimulation

Human B cells were purified from 150 ml of blood. Briefly, the blood was diluted ½ with PBS and centrifuged through a Ficoll density gradient. The B cells were isolated from the mononuclear cells by negative selection using the B cell isolation kit II from Milenyi (Auburn, Calif.). 50,000 B cells per well were then stimulated with 10 μg/ml of goat F(ab')$_2$ anti-human IgM antibodies (Jackson ImmunoResearch Laboratories, West Grove, Pa.) in a 96-well plate. Compounds were diluted in DMSO and added to the cells. Final concentration of DMSO was 0.5%. Proliferation was measured after 3 days using Promega CellTiter-Glo® (Madison, Wis.). Certain compounds of formula I were tested and found to be active.

Table 1 shows the activity of selected compounds of this invention in the in vitro Btk kinase assay. Compounds have an activity designated as "A" provided an IC$_{50}$<100 nM; compounds having an activity designated as "B" provided an IC$_{50}$ of 100-999 nM; compounds having an activity designated as "C" provided an IC$_{50}$ of 1000-10,000 nM; and compounds having an activity designated as "D" provided an IC$_{50}$ of >10,000 nM. In some instances where a compound tested has activity "D", other structurally similar compounds beyond the measurable limits of the assay are not included in Table 1.

TABLE 1

Exemplary compounds of formula I.

| Cmpd. No. | Structure | IC$_{50}$ (10 uM ATP)$^a$ |
|---|---|---|
| 1 | 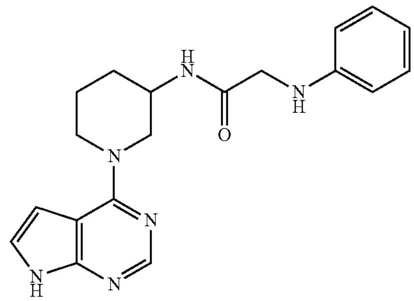 [SMILES: O=C(CNc1ccccc1)NC1CCCN(c2ncnc3[nH]ccc23)C1] | B |
| 2 | 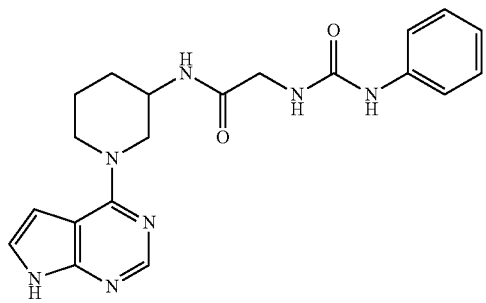 [SMILES: O=C(CNC(=O)Nc1ccccc1)NC1CCCN(c2ncnc3[nH]ccc23)C1] | B |
| 3 | 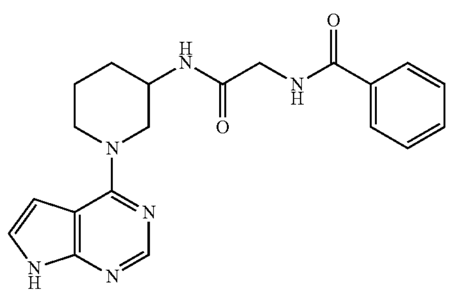 [SMILES: O=C(CNC(=O)c1ccccc1)NC1CCCN(c2ncnc3[nH]ccc23)C1] | B |
| 4 | 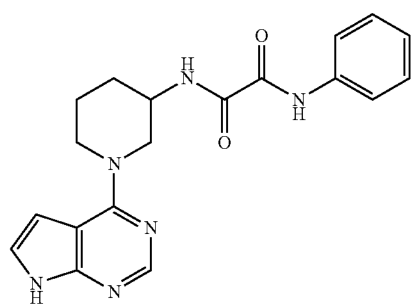 [SMILES: O=C(Nc1ccccc1)C(=O)NC1CCCN(c2ncnc3[nH]ccc23)C1] | D |
| 5 | 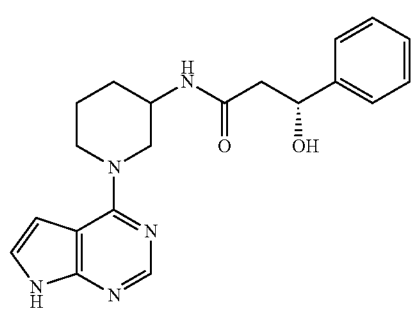 [SMILES: O=C(C[C@@H](O)c1ccccc1)NC1CCCN(c2ncnc3[nH]ccc23)C1] | |

TABLE 1-continued

Exemplary compounds of formula I.

| Cmpd. No. | Structure | IC$_{50}$ (10 uM ATP)$^a$ |
|---|---|---|
| 6 | 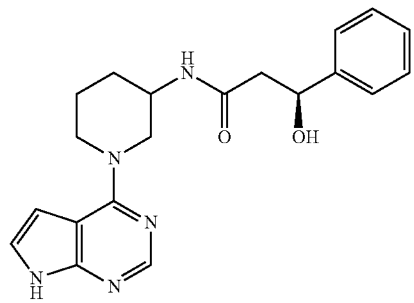 [SMILES: O=C(C[C@H](O)c1ccccc1)NC1CCCN(c2ncnc3[nH]ccc23)C1] | |
| 7 | 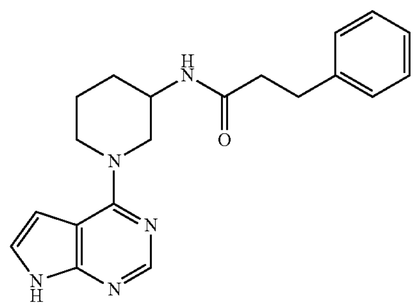 [SMILES: O=C(CCc1ccccc1)NC1CCCN(c2ncnc3[nH]ccc23)C1] | |
| 8 | 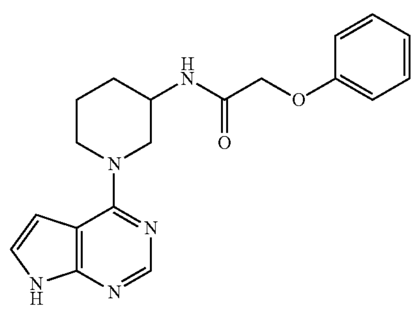 | C |
| 9 | 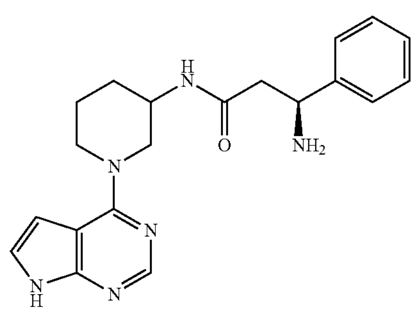 | |
| 10 | 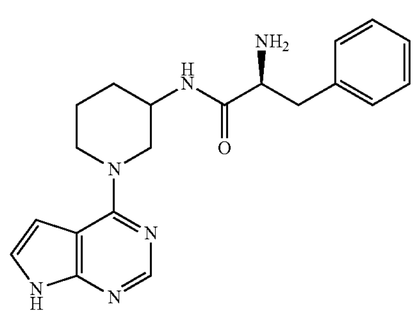 [SMILES: N[C@@H](Cc1ccccc1)C(=O)NC1CCCN(c2ncnc3[nH]ccc23)C1] | |

TABLE 1-continued

Exemplary compounds of formula I.

| Cmpd. No. | Structure | IC$_{50}$ (10 uM ATP) [a] |
|---|---|---|
| 11 | 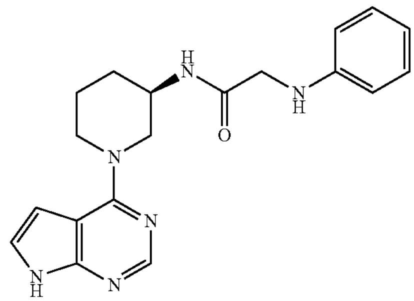 | B |
| 12 | 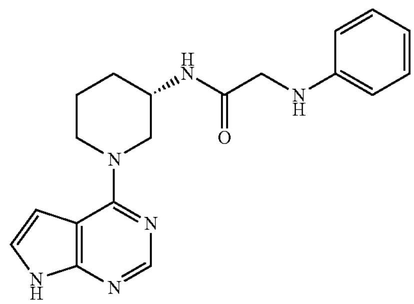 [SMILES: O=C(CNc1ccccc1)N[C@H]1CCCN(c2ncnc3[nH]ccc23)C1] | B |
| 13 | 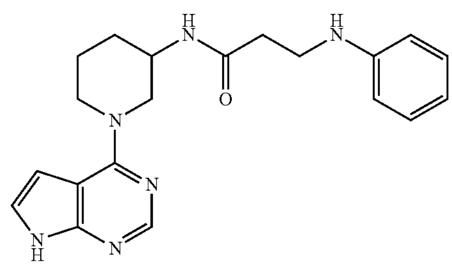 [SMILES: O=C(CCNc1ccccc1)NC1CCCN(c2ncnc3[nH]ccc23)C1] | B |
| 14 | 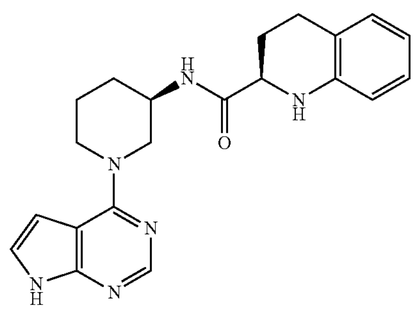 [SMILES: O=C(N[C@@H]1CCCN(c2ncnc3[nH]ccc23)C1)[C@H]1CCc2ccccc2N1] | C |
| 15 | 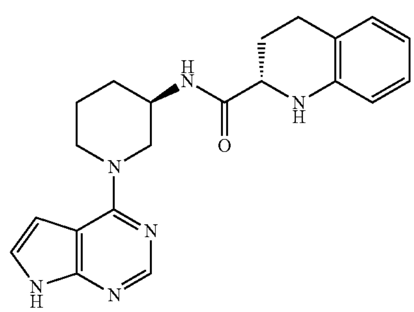 [SMILES: O=C(N[C@@H]1CCCN(c2ncnc3[nH]ccc23)C1)[C@@H]1CCc2ccccc2N1] | C |

TABLE 1-continued

Exemplary compounds of formula I.

| Cmpd. No. | Structure | IC$_{50}$ (10 uM ATP) $^a$ |
|---|---|---|
| 16 | 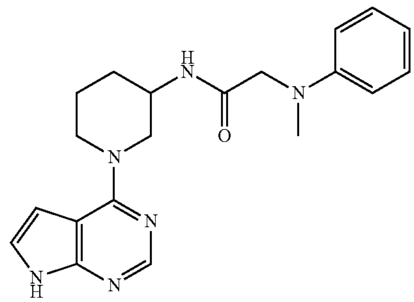 [SMILES: CN(CC(=O)NC1CCCN(c2ncnc3[nH]ccc23)C1)c1ccccc1] | C |
| 17 | 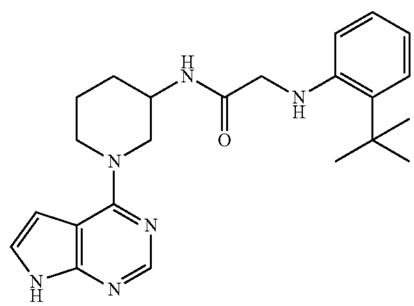 [SMILES: CC(C)(C)c1ccccc1NCC(=O)NC1CCCN(c2ncnc3[nH]ccc23)C1] | C |
| 18 | 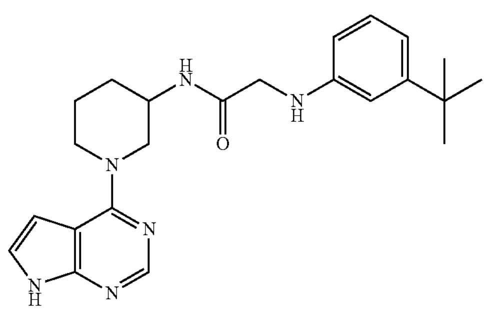 [SMILES: CC(C)(C)c1cccc(NCC(=O)NC2CCCN(c3ncnc4[nH]ccc34)C2)c1] | B |
| 19 | 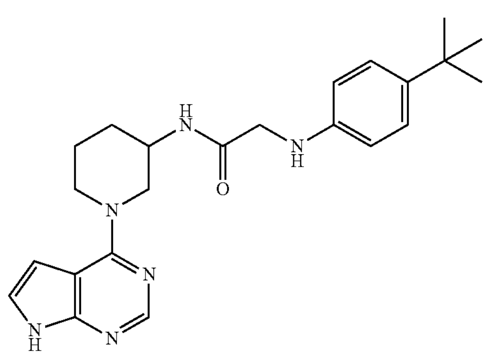 [SMILES: CC(C)(C)c1ccc(NCC(=O)NC2CCCN(c3ncnc4[nH]ccc34)C2)cc1] | D |

TABLE 1-continued

Exemplary compounds of formula I.

| Cmpd. No. | Structure | IC$_{50}$ (10 uM ATP)$^a$ |
|---|---|---|
| 20 | 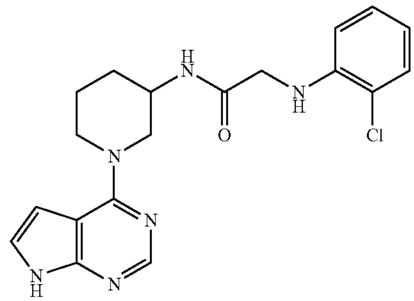 [SMILES: O=C(CNc1ccccc1Cl)NC1CCCN(c2ncnc3[nH]ccc23)C1] | B |
| 21 | 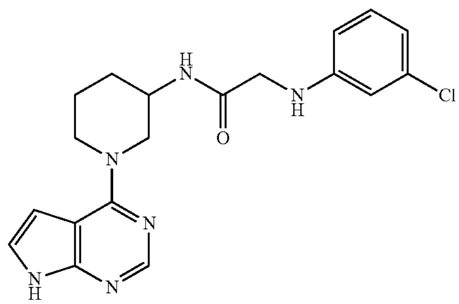 [SMILES: O=C(CNc1cccc(Cl)c1)NC1CCCN(c2ncnc3[nH]ccc23)C1] | A |
| 22 | 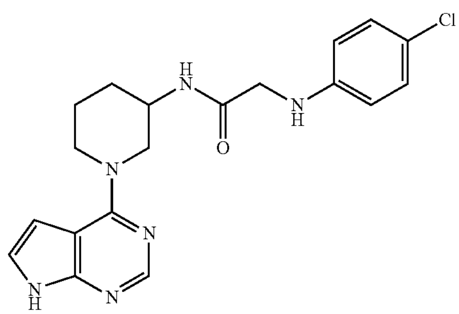 [SMILES: O=C(CNc1ccc(Cl)cc1)NC1CCCN(c2ncnc3[nH]ccc23)C1] | B |
| 23 | 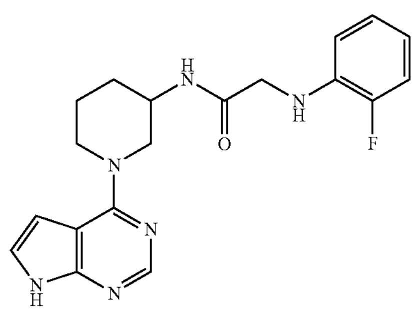 [SMILES: O=C(CNc1ccccc1F)NC1CCCN(c2ncnc3[nH]ccc23)C1] | B |
| 24 | 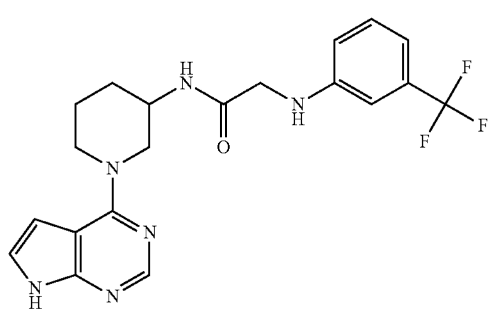 [SMILES: O=C(CNc1cccc(C(F)(F)F)c1)NC1CCCN(c2ncnc3[nH]ccc23)C1] | B |

TABLE 1-continued

Exemplary compounds of formula I.

| Cmpd. No. | Structure | IC$_{50}$ (10 uM ATP)$^a$ |
|---|---|---|
| 25 | 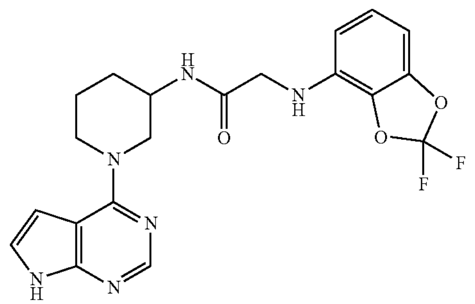 [SMILES: O=C(CNc1cccc2c1OC(F)(F)O2)NC1CCCN(c2ncnc3[nH]ccc23)C1] | A |
| 26 | 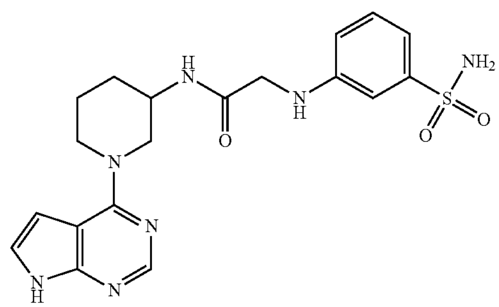 [SMILES: NS(=O)(=O)c1cccc(NCC(=O)NC2CCCN(c3ncnc4[nH]ccc34)C2)c1] | D |
| 27 | 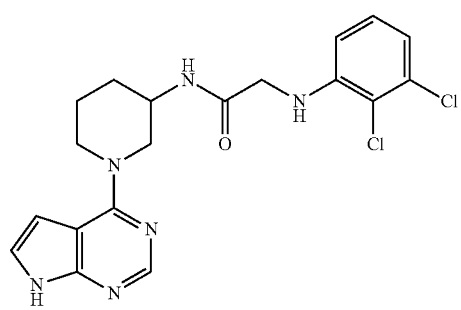 [SMILES: O=C(CNc1cccc(Cl)c1Cl)NC1CCCN(c2ncnc3[nH]ccc23)C1] | B |
| 28 | 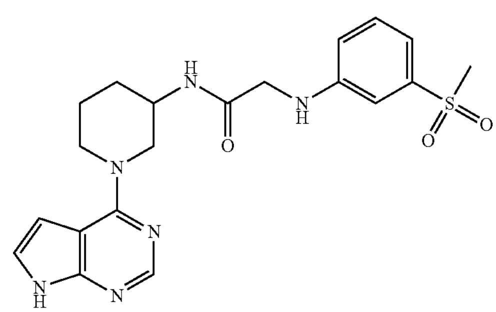 [SMILES: CS(=O)(=O)c1cccc(NCC(=O)NC2CCCN(c3ncnc4[nH]ccc34)C2)c1] | C |
| 29 | 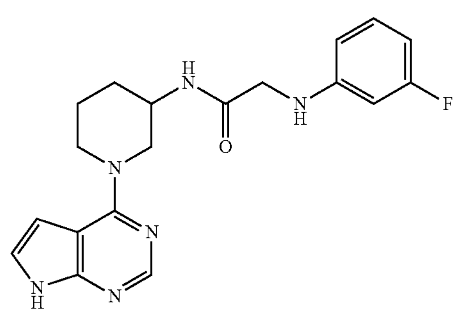 [SMILES: O=C(CNc1cccc(F)c1)NC1CCCN(c2ncnc3[nH]ccc23)C1] | B |

TABLE 1-continued
Exemplary compounds of formula I.
| Cmpd. No. | Structure | IC$_{50}$ (10 uM ATP)$^a$ |
|---|---|---|
| 30 | 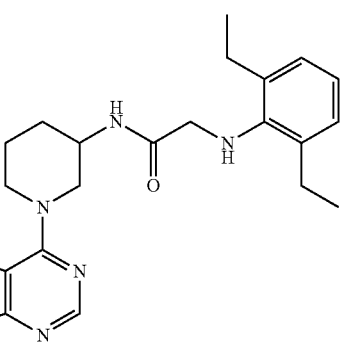 | C |
| 31 | 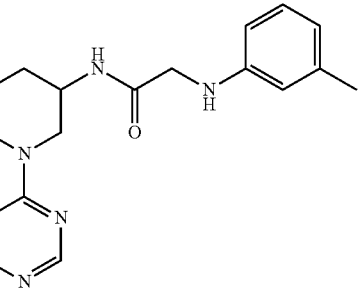 | B |
| 32 | 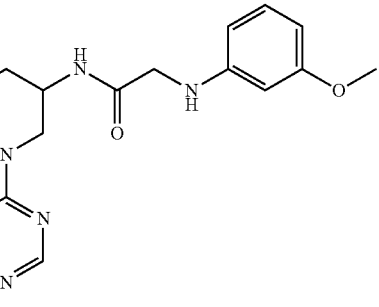 | B |
| 33 | 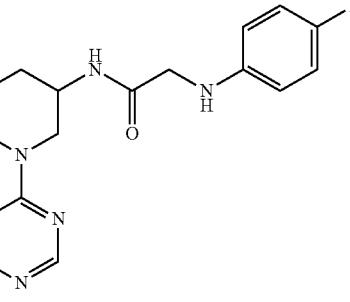 | C |

TABLE 1-continued

Exemplary compounds of formula I.

| Cmpd. No. | Structure | IC$_{50}$ (10 uM ATP)$^a$ |
|---|---|---|
| 34 | 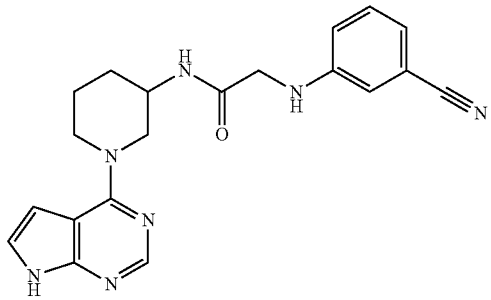 [SMILES: N#Cc1cccc(NCC(=O)NC2CCCN(c3ncnc4[nH]ccc34)C2)c1] | C |
| 35 | 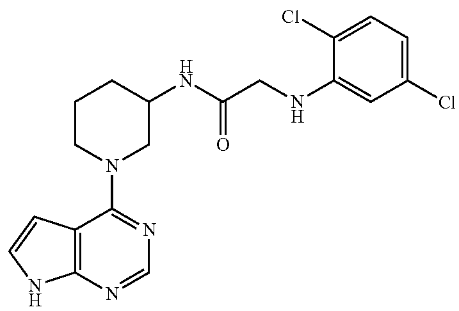 [SMILES: O=C(CNc1cc(Cl)ccc1Cl)NC1CCCN(c2ncnc3[nH]ccc23)C1] | B |
| 36 | 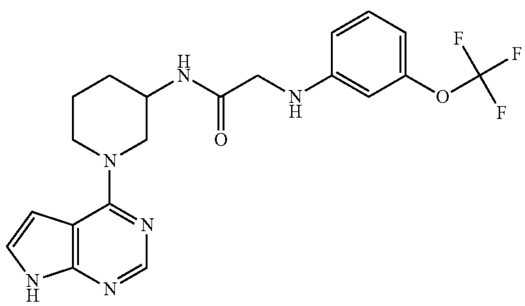 [SMILES: O=C(CNc1cccc(OC(F)(F)F)c1)NC1CCCN(c2ncnc3[nH]ccc23)C1] | B |
| 37 | 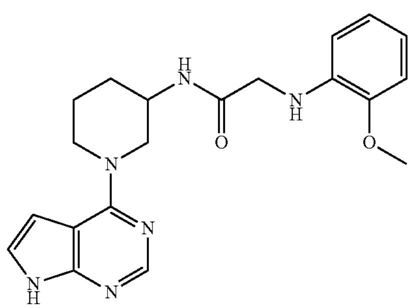 [SMILES: COc1ccccc1NCC(=O)NC1CCCN(c2ncnc3[nH]ccc23)C1] | B |
| 38 | 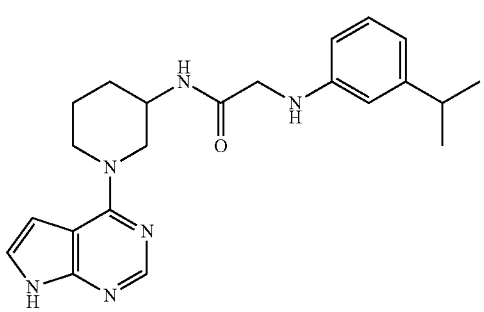 [SMILES: CC(C)c1cccc(NCC(=O)NC2CCCN(c3ncnc4[nH]ccc34)C2)c1] | A |

TABLE 1-continued

Exemplary compounds of formula I.

| Cmpd. No. | Structure | IC$_{50}$ (10 uM ATP)$^a$ |
|---|---|---|
| 39 | 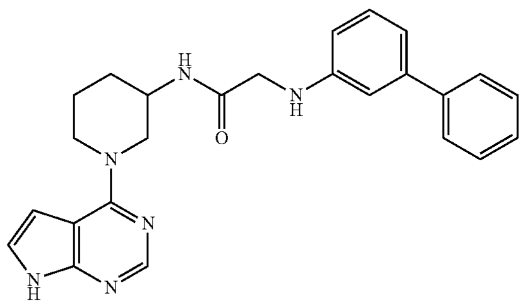 [SMILES: O=C(CNc1cccc(-c2ccccc2)c1)NC1CCCN(c2ncnc3[nH]ccc23)C1] | A |
| 40 | 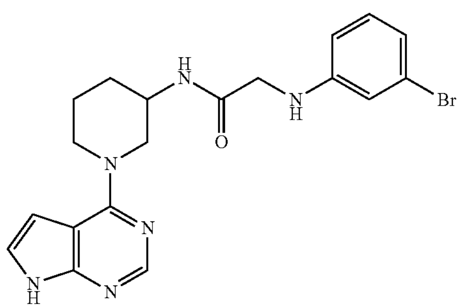 [SMILES: O=C(CNc1cccc(Br)c1)NC1CCCN(c2ncnc3[nH]ccc23)C1] | A |
| 41 | 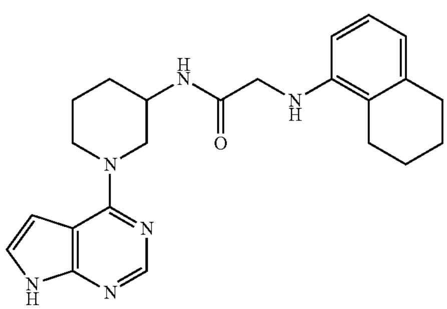 [SMILES: O=C(CNc1cccc2c1CCCC2)NC1CCCN(c2ncnc3[nH]ccc23)C1] | A |
| 42 | 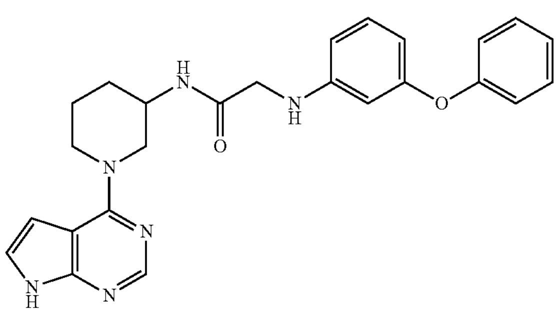 [SMILES: O=C(CNc1cccc(Oc2ccccc2)c1)NC1CCCN(c2ncnc3[nH]ccc23)C1] | B |
| 43 | 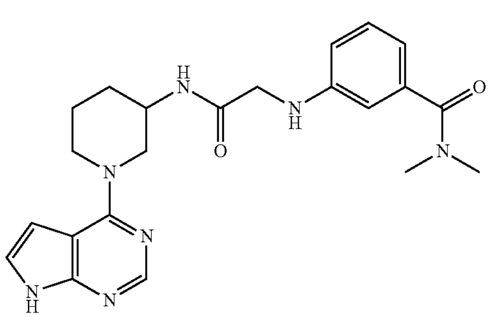 [SMILES: CN(C)C(=O)c1cccc(NCC(=O)NC2CCCN(c3ncnc4[nH]ccc34)C2)c1] | C |

TABLE 1-continued
Exemplary compounds of formula I.
| Cmpd. No. | Structure | IC$_{50}$ (10 uM ATP)$^a$ |
|---|---|---|
| 44 | 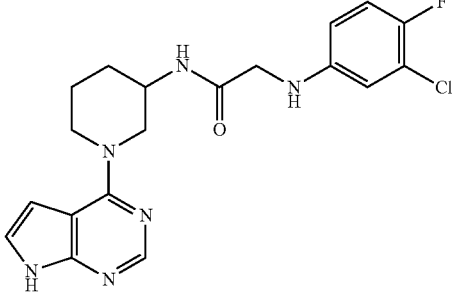 | B |
| 45 | 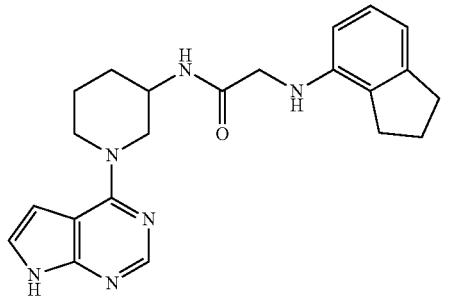 [SMILES: O=C(CNc1cccc2c1CCC2)NC1CCCN(c2ncnc3[nH]ccc23)C1] | A |
| 46 | 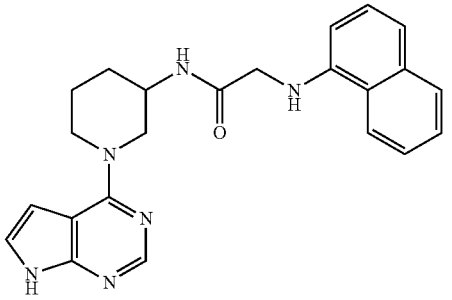 [SMILES: O=C(CNc1cccc2ccccc12)NC1CCCN(c2ncnc3[nH]ccc23)C1] | A |
| 47 | 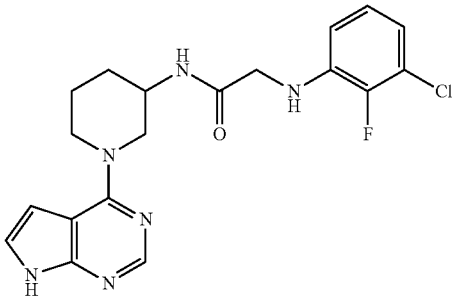 | B |

TABLE 1-continued
Exemplary compounds of formula I.
| Cmpd. No. | Structure | IC$_{50}$ (10 uM ATP)[a] |
|---|---|---|
| 48 | 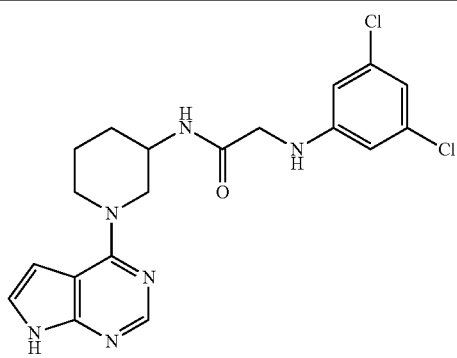 | A |
| 49 | 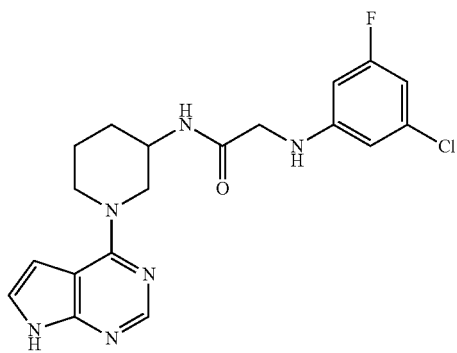 [SMILES: O=C(CNc1cc(F)cc(Cl)c1)NC1CCCN(c2ncnc3[nH]ccc23)C1] | A |
| 50 | 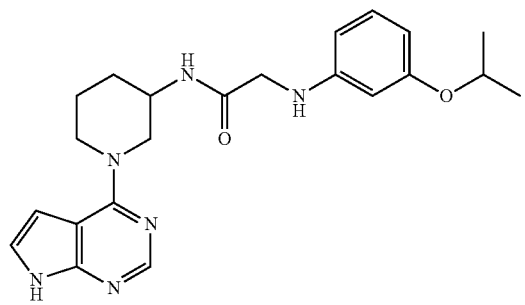 [SMILES: CC(C)Oc1cccc(NCC(=O)NC2CCCN(c3ncnc4[nH]ccc34)C2)c1] | C |
| 51 | 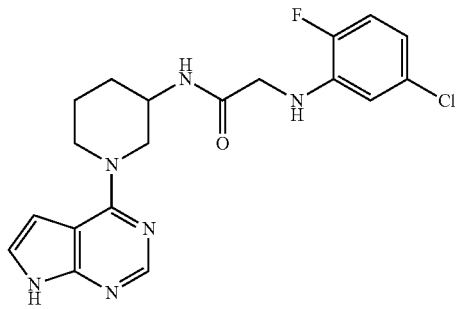 | B |

TABLE 1-continued
Exemplary compounds of formula I.
| Cmpd. No. | Structure | IC$_{50}$ (10 uM ATP)$^a$ |
|---|---|---|
| 52 | 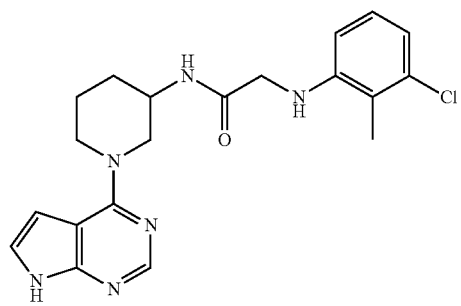 | B |
| 53 | 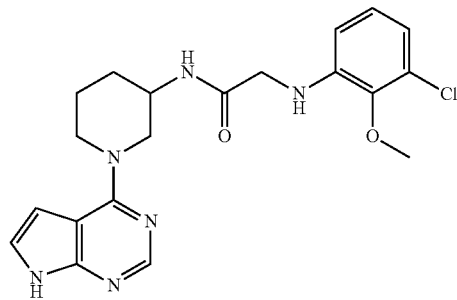 [SMILES: COc1c(Cl)cccc1NCC(=O)NC1CCCN(c2ncnc3[nH]ccc23)C1] | B |
| 54 | 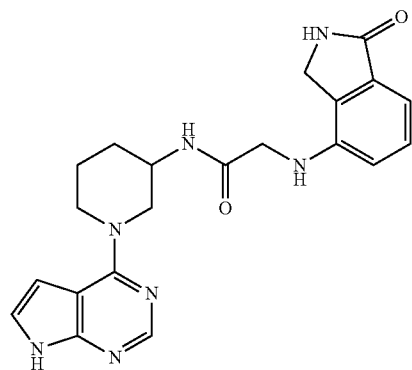 [SMILES: O=C(CNc1cccc2c1CNC2=O)NC1CCCN(c2ncnc3[nH]ccc23)C1] | D |
| 55 | 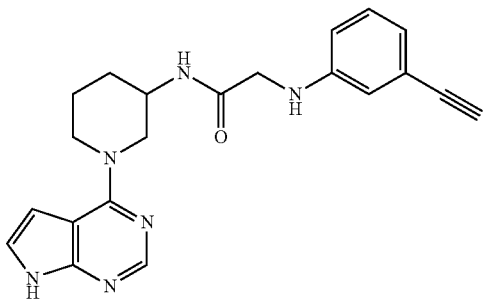 [SMILES: C#Cc1cccc(NCC(=O)NC2CCCN(c3ncnc4[nH]ccc34)C2)c1] | A |

TABLE 1-continued
Exemplary compounds of formula I.
| Cmpd. No. | Structure | IC$_{50}$ (10 uM ATP)$^a$ |
|---|---|---|
| 56 | 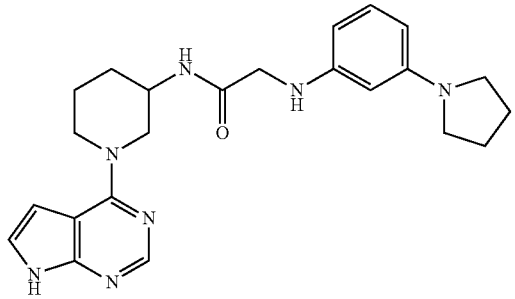 [SMILES: O=C(CNc1cccc(N2CCCC2)c1)NC1CCCN(c2ncnc3[nH]ccc23)C1] | B |
| 57 | 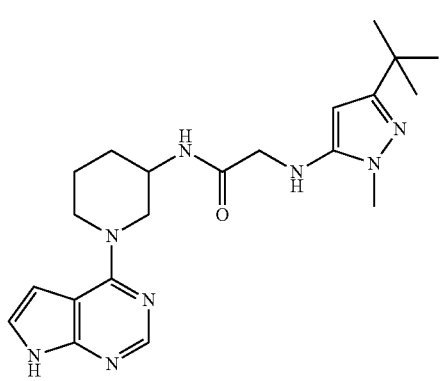 [SMILES: Cn1nc(C(C)(C)C)cc1NCC(=O)NC1CCCN(c2ncnc3[nH]ccc23)C1] | C |
| 58 | 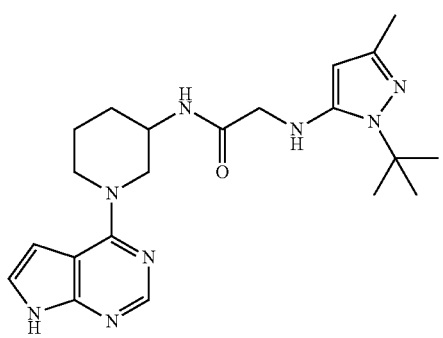 [SMILES: Cc1cc(NCC(=O)NC2CCCN(c3ncnc4[nH]ccc34)C2)n(C(C)(C)C)n1] | D |
| 59 | 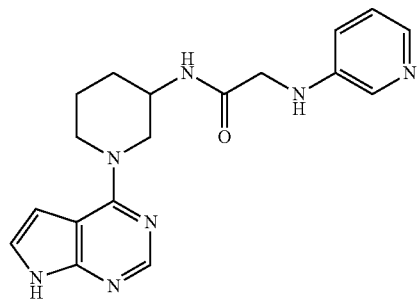 [SMILES: O=C(CNc1cccnc1)NC1CCCN(c2ncnc3[nH]ccc23)C1] | D |

TABLE 1-continued

Exemplary compounds of formula I.

| Cmpd. No. | Structure | IC$_{50}$ (10 uM ATP)$^a$ |
|---|---|---|
| 60 | 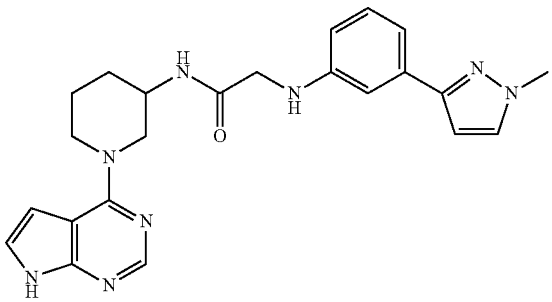 [SMILES: Cn1ccc(-c2cccc(NCC(=O)NC3CCCN(c4ncnc5[nH]ccc45)C3)c2)n1] | C |
| 61 | 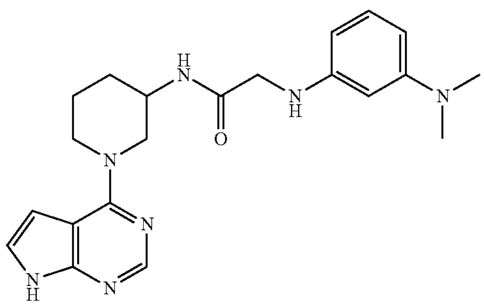 | C |
| 62 | 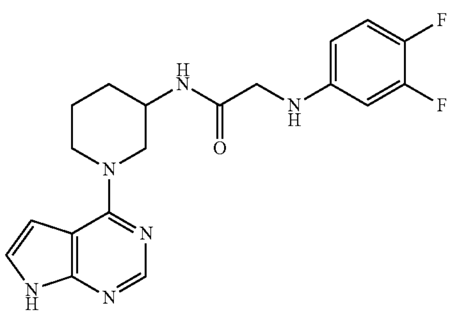 [SMILES: O=C(CNc1ccc(F)c(F)c1)NC1CCCN(c2ncnc3[nH]ccc23)C1] | B |
| 63 | 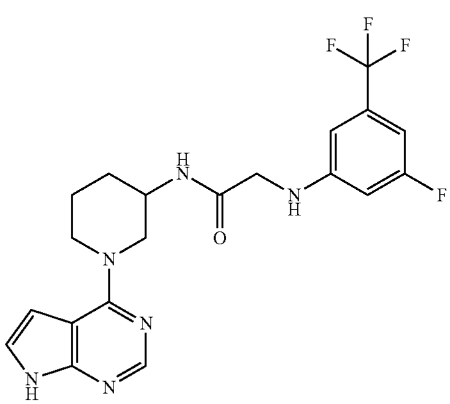 [SMILES: O=C(CNc1cc(F)cc(C(F)(F)F)c1)NC1CCCN(c2ncnc3[nH]ccc23)C1] | A |

TABLE 1-continued
Exemplary compounds of formula I.
| Cmpd. No. | Structure | IC$_{50}$ (10 uM ATP)$^a$ |
|---|---|---|
| 64 | 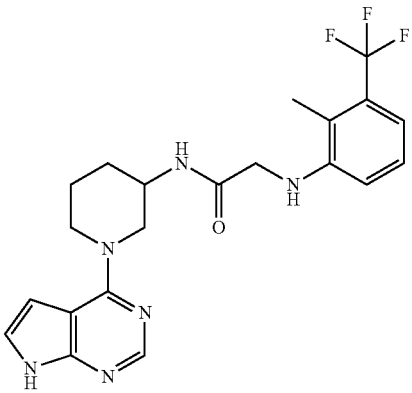 [SMILES: Cc1c(NCC(=O)NC2CCCN(c3ncnc4[nH]ccc34)C2)cccc1C(F)(F)F] | B |
| 65 | 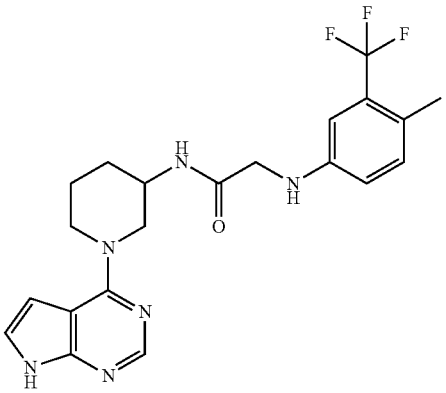 [SMILES: Cc1ccc(NCC(=O)NC2CCCN(c3ncnc4[nH]ccc34)C2)cc1C(F)(F)F] | B |
| 66 | 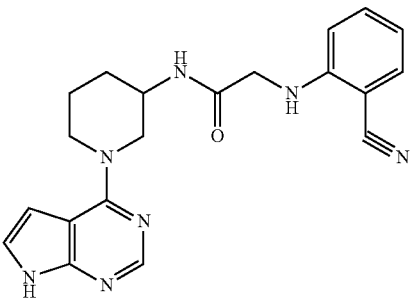 [SMILES: N#Cc1ccccc1NCC(=O)NC1CCCN(c2ncnc3[nH]ccc23)C1] | C |
| 67 | 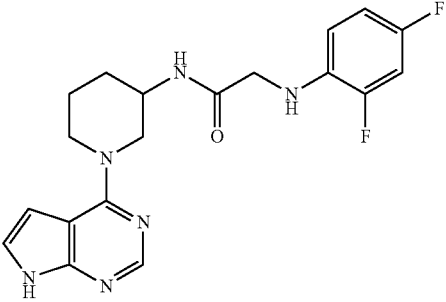 [SMILES: O=C(CNc1ccc(F)cc1F)NC1CCCN(c2ncnc3[nH]ccc23)C1] | B |

TABLE 1-continued
Exemplary compounds of formula I.
| Cmpd. No. | Structure | IC$_{50}$ (10 uM ATP)$^a$ |
|---|---|---|
| 68 | 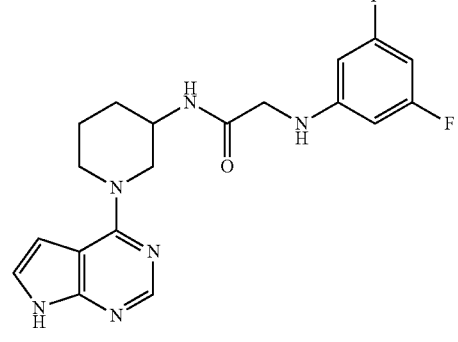 | A |
| 69 | 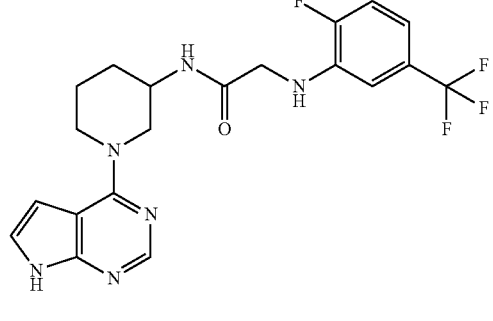 [SMILES: O=C(CNc1cccc(C(F)(F)F)c1F)NC1CCCN(c2ncnc3[nH]ccc23)C1] | C |
| 70 | 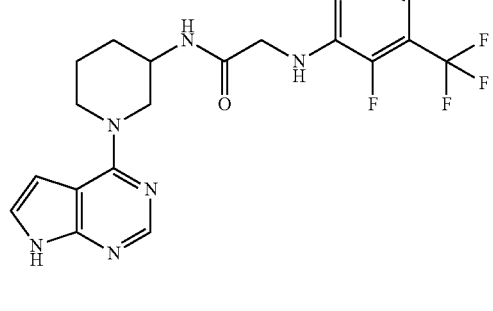 | B |
| 71 | 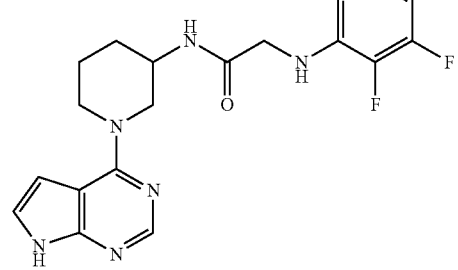 | B |

TABLE 1-continued
Exemplary compounds of formula I.
| Cmpd. No. | Structure | IC$_{50}$ (10 uM ATP)$^a$ |
|---|---|---|
| 72 | 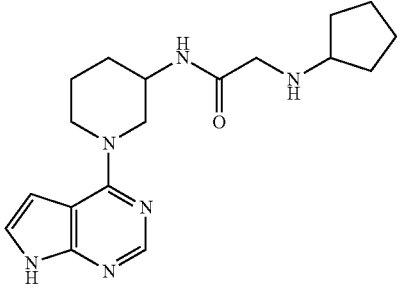 [SMILES: O=C(CNC1CCCC1)NC1CCCN(c2ncnc3[nH]ccc23)C1] | C |
| 73 | 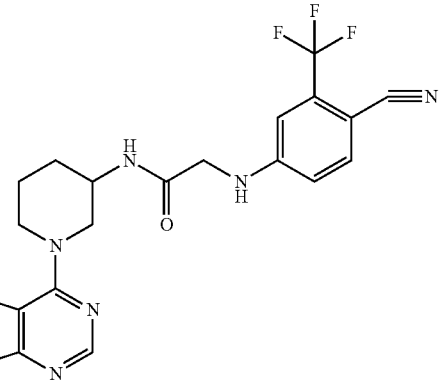 | D |
| 74 | 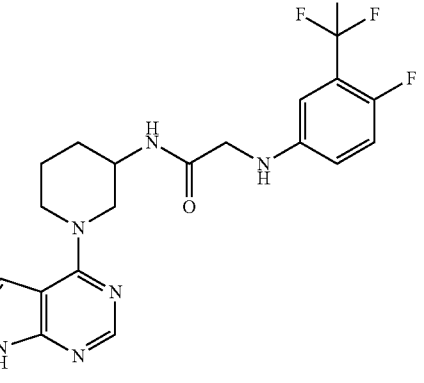 | C |
| 75 | 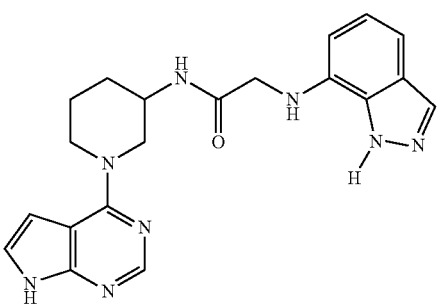 [SMILES: O=C(CNc1cccc2cn[nH]c12)NC1CCCN(c2ncnc3[nH]ccc23)C1] | C |

TABLE 1-continued
Exemplary compounds of formula I.
| Cmpd. No. | Structure | IC$_{50}$ (10 uM ATP)$^a$ |
|---|---|---|
| 76 | 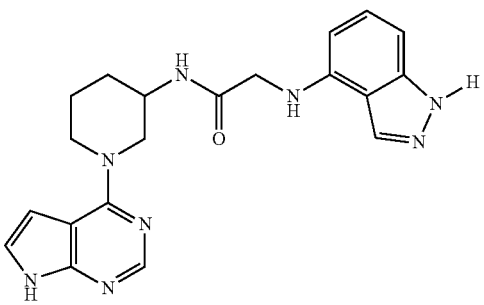 [SMILES: O=C(CNc1cccc2[nH]ncc12)NC1CCCN(c2ncnc3[nH]ccc23)C1] | B |
| 77 | 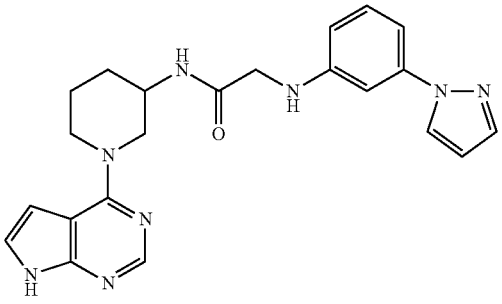 [SMILES: O=C(CNc1cccc(-n2cccn2)c1)NC1CCCN(c2ncnc3[nH]ccc23)C1] | B |
| 78 | 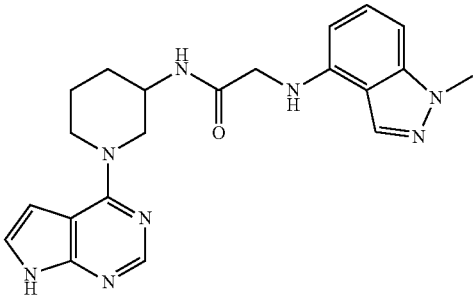 [SMILES: Cn1ncc2c(NCC(=O)NC3CCCN(c4ncnc5[nH]ccc45)C3)cccc21] | C |
| 79 | 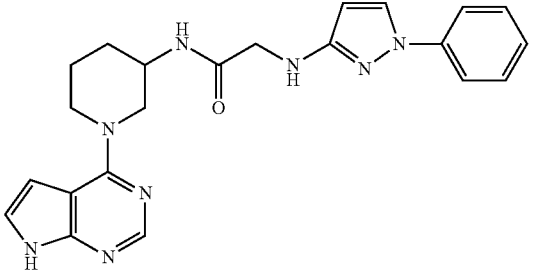 [SMILES: O=C(CNc1ccn(-c2ccccc2)n1)NC1CCCN(c2ncnc3[nH]ccc23)C1] | D |
| 80 | 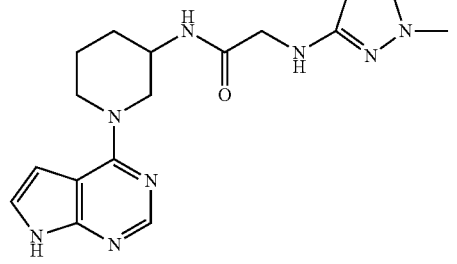 | C |

TABLE 1-continued

Exemplary compounds of formula I.

| Cmpd. No. | Structure | IC$_{50}$ (10 uM ATP) [a] |
|---|---|---|
| 81 | 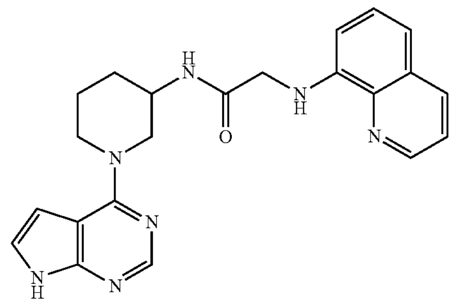 [SMILES: O=C(CNc1cccc2cccnc12)NC1CCCN(c2ncnc3[nH]ccc23)C1] | C |
| 82 | 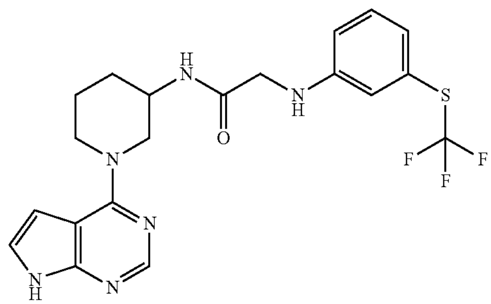 [SMILES: O=C(CNc1cccc(SC(F)(F)F)c1)NC1CCCN(c2ncnc3[nH]ccc23)C1] | B |
| 83 | 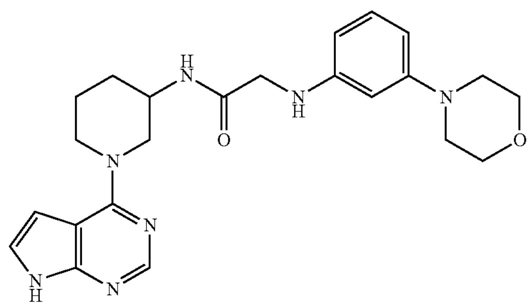 [SMILES: O=C(CNc1cccc(N2CCOCC2)c1)NC1CCCN(c2ncnc3[nH]ccc23)C1] | C |
| 84 | 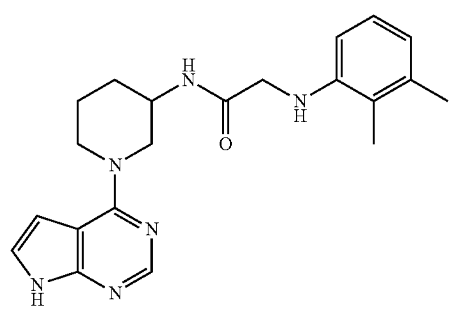 [SMILES: Cc1cccc(NCC(=O)NC2CCCN(c3ncnc4[nH]ccc34)C2)c1C] | B |
| 85 | 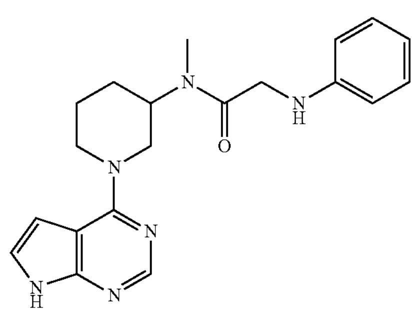 | |

TABLE 1-continued

Exemplary compounds of formula I.

| Cmpd. No. | Structure | IC$_{50}$ (10 uM ATP) [a] |
|---|---|---|
| 86 | 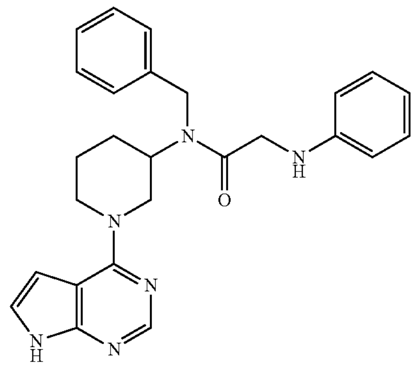 [SMILES: O=C(CNc1ccccc1)N(Cc1ccccc1)C1CCCN(c2ncnc3[nH]ccc23)C1] | C |
| 87 | 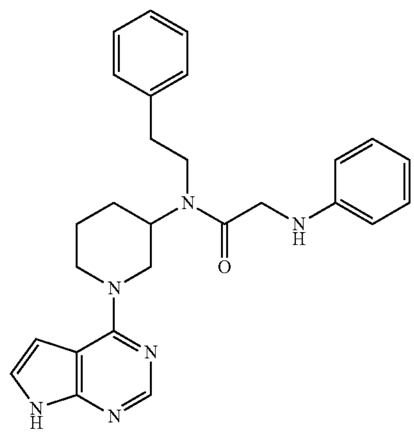 [SMILES: O=C(CNc1ccccc1)N(CCc1ccccc1)C1CCCN(c2ncnc3[nH]ccc23)C1] | B |
| 88 | 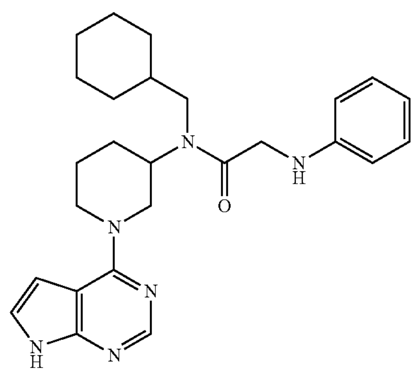 [SMILES: O=C(CNc1ccccc1)N(CC1CCCCC1)C1CCCN(c2ncnc3[nH]ccc23)C1] | C |
| 89 | 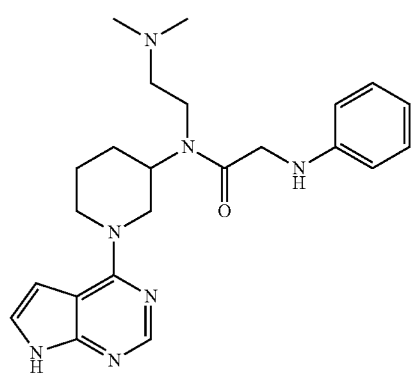 [SMILES: CN(C)CCN(C(=O)CNc1ccccc1)C1CCCN(c2ncnc3[nH]ccc23)C1] | |

TABLE 1-continued

Exemplary compounds of formula I.

| Cmpd. No. | Structure | IC$_{50}$ (10 uM ATP)$^a$ |
|---|---|---|
| 92 | 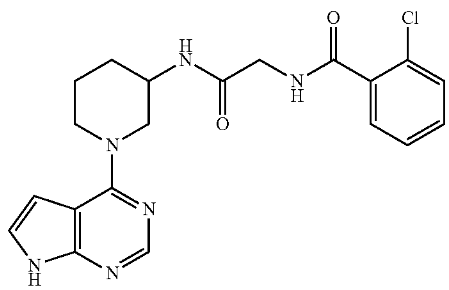 [SMILES: O=C(CNC(=O)c1ccccc1Cl)NC1CCCN(c2ncnc3[nH]ccc23)C1] | C |
| 93 | 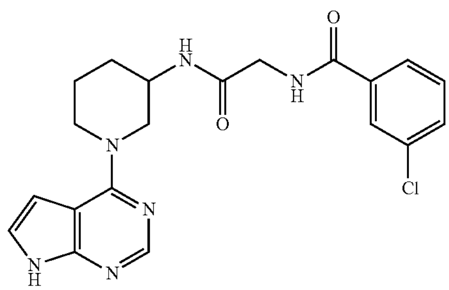 [SMILES: O=C(CNC(=O)c1cccc(Cl)c1)NC1CCCN(c2ncnc3[nH]ccc23)C1] | C |
| 94 | 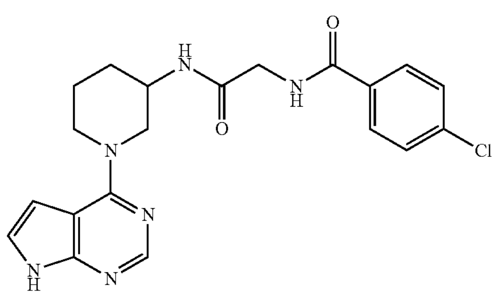 [SMILES: O=C(CNC(=O)c1ccc(Cl)cc1)NC1CCCN(c2ncnc3[nH]ccc23)C1] | C |
| 95 | 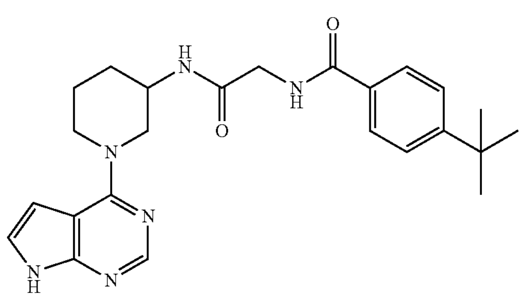 [SMILES: CC(C)(C)c1ccc(C(=O)NCC(=O)NC2CCCN(c3ncnc4[nH]ccc34)C2)cc1] | B |
| 96 | 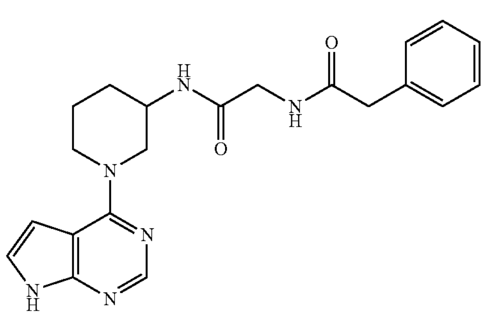 [SMILES: O=C(Cc1ccccc1)NCC(=O)NC1CCCN(c2ncnc3[nH]ccc23)C1] | C |

TABLE 1-continued

Exemplary compounds of formula I.

| Cmpd. No. | Structure | IC$_{50}$ (10 uM ATP) $^a$ |
|---|---|---|
| 97 | 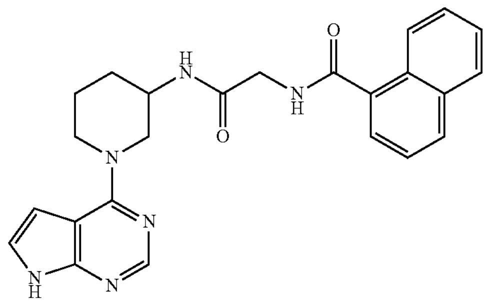 [SMILES: O=C(CNC(=O)c1cccc2ccccc12)NC1CCCN(c2ncnc3[nH]ccc23)C1] | B |
| 98 | 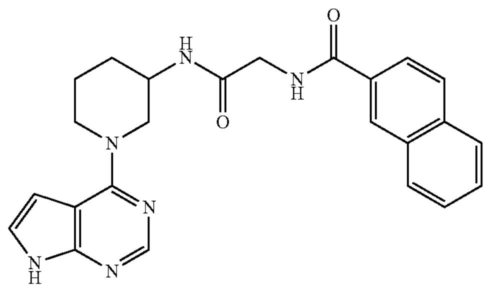 [SMILES: O=C(CNC(=O)c1ccc2ccccc2c1)NC1CCCN(c2ncnc3[nH]ccc23)C1] | B |
| 99 | 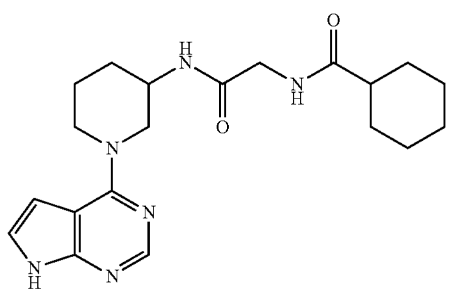 [SMILES: O=C(CNC(=O)C1CCCCC1)NC1CCCN(c2ncnc3[nH]ccc23)C1] | C |
| 100 | 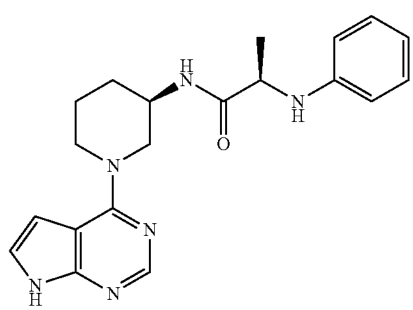 [SMILES: C[C@@H](Nc1ccccc1)C(=O)N[C@@H]1CCCN(c2ncnc3[nH]ccc23)C1] | B |
| 101 | 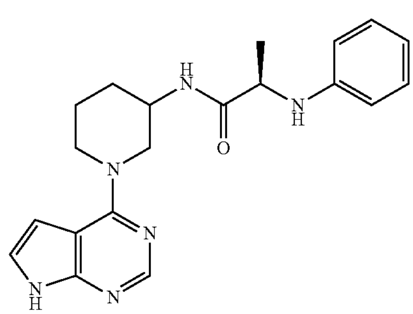 [SMILES: C[C@@H](Nc1ccccc1)C(=O)NC1CCCN(c2ncnc3[nH]ccc23)C1] | B |

TABLE 1-continued

Exemplary compounds of formula I.

| Cmpd. No. | Structure | IC$_{50}$ (10 uM ATP)$^a$ |
|---|---|---|
| 102 | 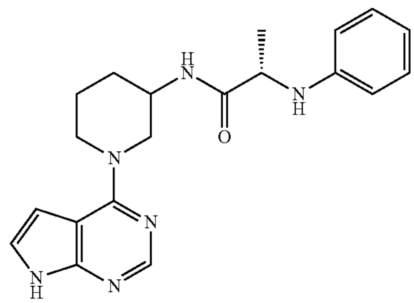 [SMILES: C[C@H](Nc1ccccc1)C(=O)NC1CCCN(c2ncnc3[nH]ccc23)C1] | D |
| 103 | 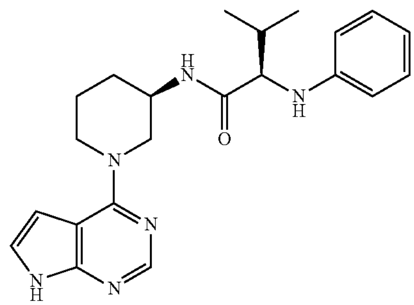 [SMILES: CC(C)[C@@H](Nc1ccccc1)C(=O)N[C@@H]1CCCN(c2ncnc3[nH]ccc23)C1] | B |
| 104 | 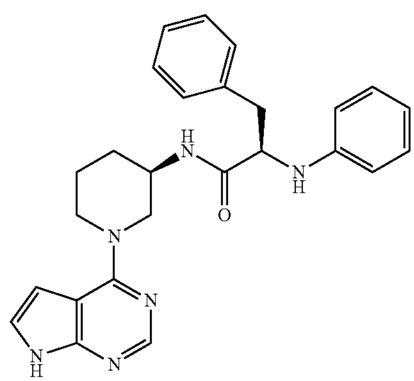 [SMILES: O=C(N[C@@H]1CCCN(c2ncnc3[nH]ccc23)C1)[C@@H](Cc1ccccc1)Nc1ccccc1] | C |
| 105 | 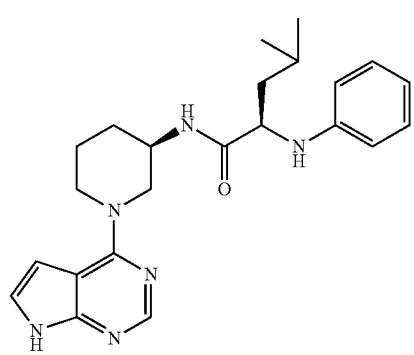 [SMILES: CC(C)C[C@@H](Nc1ccccc1)C(=O)N[C@@H]1CCCN(c2ncnc3[nH]ccc23)C1] | C |

TABLE 1-continued
Exemplary compounds of formula I.
| Cmpd. No. | Structure | IC$_{50}$ (10 uM ATP)$^a$ |
|---|---|---|
| 106 | 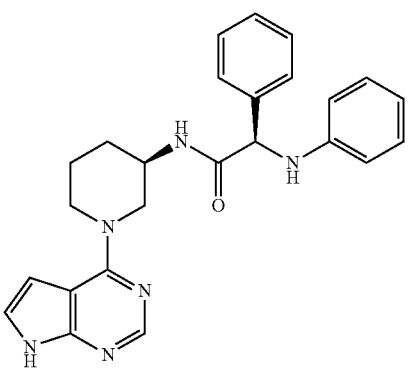 [SMILES: O=C(N[C@@H]1CCCN(c2ncnc3[nH]ccc23)C1)[C@H](Nc1ccccc1)c1ccccc1] | D |
| 107 | 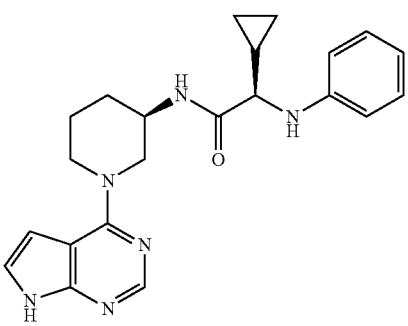 [SMILES: O=C(N[C@@H]1CCCN(c2ncnc3[nH]ccc23)C1)[C@H](Nc1ccccc1)C1CC1] | A |
| 108 | 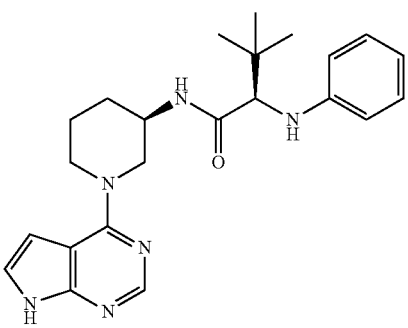 [SMILES: CC(C)(C)[C@@H](Nc1ccccc1)C(=O)N[C@@H]1CCCN(c2ncnc3[nH]ccc23)C1] | B |
| 109 | 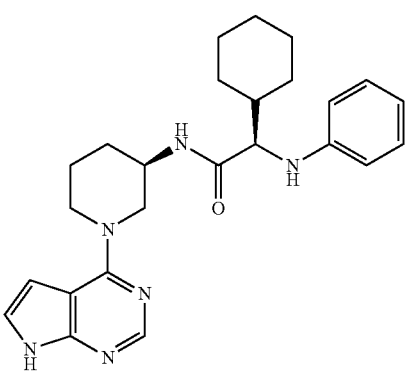 [SMILES: O=C(N[C@@H]1CCCN(c2ncnc3[nH]ccc23)C1)[C@H](Nc1ccccc1)C1CCCCC1] | C |

TABLE 1-continued

Exemplary compounds of formula I.

| Cmpd. No. | Structure | IC$_{50}$ (10 uM ATP)$^a$ |
|---|---|---|
| 110 | 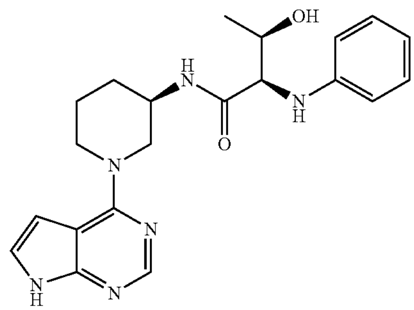 [SMILES: C[C@@H](O)[C@@H](Nc1ccccc1)C(=O)N[C@@H]1CCCN(c2ncnc3[nH]ccc23)C1] | B |
| 111 | 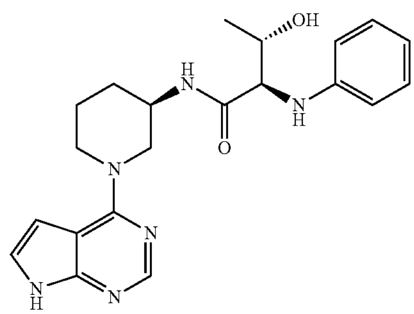 [SMILES: C[C@H](O)[C@@H](Nc1ccccc1)C(=O)N[C@@H]1CCCN(c2ncnc3[nH]ccc23)C1] | B |
| 112 | 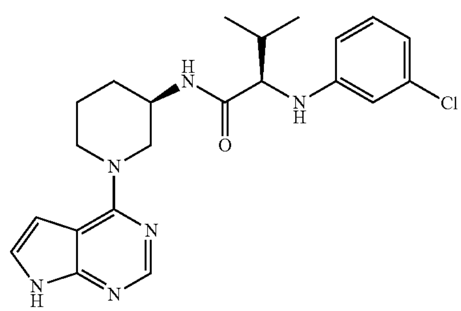 [SMILES: CC(C)[C@@H](Nc1cccc(Cl)c1)C(=O)N[C@@H]1CCCN(c2ncnc3[nH]ccc23)C1] | A |
| 113 | 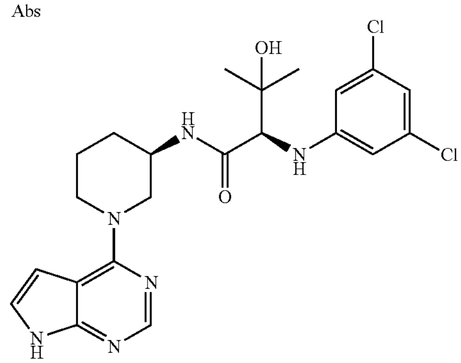 | A |

TABLE 1-continued

Exemplary compounds of formula I.

| Cmpd. No. | Structure | IC$_{50}$ (10 uM ATP)$^a$ |
|---|---|---|
| 114 | 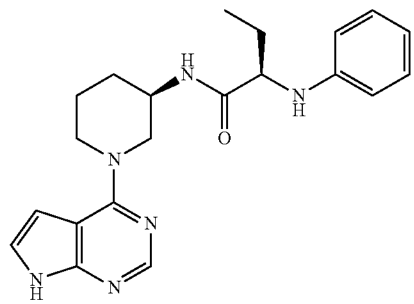 | A |
| 115 | 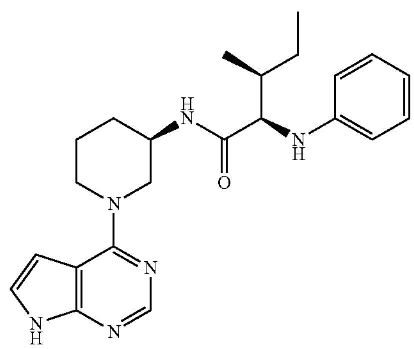 [SMILES: CC[C@H](C)[C@@H](Nc1ccccc1)C(=O)N[C@@H]1CCCN(c2ncnc3[nH]ccc23)C1] | B |
| 116 | 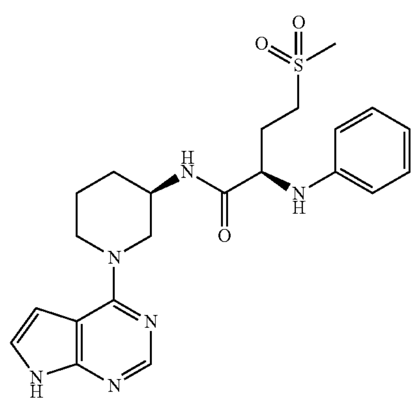 [SMILES: CS(=O)(=O)CC[C@@H](Nc1ccccc1)C(=O)N[C@@H]1CCCN(c2ncnc3[nH]ccc23)C1] | C |
| 117 | 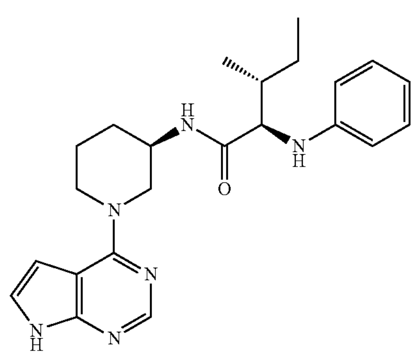 [SMILES: CC[C@@H](C)[C@@H](Nc1ccccc1)C(=O)N[C@@H]1CCCN(c2ncnc3[nH]ccc23)C1] | B |

TABLE 1-continued

Exemplary compounds of formula I.

| Cmpd. No. | Structure | IC$_{50}$ (10 uM ATP)$^a$ |
|---|---|---|
| 118 | 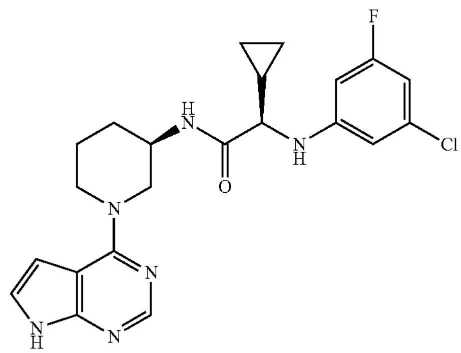 [SMILES: O=C(N[C@@H]1CCCN(c2ncnc3[nH]ccc23)C1)[C@H](Nc1cc(F)cc(Cl)c1)C1CC1] | A |
| 119 | 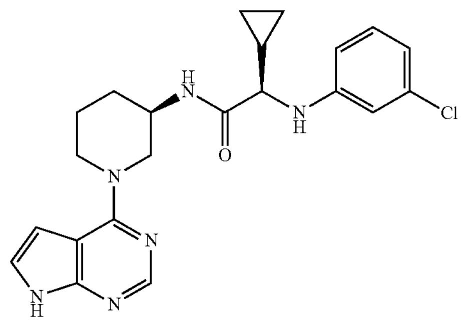 [SMILES: O=C(N[C@@H]1CCCN(c2ncnc3[nH]ccc23)C1)[C@H](Nc1cccc(Cl)c1)C1CC1] | A |
| 120 | 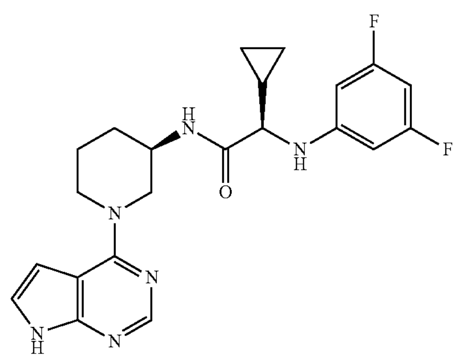 [SMILES: O=C(N[C@@H]1CCCN(c2ncnc3[nH]ccc23)C1)[C@H](Nc1cc(F)cc(F)c1)C1CC1] | A |
| 121 | 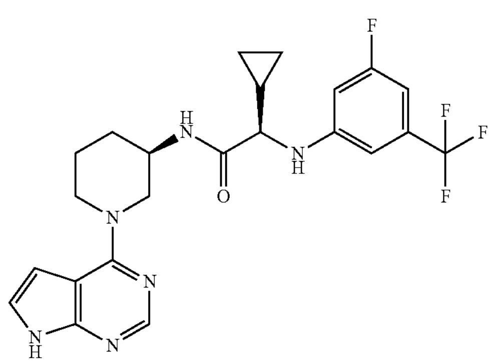 [SMILES: O=C(N[C@@H]1CCCN(c2ncnc3[nH]ccc23)C1)[C@H](Nc1cc(F)cc(C(F)(F)F)c1)C1CC1] | A |

TABLE 1-continued

Exemplary compounds of formula I.

| Cmpd. No. | Structure | IC$_{50}$ (10 uM ATP)$^a$ |
|---|---|---|
| 122 | 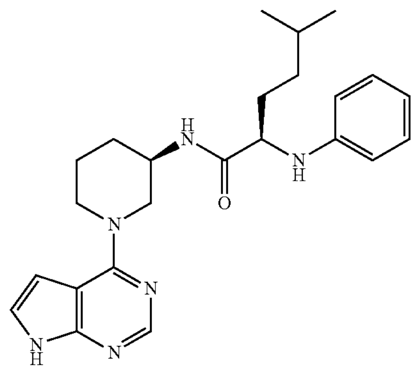 [SMILES: CC(C)CC[C@@H](Nc1ccccc1)C(=O)N[C@@H]1CCCN(c2ncnc3[nH]ccc23)C1] | C |
| 123 | 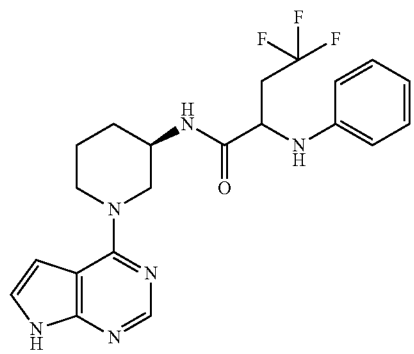 [SMILES: O=C(N[C@@H]1CCCN(c2ncnc3[nH]ccc23)C1)C(CC(F)(F)F)Nc1ccccc1] | C |
| 124 | 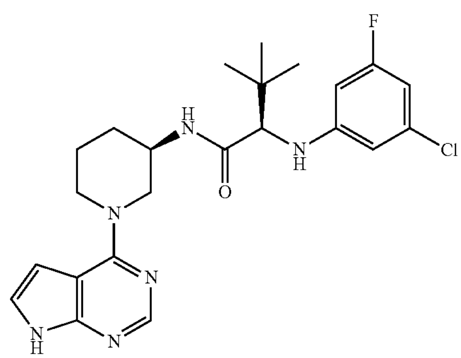 | A |
| 125 | 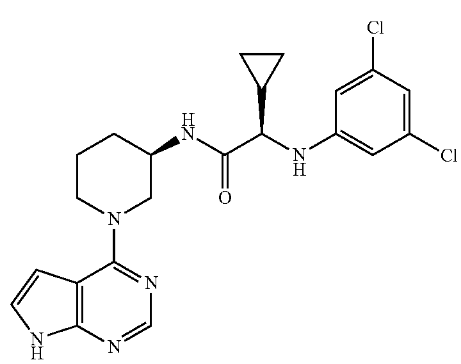 | A |

TABLE 1-continued

Exemplary compounds of formula I.

| Cmpd. No. | Structure | IC$_{50}$ (10 uM ATP)$^a$ |
|---|---|---|
| 126 | 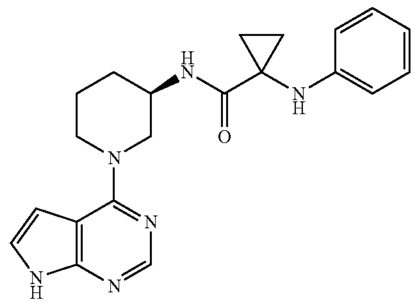 [SMILES: O=C(N[C@@H]1CCCN(c2ncnc3[nH]ccc23)C1)C1(Nc2ccccc2)CC1] | C |
| 127 | 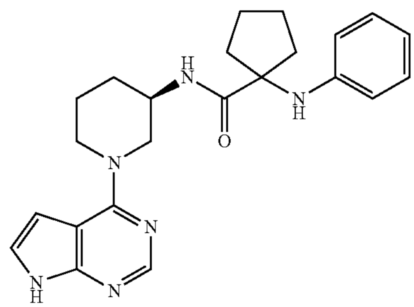 [SMILES: O=C(N[C@@H]1CCCN(c2ncnc3[nH]ccc23)C1)C1(Nc2ccccc2)CCCC1] | C |
| 128 | 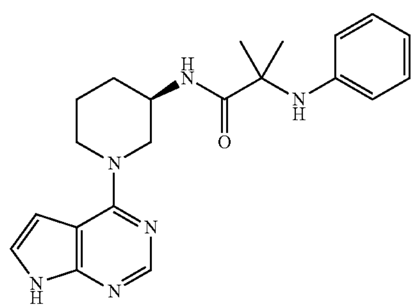 | C |
| 129 | Abs | A |

TABLE 1-continued

Exemplary compounds of formula I.

| Cmpd. No. | Structure | IC$_{50}$ (10 uM ATP)$^a$ |
|---|---|---|
| 130 | Abs | A |
| 131 | Abs | A |
| 132 | Abs | B |
| 133 | Rac | C |

TABLE 1-continued

Exemplary compounds of formula I.

| Cmpd. No. | Structure | IC$_{50}$ (10 uM ATP)$^a$ |
|---|---|---|
| 134 | 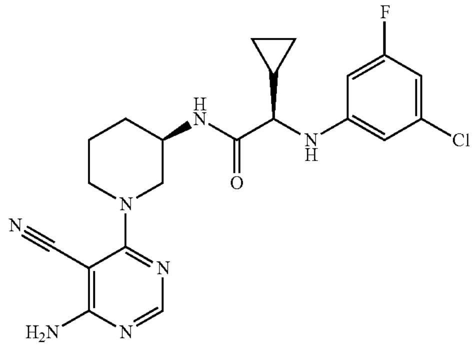 [SMILES: N#Cc1c(N)ncnc1N1CCC[C@@H](NC(=O)[C@H](Nc2cc(F)cc(Cl)c2)C2CC2)C1] | C |
| 135 | 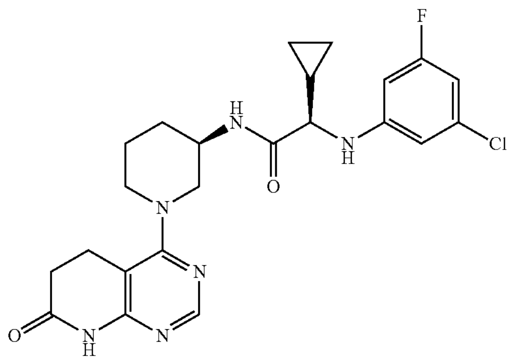 [SMILES: O=C1CCc2c(ncnc2N2CCC[C@@H](NC(=O)[C@H](Nc3cc(F)cc(Cl)c3)C3CC3)C2)N1] | B |
| 136 | 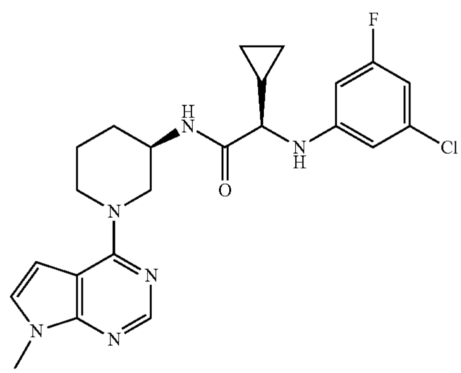 [SMILES: Cn1ccc2c(N3CCC[C@@H](NC(=O)[C@H](Nc4cc(F)cc(Cl)c4)C4CC4)C3)ncnc21] | B |
| 137 | 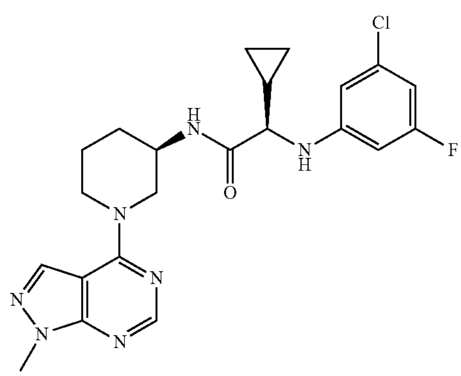 [SMILES: Cn1ncc2c(N3CCC[C@@H](NC(=O)[C@H](Nc4cc(F)cc(Cl)c4)C4CC4)C3)ncnc21] | C |

TABLE 1-continued

Exemplary compounds of formula I.

| Cmpd. No. | Structure | IC$_{50}$ (10 uM ATP)$^a$ |
|---|---|---|
| 138 | 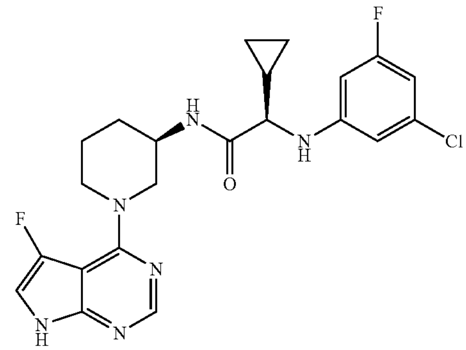 [SMILES: O=C(N[C@@H]1CCCN(c2ncnc3[nH]cc(F)c23)C1)[C@H](Nc1cc(F)cc(Cl)c1)C1CC1] | B |
| 139 | 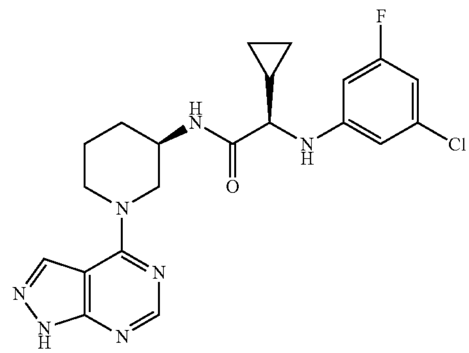 [SMILES: O=C(N[C@@H]1CCCN(c2ncnc3[nH]ncc23)C1)[C@H](Nc1cc(F)cc(Cl)c1)C1CC1] | A |
| 140 | Abs | B |
| 141 | Abs | C |

TABLE 1-continued

Exemplary compounds of formula I.

| Cmpd. No. | Structure | IC$_{50}$ (10 uM ATP)$^a$ |
|---|---|---|
| 142 | Abs | C |
| 143 | Abs | C |
| 144 | Abs | B |
| 145 | 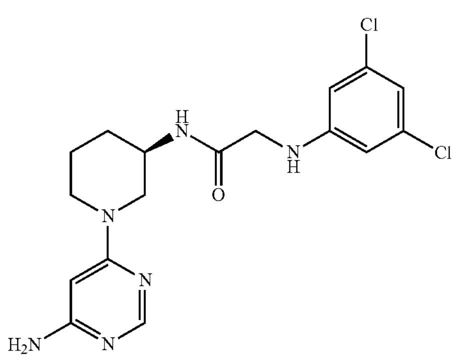 [SMILES: Nc1cc(N2CCC[C@@H](NC(=O)CNc3cc(Cl)cc(Cl)c3)C2)ncn1] | A |

TABLE 1-continued

Exemplary compounds of formula I.

| Cmpd. No. | Structure | IC$_{50}$ (10 uM ATP)$^a$ |
|---|---|---|
| 146 | 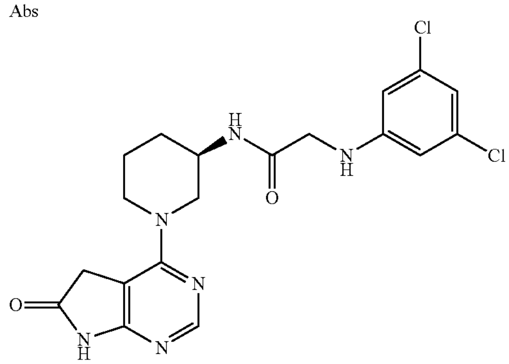 [SMILES: O=C1Cc2c(ncnc2N2CCC[C@@H](NC(=O)CNc3cc(Cl)cc(Cl)c3)C2)N1] | B |
| 147 | 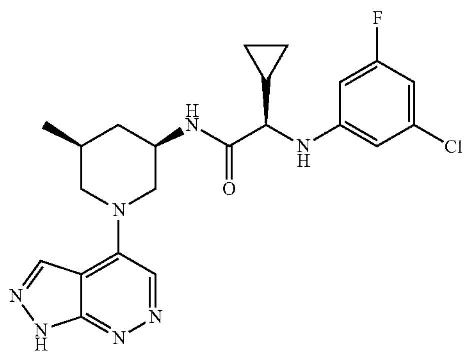 [SMILES: C[C@H]1C[C@@H](NC(=O)[C@H](Nc2cc(F)cc(Cl)c2)C2CC2)CN(c2cnnc3[nH]ncc23)C1] | A |
| 148 | 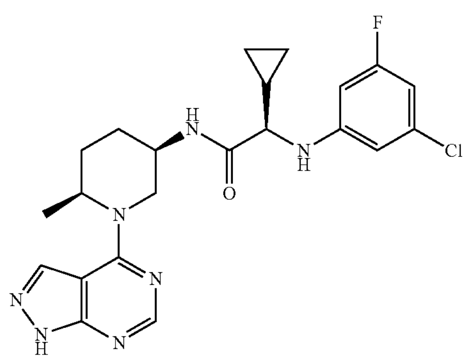 [SMILES: C[C@H]1CC[C@@H](NC(=O)[C@H](Nc2cc(F)cc(Cl)c2)C2CC2)CN1c1ncnc2[nH]ncc12] | B |
| 149 | 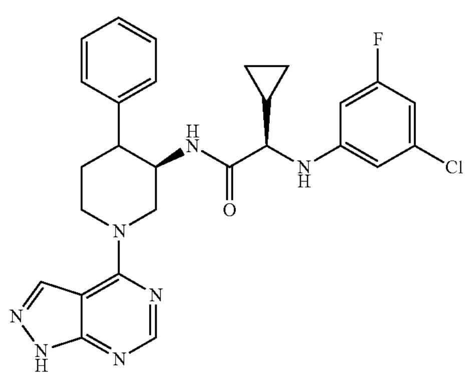 [SMILES: O=C(N[C@H]1CN(c2ncnc3[nH]ncc23)CCC1c1ccccc1)[C@H](Nc1cc(F)cc(Cl)c1)C1CC1] | A |

TABLE 1-continued

Exemplary compounds of formula I.

| Cmpd. No. | Structure | IC$_{50}$ (10 uM ATP)$^a$ |
|---|---|---|
| 150 | Abs | A |
| 151 | Abs | B |
| 152 | Abs | A |
| 153 | 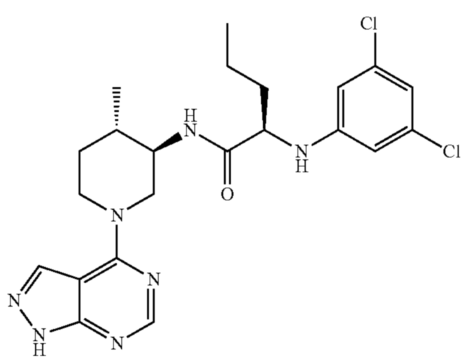 [SMILES: CCC[C@@H](Nc1cc(Cl)cc(Cl)c1)C(=O)N[C@H]1CN(c2ncnc3[nH]ncc23)CC[C@@H]1C] | A |

TABLE 1-continued

Exemplary compounds of formula I.

| Cmpd. No. | Structure | IC$_{50}$ (10 uM ATP)$^a$ |
|---|---|---|
| 154 | 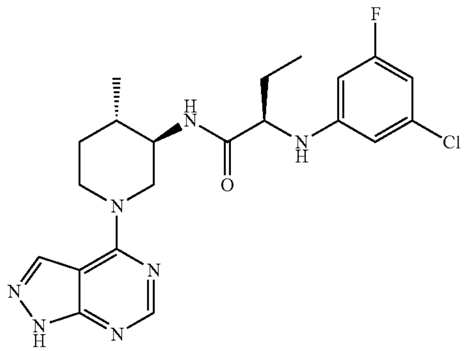 [SMILES: CC[C@@H](Nc1cc(F)cc(Cl)c1)C(=O)N[C@H]1CN(c2ncnc3[nH]ncc23)CC[C@@H]1C] | A |
| 155 | 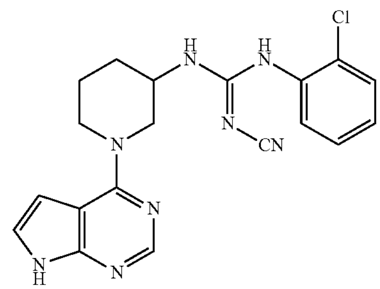 [SMILES: N#C/N=C(\Nc1ccccc1Cl)NC1CCCN(c2ncnc3[nH]ccc23)C1] | |
| 156 | 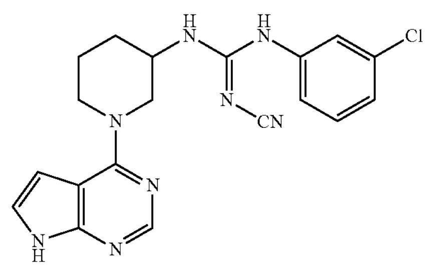 [SMILES: N#C/N=C(\Nc1cccc(Cl)c1)NC1CCCN(c2ncnc3[nH]ccc23)C1] | |
| 157 | 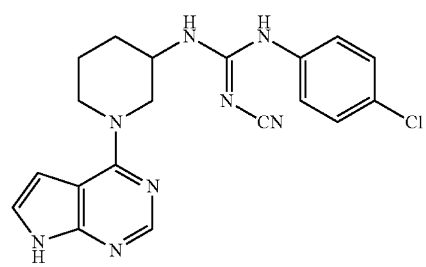 [SMILES: N#C/N=C(\Nc1ccc(Cl)cc1)NC1CCCN(c2ncnc3[nH]ccc23)C1] | |
| 158 | 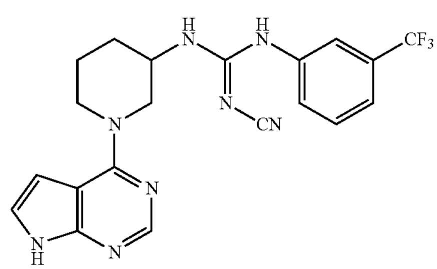 [SMILES: N#C/N=C(\Nc1cccc(C(F)(F)F)c1)NC1CCCN(c2ncnc3[nH]ccc23)C1] | |

TABLE 1-continued

Exemplary compounds of formula I.

| Cmpd. No. | Structure | IC$_{50}$ (10 uM ATP)$^a$ |
|---|---|---|
| 159 | 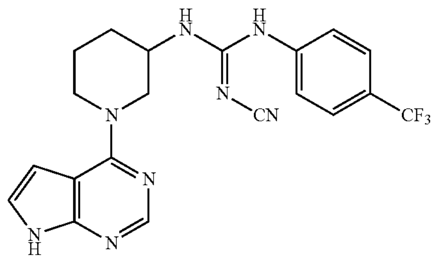 [SMILES: N#C/N=C(\Nc1ccc(C(F)(F)F)cc1)NC1CCCN(c2ncnc3[nH]ccc23)C1] | |
| 160 | 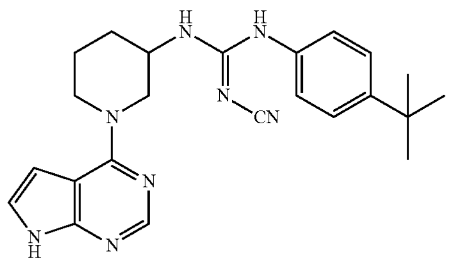 [SMILES: CC(C)(C)c1ccc(N/C(=N\C#N)NC2CCCN(c3ncnc4[nH]ccc34)C2)cc1] | |
| 163 | 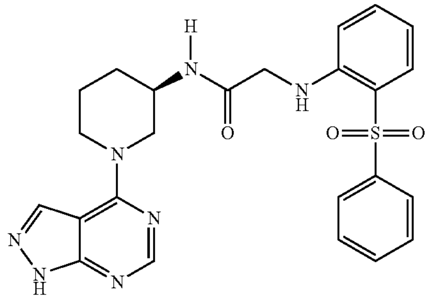 [SMILES: O=C(CNc1ccccc1S(=O)(=O)c1ccccc1)N[C@@H]1CCCN(c2ncnc3[nH]ncc23)C1] | A |
| 164 | 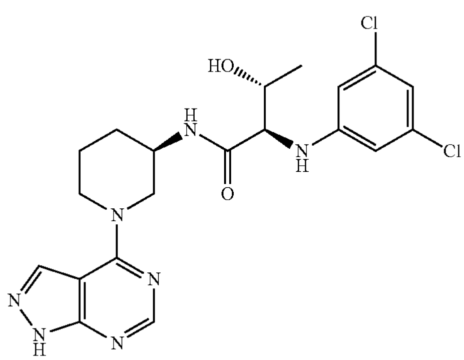 [SMILES: C[C@@H](O)[C@@H](Nc1cc(Cl)cc(Cl)c1)C(=O)N[C@@H]1CCCN(c2ncnc3[nH]ncc23)C1] | A |
| 165 | 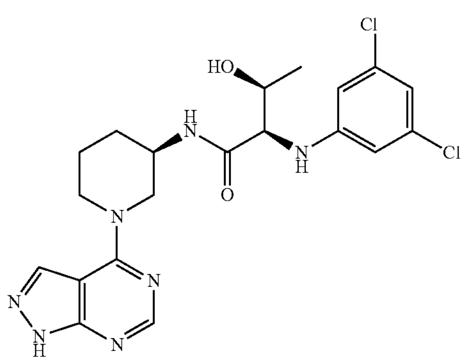 [SMILES: C[C@H](O)[C@@H](Nc1cc(Cl)cc(Cl)c1)C(=O)N[C@@H]1CCCN(c2ncnc3[nH]ncc23)C1] | A |

TABLE 1-continued

Exemplary compounds of formula I.

| Cmpd. No. | Structure | IC$_{50}$ (10 uM ATP)$^a$ |
|---|---|---|
| 166 | 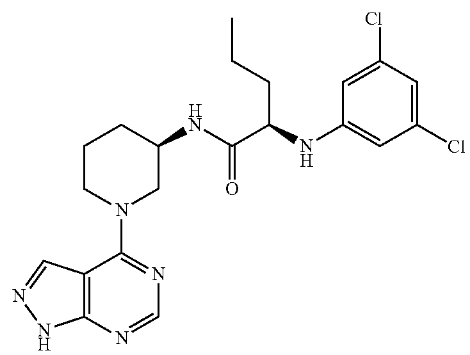 [SMILES: CCC[C@@H](Nc1cc(Cl)cc(Cl)c1)C(=O)N[C@@H]1CCCN(c2ncnc3[nH]ncc23)C1] | A |
| 167 | 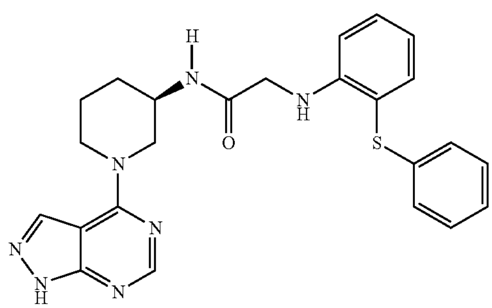 [SMILES: O=C(CNc1ccccc1Sc1ccccc1)N[C@@H]1CCCN(c2ncnc3[nH]ncc23)C1] | A |
| 168 | Abs | A |
| 169 | 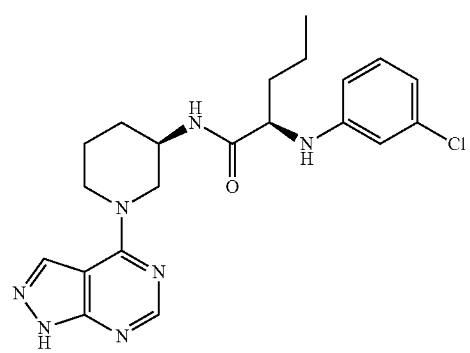 [SMILES: CCC[C@@H](Nc1cccc(Cl)c1)C(=O)N[C@@H]1CCCN(c2ncnc3[nH]ncc23)C1] | A |

TABLE 1-continued
Exemplary compounds of formula I.
| Cmpd. No. | Structure | IC$_{50}$ (10 uM ATP)$^a$ |
|---|---|---|
| 170 | 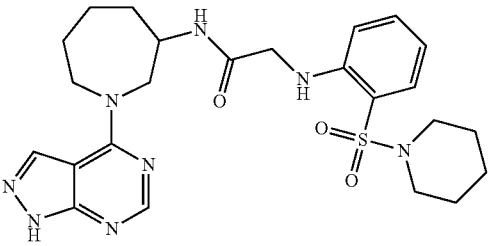 [SMILES: O=C(CNc1ccccc1S(=O)(=O)N1CCCCC1)NC1CCCCN(c2ncnc3[nH]ncc23)C1] | A |
| 171 | 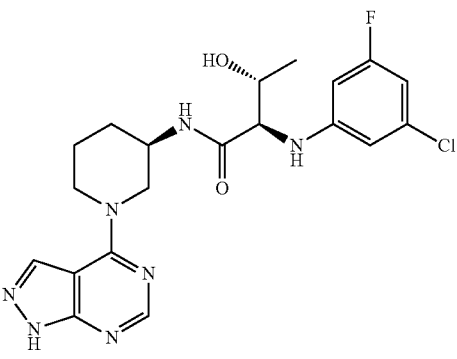 [SMILES: C[C@@H](O)[C@@H](Nc1cc(F)cc(Cl)c1)C(=O)N[C@@H]1CCCN(c2ncnc3[nH]ncc23)C1] | A |
| 172 | 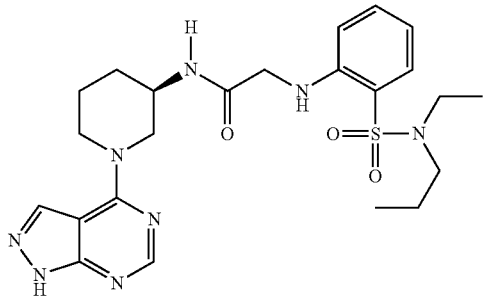 [SMILES: CCCN(CC)S(=O)(=O)c1ccccc1NCC(=O)N[C@@H]1CCCN(c2ncnc3[nH]ncc23)C1] | A |
| 173 | 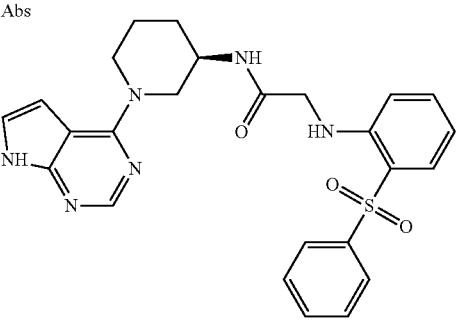 [SMILES: O=C(CNc1ccccc1S(=O)(=O)c1ccccc1)N[C@@H]1CCCN(c2ncnc3[nH]ccc23)C1] | A |

TABLE 1-continued

Exemplary compounds of formula I.

| Cmpd. No. | Structure | IC$_{50}$ (10 uM ATP)$^a$ |
|---|---|---|
| 174 | 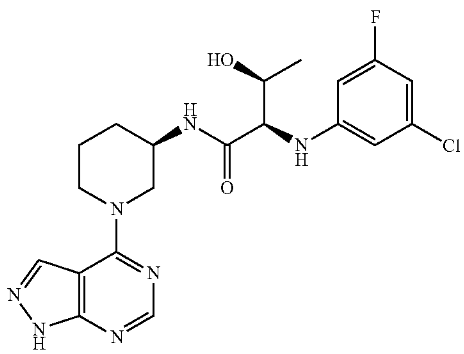 [SMILES: C[C@H](O)[C@@H](Nc1cc(F)cc(Cl)c1)C(=O)N[C@@H]1CCCN(c2ncnc3[nH]ncc23)C1] | A |
| 175 | 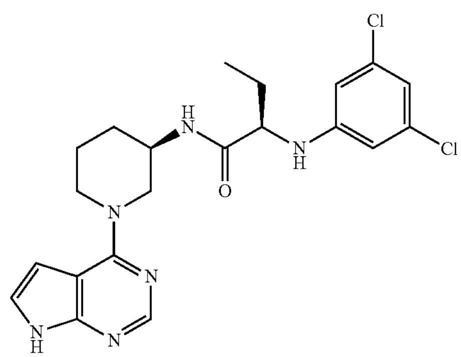 [SMILES: CC[C@@H](Nc1cc(Cl)cc(Cl)c1)C(=O)N[C@@H]1CCCN(c2ncnc3[nH]ccc23)C1] | A |
| 176 | 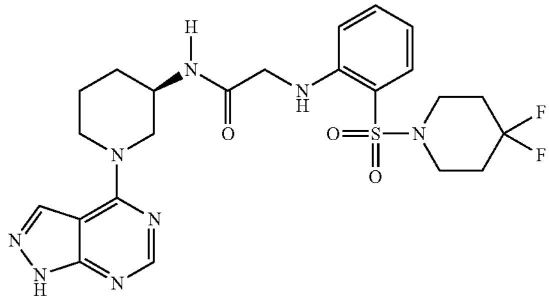 [SMILES: O=C(CNc1ccccc1S(=O)(=O)N1CCC(F)(F)CC1)N[C@@H]1CCCN(c2ncnc3[nH]ncc23)C1] | A |
| 177 | Abs | A |

TABLE 1-continued

Exemplary compounds of formula I.

| Cmpd. No. | Structure | IC$_{50}$ (10 uM ATP)$^a$ |
|---|---|---|
| 178 | 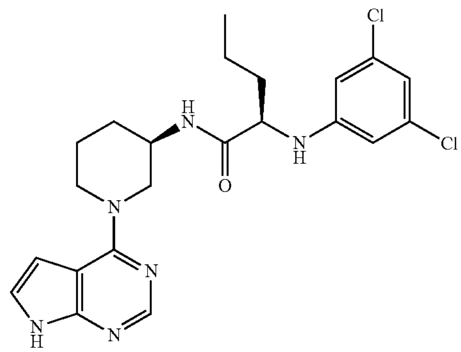 [SMILES: CCC[C@@H](Nc1cc(Cl)cc(Cl)c1)C(=O)N[C@@H]1CCCN(c2ncnc3[nH]ccc23)C1] | A |
| 179 | 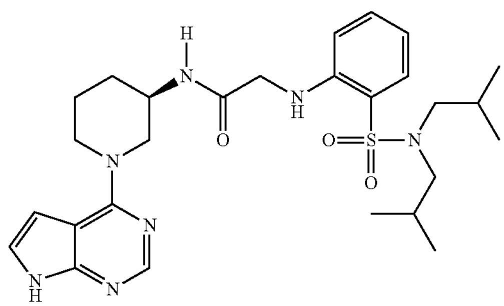 [SMILES: CC(C)CN(CC(C)C)S(=O)(=O)c1ccccc1NCC(=O)N[C@@H]1CCCN(c2ncnc3[nH]ccc23)C1] | A |
| 180 | 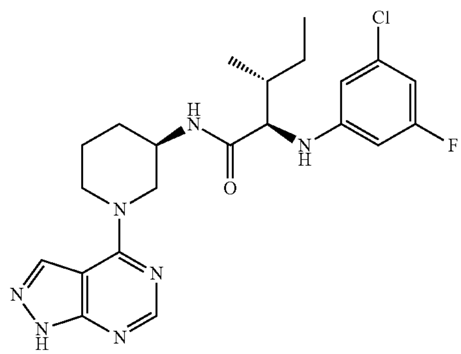 [SMILES: CC[C@@H](C)[C@@H](Nc1cc(F)cc(Cl)c1)C(=O)N[C@@H]1CCCN(c2ncnc3[nH]ncc23)C1] | A |
| 181 | 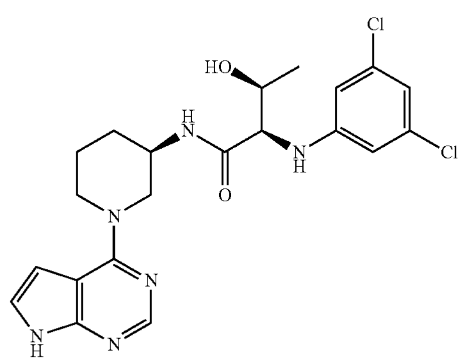 [SMILES: C[C@H](O)[C@@H](Nc1cc(Cl)cc(Cl)c1)C(=O)N[C@@H]1CCCN(c2ncnc3[nH]ccc23)C1] | A |

TABLE 1-continued

Exemplary compounds of formula I.

| Cmpd. No. | Structure | IC$_{50}$ (10 uM ATP) $^a$ |
|---|---|---|
| 182 | 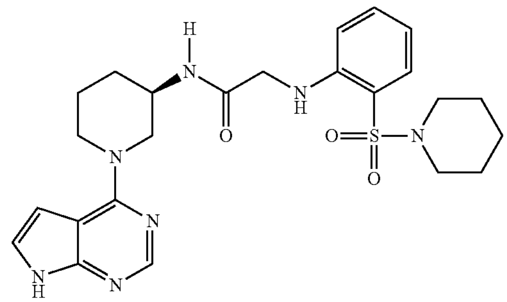 [SMILES: O=C(CNc1ccccc1S(=O)(=O)N1CCCCC1)N[C@@H]1CCCN(c2ncnc3[nH]ccc23)C1] | A |
| 183 | 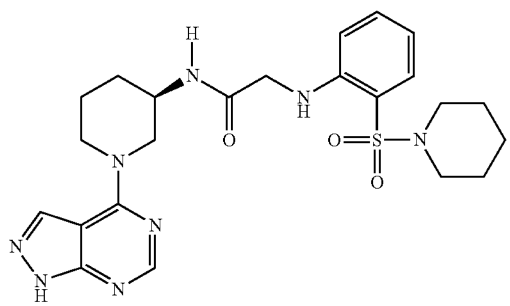 [SMILES: O=C(CNc1ccccc1S(=O)(=O)N1CCCCC1)N[C@@H]1CCCN(c2ncnc3[nH]ncc23)C1] | A |
| 184 | 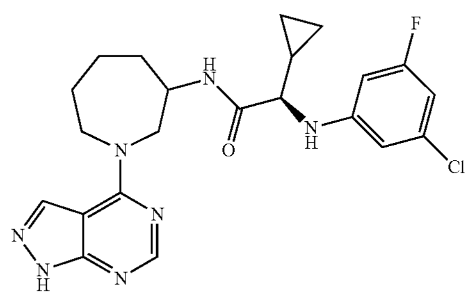 [SMILES: O=C(NC1CCCCN(c2ncnc3[nH]ncc23)C1)[C@H](Nc1cc(F)cc(Cl)c1)C1CC1] | A |
| 185 | Abs | A |

TABLE 1-continued
Exemplary compounds of formula I.
| Cmpd. No. | Structure | IC$_{50}$ (10 uM ATP)$^a$ |
|---|---|---|
| 186 | 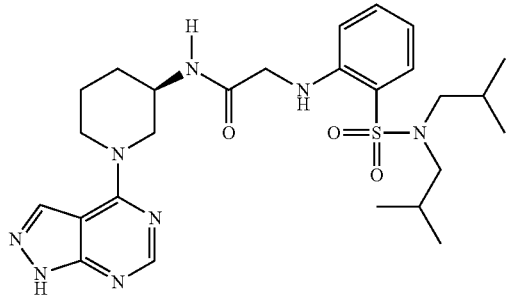 [SMILES: CC(C)CN(CC(C)C)S(=O)(=O)c1ccccc1NCC(=O)N[C@@H]1CCCN(c2ncnc3[nH]ncc23)C1] | A |
| 187 | 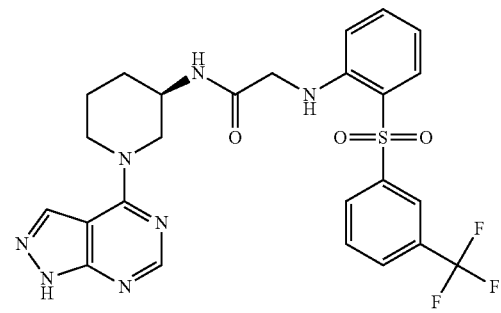 [SMILES: O=C(CNc1ccccc1S(=O)(=O)c1cccc(C(F)(F)F)c1)N[C@@H]1CCCN(c2ncnc3[nH]ncc23)C1] | A |
| 188 | 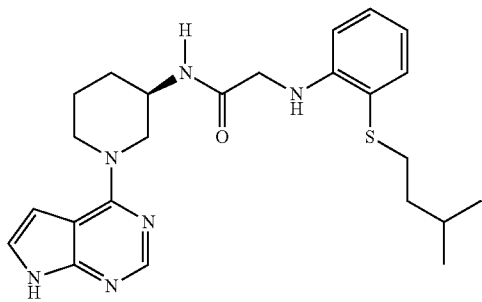 [SMILES: CC(C)CCSc1ccccc1NCC(=O)N[C@@H]1CCCN(c2ncnc3[nH]ccc23)C1] | A |
| 189 | 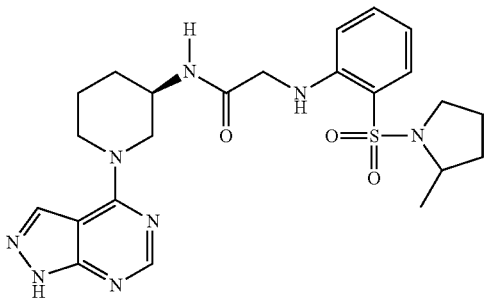 [SMILES: CC1CCCN1S(=O)(=O)c1ccccc1NCC(=O)N[C@@H]1CCCN(c2ncnc3[nH]ncc23)C1] | A |

TABLE 1-continued
Exemplary compounds of formula I.
| Cmpd. No. | Structure | IC$_{50}$ (10 uM ATP)$^a$ |
|---|---|---|
| 190 | 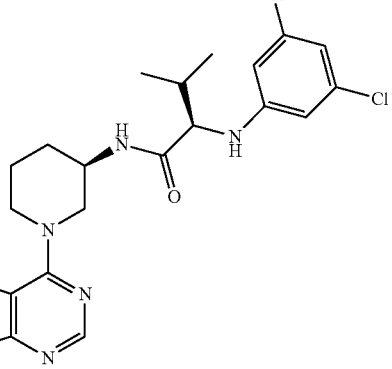 | A |
| 191 | 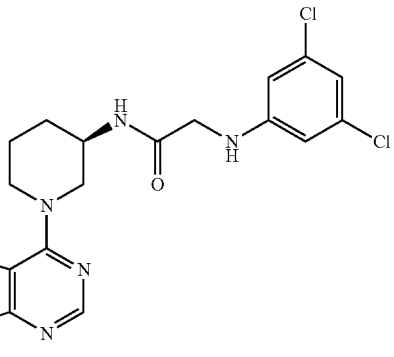 | A |
| 192 | 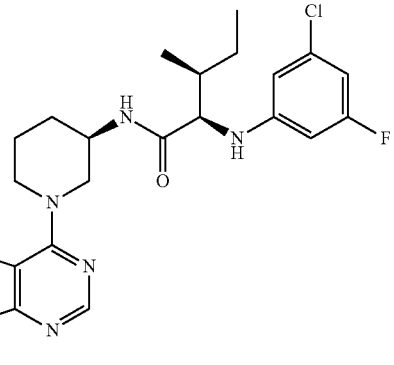 | A |
| 193 | 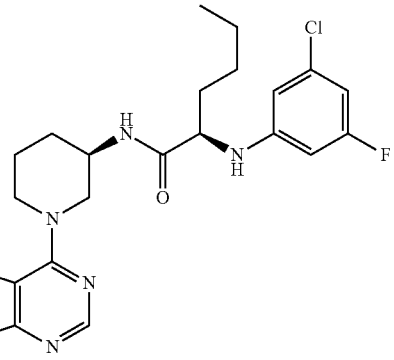 | A |

TABLE 1-continued
Exemplary compounds of formula I.
| Cmpd. No. | Structure | IC$_{50}$ (10 uM ATP)$^a$ |
|---|---|---|
| 194 | 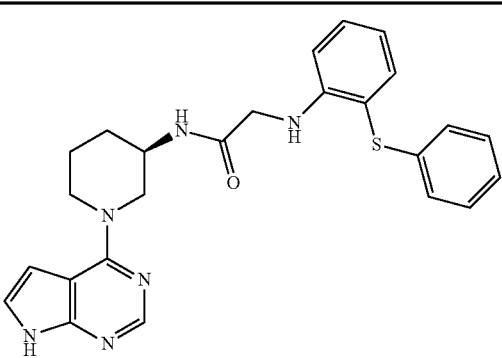 | A |
| 195 | 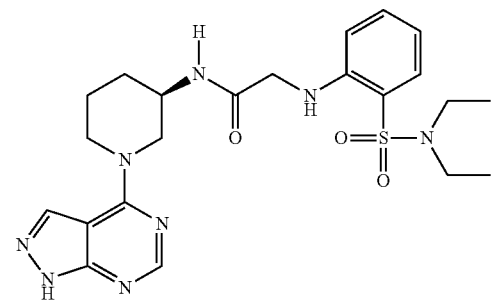 [SMILES: CCN(CC)S(=O)(=O)c1ccccc1NCC(=O)N[C@@H]1CCCN(c2ncnc3[nH]ncc23)C1] | A |
| 196 | 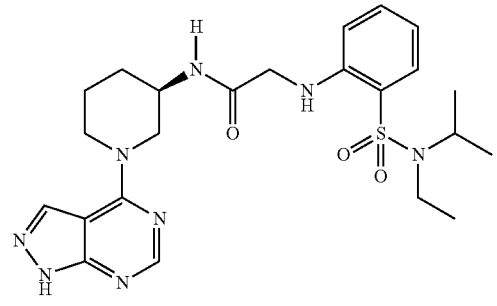 [SMILES: CCN(C(C)C)S(=O)(=O)c1ccccc1NCC(=O)N[C@@H]1CCCN(c2ncnc3[nH]ncc23)C1] | A |
| 197 | 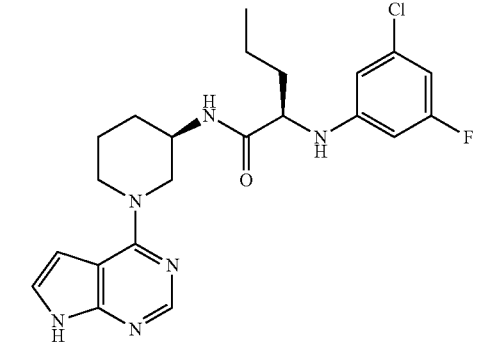 [SMILES: CCC[C@@H](Nc1cc(F)cc(Cl)c1)C(=O)N[C@@H]1CCCN(c2ncnc3[nH]ccc23)C1] | A |

TABLE 1-continued

Exemplary compounds of formula I.

| Cmpd. No. | Structure | IC$_{50}$ (10 uM ATP)$^a$ |
|---|---|---|
| 198 | 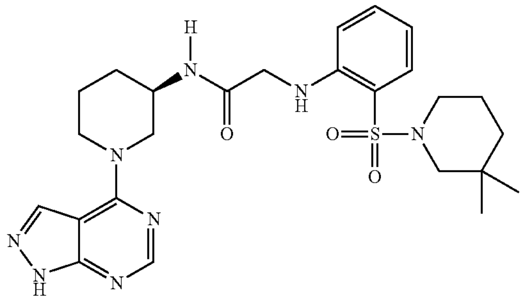 [SMILES: CC1(C)CCCN(S(=O)(=O)c2ccccc2NCC(=O)N[C@@H]2CCCN(c3ncnc4[nH]ncc34)C2)C1] | A |
| 199 | 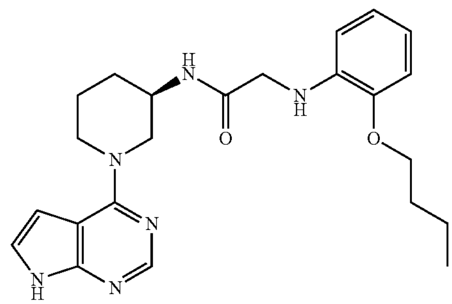 [SMILES: CCCCOc1ccccc1NCC(=O)N[C@@H]1CCCN(c2ncnc3[nH]ccc23)C1] | A |
| 200 | 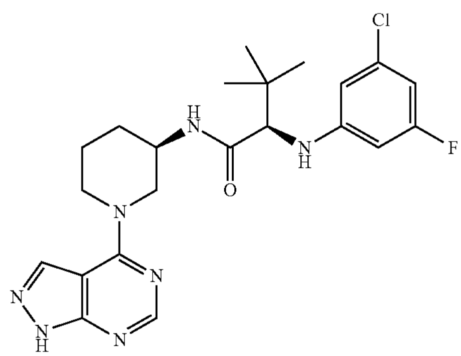 [SMILES: CC(C)(C)[C@@H](Nc1cc(F)cc(Cl)c1)C(=O)N[C@@H]1CCCN(c2ncnc3[nH]ncc23)C1] | A |
| 201 | 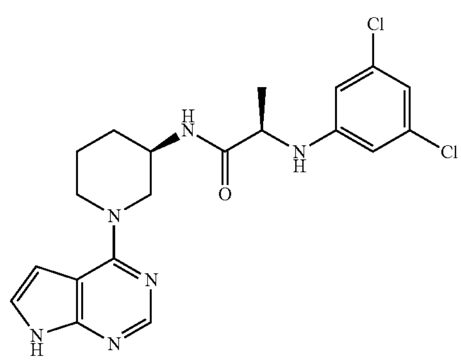 [SMILES: C[C@@H](Nc1cc(Cl)cc(Cl)c1)C(=O)N[C@@H]1CCCN(c2ncnc3[nH]ccc23)C1] | A |

TABLE 1-continued

Exemplary compounds of formula I.

| Cmpd. No. | Structure | IC$_{50}$ (10 uM ATP)$^a$ |
|---|---|---|
| 202 | 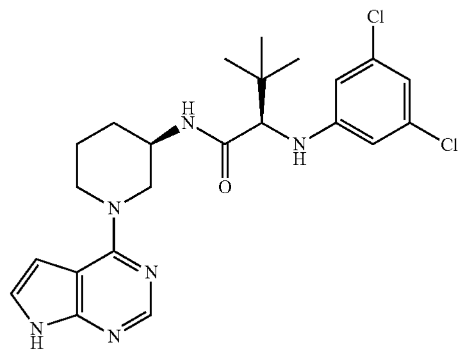 | A |
| 203 | 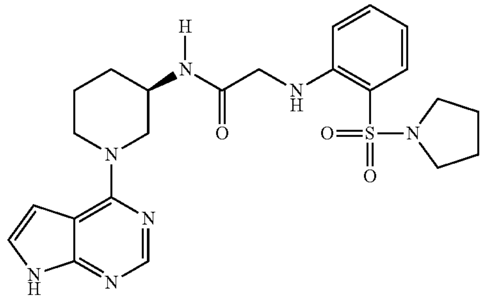 [SMILES: O=C(CNc1ccccc1S(=O)(=O)N1CCCC1)N[C@@H]1CCCN(c2ncnc3[nH]ccc23)C1] | A |
| 204 | 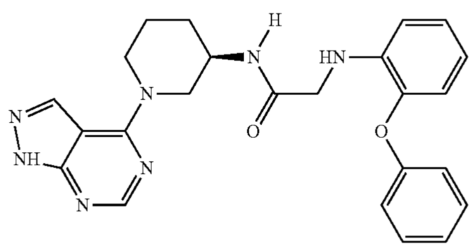 [SMILES: O=C(CNc1ccccc1Oc1ccccc1)N[C@@H]1CCCN(c2ncnc3[nH]ncc23)C1] | A |
| 205 | 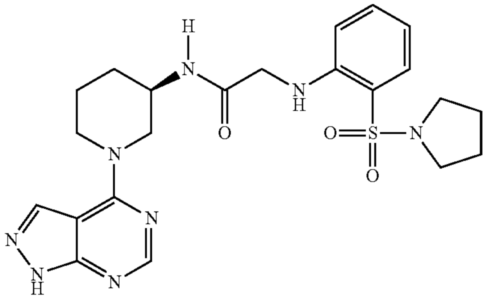 [SMILES: O=C(CNc1ccccc1S(=O)(=O)N1CCCC1)N[C@@H]1CCCN(c2ncnc3[nH]ncc23)C1] | A |
| 206 | 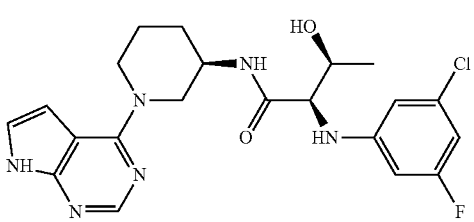 [SMILES: C[C@H](O)[C@@H](Nc1cc(F)cc(Cl)c1)C(=O)N[C@@H]1CCCN(c2ncnc3[nH]ccc23)C1] | A |

TABLE 1-continued

Exemplary compounds of formula I.

| Cmpd. No. | Structure | IC$_{50}$ (10 uM ATP)$^a$ |
|---|---|---|
| 207 | 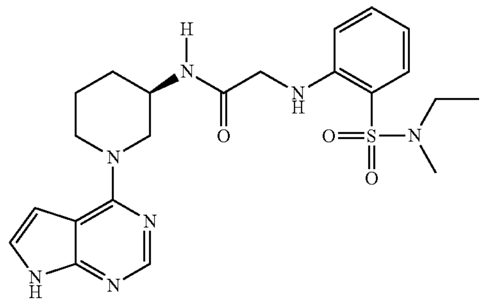 [SMILES: CCN(C)S(=O)(=O)c1ccccc1NCC(=O)N[C@@H]1CCCN(c2ncnc3[nH]ccc23)C1] | A |
| 208 | 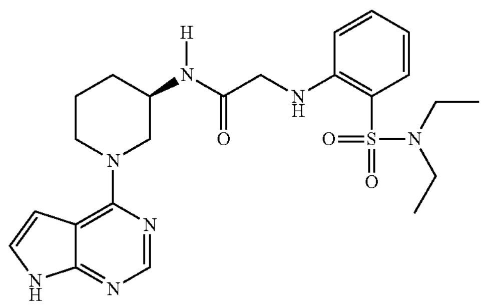 [SMILES: CCN(CC)S(=O)(=O)c1ccccc1NCC(=O)N[C@@H]1CCCN(c2ncnc3[nH]ccc23)C1] | A |
| 209 | 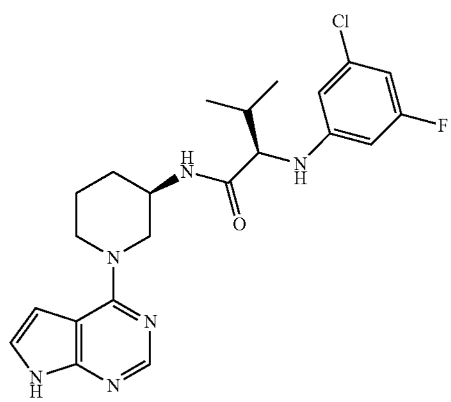 [SMILES: CC(C)[C@@H](Nc1cc(F)cc(Cl)c1)C(=O)N[C@@H]1CCCN(c2ncnc3[nH]ccc23)C1] | A |
| 210 | 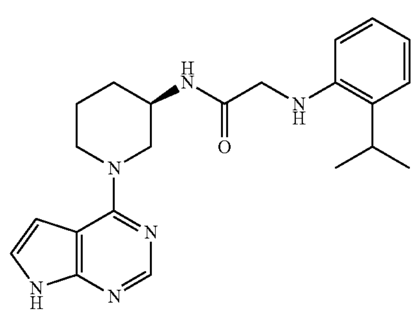 | A |

TABLE 1-continued
Exemplary compounds of formula I.
| Cmpd. No. | Structure | IC$_{50}$ (10 uM ATP)$^a$ |
|---|---|---|
| 211 | 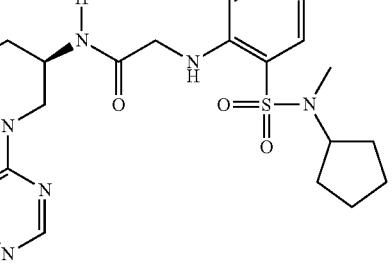 | A |
| 212 | 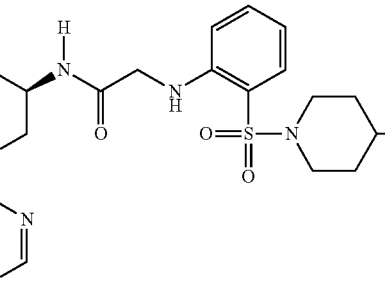 | A |
| 213 | 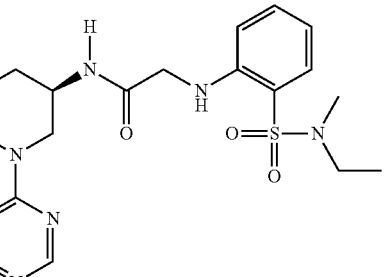 | A |
| 214 | 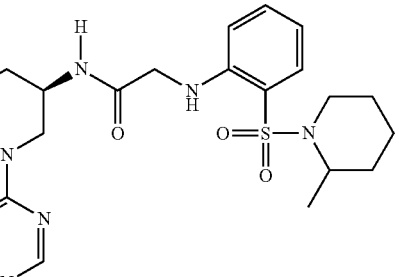 | A |

TABLE 1-continued

Exemplary compounds of formula I.

| Cmpd. No. | Structure | IC$_{50}$ (10 uM ATP)$^a$ |
|---|---|---|
| 215 | 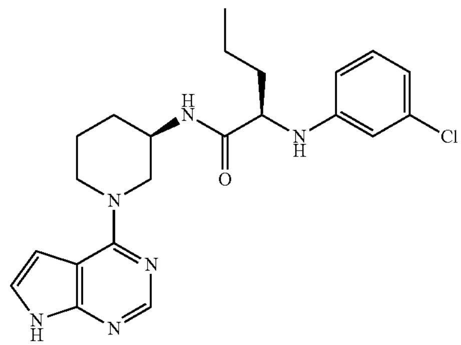 [SMILES: CCC[C@@H](Nc1cccc(Cl)c1)C(=O)N[C@@H]1CCCN(c2ncnc3[nH]ccc23)C1] | A |
| 216 | Abs | A |
| 217 | 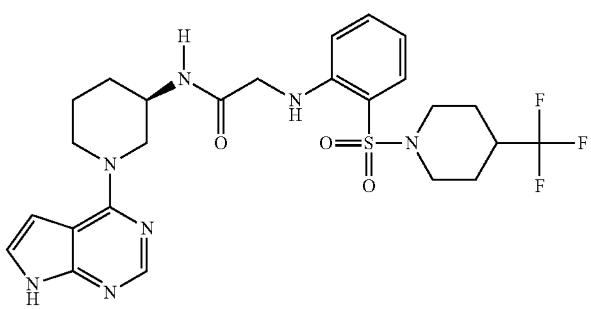 [SMILES: O=C(CNc1ccccc1S(=O)(=O)N1CCC(C(F)(F)F)CC1)N[C@@H]1CCCN(c2ncnc3[nH]ccc23)C1] | A |
| 218 | Abs | A |

TABLE 1-continued

Exemplary compounds of formula I.

| Cmpd. No. | Structure | IC$_{50}$ (10 uM ATP)$^a$ |
|---|---|---|
| 219 | Abs | A |
| 220 | 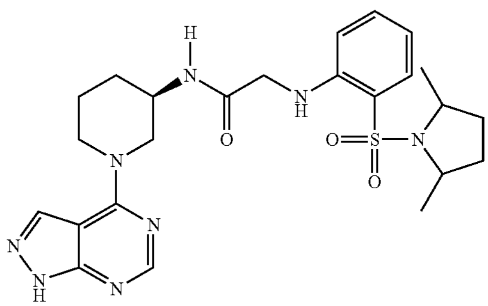 [SMILES: CC1CCC(C)N1S(=O)(=O)c1ccccc1NCC(=O)N[C@@H]1CCCN(c2ncnc3[nH]ncc23)C1] | A |
| 221 | 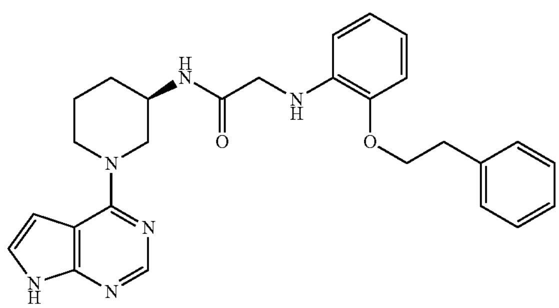 [SMILES: O=C(CNc1ccccc1OCCc1ccccc1)N[C@@H]1CCCN(c2ncnc3[nH]ccc23)C1] | A |
| 222 | 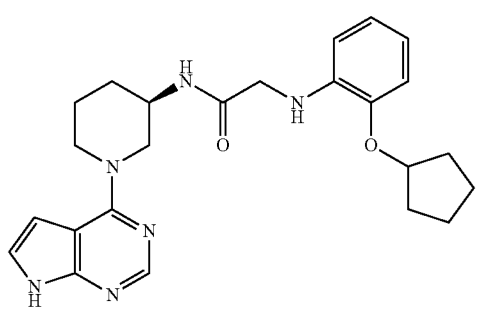 [SMILES: O=C(CNc1ccccc1OC1CCCC1)N[C@@H]1CCCN(c2ncnc3[nH]ccc23)C1] | A |

TABLE 1-continued
Exemplary compounds of formula I.
| Cmpd. No. | Structure | IC$_{50}$ (10 uM ATP)$^a$ |
|---|---|---|
| 223 | 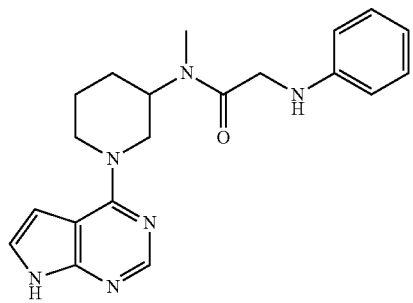 [SMILES: CN(C(=O)CNc1ccccc1)C1CCCN(c2ncnc3[nH]ccc23)C1] | B |
| 224 | 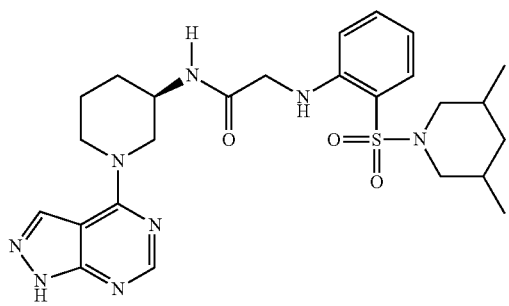 [SMILES: CC1CC(C)CN(S(=O)(=O)c2ccccc2NCC(=O)N[C@@H]2CCCN(c3ncnc4[nH]ncc34)C2)C1] | A |
| 225 | 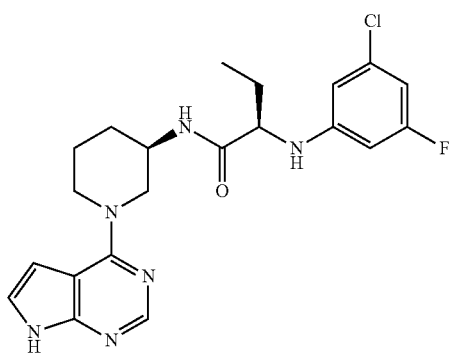 [SMILES: CC[C@@H](Nc1cc(F)cc(Cl)c1)C(=O)N[C@@H]1CCCN(c2ncnc3[nH]ccc23)C1] | A |
| 226 | 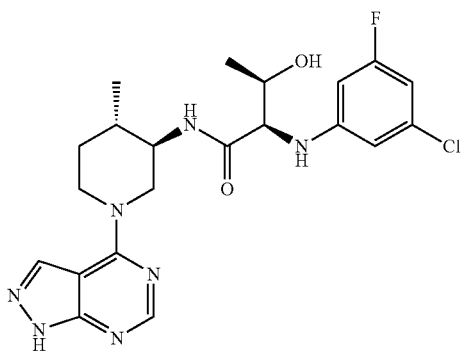 [SMILES: C[C@@H](O)[C@@H](Nc1cc(F)cc(Cl)c1)C(=O)N[C@H]1CN(c2ncnc3[nH]ncc23)CC[C@@H]1C] | A |

TABLE 1-continued

Exemplary compounds of formula I.

| Cmpd. No. | Structure | IC$_{50}$ (10 uM ATP)$^a$ |
|---|---|---|
| 227 | 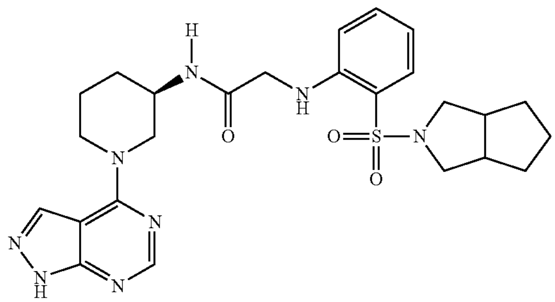 [SMILES: O=C(CNc1ccccc1S(=O)(=O)N1CC2CCCC2C1)N[C@@H]1CCCN(c2ncnc3[nH]ncc23)C1] | A |
| 228 | 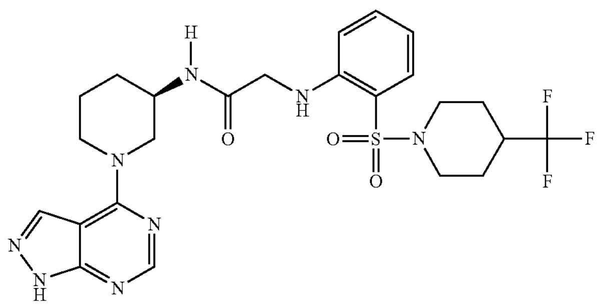 [SMILES: O=C(CNc1ccccc1S(=O)(=O)N1CCC(C(F)(F)F)CC1)N[C@@H]1CCCN(c2ncnc3[nH]ncc23)C1] | A |
| 229 | 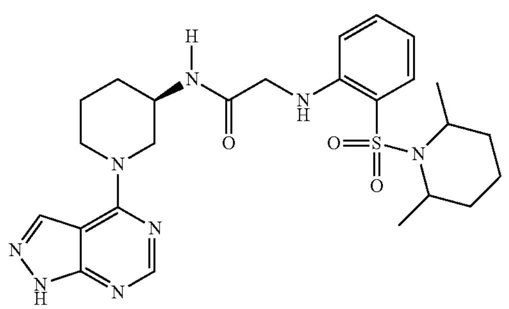 [SMILES: CC1CCCC(C)N1S(=O)(=O)c1ccccc1NCC(=O)N[C@@H]1CCCN(c2ncnc3[nH]ncc23)C1] | A |
| 230 | 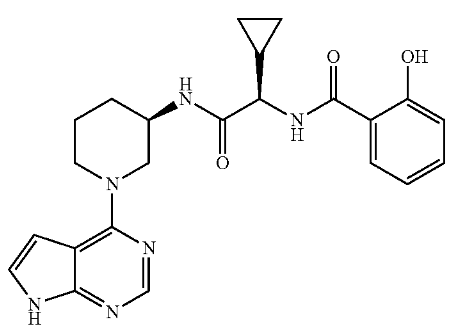 [SMILES: O=C(N[C@@H](C(=O)N[C@@H]1CCCN(c2ncnc3[nH]ccc23)C1)C1CC1)c1ccccc1O] | B |

TABLE 1-continued

Exemplary compounds of formula I.

| Cmpd. No. | Structure | IC$_{50}$ (10 uM ATP)$^a$ |
|---|---|---|
| 231 | Abs | A |
| 232 | 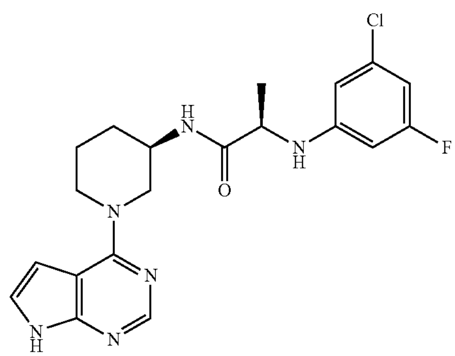 [SMILES: C[C@@H](Nc1cc(F)cc(Cl)c1)C(=O)N[C@@H]1CCCN(c2ncnc3[nH]ccc23)C1] | A |
| 233 | 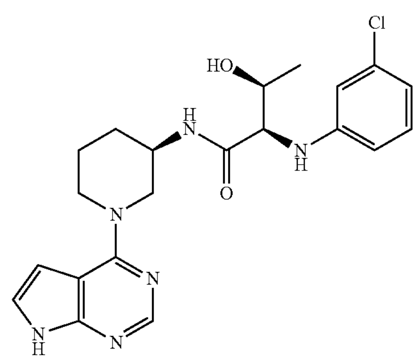 [SMILES: C[C@H](O)[C@@H](Nc1cccc(Cl)c1)C(=O)N[C@@H]1CCCN(c2ncnc3[nH]ccc23)C1] | A |
| 234 | Abs | B |

TABLE 1-continued

Exemplary compounds of formula I.

| Cmpd. No. | Structure | IC$_{50}$ (10 uM ATP) $^a$ |
|---|---|---|
| 235 | 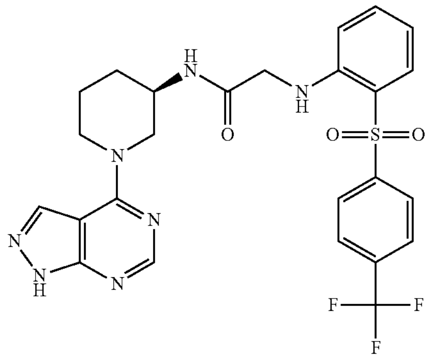 [SMILES: O=C(CNc1ccccc1S(=O)(=O)c1ccc(C(F)(F)F)cc1)N[C@@H]1CCCN(c2ncnc3[nH]ncc23)C1] | A |
| 236 | 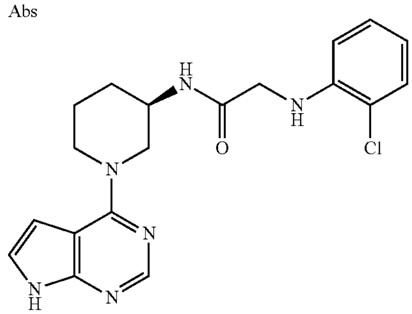 [SMILES: O=C(CNc1ccccc1Cl)N[C@@H]1CCCN(c2ncnc3[nH]ccc23)C1] | A |
| 237 | 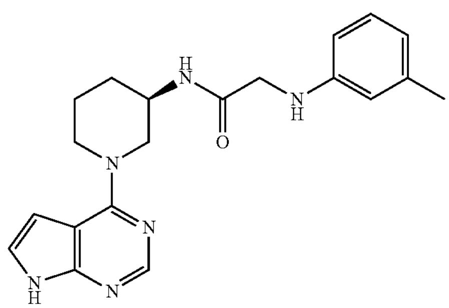 [SMILES: Cc1cccc(NCC(=O)N[C@@H]2CCCN(c3ncnc4[nH]ccc34)C2)c1] | B |
| 238 | 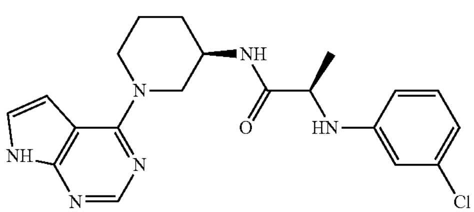 [SMILES: C[C@@H](Nc1cccc(Cl)c1)C(=O)N[C@@H]1CCCN(c2ncnc3[nH]ccc23)C1] | A |
| 239 | 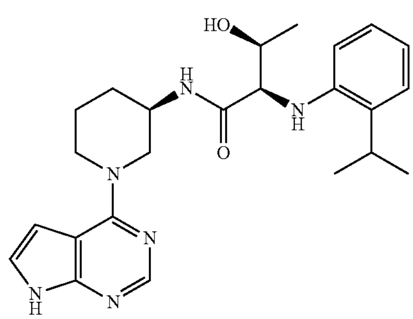 [SMILES: CC(C)c1ccccc1N[C@@H](C(=O)N[C@@H]1CCCN(c2ncnc3[nH]ccc23)C1)[C@H](C)O] | B |

TABLE 1-continued
Exemplary compounds of formula I.
| Cmpd. No. | Structure | IC$_{50}$ (10 uM ATP)$^a$ |
|---|---|---|
| 240 | 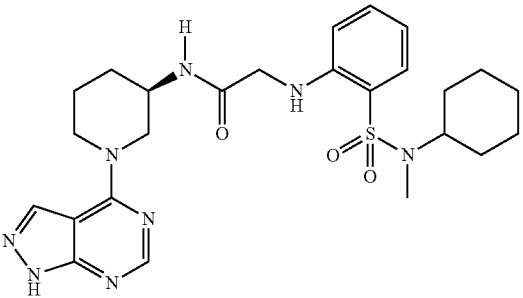 [SMILES: CN(C1CCCCC1)S(=O)(=O)c1ccccc1NCC(=O)N[C@@H]1CCCN(c2ncnc3[nH]ncc23)C1] | A |
| 241 | 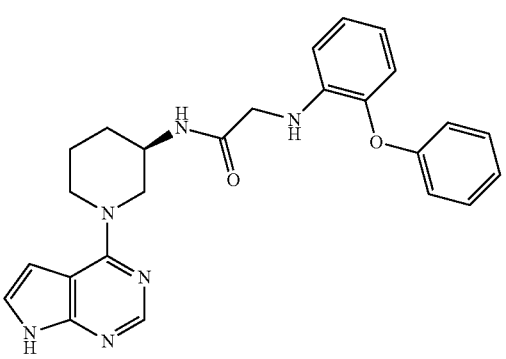 [SMILES: O=C(CNc1ccccc1Oc1ccccc1)N[C@@H]1CCCN(c2ncnc3[nH]ccc23)C1] | A |
| 242 | 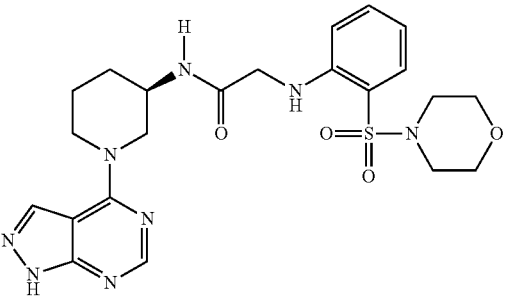 [SMILES: O=C(CNc1ccccc1S(=O)(=O)N1CCOCC1)N[C@@H]1CCCN(c2ncnc3[nH]ncc23)C1] | A |
| 243 | 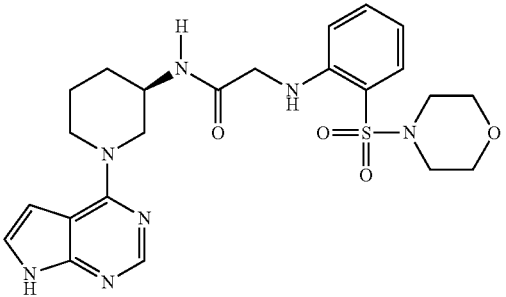 [SMILES: O=C(CNc1ccccc1S(=O)(=O)N1CCOCC1)N[C@@H]1CCCN(c2ncnc3[nH]ccc23)C1] | A |

TABLE 1-continued
Exemplary compounds of formula I.
| Cmpd. No. | Structure | IC$_{50}$ (10 uM ATP)$^a$ |
|---|---|---|
| 244 | 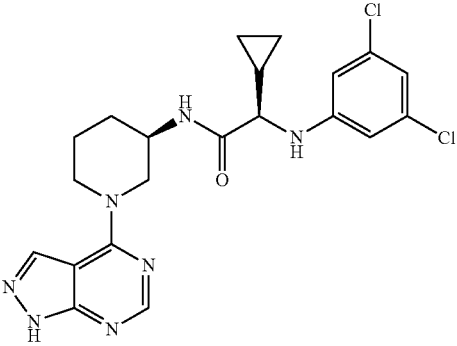 | B |
| 245 | 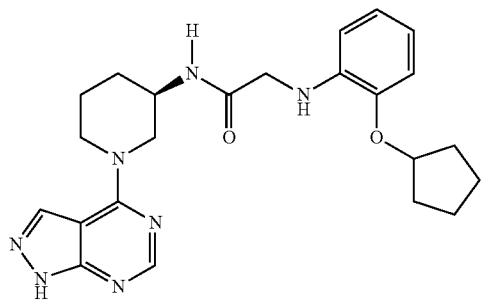 [SMILES: O=C(CNc1ccccc1OC1CCCC1)N[C@@H]1CCCN(c2ncnc3[nH]ncc23)C1] | A |
| 246 | 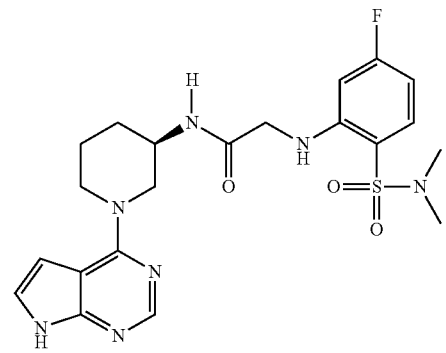 [SMILES: CN(C)S(=O)(=O)c1ccc(F)cc1NCC(=O)N[C@@H]1CCCN(c2ncnc3[nH]ccc23)C1] | B |
| 247 | 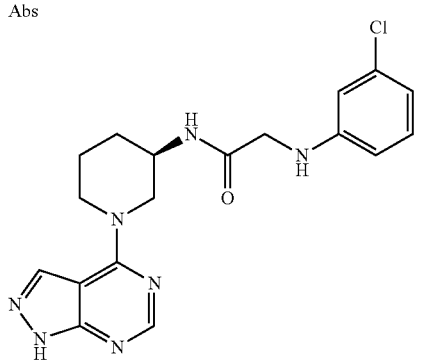 [SMILES: O=C(CNc1cccc(Cl)c1)N[C@@H]1CCCN(c2ncnc3[nH]ncc23)C1] | A |

TABLE 1-continued
Exemplary compounds of formula I.
| Cmpd. No. | Structure | IC$_{50}$ (10 uM ATP)$^a$ |
|---|---|---|
| 248 | 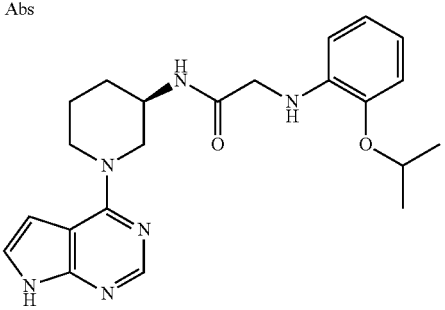 [SMILES: CC(C)Oc1ccccc1NCC(=O)N[C@@H]1CCCN(c2ncnc3[nH]ccc23)C1] | B |
| 249 | 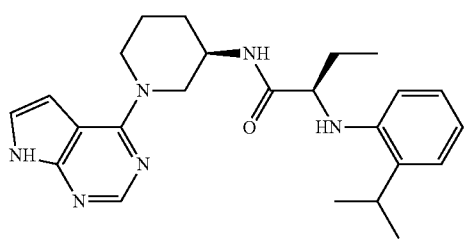 [SMILES: CC[C@@H](Nc1ccccc1C(C)C)C(=O)N[C@@H]1CCCN(c2ncnc3[nH]ccc23)C1] | B |
| 250 | 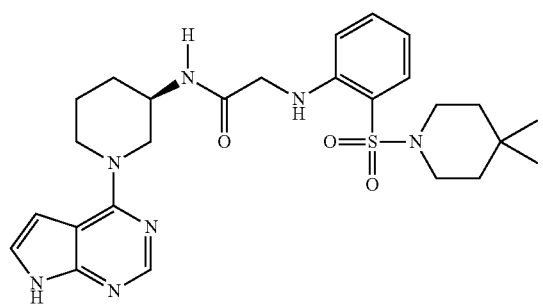 [SMILES: CC1(C)CCN(S(=O)(=O)c2ccccc2NCC(=O)N[C@@H]2CCCN(c3ncnc4[nH]ccc34)C2)CC1] | A |
| 251 | 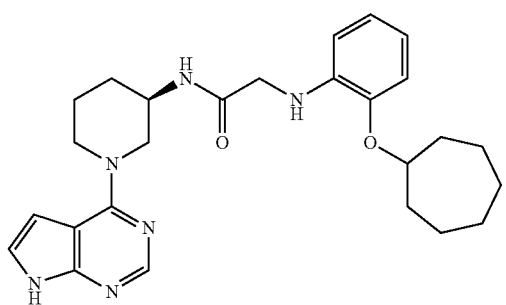 [SMILES: O=C(CNc1ccccc1OC1CCCCCC1)N[C@@H]1CCCN(c2ncnc3[nH]ccc23)C1] | A |

TABLE 1-continued

Exemplary compounds of formula I.

| Cmpd. No. | Structure | IC$_{50}$ (10 uM ATP)$^a$ |
|---|---|---|
| 252 | 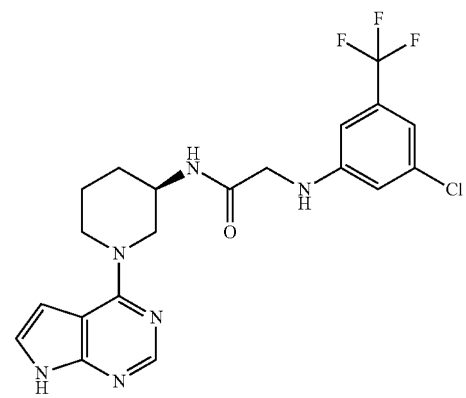 [SMILES: O=C(CNc1cc(Cl)cc(C(F)(F)F)c1)N[C@@H]1CCCN(c2ncnc3[nH]ccc23)C1] | A |
| 253 | 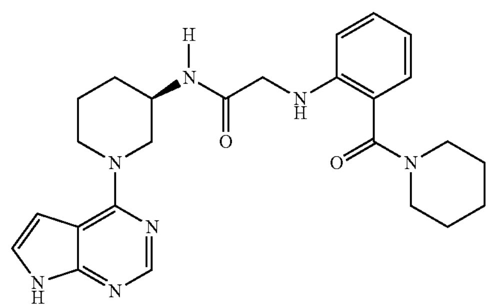 [SMILES: O=C(CNc1ccccc1C(=O)N1CCCCC1)N[C@@H]1CCCN(c2ncnc3[nH]ccc23)C1] | B |
| 254 | 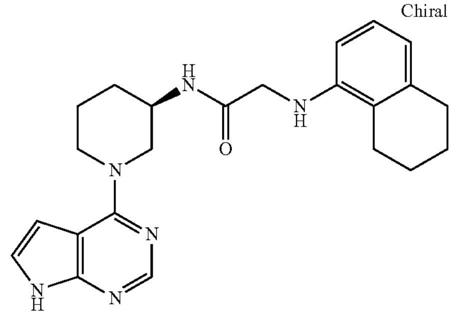 [SMILES: O=C(CNc1cccc2c1CCCC2)N[C@@H]1CCCN(c2ncnc3[nH]ccc23)C1] | A |
| 255 | 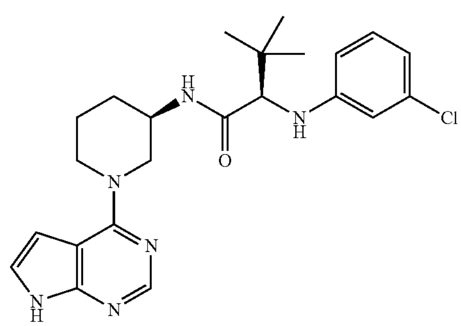 [SMILES: CC(C)(C)[C@@H](Nc1cccc(Cl)c1)C(=O)N[C@@H]1CCCN(c2ncnc3[nH]ccc23)C1] | A |

TABLE 1-continued

Exemplary compounds of formula I.

| Cmpd. No. | Structure | IC$_{50}$ (10 uM ATP)$^a$ |
|---|---|---|
| 256 | 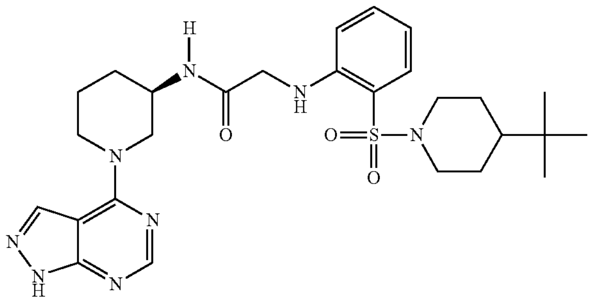 [SMILES: CC(C)(C)C1CCN(S(=O)(=O)c2ccccc2NCC(=O)N[C@@H]2CCCN(c3ncnc4[nH]ncc34)C2)CC1] | A |
| 257 | 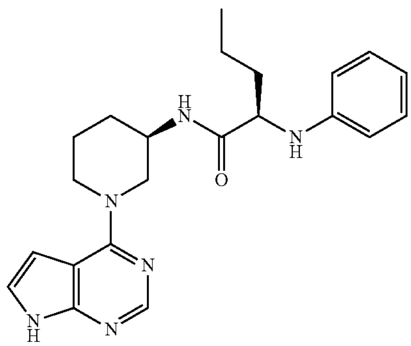 [SMILES: CCC[C@@H](Nc1ccccc1)C(=O)N[C@@H]1CCCN(c2ncnc3[nH]ccc23)C1] | B |
| 258 | 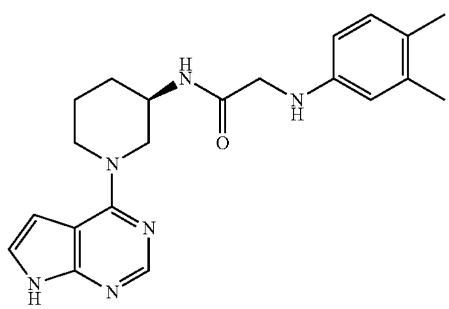 [SMILES: Cc1ccc(NCC(=O)N[C@@H]2CCCN(c3ncnc4[nH]ccc34)C2)cc1C] | B |
| 259 | 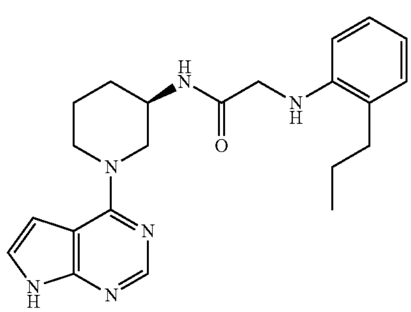 [SMILES: CCCc1ccccc1NCC(=O)N[C@@H]1CCCN(c2ncnc3[nH]ccc23)C1] | A |

TABLE 1-continued

Exemplary compounds of formula I.

| Cmpd. No. | Structure | IC$_{50}$ (10 uM ATP)$^a$ |
|---|---|---|
| 260 | Abs | B |
| 261 | 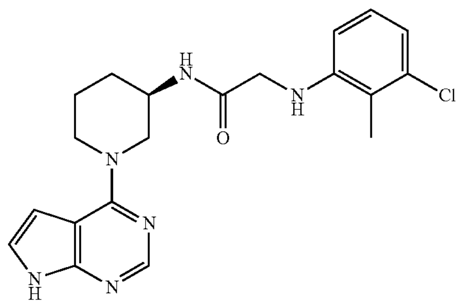 [SMILES: Cc1c(Cl)cccc1NCC(=O)N[C@@H]1CCCN(c2ncnc3[nH]ccc23)C1] | B |
| 262 | 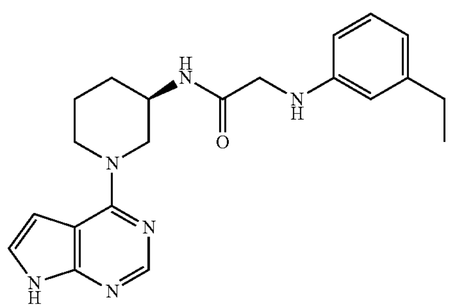 [SMILES: CCc1cccc(NCC(=O)N[C@@H]2CCCN(c3ncnc4[nH]ccc34)C2)c1] | A |
| 263 | 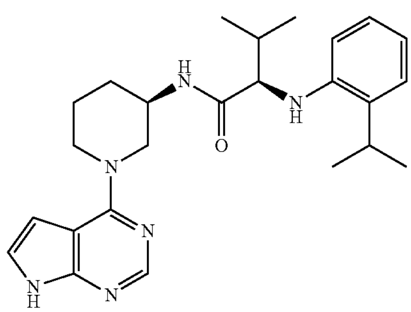 [SMILES: CC(C)c1ccccc1N[C@@H](C(=O)N[C@@H]1CCCN(c2ncnc3[nH]ccc23)C1)C(C)C] | B |

TABLE 1-continued
Exemplary compounds of formula I.
| Cmpd. No. | Structure | IC$_{50}$ (10 uM ATP)$^a$ |
|---|---|---|
| 264 | 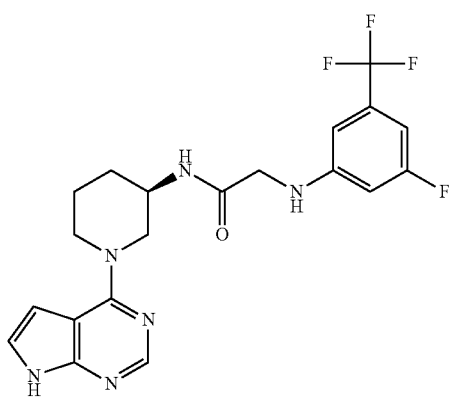 [SMILES: O=C(CNc1cc(F)cc(C(F)(F)F)c1)N[C@@H]1CCCN(c2ncnc3[nH]ccc23)C1] | A |
| 265 | 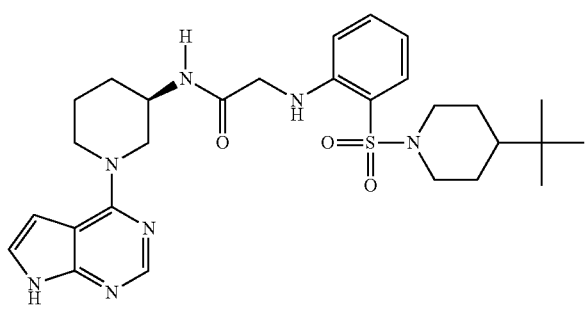 [SMILES: CC(C)(C)C1CCN(S(=O)(=O)c2ccccc2NCC(=O)N[C@@H]2CCCN(c3ncnc4[nH]ccc34)C2)CC1] | A |
| 266 | 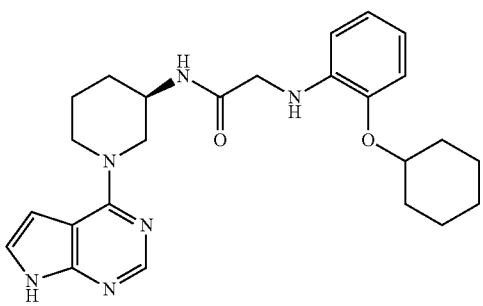 [SMILES: O=C(CNc1ccccc1OC1CCCCC1)N[C@@H]1CCCN(c2ncnc3[nH]ccc23)C1] | A |
| 267 | 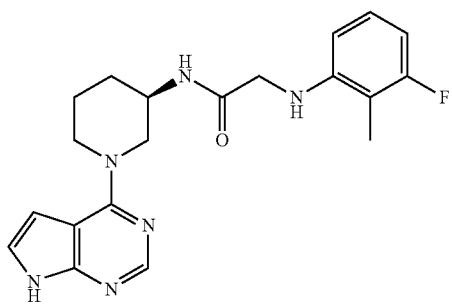 [SMILES: Cc1c(F)cccc1NCC(=O)N[C@@H]1CCCN(c2ncnc3[nH]ccc23)C1] | B |

TABLE 1-continued

Exemplary compounds of formula I.

| Cmpd. No. | Structure | IC$_{50}$ (10 uM ATP)$^a$ |
|---|---|---|
| 268 | 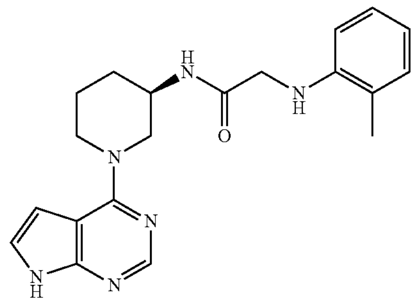 | B |
| 269 | 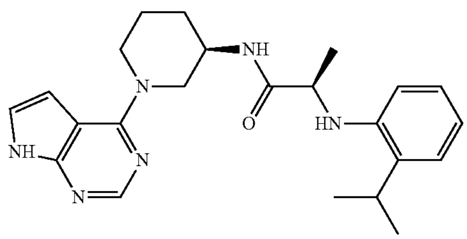 [SMILES: CC(C)c1ccccc1N[C@H](C)C(=O)N[C@@H]1CCCN(c2ncnc3[nH]ccc23)C1] | B |
| 270 | 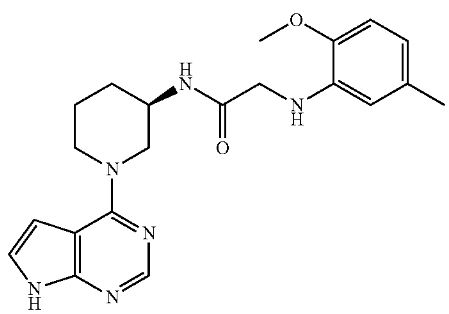 [SMILES: COc1ccc(C)cc1NCC(=O)N[C@@H]1CCCN(c2ncnc3[nH]ccc23)C1] | A |
| 271 | 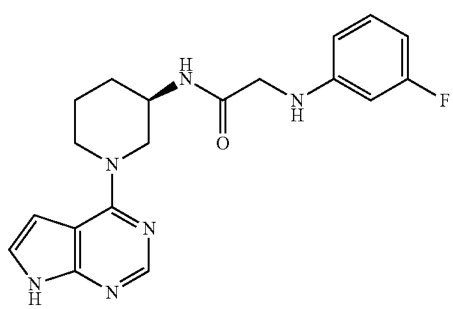 [SMILES: O=C(CNc1cccc(F)c1)N[C@@H]1CCCN(c2ncnc3[nH]ccc23)C1] | B |
| 272 | 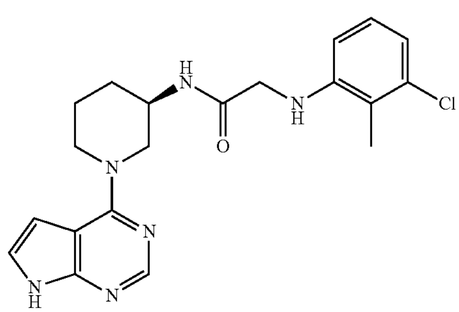 [SMILES: Cc1c(Cl)cccc1NCC(=O)N[C@@H]1CCCN(c2ncnc3[nH]ccc23)C1] | A |

TABLE 1-continued

Exemplary compounds of formula I.

| Cmpd. No. | Structure | IC$_{50}$ (10 uM ATP)$^a$ |
|---|---|---|
| 273 | 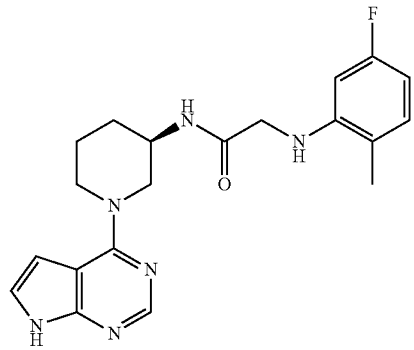 | A |
| 274 | 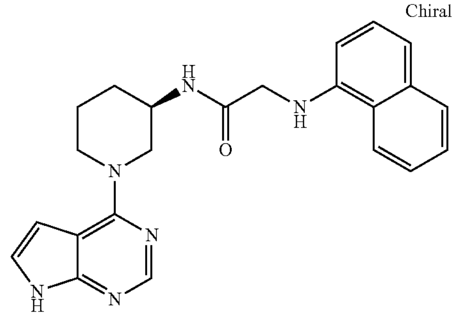 [SMILES: O=C(CNc1cccc2ccccc12)N[C@@H]1CCCN(c2ncnc3[nH]ccc23)C1] | B |
| 275 | 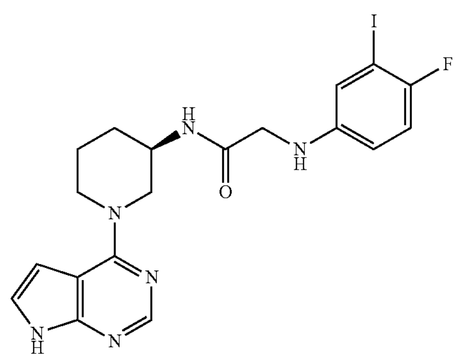 [SMILES: O=C(CNc1ccc(F)c(I)c1)N[C@@H]1CCCN(c2ncnc3[nH]ccc23)C1] | B |
| 276 | 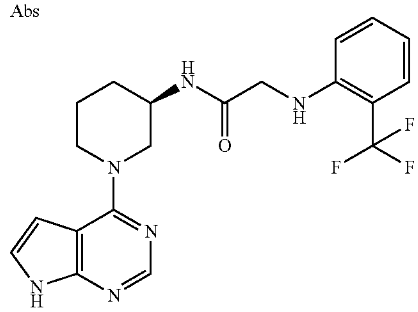 [SMILES: O=C(CNc1ccccc1C(F)(F)F)N[C@@H]1CCCN(c2ncnc3[nH]ccc23)C1] | B |

TABLE 1-continued

Exemplary compounds of formula I.

| Cmpd. No. | Structure | IC$_{50}$ (10 uM ATP)$^a$ |
|---|---|---|
| 277 | 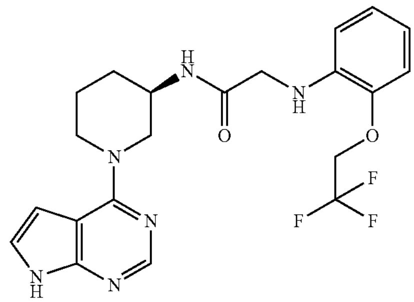 [SMILES: O=C(CNc1ccccc1OCC(F)(F)F)N[C@@H]1CCCN(c2ncnc3[nH]ccc23)C1] | B |
| 278 | 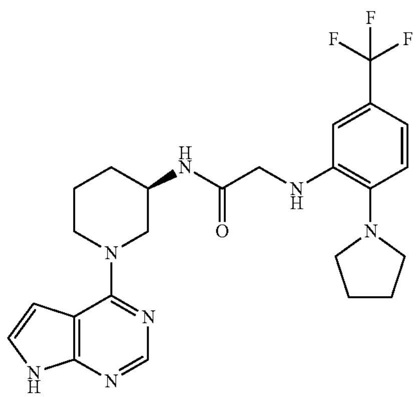 [SMILES: O=C(CNc1cc(C(F)(F)F)ccc1N1CCCC1)N[C@@H]1CCCN(c2ncnc3[nH]ccc23)C1] | B |
| 279 | 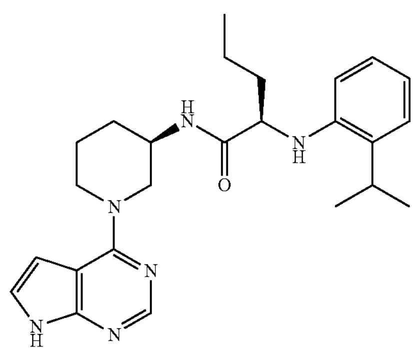 [SMILES: CCC[C@@H](Nc1ccccc1C(C)C)C(=O)N[C@@H]1CCCN(c2ncnc3[nH]ccc23)C1] | B |
| 280 | 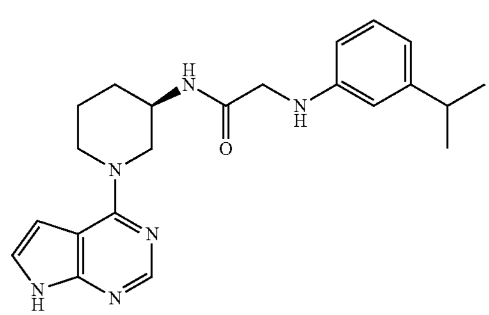 [SMILES: CC(C)c1cccc(NCC(=O)N[C@@H]2CCCN(c3ncnc4[nH]ccc34)C2)c1] | A |

TABLE 1-continued

Exemplary compounds of formula I.

| Cmpd. No. | Structure | IC$_{50}$ (10 uM ATP)$^a$ |
|---|---|---|
| 281 | 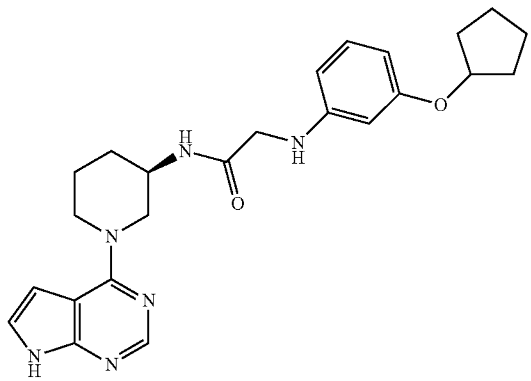 [SMILES: O=C(CNc1cccc(OC2CCCC2)c1)N[C@@H]1CCCN(c2ncnc3[nH]ccc23)C1] | B |
| 282 | 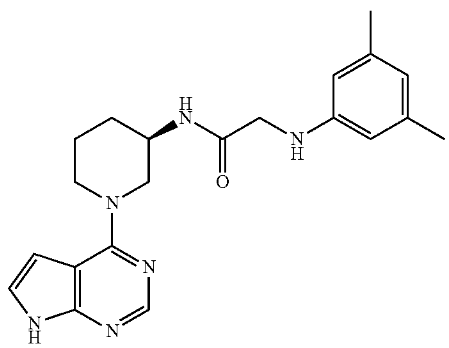 [SMILES: Cc1cc(C)cc(NCC(=O)N[C@@H]2CCCN(c3ncnc4[nH]ccc34)C2)c1] | B |
| 283 | 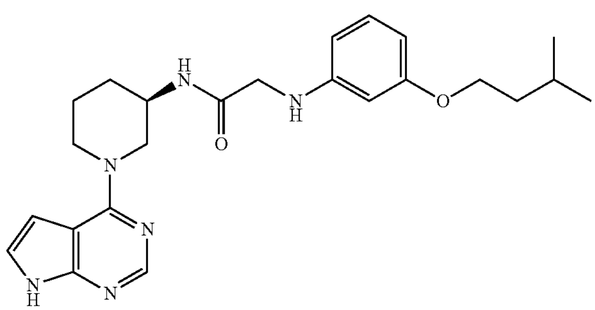 [SMILES: CC(C)CCOc1cccc(NCC(=O)N[C@@H]2CCCN(c3ncnc4[nH]ccc34)C2)c1] | A |
| 284 | Abs | B |

TABLE 1-continued
Exemplary compounds of formula I.
| Cmpd. No. | Structure | IC$_{50}$ (10 uM ATP)$^a$ |
|---|---|---|
| 285 | 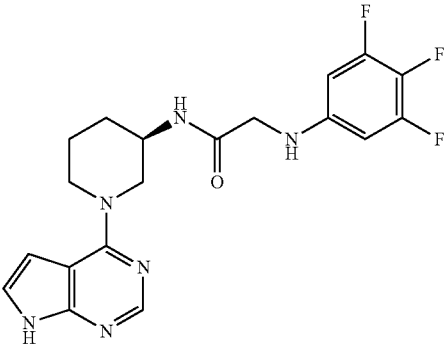 [SMILES: O=C(CNc1cc(F)c(F)c(F)c1)N[C@@H]1CCCN(c2ncnc3[nH]ccc23)C1] | B |
| 286 | 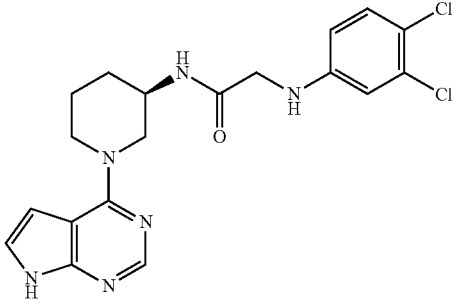 [SMILES: O=C(CNc1ccc(Cl)c(Cl)c1)N[C@@H]1CCCN(c2ncnc3[nH]ccc23)C1] | B |
| 287 | 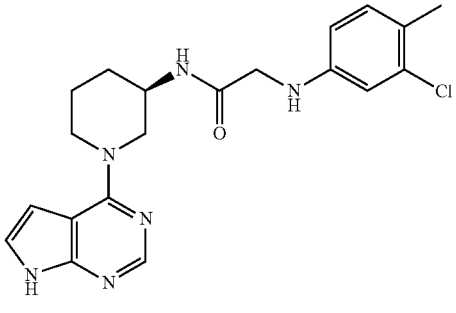 [SMILES: Cc1ccc(NCC(=O)N[C@@H]2CCCN(c3ncnc4[nH]ccc34)C2)cc1Cl] | B |
| 288 | 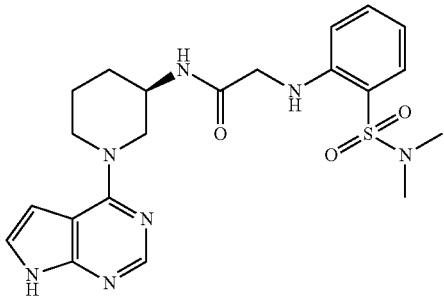 | B |

TABLE 1-continued
Exemplary compounds of formula I.
| Cmpd. No. | Structure | IC$_{50}$ (10 uM ATP)$^a$ |
|---|---|---|
| 289 | 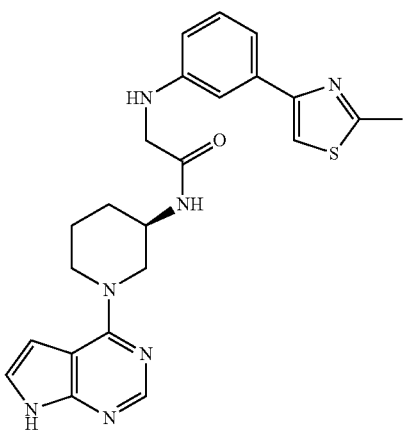 [SMILES: Cc1nc(-c2cccc(NCC(=O)N[C@@H]3CCCN(c4ncnc5[nH]ccc45)C3)c2)cs1] | B |
| 290 | 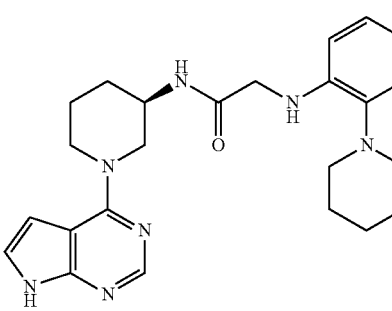 | B |
| 291 | 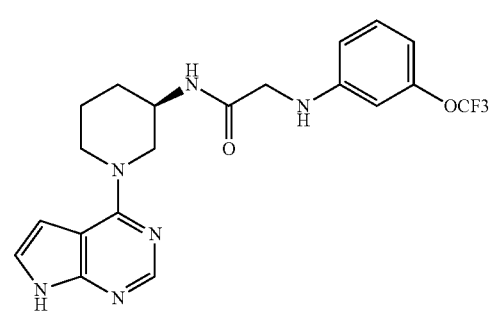 [SMILES: O=C(CNc1cccc(OC(F)(F)F)c1)N[C@@H]1CCCN(c2ncnc3[nH]ccc23)C1] | B |
| 292 | 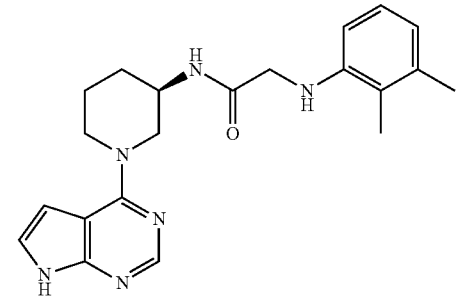 [SMILES: Cc1cccc(NCC(=O)N[C@@H]2CCCN(c3ncnc4[nH]ccc34)C2)c1C] | B |

TABLE 1-continued
Exemplary compounds of formula I.
| Cmpd. No. | Structure | IC$_{50}$ (10 uM ATP) [a] |
|---|---|---|
| 293 | 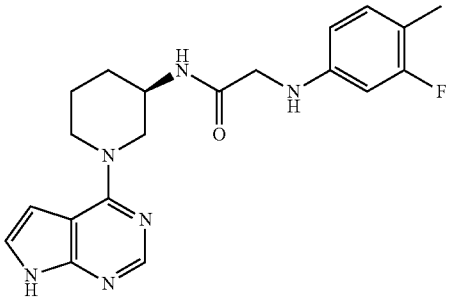 [SMILES: Cc1ccc(NCC(=O)N[C@@H]2CCCN(c3ncnc4[nH]ccc34)C2)cc1F] | B |
| 294 | Abs 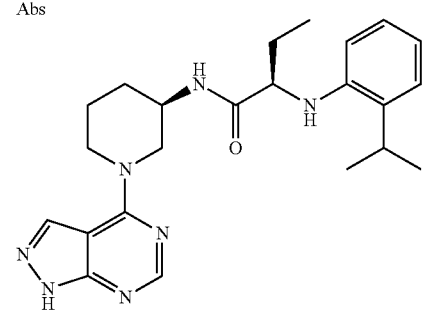 [SMILES: CC[C@@H](Nc1ccccc1C(C)C)C(=O)N[C@@H]1CCCN(c2ncnc3[nH]ncc23)C1] | B |
| 295 | 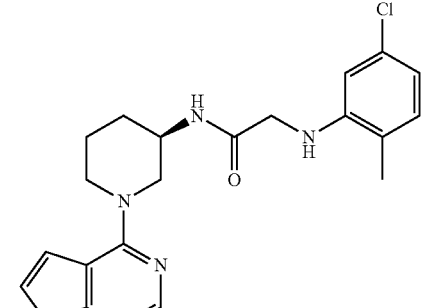 | B |
| 296 | Abs 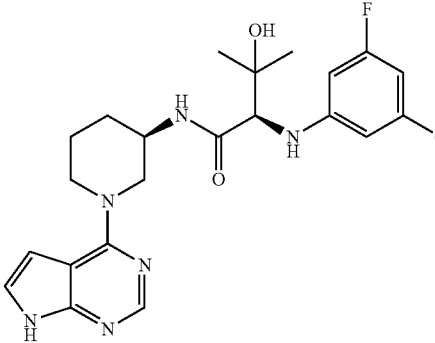 | B |

TABLE 1-continued

Exemplary compounds of formula I.

| Cmpd. No. | Structure | IC$_{50}$ (10 uM ATP)$^a$ |
|---|---|---|
| 297 | 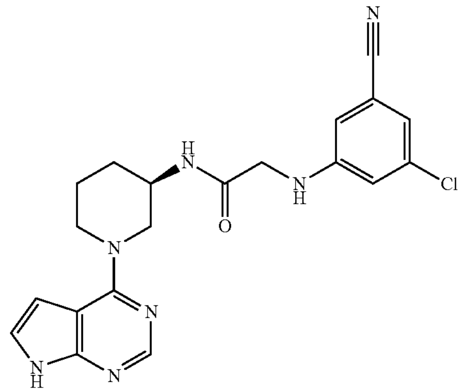 [SMILES: N#Cc1cc(Cl)cc(NCC(=O)N[C@@H]2CCCN(c3ncnc4[nH]ccc34)C2)c1] | B |
| 298 | 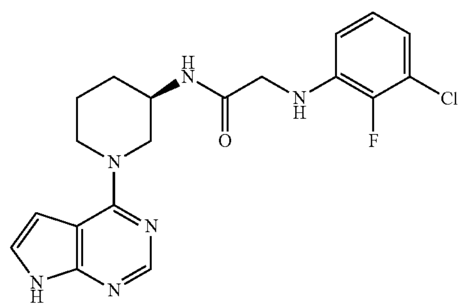 [SMILES: O=C(CNc1cccc(Cl)c1F)N[C@@H]1CCCN(c2ncnc3[nH]ccc23)C1] | B |
| 299 | 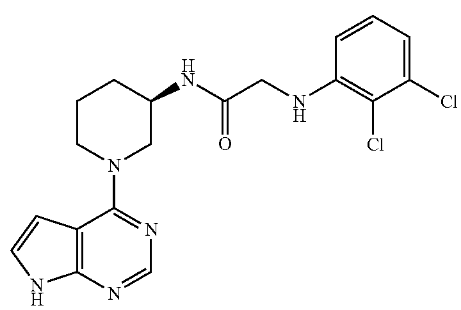 | B |
| 300 | 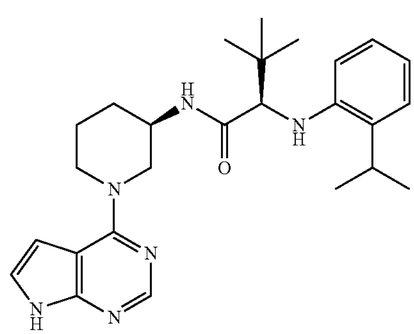 [SMILES: CC(C)c1ccccc1N[C@@H](C(=O)N[C@@H]1CCCN(c2ncnc3[nH]ccc23)C1)C(C)(C)C] | B |

TABLE 1-continued
Exemplary compounds of formula I.
| Cmpd. No. | Structure | IC$_{50}$ (10 uM ATP)$^a$ |
|---|---|---|
| 301 | 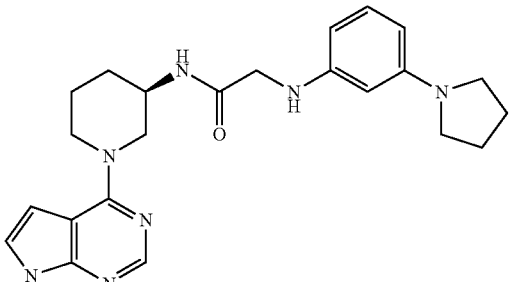 | B |
| 302 | 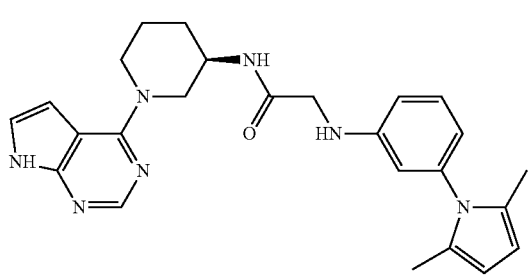 [SMILES: Cc1ccc(C)n1-c1cccc(NCC(=O)N[C@@H]2CCCN(c3ncnc4[nH]ccc34)C2)c1] | B |
| 303 | 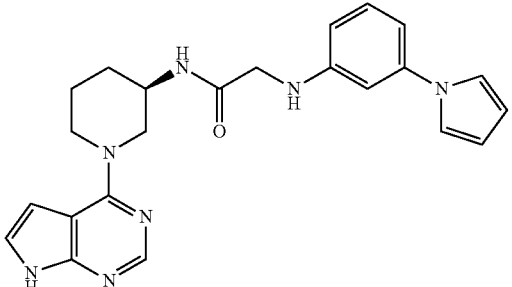 | B |
| 304 | 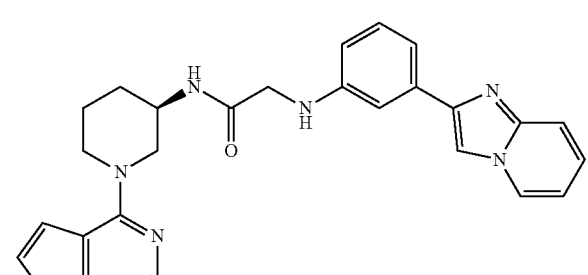 | B |
| 305 | 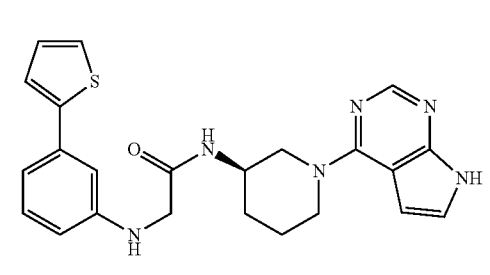 [SMILES: O=C(CNc1cccc(-c2cccs2)c1)N[C@@H]1CCCN(c2ncnc3[nH]ccc23)C1] | B |

TABLE 1-continued

Exemplary compounds of formula I.

| Cmpd. No. | Structure | IC$_{50}$ (10 uM ATP)$^a$ |
|---|---|---|
| 306 | 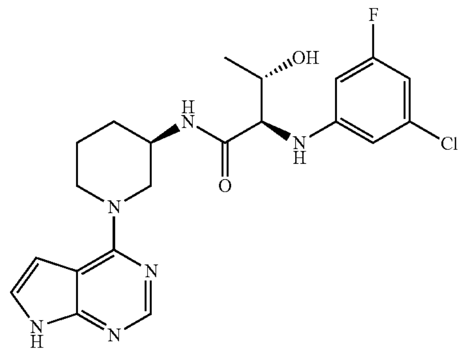 [SMILES: C[C@H](O)[C@@H](Nc1cc(F)cc(Cl)c1)C(=O)N[C@@H]1CCCN(c2ncnc3[nH]ccc23)C1] | B |
| 307 | Abs | B |
| 308 | 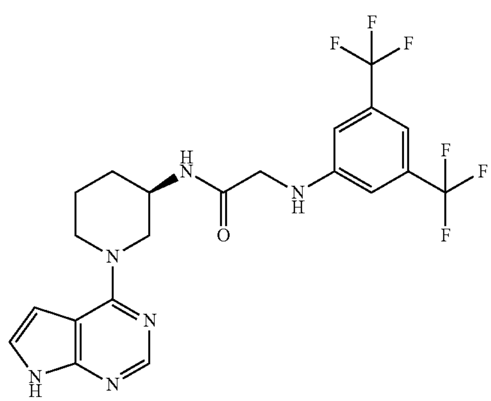 [SMILES: O=C(CNc1cc(C(F)(F)F)cc(C(F)(F)F)c1)N[C@@H]1CCCN(c2ncnc3[nH]ccc23)C1] | B |
| 309 | 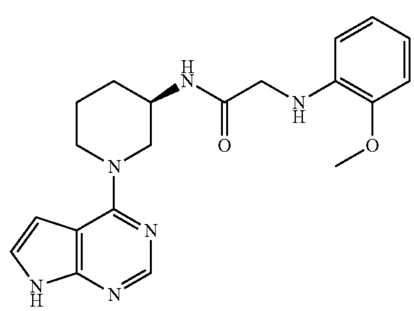 [SMILES: COc1ccccc1NCC(=O)N[C@@H]1CCCN(c2ncnc3[nH]ccc23)C1] | B |

TABLE 1-continued
Exemplary compounds of formula I.
| Cmpd. No. | Structure | IC$_{50}$ (10 uM ATP)$^a$ |
|---|---|---|
| 310 | 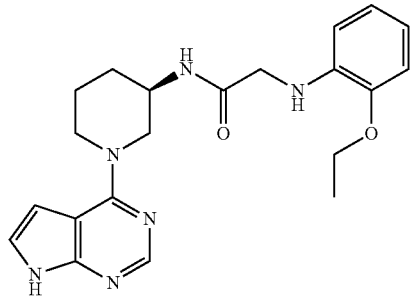 | B |
| 311 | 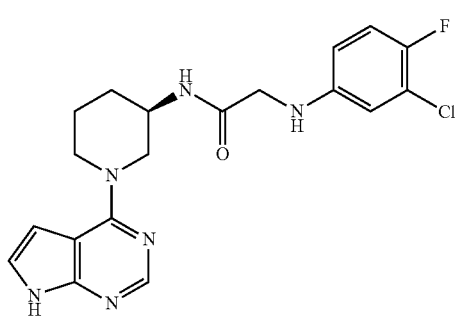 [SMILES: O=C(CNc1ccc(F)c(Cl)c1)N[C@@H]1CCCN(c2ncnc3[nH]ccc23)C1] | B |
| 312 | 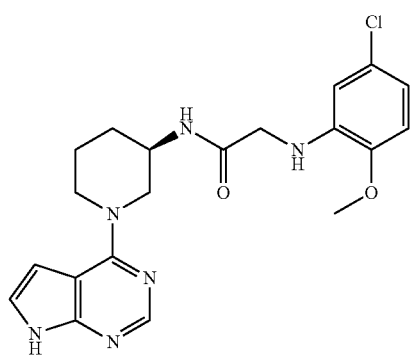 [SMILES: COc1ccc(Cl)cc1NCC(=O)N[C@@H]1CCCN(c2ncnc3[nH]ccc23)C1] | B |
| 313 | 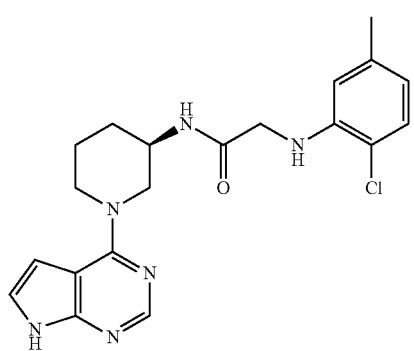 [SMILES: Cc1ccc(Cl)c(NCC(=O)N[C@@H]2CCCN(c3ncnc4[nH]ccc34)C2)c1] | B |

TABLE 1-continued
Exemplary compounds of formula I.
| Cmpd. No. | Structure | IC$_{50}$ (10 uM ATP)$^a$ |
|---|---|---|
| 314 | Abs 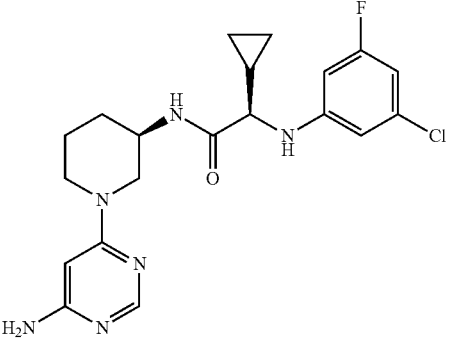 | B |
| 315 | 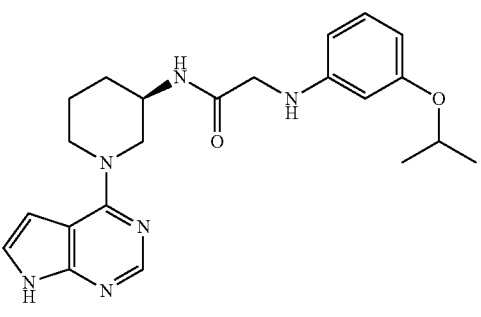 [SMILES: CC(C)Oc1cccc(NCC(=O)N[C@@H]2CCCN(c3ncnc4[nH]ccc34)C2)c1] | B |
| 316 | 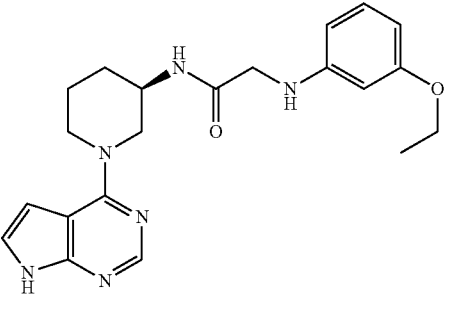 [SMILES: CCOc1cccc(NCC(=O)N[C@@H]2CCCN(c3ncnc4[nH]ccc34)C2)c1] | B |
| 317 | 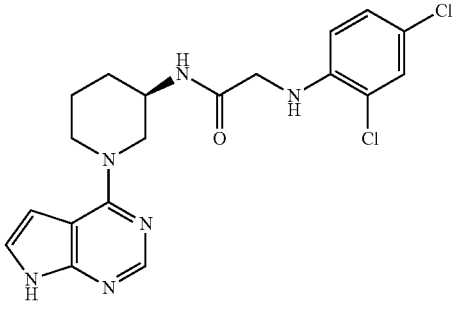 [SMILES: O=C(CNc1ccc(Cl)cc1Cl)N[C@@H]1CCCN(c2ncnc3[nH]ccc23)C1] | B |

TABLE 1-continued

Exemplary compounds of formula I.

| Cmpd. No. | Structure | IC$_{50}$ (10 uM ATP)$^a$ |
|---|---|---|
| 318 | 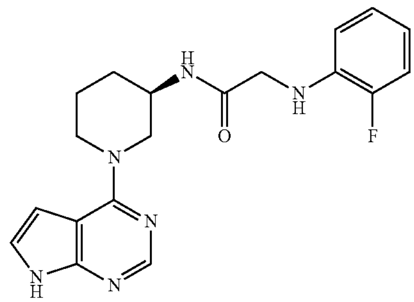 | B |
| 319 | 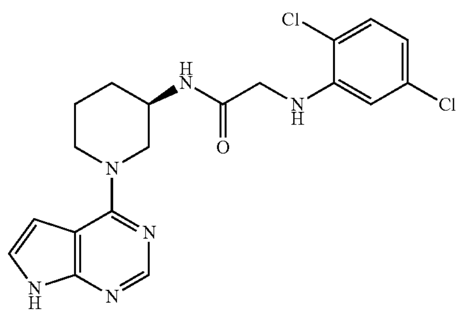 [SMILES: O=C(CNc1cc(Cl)ccc1Cl)N[C@@H]1CCCN(c2ncnc3[nH]ccc23)C1] | B |
| 320 | 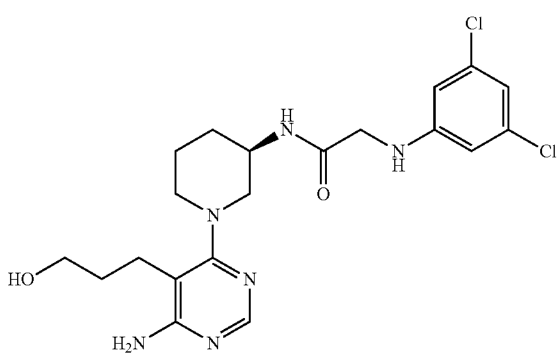 [SMILES: Nc1ncnc(N2CCC[C@@H](NC(=O)CNc3cc(Cl)cc(Cl)c3)C2)c1CCCO] | B |
| 321 | 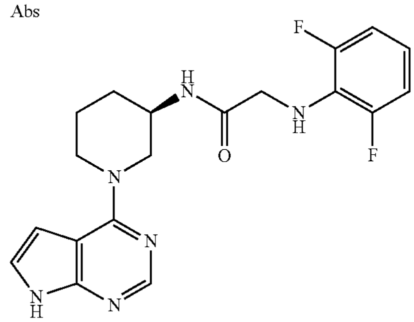 [SMILES: O=C(CNc1c(F)cccc1F)N[C@@H]1CCCN(c2ncnc3[nH]ccc23)C1] | B |

TABLE 1-continued
Exemplary compounds of formula I.
| Cmpd. No. | Structure | IC$_{50}$ (10 uM ATP)$^a$ |
|---|---|---|
| 322 | 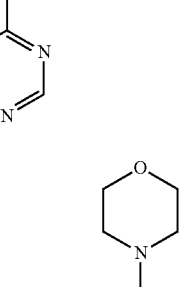 | B |
| 323 | 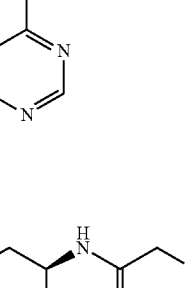 | B |
| 324 | Chiral 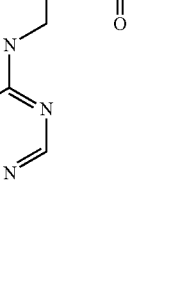 | B |
| 325 | Abs 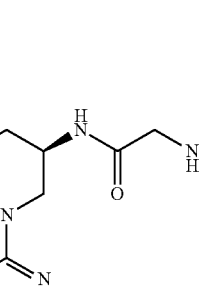 | B |

TABLE 1-continued

Exemplary compounds of formula I.

| Cmpd. No. | Structure | IC$_{50}$ (10 uM ATP)$^a$ |
|---|---|---|
| 326 | Abs | B |
| 327 | Abs | B |
| 328 | 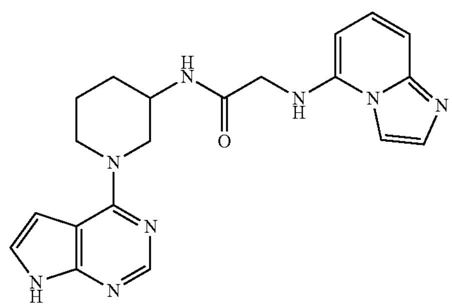 [SMILES: O=C(CNc1cccc2nccn12)NC1CCCN(c2ncnc3[nH]ccc23)C1] | D |
| 329 | 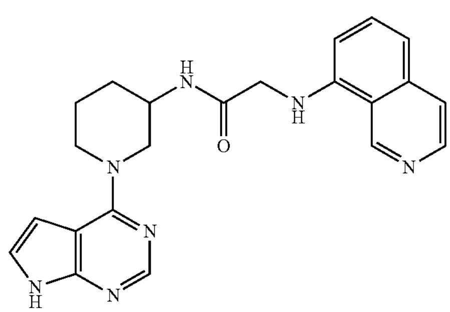 [SMILES: O=C(CNc1cccc2ccncc12)NC1CCCN(c2ncnc3[nH]ccc23)C1] | D |
| 330 | 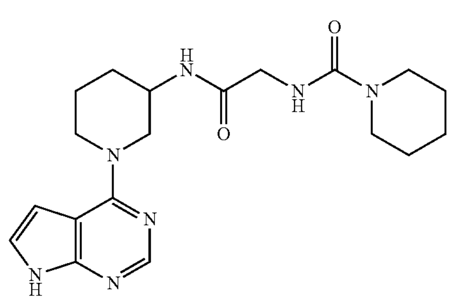 [SMILES: O=C(CNC(=O)N1CCCCC1)NC1CCCN(c2ncnc3[nH]ccc23)C1] | D |

TABLE 1-continued
Exemplary compounds of formula I.
| Cmpd. No. | Structure | IC$_{50}$ (10 uM ATP)$^a$ |
|---|---|---|
| 331 | 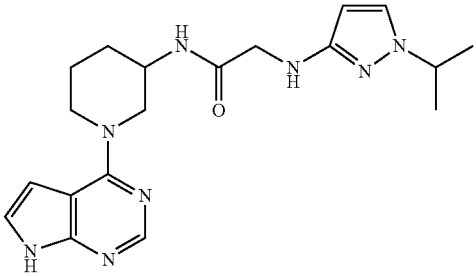 [SMILES: CC(C)n1ccc(NCC(=O)NC2CCCN(c3ncnc4[nH]ccc34)C2)n1] | D |
| 332 | 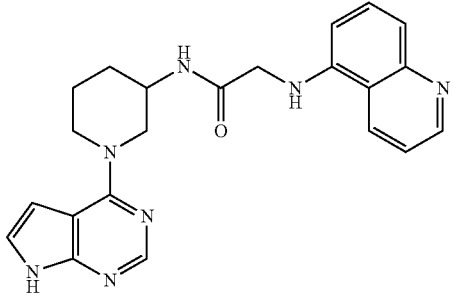 [SMILES: O=C(CNc1cccc2ncccc12)NC1CCCN(c2ncnc3[nH]ccc23)C1] | D |
| 333 | 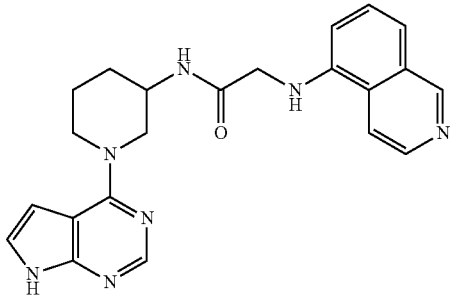 [SMILES: O=C(CNc1cccc2cnccc12)NC1CCCN(c2ncnc3[nH]ccc23)C1] | C |
| 334 | 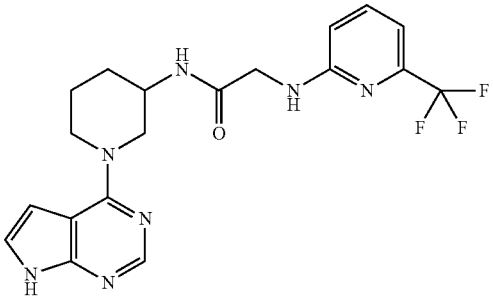 [SMILES: O=C(CNc1cccc(C(F)(F)F)n1)NC1CCCN(c2ncnc3[nH]ccc23)C1] | C |
| 335 | 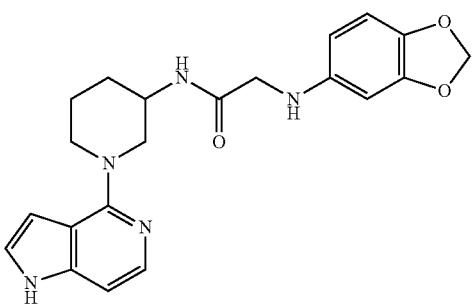 [SMILES: O=C(CNc1ccc2c(c1)OCO2)NC1CCCN(c2nccc3[nH]ccc23)C1] | D |

TABLE 1-continued
Exemplary compounds of formula I.
| Cmpd. No. | Structure | IC$_{50}$ (10 uM ATP)$^a$ |
|---|---|---|
| 336 | 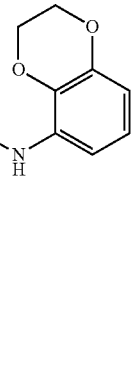 | D |
| 337 | 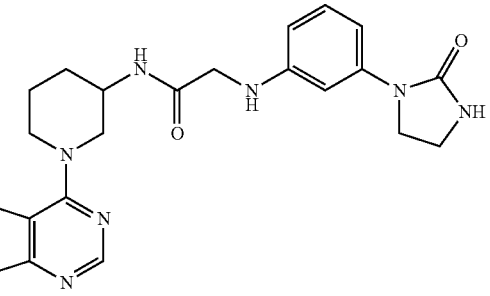 | D |
| 338 | 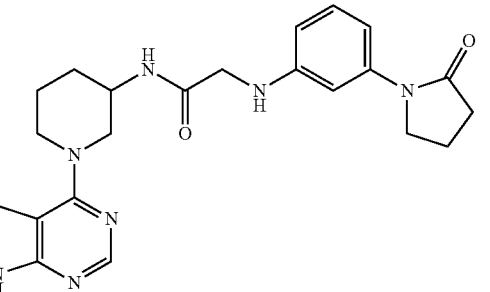 | C |
| 339 | 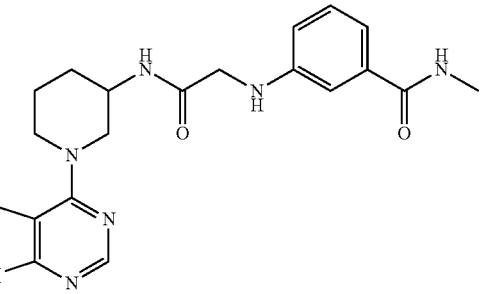 | D |

TABLE 1-continued

Exemplary compounds of formula I.

| Cmpd. No. | Structure | IC$_{50}$ (10 uM ATP)$^a$ |
|---|---|---|
| 340 | 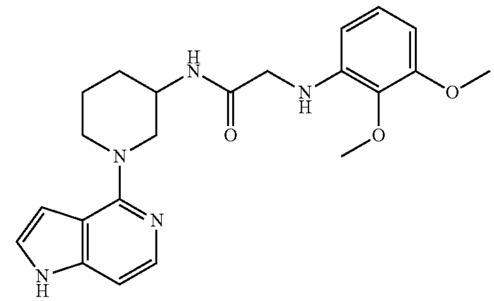 [SMILES: COc1cccc(NCC(=O)NC2CCCN(c3nccc4[nH]ccc34)C2)c1OC] | D |
| 341 | 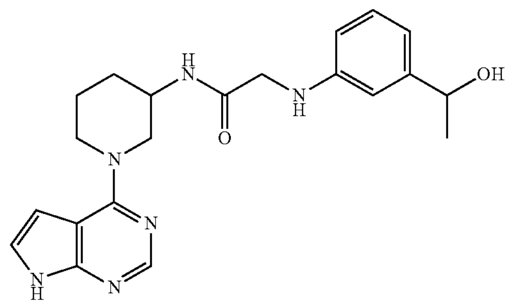 [SMILES: CC(O)c1cccc(NCC(=O)NC2CCCN(c3ncnc4[nH]ccc34)C2)c1] | D |
| 342 | 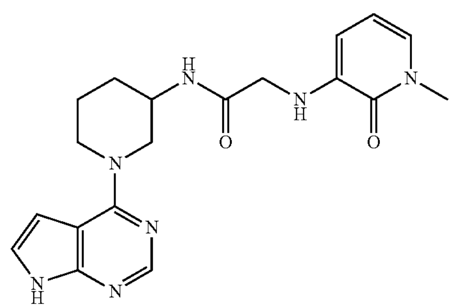 [SMILES: Cn1cccc(NCC(=O)NC2CCCN(c3ncnc4[nH]ccc34)C2)c1=O] | D |
| 343 | 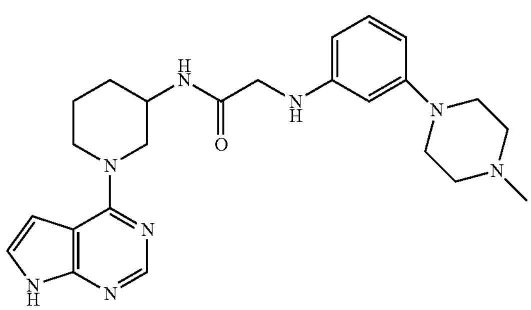 [SMILES: CN1CCN(c2cccc(NCC(=O)NC3CCCN(c4ncnc5[nH]ccc45)C3)c2)CC1] | D |
| 344 | 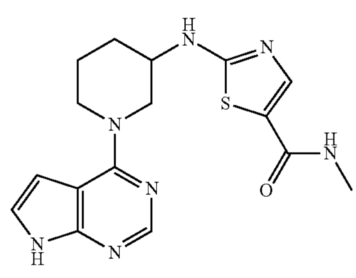 [SMILES: CNC(=O)c1cnc(NC2CCCN(c3ncnc4[nH]ccc34)C2)s1] | D |

TABLE 1-continued

Exemplary compounds of formula I.

| Cmpd. No. | Structure | IC$_{50}$ (10 uM ATP)$^a$ |
|---|---|---|
| 345 | 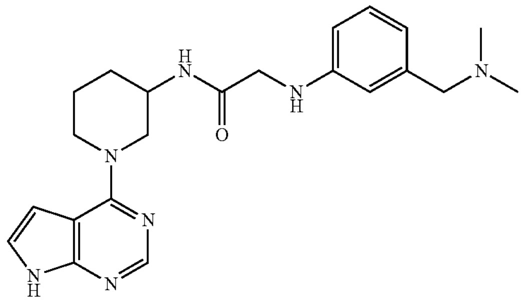 [SMILES: CN(C)Cc1cccc(NCC(=O)NC2CCCN(c3ncnc4[nH]ccc34)C2)c1] | D |
| 346 | 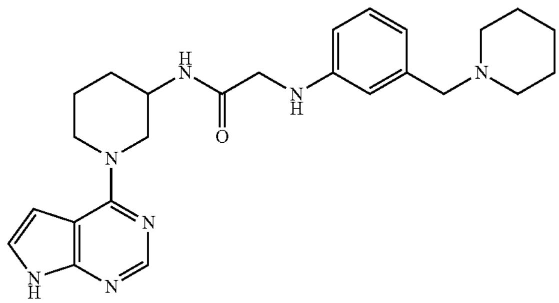 [SMILES: O=C(CNc1cccc(CN2CCCCC2)c1)NC1CCCN(c2ncnc3[nH]ccc23)C1] | D |
| 347 | 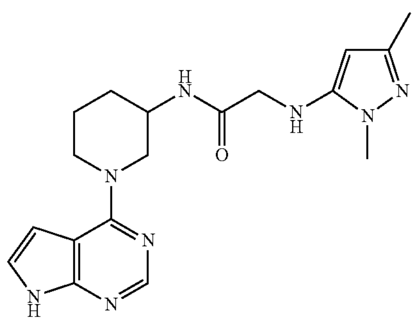 [SMILES: Cc1cc(NCC(=O)NC2CCCN(c3ncnc4[nH]ccc34)C2)n(C)n1] | D |
| 348 | 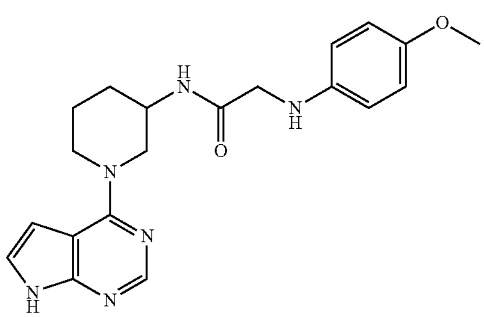 [SMILES: COc1ccc(NCC(=O)NC2CCCN(c3ncnc4[nH]ccc34)C2)cc1] | D |
| 349 | 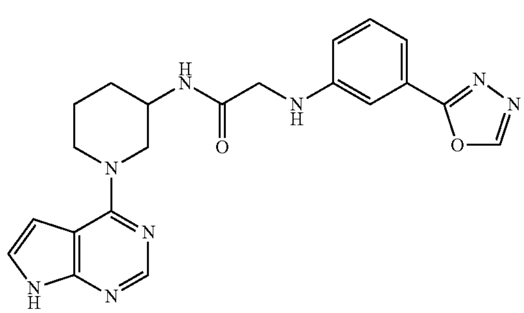 [SMILES: O=C(CNc1cccc(-c2nnco2)c1)NC1CCCN(c2ncnc3[nH]ccc23)C1] | D |

TABLE 1-continued

Exemplary compounds of formula I.

| Cmpd. No. | Structure | IC$_{50}$ (10 uM ATP)$^a$ |
|---|---|---|
| 350 | 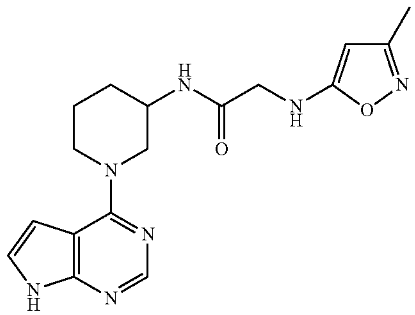 [SMILES: Cc1cc(NCC(=O)NC2CCCN(c3ncnc4[nH]ccc34)C2)on1] | D |
| 351 | 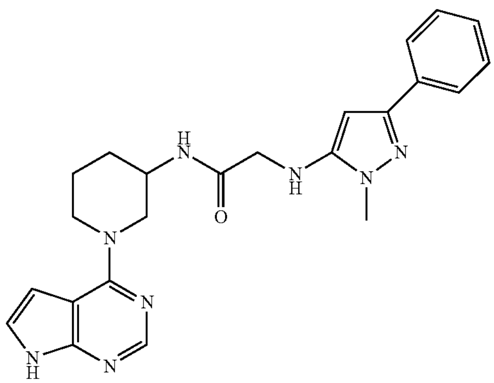 [SMILES: Cn1nc(-c2ccccc2)cc1NCC(=O)NC1CCCN(c2ncnc3[nH]ccc23)C1] | D |
| 352 | 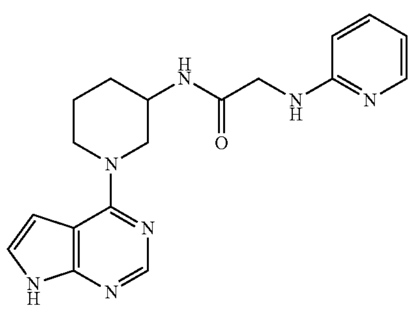 | C |
| 353 | 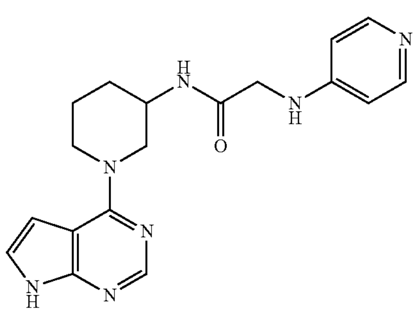 [SMILES: O=C(CNc1ccncc1)NC1CCCN(c2ncnc3[nH]ccc23)C1] | D |

TABLE 1-continued

Exemplary compounds of formula I.

| Cmpd. No. | Structure | IC$_{50}$ (10 uM ATP)$^a$ |
|---|---|---|
| 354 | 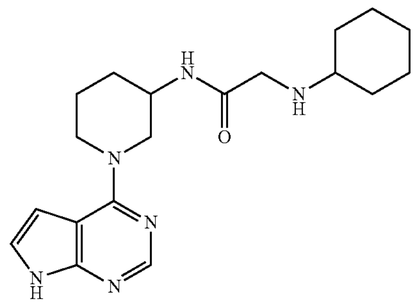 [SMILES: O=C(CNC1CCCCC1)NC1CCCN(c2ncnc3[nH]ccc23)C1] | D |
| 355 | 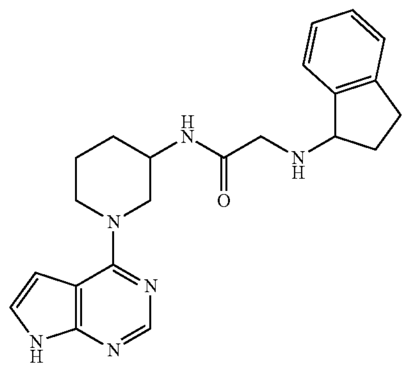 [SMILES: O=C(CNC1CCc2ccccc21)NC1CCCN(c2ncnc3[nH]ccc23)C1] | D |
| 356 | 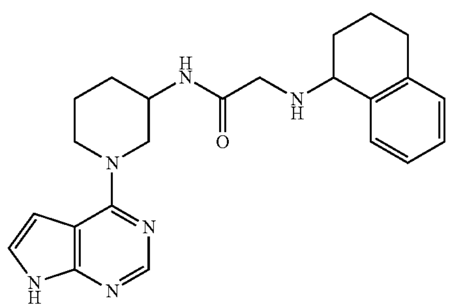 [SMILES: O=C(CNC1CCCc2ccccc21)NC1CCCN(c2ncnc3[nH]ccc23)C1] | D |
| 357 | 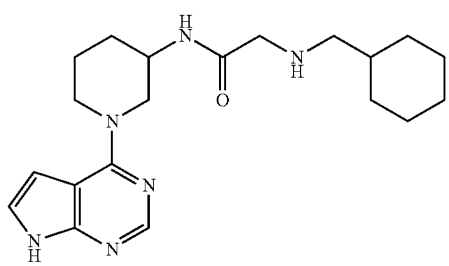 [SMILES: O=C(CNCC1CCCCC1)NC1CCCN(c2ncnc3[nH]ccc23)C1] | D |
| 358 | 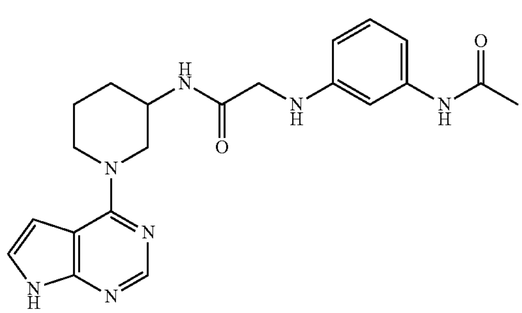 [SMILES: CC(=O)Nc1cccc(NCC(=O)NC2CCCN(c3ncnc4[nH]ccc34)C2)c1] | D |

TABLE 1-continued
Exemplary compounds of formula I.
| Cmpd. No. | Structure | IC$_{50}$ (10 uM ATP) $^a$ |
|---|---|---|
| 359 | 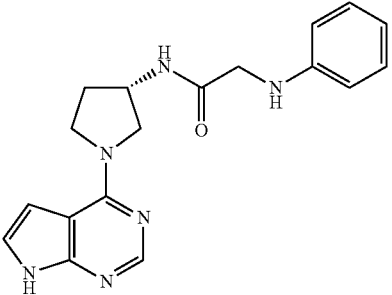 [SMILES: O=C(CNc1ccccc1)N[C@H]1CCN(c2ncnc3[nH]ccc23)C1] | D |
| 360 | 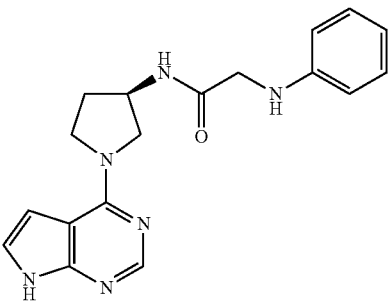 [SMILES: O=C(CNc1ccccc1)N[C@@H]1CCN(c2ncnc3[nH]ccc23)C1] | D |
| 361 | 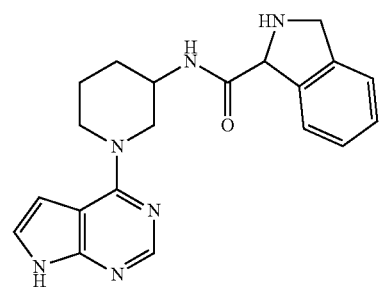 [SMILES: O=C(NC1CCCN(c2ncnc3[nH]ccc23)C1)C1NCc2ccccc21] | D |
| 362 | 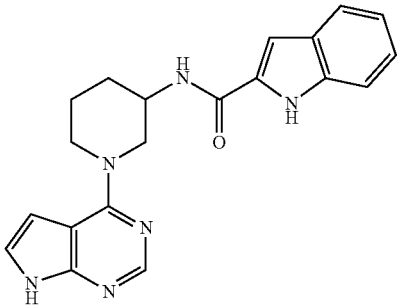 [SMILES: O=C(NC1CCCN(c2ncnc3[nH]ccc23)C1)c1cc2ccccc2[nH]1] | C |
| 363 | 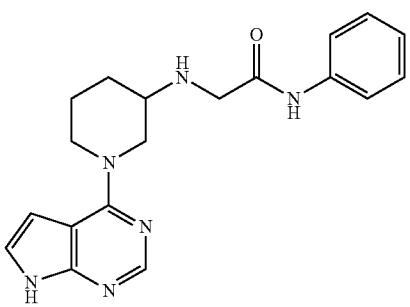 [SMILES: O=C(CNC1CCCN(c2ncnc3[nH]ccc23)C1)Nc1ccccc1] | D |

TABLE 1-continued
Exemplary compounds of formula I.
| Cmpd. No. | Structure | IC$_{50}$ (10 uM ATP)$^a$ |
|---|---|---|
| 364 | 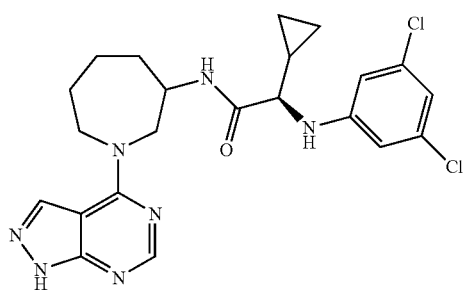 [SMILES: O=C(NC1CCCCN(c2ncnc3[nH]ncc23)C1)[C@H](Nc1cc(Cl)cc(Cl)c1)C1CC1] | A |
| 365 | 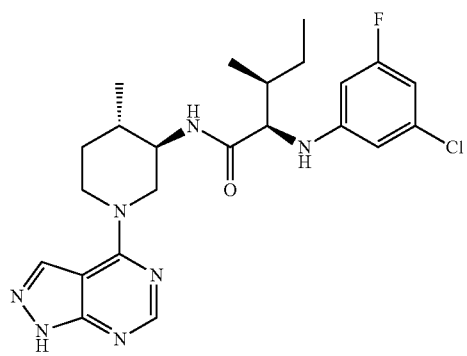 [SMILES: CC[C@H](C)[C@@H](Nc1cc(F)cc(Cl)c1)C(=O)N[C@H]1CN(c2ncnc3[nH]ncc23)CC[C@@H]1C] | A |
| 366 | 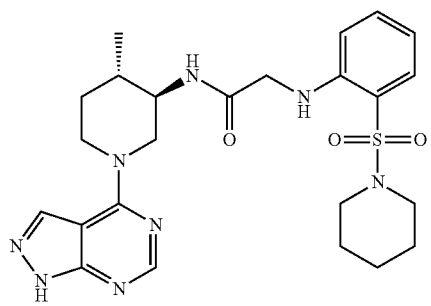 [SMILES: C[C@H]1CCN(c2ncnc3[nH]ncc23)C[C@@H]1NC(=O)CNc1ccccc1S(=O)(=O)N1CCCCC1] | A |
| 367 | 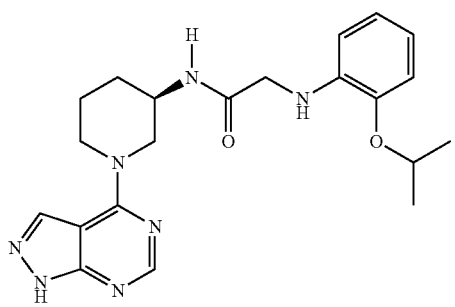 [SMILES: CC(C)Oc1ccccc1NCC(=O)N[C@@H]1CCCN(c2ncnc3[nH]ncc23)C1] | B |

TABLE 1-continued
Exemplary compounds of formula I.
| Cmpd. No. | Structure | IC$_{50}$ (10 uM ATP) [a] |
|---|---|---|
| 368 | 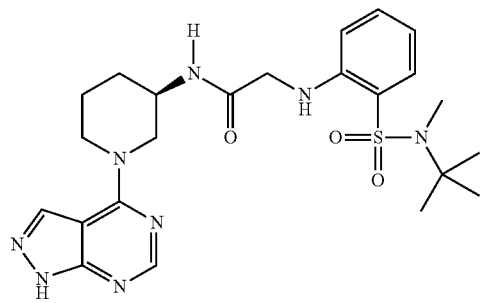 [SMILES: CN(C(C)(C)C)S(=O)(=O)c1ccccc1NCC(=O)N[C@@H]1CCCN(c2ncnc3[nH]ncc23)C1] | B |
| 369 | Abs 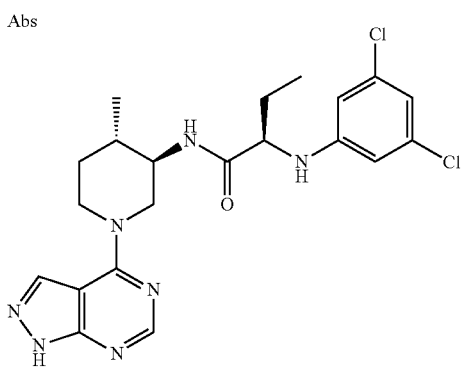 [SMILES: CC[C@@H](Nc1cc(Cl)cc(Cl)c1)C(=O)N[C@H]1CN(c2ncnc3[nH]ncc23)CC[C@@H]1C] | B |
| 370 | 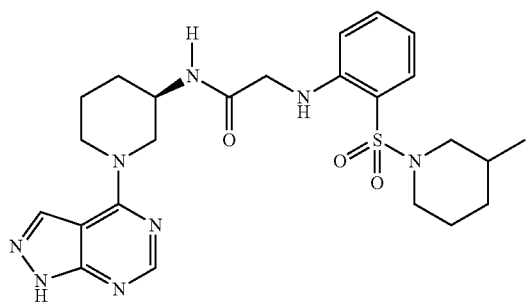 [SMILES: CC1CCCN(S(=O)(=O)c2ccccc2NCC(=O)N[C@@H]2CCCN(c3ncnc4[nH]ncc34)C2)C1] | A |
| 371 | 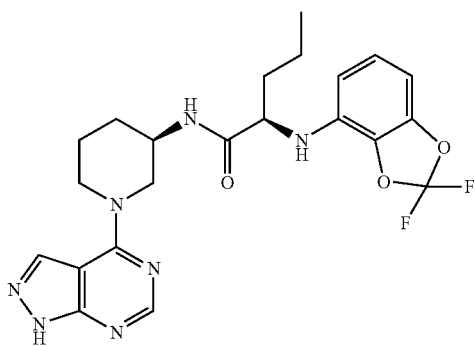 [SMILES: CCC[C@@H](Nc1cccc2c1OC(F)(F)O2)C(=O)N[C@@H]1CCCN(c2ncnc3[nH]ncc23)C1] | B |

TABLE 1-continued

Exemplary compounds of formula I.

| Cmpd. No. | Structure | IC$_{50}$ (10 uM ATP)$^a$ |
|---|---|---|
| 372 | 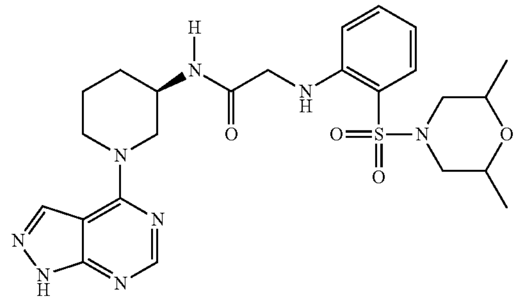 [SMILES: CC1CN(S(=O)(=O)c2ccccc2NCC(=O)N[C@@H]2CCCN(c3ncnc4[nH]ncc34)C2)CC(C)O1] | B |
| 373 | 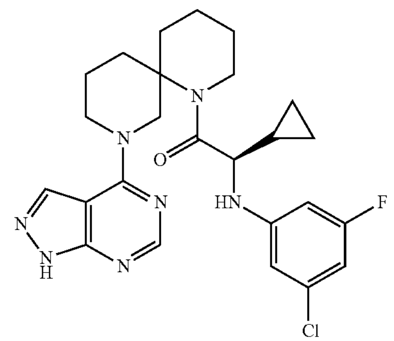 [SMILES: O=C([C@H](Nc1cc(F)cc(Cl)c1)C1CC1)N1CCCCC12CCCN(c1ncnc3[nH]ncc13)C2] | C |
| 374 | 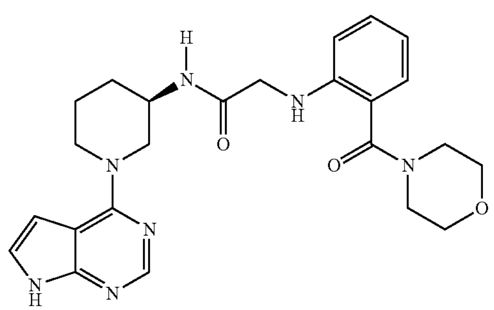 [SMILES: O=C(CNc1ccccc1C(=O)N1CCOCC1)N[C@@H]1CCCN(c2ncnc3[nH]ccc23)C1] | B |
| 375 | 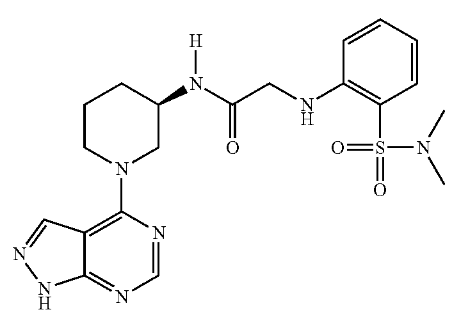 [SMILES: CN(C)S(=O)(=O)c1ccccc1NCC(=O)N[C@@H]1CCCN(c2ncnc3[nH]ncc23)C1] | B |

TABLE 1-continued

Exemplary compounds of formula I.

| Cmpd. No. | Structure | IC$_{50}$ (10 uM ATP)$^a$ |
|---|---|---|
| 376 | 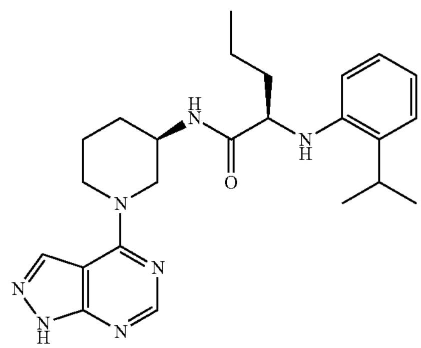 [SMILES: CCC[C@@H](Nc1ccccc1C(C)C)C(=O)N[C@@H]1CCCN(c2ncnc3[nH]ncc23)C1] | B |
| 377 | 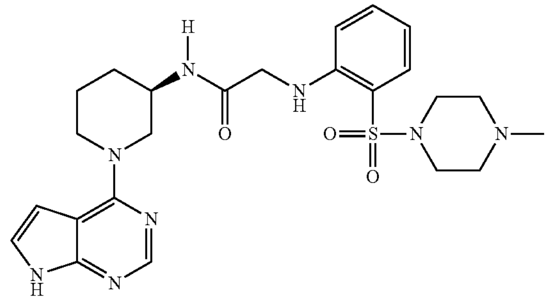 [SMILES: CN1CCN(S(=O)(=O)c2ccccc2NCC(=O)N[C@@H]2CCCN(c3ncnc4[nH]ccc34)C2)CC1] | C |
| 378 | 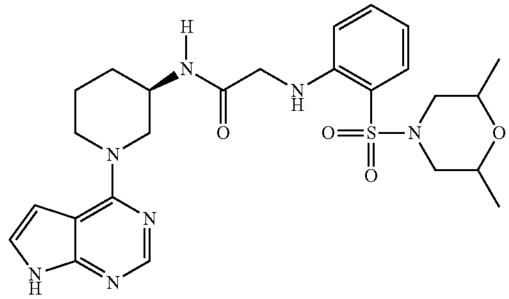 [SMILES: CC1CN(S(=O)(=O)c2ccccc2NCC(=O)N[C@@H]2CCCN(c3ncnc4[nH]ccc34)C2)CC(C)O1] | B |
| 379 | 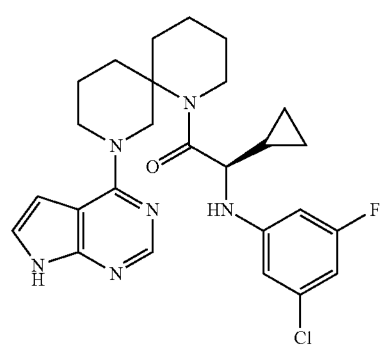 [SMILES: O=C([C@H](Nc1cc(F)cc(Cl)c1)C1CC1)N1CCCCC12CCCN(c1ncnc3[nH]ccc13)C2] | C |

TABLE 1-continued
Exemplary compounds of formula I.
| Cmpd. No. | Structure | IC$_{50}$ (10 uM ATP)$^a$ |
|---|---|---|
| 380 | 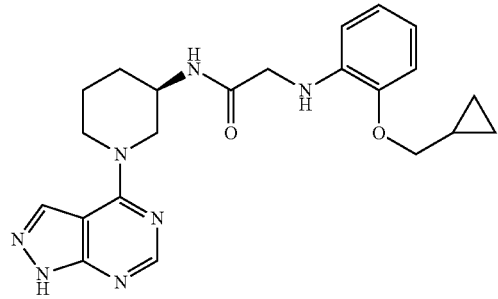 [SMILES: O=C(CNc1ccccc1OCC1CC1)N[C@@H]1CCCN(c2ncnc3[nH]ncc23)C1] | B |
| 381 | 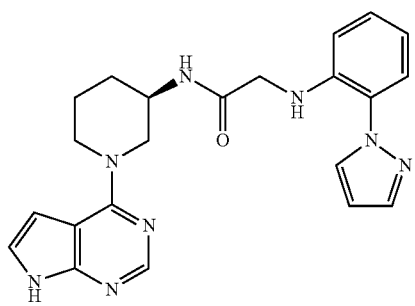 [SMILES: O=C(CNc1ccccc1-n1cccn1)N[C@@H]1CCCN(c2ncnc3[nH]ccc23)C1] | C |
| 382 | 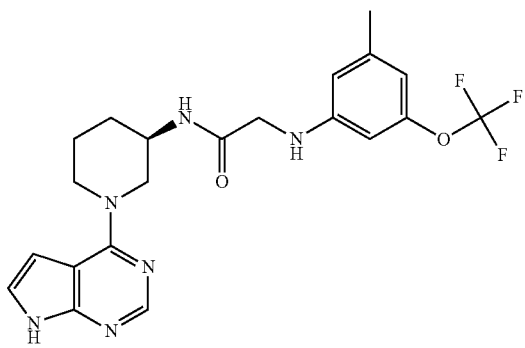 [SMILES: Cc1cc(NCC(=O)N[C@@H]2CCCN(c3ncnc4[nH]ccc34)C2)cc(OC(F)(F)F)c1] | A |
| 383 | 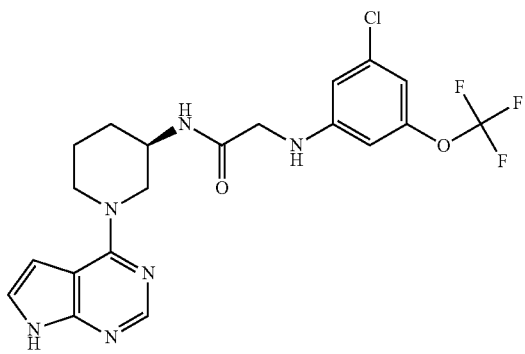 [SMILES: O=C(CNc1cc(Cl)cc(OC(F)(F)F)c1)N[C@@H]1CCCN(c2ncnc3[nH]ccc23)C1] | A |

TABLE 1-continued

Exemplary compounds of formula I.

| Cmpd. No. | Structure | IC$_{50}$ (10 uM ATP)$^a$ |
|---|---|---|
| 384 | 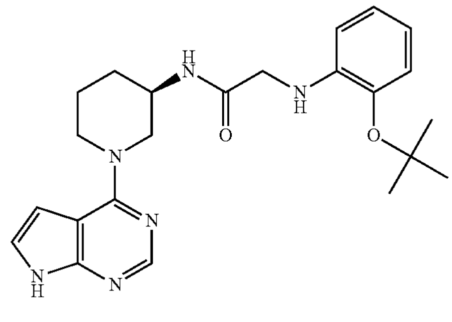 [SMILES: CC(C)(C)Oc1ccccc1NCC(=O)N[C@@H]1CCCN(c2ncnc3[nH]ccc23)C1] | B |
| 385 | Abs | A |
| 386 | 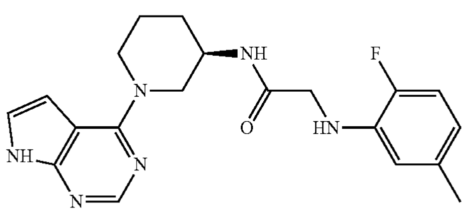 [SMILES: Cc1ccc(F)c(NCC(=O)N[C@@H]2CCCN(c3ncnc4[nH]ccc34)C2)c1] | B |
| 387 | 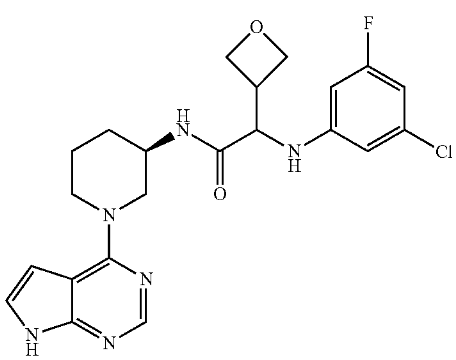 [SMILES: O=C(N[C@@H]1CCCN(c2ncnc3[nH]ccc23)C1)C(Nc1cc(F)cc(Cl)c1)C1COC1] | C |

TABLE 1-continued

Exemplary compounds of formula I.

| Cmpd. No. | Structure | IC$_{50}$ (10 uM ATP)$^a$ |
|---|---|---|
| 388 | Abs | C |
| 389 | 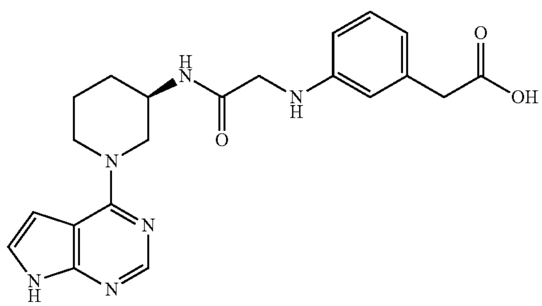 [SMILES: O=C(O)Cc1cccc(NCC(=O)N[C@@H]2CCCN(c3ncnc4[nH]ccc34)C2)c1] | C |
| 390 | 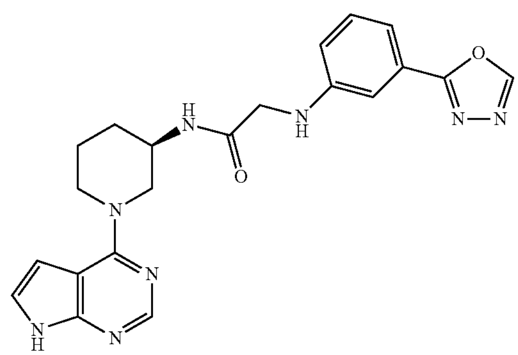 [SMILES: O=C(CNc1cccc(-c2nnco2)c1)N[C@@H]1CCCN(c2ncnc3[nH]ccc23)C1] | C |
| 391 | Abs | C |

TABLE 1-continued

Exemplary compounds of formula I.

| Cmpd. No. | Structure | IC$_{50}$ (10 uM ATP)$^a$ |
|---|---|---|
| 392 | 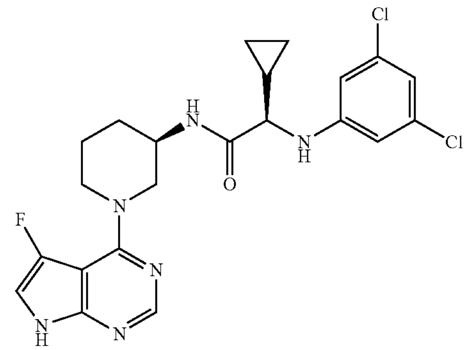 [SMILES: O=C(N[C@@H]1CCCN(c2ncnc3[nH]cc(F)c23)C1)[C@H](Nc1cc(Cl)cc(Cl)c1)C1CC1] | C |
| 393 | 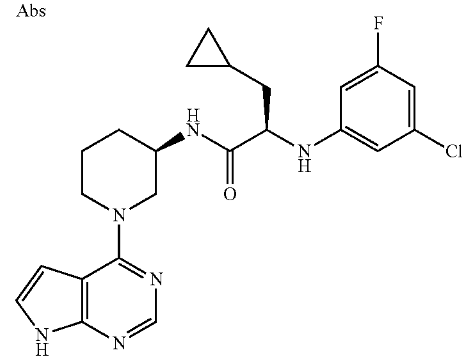 [SMILES: O=C(N[C@@H]1CCCN(c2ncnc3[nH]ccc23)C1)[C@@H](CC1CC1)Nc1cc(F)cc(Cl)c1] | C |
| 394 | 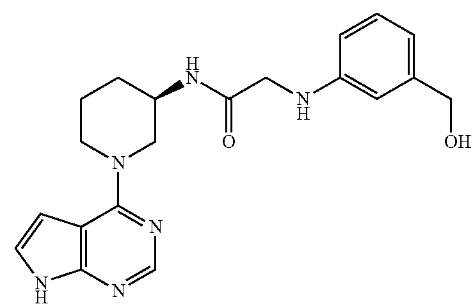 [SMILES: O=C(CNc1cccc(CO)c1)N[C@@H]1CCCN(c2ncnc3[nH]ccc23)C1] | C |
| 395 | 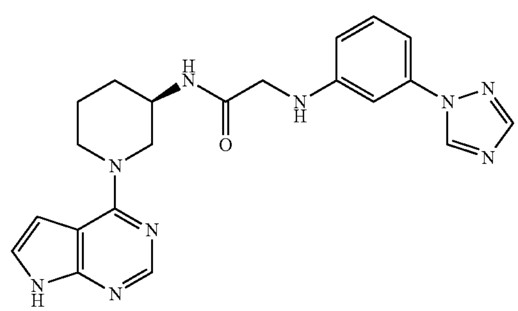 [SMILES: O=C(CNc1cccc(-n2cncn2)c1)N[C@@H]1CCCN(c2ncnc3[nH]ccc23)C1] | C |

TABLE 1-continued

Exemplary compounds of formula I.

| Cmpd. No. | Structure | IC$_{50}$ (10 uM ATP) $^a$ |
|---|---|---|
| 396 | 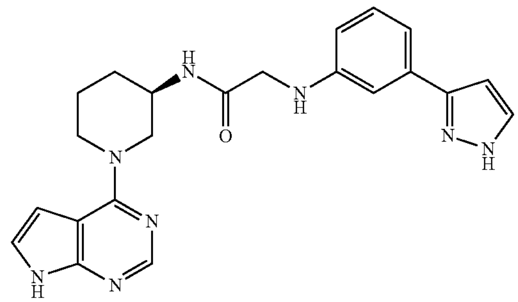 [SMILES: O=C(CNc1cccc(-c2cc[nH]n2)c1)N[C@@H]1CCCN(c2ncnc3[nH]ccc23)C1] | C |
| 397 | 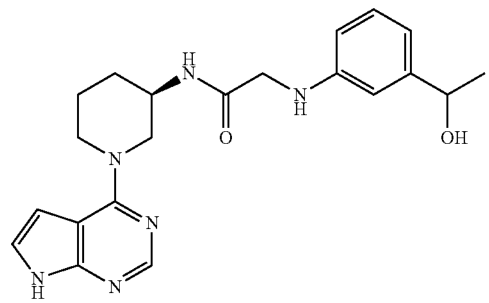 [SMILES: CC(O)c1cccc(NCC(=O)N[C@@H]2CCCN(c3ncnc4[nH]ccc34)C2)c1] | C |
| 398 | 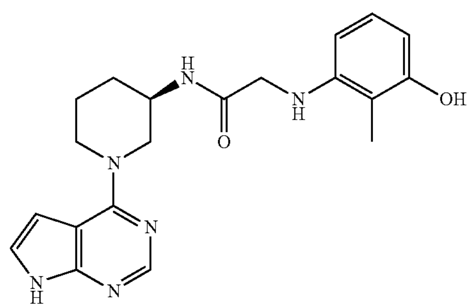 [SMILES: Cc1c(O)cccc1NCC(=O)N[C@@H]1CCCN(c2ncnc3[nH]ccc23)C1] | C |
| 399 | 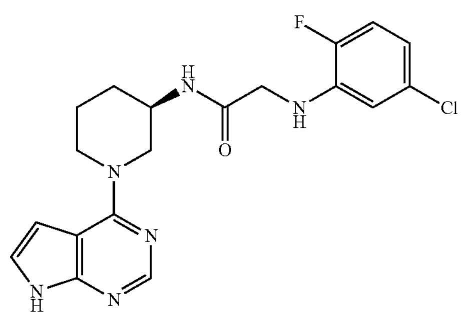 | B |
| 400 | 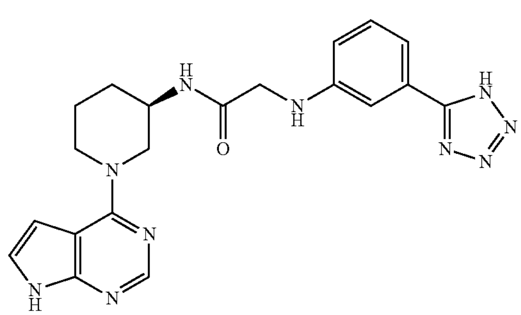 [SMILES: O=C(CNc1cccc(-c2nnn[nH]2)c1)N[C@@H]1CCCN(c2ncnc3[nH]ccc23)C1] | C |

TABLE 1-continued
Exemplary compounds of formula I.
| Cmpd. No. | Structure | IC$_{50}$ (10 uM ATP)$^a$ |
|---|---|---|
| 401 | 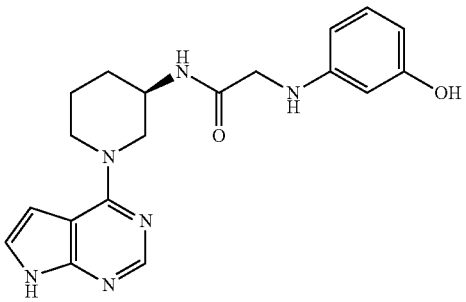 [SMILES: O=C(CNc1cccc(O)c1)N[C@@H]1CCCN(c2ncnc3[nH]ccc23)C1] | C |
| 402 | 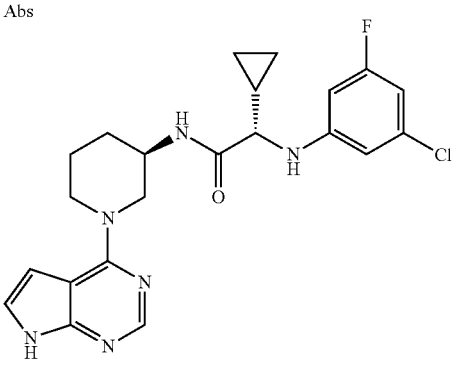 [SMILES: O=C(N[C@@H]1CCCN(c2ncnc3[nH]ccc23)C1)[C@@H](Nc1cc(F)cc(Cl)c1)C1CC1] | C |
| 403 | 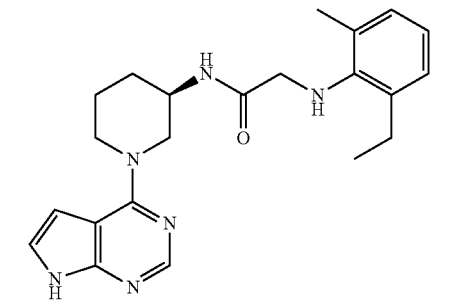 | C |
| 404 | 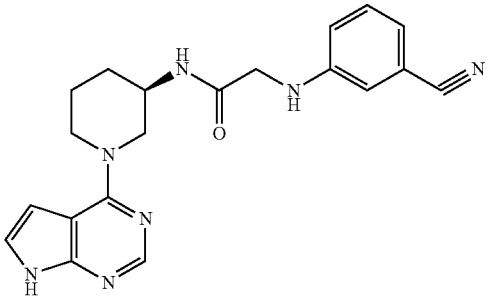 [SMILES: N#Cc1cccc(NCC(=O)N[C@@H]2CCCN(c3ncnc4[nH]ccc34)C2)c1] | C |

TABLE 1-continued

Exemplary compounds of formula I.

| Cmpd. No. | Structure | IC$_{50}$ (10 uM ATP)$^a$ |
|---|---|---|
| 405 | 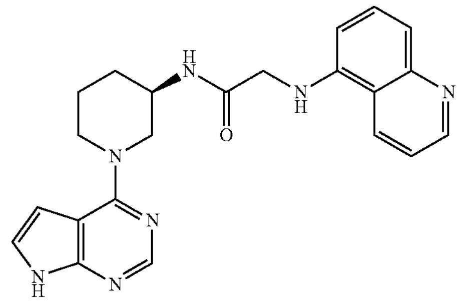 [SMILES: O=C(CNc1cccc2ncccc12)N[C@@H]1CCCN(c2ncnc3[nH]ccc23)C1] | C |
| 406 | 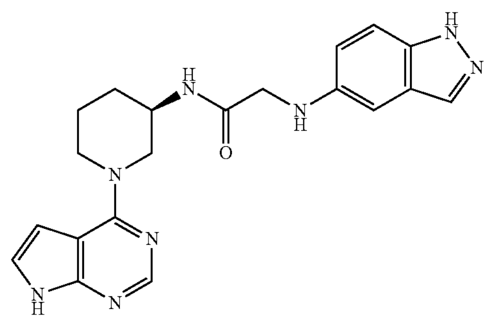 [SMILES: O=C(CNc1ccc2[nH]ncc2c1)N[C@@H]1CCCN(c2ncnc3[nH]ccc23)C1] | C |
| 407 | 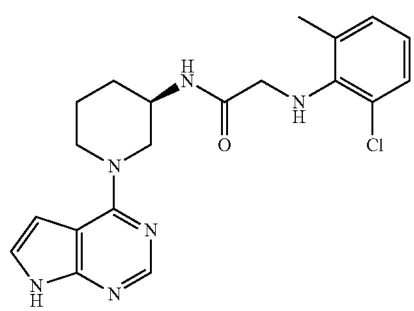 [SMILES: Cc1cccc(Cl)c1NCC(=O)N[C@@H]1CCCN(c2ncnc3[nH]ccc23)C1] | C |
| 408 | 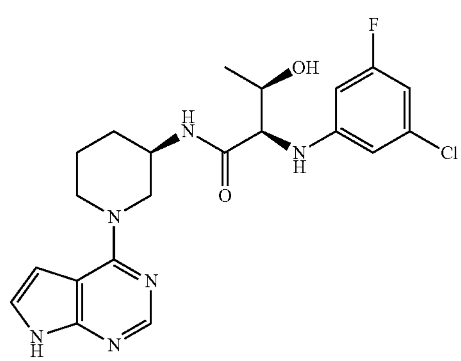 [SMILES: C[C@@H](O)[C@@H](Nc1cc(F)cc(Cl)c1)C(=O)N[C@@H]1CCCN(c2ncnc3[nH]ccc23)C1] | C |

TABLE 1-continued
Exemplary compounds of formula I.
| Cmpd. No. | Structure | IC$_{50}$ (10 uM ATP)$^a$ |
|---|---|---|
| 409 | 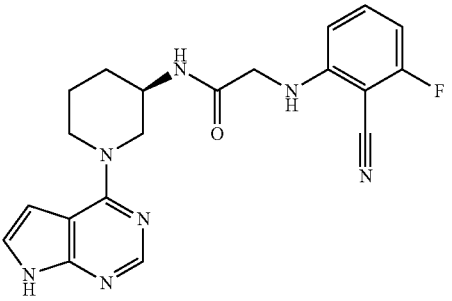 [SMILES: N#Cc1c(F)cccc1NCC(=O)N[C@@H]1CCCN(c2ncnc3[nH]ccc23)C1] | C |
| 410 | 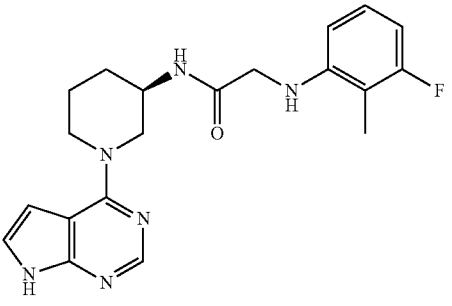 [SMILES: Cc1c(F)cccc1NCC(=O)N[C@@H]1CCCN(c2ncnc3[nH]ccc23)C1] | B |
| 411 | 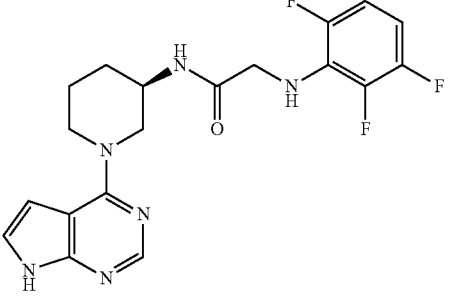 | B |
| 412 | 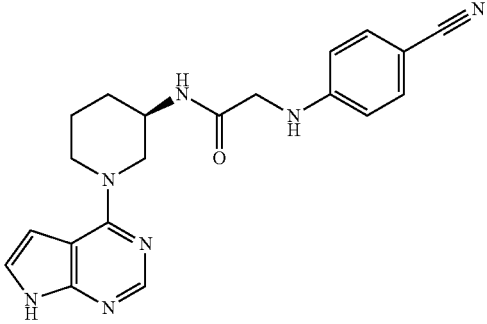 [SMILES: N#Cc1ccc(NCC(=O)N[C@@H]2CCCN(c3ncnc4[nH]ccc34)C2)cc1] | C |

TABLE 1-continued

Exemplary compounds of formula I.

| Cmpd. No. | Structure | IC$_{50}$ (10 uM ATP)$^a$ |
|---|---|---|
| 413 | 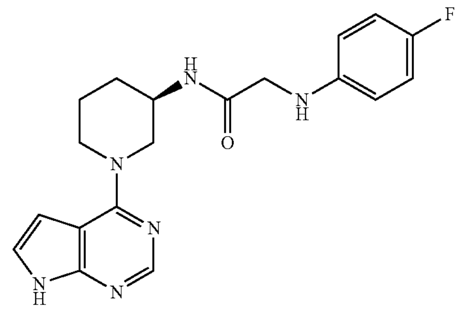 [SMILES: O=C(CNc1ccc(F)cc1)N[C@@H]1CCCN(c2ncnc3[nH]ccc23)C1] | B |
| 414 | 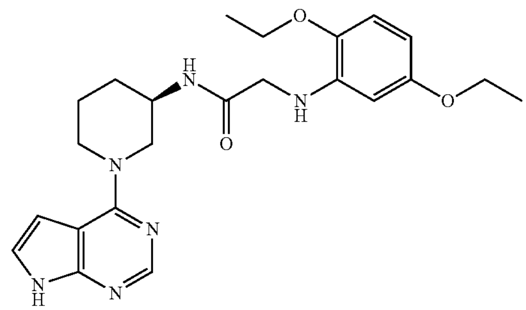 [SMILES: CCOc1ccc(OCC)c(NCC(=O)N[C@@H]2CCCN(c3ncnc4[nH]ccc34)C2)c1] | C |
| 415 | 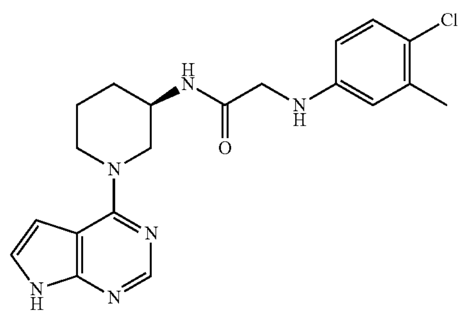 [SMILES: Cc1cc(NCC(=O)N[C@@H]2CCCN(c3ncnc4[nH]ccc34)C2)ccc1Cl] | C |
| 416 | 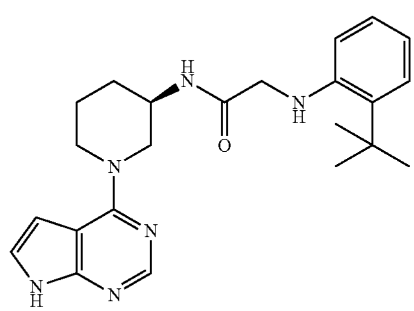 [SMILES: CC(C)(C)c1ccccc1NCC(=O)N[C@@H]1CCCN(c2ncnc3[nH]ccc23)C1] | C |
| 417 | 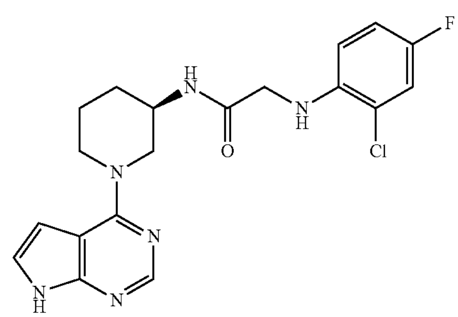 [SMILES: O=C(CNc1ccc(F)cc1Cl)N[C@@H]1CCCN(c2ncnc3[nH]ccc23)C1] | B |

TABLE 1-continued
Exemplary compounds of formula I.
| Cmpd. No. | Structure | IC$_{50}$ (10 uM ATP) [a] |
|---|---|---|
| 418 | 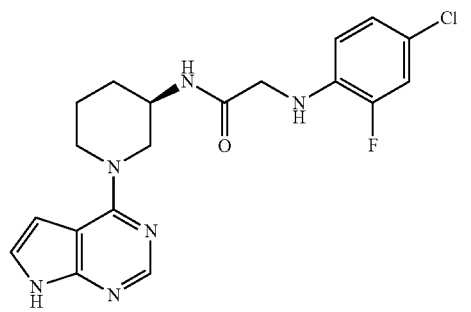 | C |
| 419 | 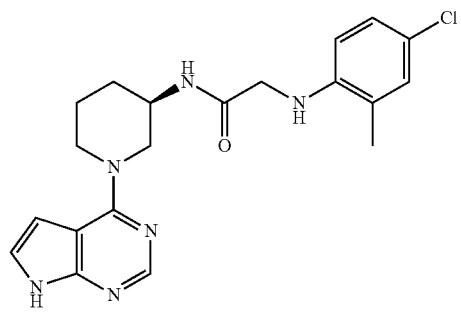 [SMILES: Cc1cc(Cl)ccc1NCC(=O)N[C@@H]1CCCN(c2ncnc3[nH]ccc23)C1] | B |
| 420 | 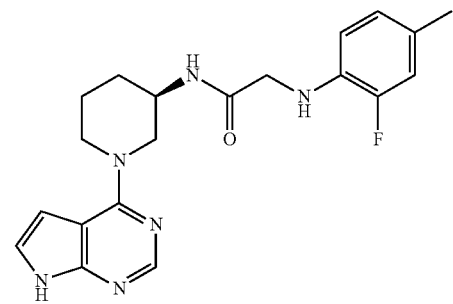 [SMILES: Cc1ccc(NCC(=O)N[C@@H]2CCCN(c3ncnc4[nH]ccc34)C2)c(F)c1] | C |
| 421 | 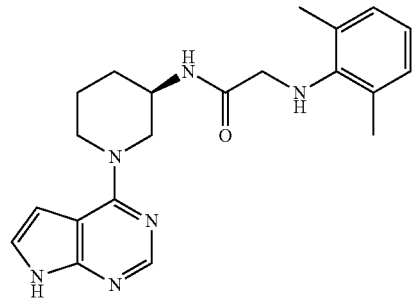 [SMILES: Cc1cccc(C)c1NCC(=O)N[C@@H]1CCCN(c2ncnc3[nH]ccc23)C1] | C |

TABLE 1-continued

Exemplary compounds of formula I.

| Cmpd. No. | Structure | IC$_{50}$ (10 uM ATP)$^a$ |
|---|---|---|
| 422 | 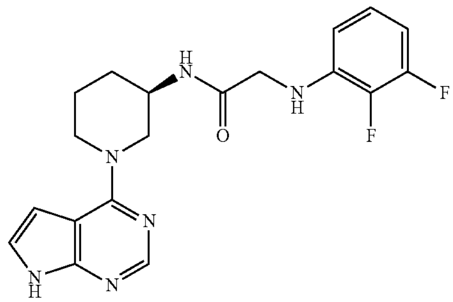 | B |
| 423 | 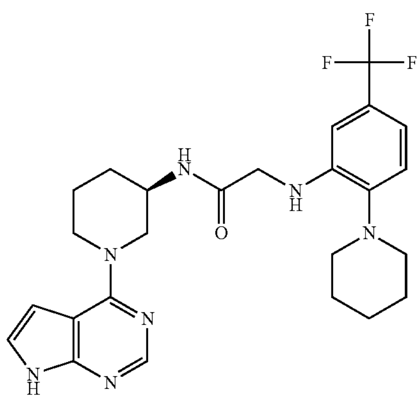 [SMILES: O=C(CNc1cc(C(F)(F)F)ccc1N1CCCCC1)N[C@@H]1CCCN(c2ncnc3[nH]ccc23)C1] | C |
| 424 | Abs | C |
| 425 | Abs | C |

TABLE 1-continued

Exemplary compounds of formula I.

| Cmpd. No. | Structure | IC$_{50}$ (10 uM ATP)$^a$ |
|---|---|---|
| 426 | 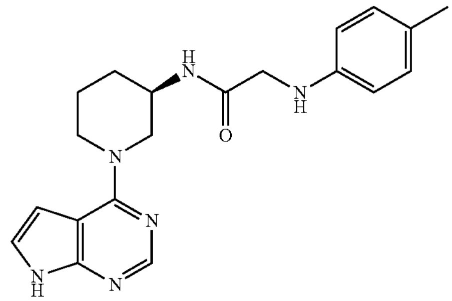 [SMILES: Cc1ccc(NCC(=O)N[C@@H]2CCCN(c3ncnc4[nH]ccc34)C2)cc1] | B |
| 427 | 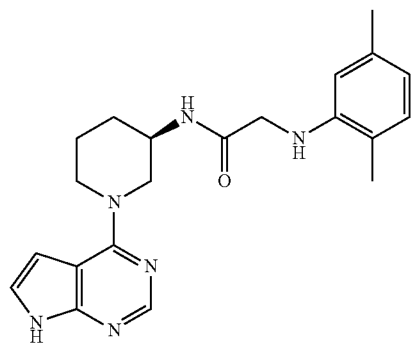 | C |
| 428 | 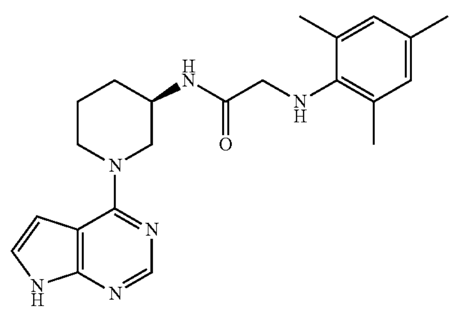 [SMILES: Cc1cc(C)c(NCC(=O)N[C@@H]2CCCN(c3ncnc4[nH]ccc34)C2)c(C)c1] | C |
| 429 | 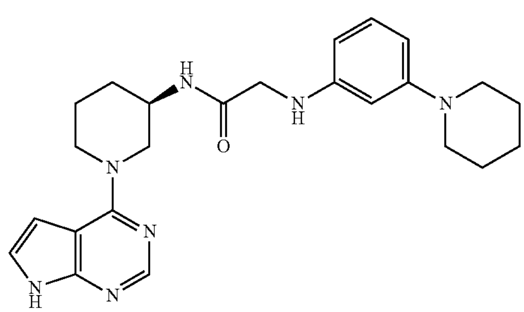 [SMILES: O=C(CNc1cccc(N2CCCCC2)c1)N[C@@H]1CCCN(c2ncnc3[nH]ccc23)C1] | C |

TABLE 1-continued

Exemplary compounds of formula I.

| Cmpd. No. | Structure | IC$_{50}$ (10 uM ATP)$^a$ |
|---|---|---|
| 430 | 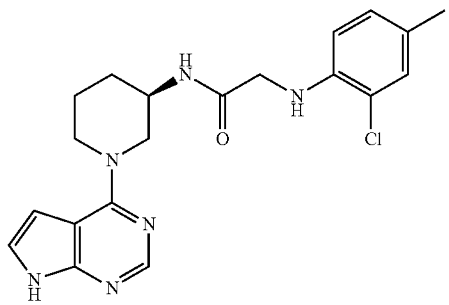 [SMILES: Cc1ccc(NCC(=O)N[C@@H]2CCCN(c3ncnc4[nH]ccc34)C2)c(Cl)c1] | C |
| 431 | Abs | C |
| 432 | Abs | C |
| 433 | 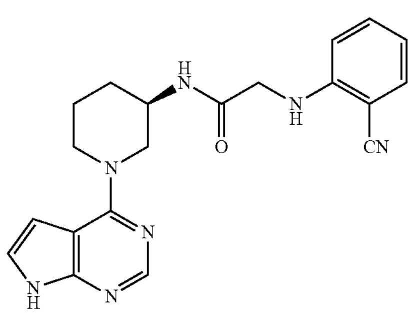 [SMILES: N#Cc1ccccc1NCC(=O)N[C@@H]1CCCN(c2ncnc3[nH]ccc23)C1] | C |

TABLE 1-continued
Exemplary compounds of formula I.
| Cmpd. No. | Structure | IC$_{50}$ (10 uM ATP) [a] |
|---|---|---|
| 434 | 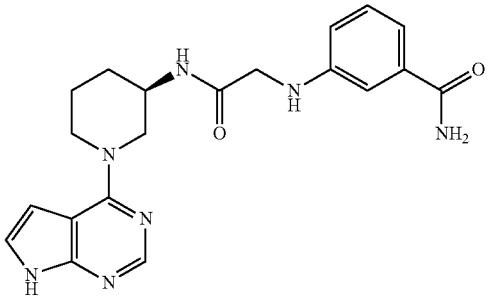 [SMILES: NC(=O)c1cccc(NCC(=O)N[C@@H]2CCCN(c3ncnc4[nH]ccc34)C2)c1] | C |
| 435 | 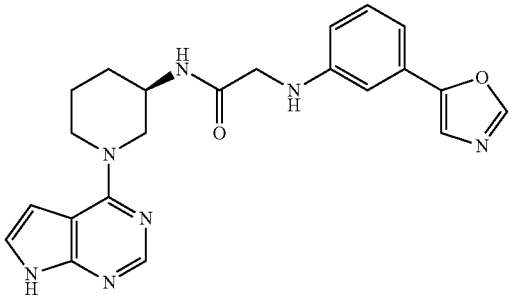 [SMILES: O=C(CNc1cccc(-c2cnco2)c1)N[C@@H]1CCCN(c2ncnc3[nH]ccc23)C1] | C |
| 436 | 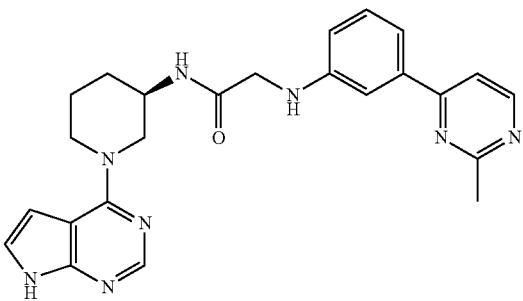 [SMILES: Cc1nccc(-c2cccc(NCC(=O)N[C@@H]3CCCN(c4ncnc5[nH]ccc45)C3)c2)n1] | C |
| 437 | 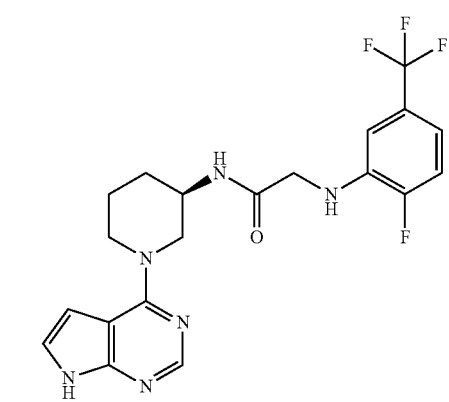 [SMILES: O=C(CNc1cc(C(F)(F)F)ccc1F)N[C@@H]1CCCN(c2ncnc3[nH]ccc23)C1] | C |

TABLE 1-continued

Exemplary compounds of formula I.

| Cmpd. No. | Structure | IC$_{50}$ (10 uM ATP)$^a$ |
|---|---|---|
| 438 | 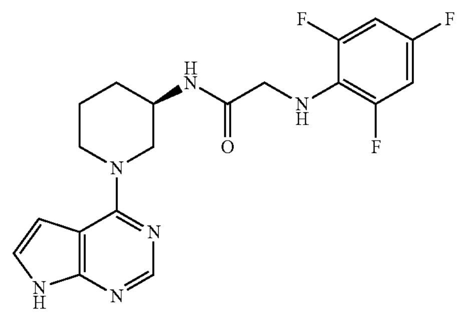 [SMILES: O=C(CNc1c(F)cc(F)cc1F)N[C@@H]1CCCN(c2ncnc3[nH]ccc23)C1] | C |
| 439 | 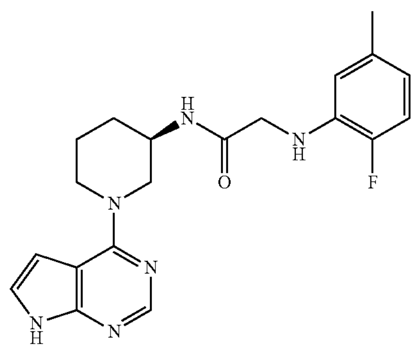 | B |
| 440 | 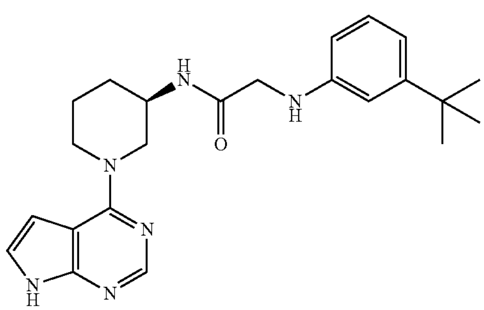 [SMILES: CC(C)(C)c1cccc(NCC(=O)N[C@@H]2CCCN(c3ncnc4[nH]ccc34)C2)c1] | B |
| 441 | 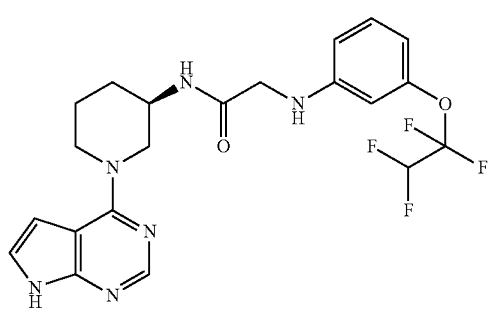 [SMILES: O=C(CNc1cccc(OC(F)(F)C(F)F)c1)N[C@@H]1CCCN(c2ncnc3[nH]ccc23)C1] | B |

TABLE 1-continued
Exemplary compounds of formula I.
| Cmpd. No. | Structure | IC$_{50}$ (10 uM ATP)$^a$ |
|---|---|---|
| 442 | 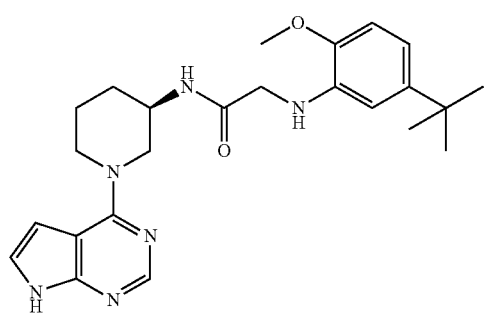 [SMILES: COc1ccc(C(C)(C)C)cc1NCC(=O)N[C@@H]1CCCN(c2ncnc3[nH]ccc23)C1] | C |
| 443 | 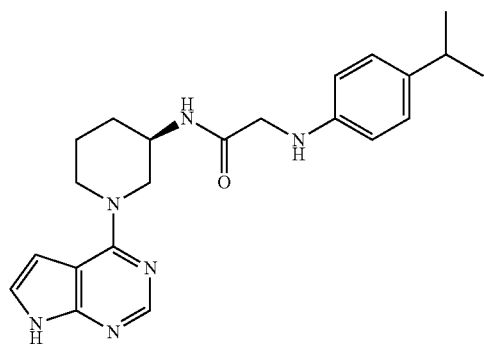 [SMILES: CC(C)c1ccc(NCC(=O)N[C@@H]2CCCN(c3ncnc4[nH]ccc34)C2)cc1] | C |
| 444 | 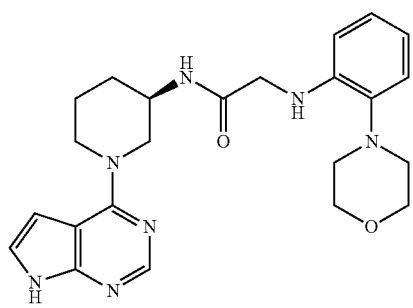 [SMILES: O=C(CNc1ccccc1N1CCOCC1)N[C@@H]1CCCN(c2ncnc3[nH]ccc23)C1] | C |
| 445 | 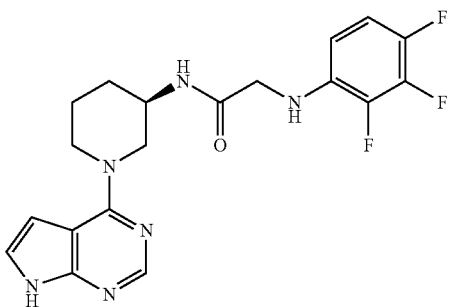 [SMILES: O=C(CNc1ccc(F)c(F)c1F)N[C@@H]1CCCN(c2ncnc3[nH]ccc23)C1] | B |

TABLE 1-continued

Exemplary compounds of formula I.

| Cmpd. No. | Structure | IC$_{50}$ (10 uM ATP)$^a$ |
|---|---|---|
| 446 | 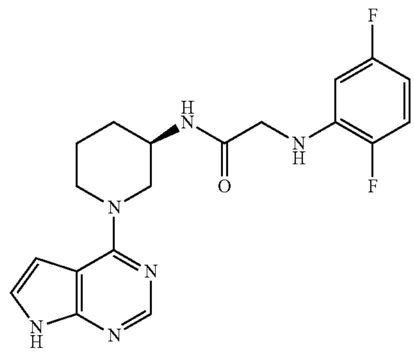 [SMILES: O=C(CNc1cc(F)ccc1F)N[C@@H]1CCCN(c2ncnc3[nH]ccc23)C1] | B |
| 447 | 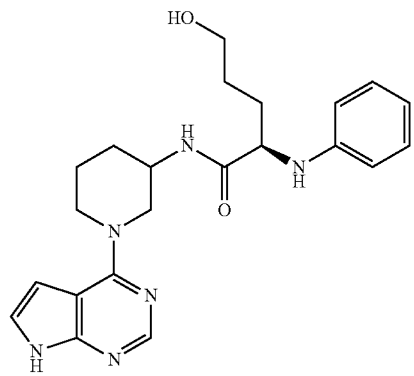 [SMILES: O=C(NC1CCCN(c2ncnc3[nH]ccc23)C1)[C@@H](CCCO)Nc1ccccc1] | C |
| 448 | 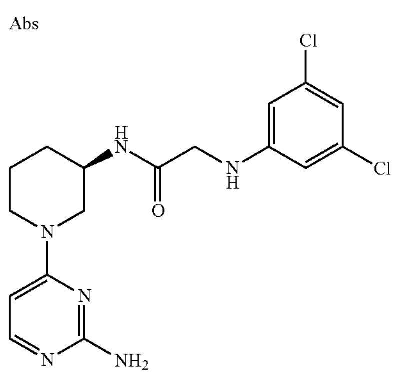 [SMILES: Nc1nccc(N2CCC[C@@H](NC(=O)CNc3cc(Cl)cc(Cl)c3)C2)n1] | C |
| 449 | 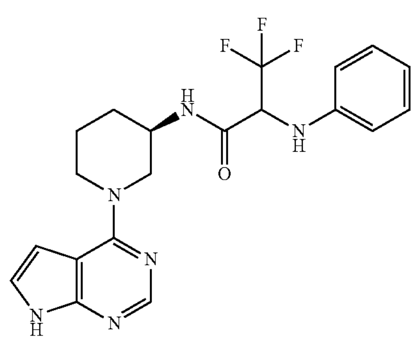 [SMILES: O=C(N[C@@H]1CCCN(c2ncnc3[nH]ccc23)C1)C(Nc1ccccc1)C(F)(F)F] | C |

TABLE 1-continued

Exemplary compounds of formula I.

| Cmpd. No. | Structure | IC$_{50}$ (10 uM ATP) $^a$ |
|---|---|---|
| 450 | Abs | C |
| 451 | 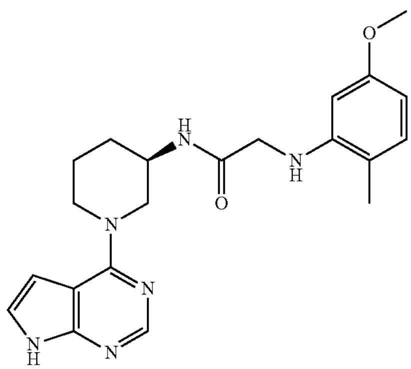 [SMILES: COc1ccc(C)c(NCC(=O)N[C@@H]2CCCN(c3ncnc4[nH]ccc34)C2)c1] | C |
| 452 | 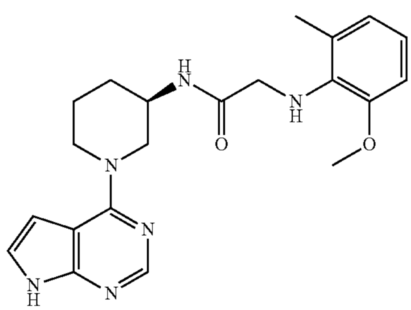 [SMILES: COc1cccc(C)c1NCC(=O)N[C@@H]1CCCN(c2ncnc3[nH]ccc23)C1] | C |
| 453 | 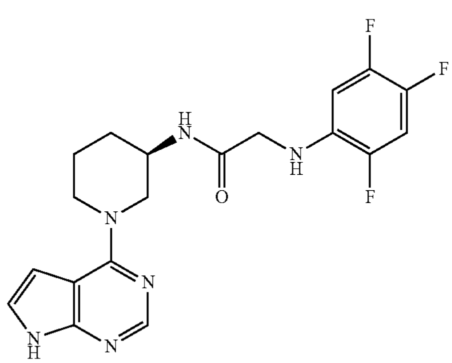 [SMILES: O=C(CNc1cc(F)c(F)cc1F)N[C@@H]1CCCN(c2ncnc3[nH]ccc23)C1] | B |

TABLE 1-continued

Exemplary compounds of formula I.

| Cmpd. No. | Structure | IC$_{50}$ (10 uM ATP)$^a$ |
|---|---|---|
| 454 | 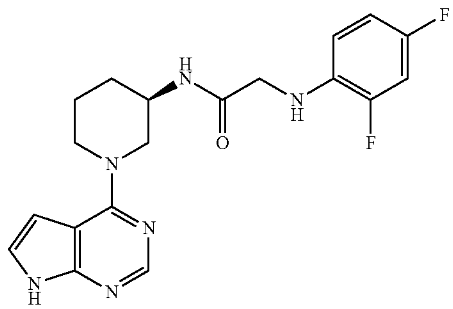 [SMILES: O=C(CNc1ccc(F)cc1F)N[C@@H]1CCCN(c2ncnc3[nH]ccc23)C1] | C |
| 455 | Abs | B |
| 456 | 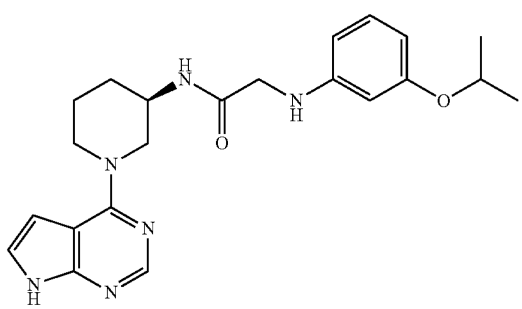 [SMILES: CC(C)Oc1cccc(NCC(=O)N[C@@H]2CCCN(c3ncnc4[nH]ccc34)C2)c1] | C |
| 457 | Abs | C |

TABLE 1-continued
Exemplary compounds of formula I.
| Cmpd. No. | Structure | IC$_{50}$ (10 uM ATP) $^a$ |
|---|---|---|
| 458 | Abs 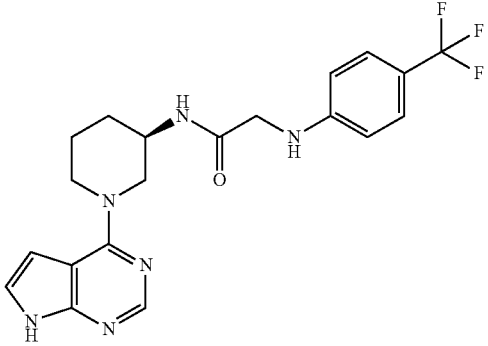 | C |
| 459 | Abs 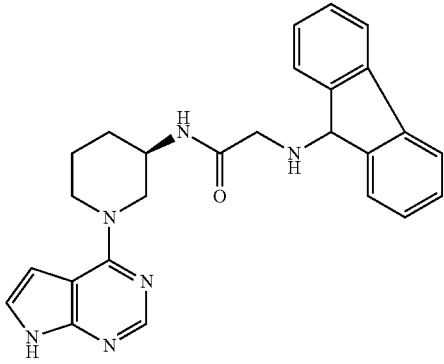 | C |
| 460 | Abs 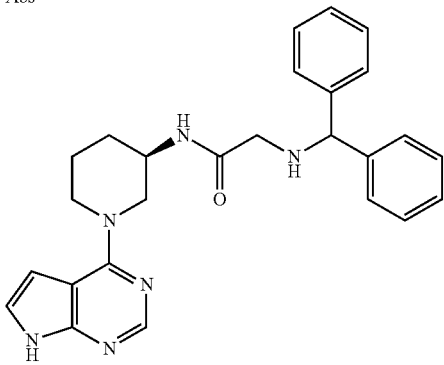 | C |
| 461 | 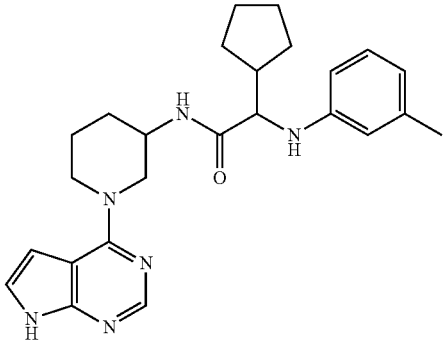 [SMILES: Cc1cccc(NC(C(=O)NC2CCCN(c3ncnc4[nH]ccc34)C2)C2CCCC2)c1] | C |

TABLE 1-continued

Exemplary compounds of formula I.

| Cmpd. No. | Structure | IC$_{50}$ (10 uM ATP) $^a$ |
|---|---|---|
| 462 | 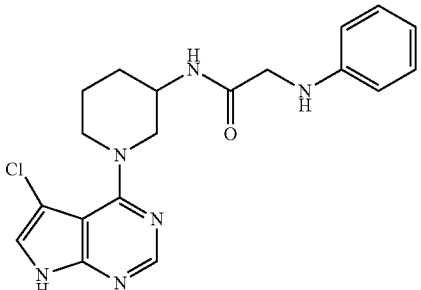 | D |
| 463 | 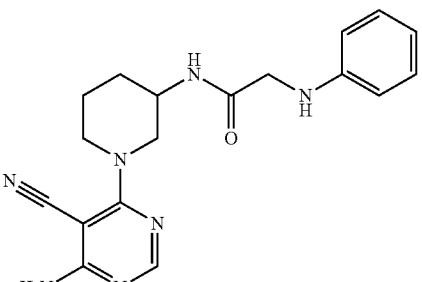 | D |
| 464 | 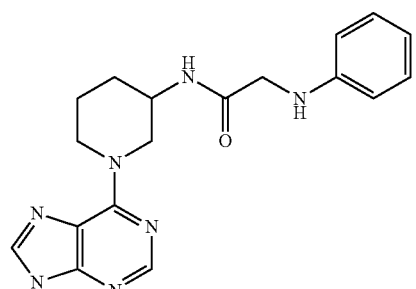 | D |

$^a$ See Example 161.

What is claimed is:

1. A compound having the formula:

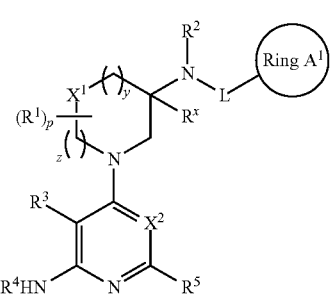

wherein:
$X^1$ is —CR$^6$R$^7$—;
$X^2$ is =N—;
p is 0 or 1;
y is 0 or 1;
z is 2;

each R$^1$ is independently an optionally substituted group selected from C$_{1-12}$ aliphatic, phenyl, a 3-7 membered saturated or partially unsaturated monocyclic carbocyclic ring, a 3-7 membered saturated or partially unsaturated monocyclic heterocyclic ring having 1-2 heteroatoms independently selected from nitrogen, oxygen, or sulfur, or a 5-6 membered heteroaryl ring having 1-3 heteroatoms independently selected from nitrogen, oxygen, or sulfur, R$^2$ is R;

R$^4$ is R, —C(O)R, —CO$_2$R, —C(O)C(O)R, —C(O)CH$_2$C(O)R, —C(O)N(R)$_2$, —S(O)R, —S(O)$_2$R, or —S(O)$_2$N(R)$_2$;

R$^3$ is R, halogen, —CN, —C(O)R, —CO$_2$R, —C(O)C(O)R, —C(O)CH$_2$C(O)R, —S(O)R, —S(O)$_2$R, —C(O)N(R)$_2$, or —SO$_2$N(R)$_2$; or:

R$^3$ and R$^4$ are optionally taken together with their intervening atoms to form an optionally substituted ring selected from pyrrole, pyrazole, or 5-6 membered partially unsaturated monocyclic heterocyclic having 1-2 heteroatoms independently selected from nitrogen, oxygen, or sulfur;

$R^5$ is hydrogen or —$NH_2$;

each of $R^6$ and $R^7$ is independently R;

$R^x$ is hydrogen, or:

$R^x$ and $R^2$ are taken together to form an optionally substituted spirocyclic heterocyclic ring selected from a 5-6 membered saturated or partially unsaturated monocyclic heterocyclic ring having 1-2 heteroatoms independently selected from nitrogen, oxygen, or sulfur;

Ring $A^1$ is an optionally substituted ring selected from phenyl, a 3-7 membered saturated or partially unsaturated monocyclic carbocyclic ring, a 7-10 membered saturated or partially unsaturated bicyclic carbocyclic ring, a 3-7 membered saturated or partially unsaturated monocyclic heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, an 8-10 membered bicyclic aryl ring, a 5-6 membered heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur;

L is —C(O)C(R)$_2$NR—; and each R is independently hydrogen or an optionally substituted group selected from $C_{1-6}$ aliphatic or 3-7 membered saturated carbocyclic, wherein a substituent on R is selected from —$CF_3$ or —OH.

2. The compound of claim 1, wherein the compound is of formula IV-a:

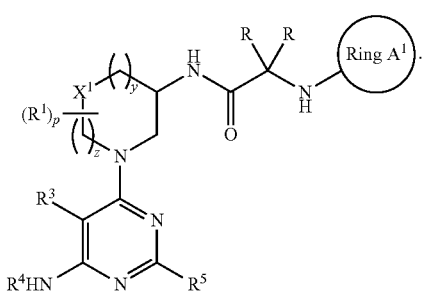

IV-a

3. The compound of claim 1, wherein L is:

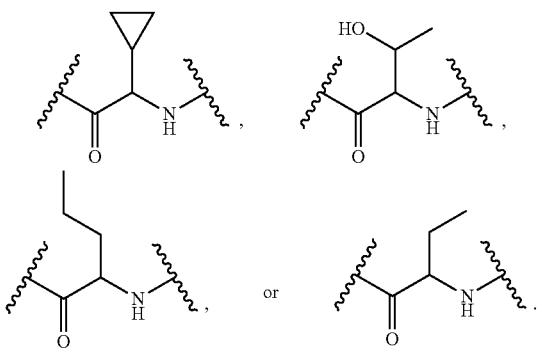

4. The compound of claim 1, wherein p is 0.

5. The compound of claim 1, wherein $R^2$ is hydrogen or optionally substituted $C_{1-6}$ aliphatic.

6. The compound of claim 1, wherein $R^x$ is hydrogen.

7. The compound of claim 1, wherein $R^5$ is hydrogen.

8. The compound of claim 1, wherein $R^3$ and $R^4$ are taken together with their intervening atoms to form an optionally substituted ring selected from pyrrole or pyrazole.

9. The compound of claim 8, wherein the compound is of formula VII-a, or VIII-a:

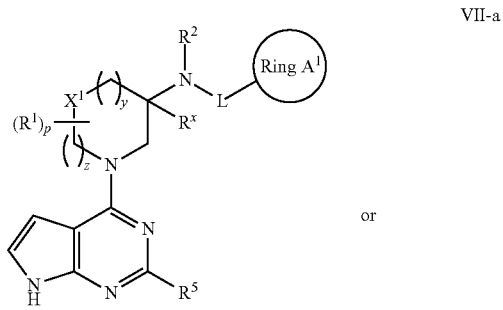

VII-a or

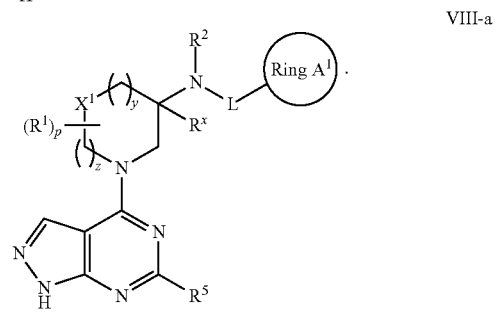

VIII-a

10. The compound of claim 1, wherein $R^4$ is hydrogen, —C(O)R, or optionally substituted $C_{1-6}$ aliphatic.

11. The compound of claim 1, wherein $R^3$ is halogen, —CN, or substituted or unsubstituted $C_{1-6}$ alkyl.

12. The compound of claim 1, wherein Ring $A^1$ is an optionally substituted ring selected from phenyl, an 8-10 membered bicyclic aryl ring, a 5-6 membered heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur.

13. The compound of claim 12, wherein Ring $A^1$ is bicyclic.

14. The compound of claim 12, wherein Ring $A^1$ is substituted phenyl.

15. The compound of claim 14, wherein substituents on Ring $A^1$ are selected from halogen, —CN, —$CF_3$, —OH, —$NH_2$, —$N(R)_2$, —COOH, —SR, —S(O)R, —S(O)$_2$R, —S(O)N(R)$_2$, —S(O)$_2$N(R)$_2$, or $C_{1-6}$ aliphatic.

16. A compound as shown in Table 1.

17. A pharmaceutical formulation comprising a compound of claim 1 and a pharmaceutically acceptable excipient.

18. A method of reducing the enzymatic activity of Bruton's tyrosine kinase comprising contacting Bruton's tyrosine kinase with an effective amount of a compound of claim 1 or a composition thereof.

* * * * *